US008198479B2

(12) United States Patent
Arhancet et al.

(10) Patent No.: US 8,198,479 B2
(45) Date of Patent: Jun. 12, 2012

(54) TRANSITION METAL-CONTAINING CATALYSTS AND CATALYST COMBINATIONS INCLUDING TRANSITION METAL-CONTAINING CATALYSTS AND PROCESSES FOR THEIR PREPARATION AND USE AS OXIDATION CATALYSTS

(75) Inventors: Juan P. Arhancet, Creve Coeur, MO (US); Fuchen Liu, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1647 days.

(21) Appl. No.: 11/357,900

(22) Filed: Feb. 17, 2006

(65) Prior Publication Data
US 2006/0229466 A1 Oct. 12, 2006

Related U.S. Application Data

(60) Provisional application No. 60/654,085, filed on Feb. 17, 2005, provisional application No. 60/654,086, filed on Feb. 17, 2005, provisional application No. 60/656,153, filed on Feb. 24, 2005.

(51) Int. Cl.
C07C 227/18 (2006.01)
(52) U.S. Cl. ...................................................... 562/575
(58) Field of Classification Search .................. 562/575
See application file for complete search history.

(56) References Cited

U.S. PATENT DOCUMENTS

| | | | |
|---|---|---|---|
| 2,384,817 A | 9/1945 | Chitwood | |
| 3,143,511 A | 8/1964 | Bichard et al. | |
| 3,702,886 A | 11/1972 | Argauer et al. | |
| 3,799,758 A | 3/1974 | Franz | |
| 3,871,998 A | 3/1975 | Rase et al. | |
| 3,950,402 A | 4/1976 | Franz | |
| 3,969,398 A | 7/1976 | Hershman | |
| 4,264,776 A | 4/1981 | Hershman et al. | |
| 4,325,842 A | 4/1982 | Slaugh et al. | |
| 4,325,843 A | 4/1982 | Slaugh et al. | |
| 4,326,992 A | 4/1982 | Slaugh et al. | |
| 4,333,916 A | 6/1982 | Iwai et al. | |
| 4,345,038 A | 8/1982 | McCandish et al. | |
| 4,410,501 A | 10/1983 | Taramasso et al. | |
| 4,476,102 A | 10/1984 | McCandish et al. | |
| 4,480,135 A | 10/1984 | Esposito et al. | |
| 4,522,708 A | 6/1985 | Leclercq et al. | |
| 4,526,878 A | 7/1985 | Takegami et al. | |
| 4,579,689 A | 4/1986 | Hershman et al. | |
| 4,582,650 A | 4/1986 | Felthouse | |
| 4,624,937 A | 11/1986 | Chou | |
| 4,686,203 A | 8/1987 | Desmond et al. | |
| 4,696,772 A | 9/1987 | Chou | |
| 4,775,498 A | 10/1988 | Gentilcore | |
| 4,782,183 A | 11/1988 | Goto et al. | |
| 4,853,159 A | 8/1989 | Riley et al. | |
| 4,895,680 A | 1/1990 | Ellis, Jr. et al. | |
| 5,023,369 A | 6/1991 | Fields, Jr. | |
| 5,043,475 A | 8/1991 | Fields, Jr. | |
| 5,098,684 A | 3/1992 | Kresge et al. | |
| 5,138,111 A | 8/1992 | Kugler et al. | |
| 5,179,228 A | 1/1993 | Martin Ramon et al. | |
| 5,292,936 A | 3/1994 | Franczyk | |
| 5,338,716 A | 8/1994 | Triplett et al. | |
| 5,367,112 A | 11/1994 | Franczyk | |
| 5,372,981 A | 12/1994 | Witherspoon | |
| 5,427,761 A | 6/1995 | Grindatto et al. | |
| 5,500,199 A | 3/1996 | Bellussi et al. | |
| 5,525,563 A | 6/1996 | Thiele et al. | |
| 5,606,107 A | 2/1997 | Smith | |
| 5,627,125 A | 5/1997 | Ebner et al. | |
| 5,739,390 A | 4/1998 | Franczyk et al. | |
| 5,977,009 A | 11/1999 | Faraj | |
| 5,989,648 A | 11/1999 | Phillips | |
| 6,005,140 A | 12/1999 | Morgenstern et al. | |
| 6,106,803 A | 8/2000 | Hasenzahl et al. | |
| 6,169,152 B1 | 1/2001 | Sakai | |
| 6,265,339 B1 | 7/2001 | Bidell et al. | |
| 6,309,772 B1 | 10/2001 | Zuber et al. | |
| 6,329,478 B1 | 12/2001 | Katayama et al. | |
| 6,376,708 B1 | 4/2002 | Morgenstern et al. | |
| 6,391,278 B1 | 5/2002 | Pinnavaia et al. | |
| 6,403,514 B1 | 6/2002 | Mantegazza et al. | |
| 6,417,133 B1 | 7/2002 | Ebner et al. | |
| 6,436,816 B1 | 8/2002 | Lee et al. | |

(Continued)

FOREIGN PATENT DOCUMENTS

DE 4 336 829 5/1995

(Continued)

OTHER PUBLICATIONS

Non-Final Office Action dated Dec. 15, 2009, U.S. Appl. No. 10/919,028, 8 pages.
Amendment G submitted Mar. 15, 2010 in connection with U.S. Appl. No. 10/919,028 in response to Office action dated Dec. 15, 2009.
Final Office action dated Dec. 9, 2008 in connection with U.S. Appl. No. 10/919,028.
Amendment E submitted Aug. 19, 2008 in connection with U.S. Appl. No. 10/919,028 in response to the Non-Final Office action dated Mar. 19, 2008.

(Continued)

Primary Examiner — Peter O Sullivan
(74) Attorney, Agent, or Firm — Senniger Powers LLP; Joseph A. Schaper

(57) ABSTRACT

This invention relates to the field of heterogeneous catalysis, and more particularly to catalysts including carbon supports having compositions which comprise one or more transition metals in combination with nitrogen and/or carbon formed on or over the surface of the carbon support. The present invention also relates to catalyst combinations comprising catalysts including carbon supports having compositions which comprise one or more transition metals in combination with nitrogen and/or carbon formed on or over the surface of a carbon support and a secondary catalyst or, co-catalyst, including a secondary transition metal. The invention further relates to the field of catalytic oxidation reactions, including the preparation of secondary amines by the catalytic oxidation of tertiary amines.

98 Claims, 73 Drawing Sheets

U.S. PATENT DOCUMENTS

| | | | |
|---|---|---|---|
| 6,528,680 | B1 | 3/2003 | Aust et al. |
| 6,667,023 | B2 | 12/2003 | Ludvig |
| 6,683,018 | B1 | 1/2004 | Kristen et al. |
| 6,689,711 | B2 | 2/2004 | Lefebvre |
| 6,696,384 | B2 | 2/2004 | McCrae et al. |
| 6,764,874 | B1 | 7/2004 | Zhang et al. |
| 6,841,144 | B2 | 1/2005 | Hasenzahl et al. |
| 6,849,114 | B2 | 2/2005 | Oswald et al. |
| 6,849,570 | B2 | 2/2005 | Hasenzahl et al. |
| 6,849,752 | B2 | 2/2005 | Tsujioka et al. |
| 6,963,009 | B2 | 11/2005 | Leiber et al. |
| 2002/0013222 | A1 | 1/2002 | Rei et al. |
| 2002/0068836 | A1 | 6/2002 | Haupfear et al. |
| 2002/0121460 | A1 | 9/2002 | Moy et al. |
| 2003/0092565 | A1 | 5/2003 | Chaudhari et al. |
| 2003/0228972 | A1 | 12/2003 | Birss et al. |
| 2004/0000456 | A1 | 12/2003 | Green et al. |
| 2004/0081877 | A1 | 4/2004 | Kim et al. |
| 2005/0014635 | A1 | 1/2005 | Zhou et al. |
| 2005/0142428 | A1 | 6/2005 | Daimon et al. |
| 2005/0250863 | A1 | 11/2005 | Green et al. |
| 2006/0088741 | A1 | 4/2006 | Yan et al. |

FOREIGN PATENT DOCUMENTS

| | | |
|---|---|---|
| EP | 0 100 119 A1 | 2/1984 |
| EP | 0 115 697 A1 | 8/1984 |
| EP | 0439445 | 7/1991 |
| EP | 1 236 509 A1 | 9/2002 |
| EP | 1 494 304 A1 | 1/2005 |
| EP | 1 604 964 A1 | 12/2005 |
| FR | 2 798 079 A1 | 3/2001 |
| FR | 2798 135 A1 | 3/2001 |
| GB | 2116974 A | 10/1983 |
| WO | WO 95/32150 A1 | 11/1995 |
| WO | WO 00/62926 A1 | 10/2000 |
| WO | WO 01/28679 A1 | 4/2001 |
| WO | WO 01/77052 A1 | 10/2001 |
| WO | WO 02/098557 A1 | 12/2002 |
| WO | WO 03/068387 A1 | 8/2003 |
| WO | WO 2005016519 A1 | 2/2005 |
| WO | WO 2005080269 A2 | 9/2005 |
| WO | 2006/031938 A2 | 3/2006 |

OTHER PUBLICATIONS

Allum, K.G., et al., "Supported Transition Metal Complexes V. Liquid Phase Catalytic Hydrogenation of Hexene-1; Cyclohexene and Isoprene under Continuous Flow Conditions," Journal of Catalysis, 1976, pp. 331-338, vol. 43.

Allum, K.G., et al., "Supported Transition Metal Complexes IV. Rhodium Catalysts for the Liquid Phase Hydrogormylation of Hexene-1," Journal of Catalysis, 1976, pp. 322-330, vol. 43.

Arana, C., et al., "Electrocatalytic Reduction of Carbon Dioxide with Iron, Cobalt, and Nickel Complexes of Terdentate Ligands," Inorg. Chem., 1992, pp. 3680-3682, vol. 31.

Frostin-Rio, M., et al., "Oxidation of Phenois by Molecular Oxygen Catalysed by Transition Metal Complexes. Comparison Between the Activity of Various Cobalt and manganese Complexes and the Role of Peroxy Intermediates," J. Chem. Soc. Perkin Trans., 1984, pp. 1971-1979, vol. 1.

Hesse, D., et al., "Advantages and Problems in the Use of Transition-Metal Complexes as SLPC," Annual AIChE Meeting, Session 114, 1985, pp. 1-8.

Non-final Office action dated Oct. 29, 2008 in connection with U.S. Appl. No. 11/274,555.

Liu et al., "Advances in CNx Nanotube Growth," Mat. Res. Soc. Symp. Proc., 2003, pp. M2.5.1-M2.5.7, vol. 772.

Notice of Allowance dated Feb. 4, 2008 in connection with U.S. Appl. No. 10/923,416.

Supplemental Notice of Allowance dated Mar. 5, 2008 in connection with U.S. Appl. No. 10/923,416.

Supplemental Notice of Allowance dated Mar. 18, 2008 in connection with U.S. Appl. No. 10/923,416.

Supplemental Notice of Allowance dated May 19, 2008 in connection with U.S. Appl. No. 10/923,416.

Supplemental Notice of Allowance dated Jun. 4, 2008 in connection with U.S. Appl. No. 10/923,416.

Non-Final Office action dated Mar. 19, 2008 in connection with U.S. Appl. No. 10/919,028.

Non-Final Office action dated Dec. 26, 2008 in connection with U.S. Appl. No. 12/124,497.

Allum, K.G. et al., "Supported Transition Metal Complexes IV. Rhodium Catalysts for the Liquid Phase Hydroformylation of Hexene-1", Journal of Catalysis, (1976), pp. 322-330, vol. 43.

Allum, K.G. et al., "Supported Transition Metal Complexes V. Liquid Phase Catalytic Hydrogenation of Hexene-1; Cyclohexene and Isoprene Under Continuous Flow Conditions", Journal of Catalysis, (1976), pp. 331-338, vol. 43.

Alvarez-Merino, M. et al., "Tungsten Catalysts Supported on Activated Carbon," Journal of Catalysis, (2000), pp. 363-373, vol. 192, Academic Press.

Alves, M.C.M. et al., Characterization of New Systems for the Catalytic Electroreduction of Oxygen by Electrochemistry and X-Ray Absorption Spectroscopy, NATO ASI Series, Series C: Mathematical and Physical Sciences, Synchrotron Techniques in Interfacial Electrochemistry, (1994), pp. 281-293, vol. 432, Kluwer Academic Press, The Netherlands.

Arana, C. et al., "Electrocatalytic Reduction of Carbon Dioxide with Iron, Cobalt, and Nickel Complexes of Terdentate Ligands", Inorg. Chem., (1992), pp. 3680-3682, vol. 31.

Bachiller-Baeza B. et al., "Ruthenium-Supported Catalysts for the Steroselective Hydrogenation of Paracetamol to 4-*trans*-acetamidocyclohexanol: Effect of Support, Metal Precursor, and Solvent", Journal of Catalysis, (2005), pp. 439-445, vol. 229.

Berger, R. et al., "Magnetic Resonance of Superparamagnetic Iron-Containing Nanoparticles in Annealed Glass", Journal of Applied Physics, (2000), pp. 7389-7396, vol. 87:10.

Besson, M. et al., "Active Carbons as Catalysts for Liquid Phase Reactions", Catalysis Today, (2005), pp. 160-165, vol. 102-103.

Bett, J.S. et al., "Platinum-macrocycle co-catalysts for the Electrochemical Oxidation of Methanol", Electrochimica Acta, (1998), pp. 3645-3655, vol. 43:24, Elsevier Science Ltd., Great Britain.

Birss, V. I. et al., "Non-Noble Metal Catalysts for PEM Oxygen Reduction Based on Sol Gel Derived Cobalt Nigrogen Compounds," *Electrochemical Society Proceedings*, (2002), pp. 89-98, vol. 2002-31, Electrochemical Society.

Bouwkamp-Wijnoltz, A.L. et al., "Electrochemical Reduction of Oxygen: An Alternative Method to Prepare Active $CoN_4$ Catalysts", Electrochimica Acta., (1999), pp. 379-386, vol. 45.

Bouwkamp-Wijnoltz, A.L. et al., "On Active-Site Heterogeneity in Pyrolyzed Carbon-Supported Iron Porphyrin Catalysts for the Electrochemical Reduction of Oxygen: An In Situ Mossbauer Study", J. Phys. Chem., (2002), pp. 12993-13001, vol. 106:50.

Bridgewater, A. J. et al., "Reactions of Carbon Monoxide with Hydrogen Over Molybdenum/Charcoal Catalysts," Journal of Catalysis, (1982), pp. 116-125, vol. 78.

Brunetta, A. et al., "Epoxidation Versus Baeyer—Villiger Oxidation: The Possible Role of Lewis Acidity in the Control of Selectivity in Catalysis by Transition Metal Complexes", Eur. J. Inorg. Chem., (2004), pp. 1030-1038.

Camblor, M.A. et al., "Synthesis of a Titaniumsilicoaluminate Isomorphous to Zeolite Beta and its Application as a Catalyst for the Selective Oxidation of Large Organic Molecules", Journal of the Chemical Society, Chemical Communications, (1992), pp. 589-590, vol. 8.

Collman, J.P. et al., "Electrode Catalysis of the Four-Electron Reduction of Oxygen to Water by Dicobalt Face-to-Face Porphyrins," *Journal of American Chemical Society*, (1980), pp. 6027-6036, vol. 102, American Chemical Society.

Cote, R. et al., "Non-Noble Metal-Based Catalysts for the Reduction of Oxygen in Polymer Electrolyte Fuel Cells," Journal of New Materials for Electrochemical Systems I, (1998), pp. 7-16.

Dandekar A. et al., "Carbon-Supported Copper Catalysts," Journal of Catalysis, (1999), pp. 131-154, vol. 183, Academic Press.

Deng, Charles Z. et al., "Sputtered Cobalt-Carbon-Nitrogen Thin Films as Oxygen Reduction Electrocatalysts", J. Electrochem. Soc., Oct. 1998, pp. 3507-3512, vol. 145:10.

Dignard-Bailey, L. et al., "Graphitization and Particle Size Analysis of Pyrolyzed Cobalt Phthalocyanine/Carbon Catalysts for Oxygen Reduction in Fuel Cells," *Journal of Materials Research*, (1994), pp. 3203-3209, vol. 9:12, Materials Research Society.

Drago, R.S., "Electron Paramagnetic Resonance Spectroscopy", Physical Methods in Chemistry, University of Illinois, Urbana, pp. 316-329, W.B. Saunders Company, (1997).

Durand, Jr., R.R. et al., "Catalysis of Dioxygen Reduction at Graphite Electrodes by an Adsorbed Cobalt(II) Porphyrin," *Journal of Electroanalytical Chemistry*, (1982), pp. 273-289, vol. 134:2, Elsevier Sequoia S.A., Lausanne, The Netherlands.

Eisch, J.J. et al., "The Roles of Oxidation State, Lewis Acid Cocatalyst and Solvent Polarity in Activating Titanium compounds for Olefin Polymerization", Macromol. Symp., (1995), pp. 221-229, vol. 89.

Ewen, R.J. et al., "X-Ray Photoelectron Spectroscopy of Clean and Gas-Doped Films of Phthalocyanines," *Journal of Physics Condensed Matter*, (1991), pp. S303-S310, vol. 3, IOP Publishing Ltd., An Institute of Physics Journal, United Kingdom.

Faubert, G. et al., "Activation and Characterization of Fe-Based Catalysts for the Reduction of Oxygen in Polymer Electrolyte Fuel Cells," Electrochimica Acta., (1998), pp. 1969-1984, vol. 43:14-15, Elsevier Science Ltd., Great Britain.

Faubert, G. et al., "Heat-Treated Iron and Cobalt Tetraphenylporphyrins Adsorbed on Carbon Black: Physical Characterization and Catalytic Properties of these Materials for the Reduction of Oxygen in Polymer Electrolyte Fuel Cells," *Electrochimica Acta*, (1996), pp. 1689-1701, vol. 41:10, Elsevier Science Ltd., Great Britain.

Faubert, G. et al., "Iron Catalysts Prepared by High-Temperature Pyrolysis of Tetraphenylporphyrins Adsorbed on Carbon Black for Oxygen Reduction in Polymer Electrolyte Fuel Cells," Electrochimica Acta., (1998), pp. 341-353, vol. 43:3-4, Elsevier Science Ltd. Great Britain.

Faubert, G. et al., "Oxygen Reduction Catalysts for Polymer Electrolyte Fuel Cells from the Pyrolysis of Fel Acetate Adsorbed on 3,4,9,10-Perylenetetracarboxylic Dianhydride," Electrochimica Acta, (1999), pp. 2589-2603, vol. 44, Elsevier Science Ltd.

Flanigen, E.M. et al., "Silicalite, A New Hydrophobic Crystalline Silica Molecular Sieve", Nature, (1978), pp. 512-516, vol. 271:5645.

Fournier, J. et al., "Activation of Various Fe-Based Precursors on Carbon Black and Graphite Supports to Obtain Catalysts for the Reduction of Oxygen in Fuel Cells", J. Electrochem. Soc., (1997), pp. 218-226, vol. 144:1.

Franz, J. E. et al., Glyphosate: A Unique Global Herbicide, Chapter 8—"Methods of Preparing Glyphosate," American Chemical Society, (1997), pp. 233-262, Washington, D.C.

Frostin-Rio, M. et al., "Oxidation of Phenols by Molecular Oxygen Catalysed by Transition Metal Complexes. Comparison between the Activity of Various Cobalt and Manganese Complexes and the Role of Peroxy Intermediates", J. Chem. Soc. Perkin Trans., (1984), pp. 1971-1979, vol. 1.

Fu, Z. et al., "HMS Catalysts Containing Transition Metals or Transition Metal Complexes", Studies in Surface Science and Catalysis, (2001), pp. 1-7, vol. 135.

Glerup, M. et al., "Synthesis of Highly Nitrogen-Doped Multi-Walled Carbon Nanotubes", Chem. Commun., (2003), pp. 2542-2543, The Royal Society of Chemistry.

Gontier, S. et al., "Oxidation of Aniline Over TS-1, the Titanium Substituted Silicalite-1", Applied Catalysis A: General, (1994), pp. 173-186, vol. 118.

Granger, P., et al., "Kinetics of the NO And CO Reaction Over Platinum Catalysts," Journal of Catalysis, (1998), pp. 304-314, Academic Press.

Gupta, S. et al., "Methanol-Tolerant Electrocatalysts for Oxygen Reduction in a Polymer Electrolyte Membrane Fuel Cell", J. Appl. Electrochem., (1998), pp. 673-682, vol. 28:7.

He, P. et al., "Oxygen Reduction Catalysts for Polymer Electrolyte Fuel Cells From the Pyrolysis of Various Transition Metal Acetates Adsorbed on 3,4,9,10-Perylenetetracarboxylic Dianhydride," Journal of New Material for Electrochemical Systems, (1999), pp. 243-251, vol. 2, Journal of New Material Electrochemical Systems.

Hesse, D. et al., "Advantages and Problems in the Use of Transition-Metal Complexes as SLPC", Annual AIChE Meeting, Session 114, (1985), pp. 1-8.

Hirai, H. et al., "Selective Hydrogenation of Cyclopentadiene to Cyclopentene Using Colloidal Palladium Supported on Chelate Resin", The Chemical Society of Japan, (1984), pp. 488-494, vol. 57:2.

Hirai, Toshiro et al., "The Influence of Catalyst-Supporting Methods on Electrochemical Activity and the Resultant Stability of Air Electrodes Activated with Iron Pythalocyanine", Journal of Applied Electrochemistry, (1985), pp. 441-445, Chapman and Hall Ltd.

Hiromoto, S. et al., "Surface Characterization and Anodic Polarization of Nitrogen-Ion-Implanted Nickel-Free Co—Cr—Mo Alloy", Materials Transactions, (2005), pp. 1627-1632, vol. 46:7.

Huybrechts, D.R.C. et al., "Oxyfunctionalization of Alkanes with Hydrogen Peroxide on Titanium Silicalite", Nature, (1990), pp. 240-242, vol. 345:6272.

Jasinski, R., "Cobalt Phthalocyanine as a Fuel Cell Cathode,"Journal of the Electrochemical Society, (1965), pp. 526-528, vol. 112:5.

Kaliya, M.L. et al., "Highly Effective Oxidative Cracking of $n$-butane in Light Olefins on a Novel Cobalt Catalyst", Catalysis Today, (2005), pp. 95-98, vol. 106.

Kalvelage, H. et al., "Electrochemical Reduction of Oxygen at Pyrolyzed Iron and Cobalt N4-Chelates on Carbon Black Supports", Chem. Eng. Technol., (2000), pp. 803-807, vol. 23:9.

Kim, D-W et al., "CoMo Bimetallic Nitride Catalysts for Thiophene HDS," *Catalysis Letters*, (1997), pp. 91-95, vol. 43:1-2, J.C. Baltzer AG, Science Publishers.

Kimbara, N. et al., "New Type of TiN Support for Hydroprocessing Catalyst Yst.," Catal. Lett., (1990), pp. 3-6, vol. 6.

Kirk-Othmer Encyclopedia of Chemical Technology, Molecular Sieves, (1999), pp. 1330-1333, 4th Edition, John Wiley & Sons, New York.

Kliava, J. et al., "Size and Shape Distribution of Magnetic Nanoparticles in Disordered Systems: Computer Simulations of Superparamagnetic Resonance Spectra", Journal of Magnetism and Magnetic Materials, (1999), pp. 328-342, vol. 205.

Lalande, G. et al., "Catalytic Activity and Stability of Heat-Treated Iron Phthalocyanines for the Electroreduction of Oxygen in Polymer Electrolyte Fuel Cells," *Journal of Power Sources*, (1996), pp. 227-237, vol. 61, Elsevier Science S.A.

Lalande, G. et al., "Chromium-Based Electrocatalysts for Oxygen Reduction in Polymer Electrolyte Fuel Cells,"New Materials for Fuel Cell and Modern Battery Systems II, Proceedings of the International Symposium on New Materials for Fuel Cell and Modern Battery Systems, 2nd Montreal, (1997), pp. 768-777, Ecole Polytechnique De Montreal, Montreal Que.

Lalande, G., et al., "Electroreduction of Oxygen in Polymer Electrolyte Fuel Cells by Activated Carbon Coated Cobalt Nanocrystallites Produced by Electric Arc Discharge,"Chemistry of Materials, (1997), pp. 784-790, vol. 9:3, American Chemical Society.

Lalande, G. et al., "Is Nitrogen Important in the Formulation of Fe-based Catalysts for Oxygen Reduction in Solid Polymer Fuel Cells?", Electrochimica Acta., (1997), pp. 1379-1388, vol. 42:9, Great Britain.

Lalande, G. et al., "Rotating Disk Electrode Measurements on the Electrocatalytic Activity of Heat-Treated Carbon Supported Cobalt Phthalocyanine Catalysts for Oxygen Reduction,"Electrochemical Society Proceedings, (1994), pp. 418-429, Electrochemical Society.

Lefevre, M. et al., "Functionalities of a Fe-Based Catalyst Evidenced by ToF-SIMS in Relation with the Electroreduction of Oxygen in Polymer Electrolyte Fuel Cells,"Secondary Ion Mass Spectrometry, SIMS XII, Proceedings of the International Conference on Secondary Ion Mass Spectrometry, (1999), pp. 447-450, Elsevier Science, Amsterdam, Netherlands.

Lefévre, M. et al., "Molecular Oxygen Reduction in PEM Fuel Cells: Evidence for the Simultaneous Presence of Two Active Sites in Fe-Based Catalysts," Journal of Physical Chemistry, (2002), pp. 8705-8713, vol. 106:34.

Lefévre, M. et al., "Molecular Oxygen Reduction in PEM Fuel Cells: ToF-SIMS Analysis of Co-Based Electrocatalysts", J. Phys. Chem. B. (2005), pp. 16718-16724, vol. 109:35.

Lefévre, M. et al., "O₂ Reduction in PEM Fuel Cells: Activity and Active Site Structural Information for Catalysts Obtained by the Pyrolysis at High Temperature of Fe Precursors," Journal of Physical Chemistry B, (2000), pp. 11238-11247, vol. 104, American Chemical Society.

Lekhal, A. et al., "Influence of pH and Ionic strength on the Metal Profile of Impregnation Catalysts", Chemical Engineering Science, (2004), pp. 1063-1077, vol. 59.

Levy, R. B. et al., "Platinum-Like Behavior of Tungsten Carbide in Surface Catalysis," Science, (1973), pp. 547-549, vol. 181.

Liang, C., et al., "Activated Carbon Supported Bimetallic CoMo Carbides Synthesized by Carbothermal Hydrogen Reduction," Carbon, (2003), pp. 1833-1839, vol. 41, Elsevier Science.

Lin, C-A et al., "Characterization of Boron-Nitride-Supported Pt Catalysts for the Deep Oxidation of Benzene," Journal of Catalysis, (2002), pp. 39-45, vol. 210, Elsevier Science, USA.

Lin, W-F et al., "On-Line FTIR Spectroscopic Investigations of Methanol Oxidation in a Direct Methanol Fuel Cell", J. Electrochem. Soc., (1997), pp. 1917-1922, vol. 144:6.

Marcotte, S. et al., "Electroreduction of Oxygen on Co-based Catalysts: Determination of the Parameters Affecting the Two-Electron Transfer Reaction in an Acid Medium," Electrochimica Acta, (2004), pp. 179-188, vol. 50:1, Elsevier Ltd.

Markusse, A.P. et al., "Platinum Deactivation: in situ EXAFS During Aqueous Alcohol Oxidation Reaction", Catalysis Letters, (1998), pp. 141-145.

Martens, J.A. et al., "Hydroxylation of Phenol with Hydrogen Peroxide on EUROTS-1 Catalyst", Applied Catalysis A: General, (1993), pp. 71-84, vol. 99.

Mehn, D. et al., "A Comparison of Different Preparation Methods of Fe/Mo/Al₂O₃ Sol-Gel Catalyst for Synthesis of Single Wall Carbon Nanotubes", Chemical Physics Letters, (2004), pp. 378-384, vol. 393.

Milad, Issa K. et al., "A Comparison of Bulk Metal Nitride Catalysts for Pyridine Hydrodenitrogenation," Catalysis Letters, (1998), pp. 113-119, vol. 52:1-2, J.C. Baltzer AG, Science Publishers.

Mordenti, D. et al., "New Synthesis of Mo₂ 14 nm in Average Size Supported on a High Specific Surface Area Carbon Material," Journal of Solid State Chemistry, (1998), pp. 114-120, vol. 141, Academic Press.

Mukerjee, S. et al., "An in Situ X-Ray Absorption Spectroscopy Investigation of the Effect of Sn Additions to Carbon-Supported Pt Electrocatalysts", Journal of The Electrochemical Society, (1999), pp. 600-606, vol. 146:2.

Murav'ev, V. I., "Carbonitriding in a Fluidized Bed of Carbon-Graphite Materials," Metal Science and Heat Treatment, (1976), pp. 492-495, vol. 18:5-6, Consultants Bureau, New York.

Nagai, M. et al., "Catalytic Activity and Surface Properties of Nitride Molybdena-Alumina for Carbazole Hydrodenitrogenation," Journal of Catalysis, (2000), pp. 128-137, vol. 191, Academic Press.

Nhut, J.M. et al., "Synthesis and Catalytic Uses of Carbon and Silicon Carbide Nanostructures," Catalysis Today, (2002), pp. 11-32, vol. 76, Elsevier Science B. V.

Nishihara, H. et al., "Electrochemical Olefin Epoxidation with Manganese meso-Tetraphenylporphyrin Catalyst and Hydrogen Peroxide Generation at Polymer-Coated Electrodes,"Inorganic Chemistry, (1990), pp. 1000-1006, vol. 29:5, American Chemical Society.

Ohta, R. et al., "Origin of N 1s Spectrum in Amorphous Carbon Nitride Obtained by X-Ray Photoelectron Spectroscopy," Thin Solid Films, (2003), pp. 296-302, vol. 434, Elsevier.

Okada, T., et al., "Oxygen Reduction Characteristics of Graphite Electrodes Modified with Cobalt Di-Quinolyldiamine Derivatives", Electrochimica Acta, (2000), pp. 4419-4429, vol. 45, Elsevier Science Ltd., Great Britain.

Okada, T. et al., "Oxygen Reduction Characteristics of Heat-Treated Catalysts Based on Cobalt-Porphyrin Ion Complexes", J. Electrochem. Soc., Mar. 1998, pp. 815-822, vol. 145:3.

Oyama, S. T. et al., "Preparation and Characterization of Early Transition-Metal Carbides and Nitrides," Industrial & Engineering Chemistry Research, (1988), pp. 1639-1648, vol. 27:9, American Chemical Society.

Oyama, S. T., "Preparation and Catalytic Properties of Transition Metal Carbides and Nitrides," Catalysis Today, (1992), pp. 179-200, vol. 15, Elsevier Science Publishers, B. V., Amsterdam.

Pilbrow, J.R., Transition Ion Electron Paramagnetic Resonance, (1990), pp. 3-7, Clarendon Press, Oxford.

Pinel, C. et al., "Effect of the Nature of Carbon Catalysts on Glyphosate Synthesis," *Academic Press*, (1999), pp. 515-519.

Sedunov, V. K. et al., "Structure and Phase Composition of Surface Zones of Carburized and Carbonitrided Layers," Metal Science and Heat Treatment, (1977), pp. 742-745, vol. 19:9-10, Consultants Bureau, New York.

Singh, A. et al., "X-Ray Photoelectron Spectroscopy of Nitrogen-Implanted Cemented Tungsten Carbide (WC-Co)," Journal of Materials Science Letters, (1990), pp. 1101-1102, vol. 9, Chapman and Hall Ltd.

Soto, G. et al., "XPS AES, and EELS Characterization of Nitrogen-Containing Thin Films,"Journal of Electron Spectroscopy and Related Phenomena, (2004), pp. 27-39, vol. 135, Elsevier B.V.

Takano, I. et al., "Nitrogenation of Various Transition Metals by N₂+-Ion Implantation,"Applied Surface Science, (1989), pp. 25-32, vol. 37, Elsevier Science Publishers B.V., North-Holland, Amsterdam.

Tang, C. et al., "Synthesis and Field Emission of Carbon Nanotubular Fibers Doped with High Nitrogen Content", Chem Commun., (2003), pp. 3050-3051, The Royal Society of Chemistry.

Tavadyan, L.A. et al., "Catalysis of the Liquid-Phase Oxidation of Organic Compounds by Metal-Complex Compounds of Nitrogen-Containing Carbon: III. Oxidation of Benzaldehyde", Kinetics and Catalysis, (1997), pp. 375-380, vol. 38:3.

Thangaraj, A. et al., "Direct Catalytic Hydroxylation of Benzene with Hydorgen Peroxide over Titanium—Silicate Zeolites", Applied Catalysis, (1990), pp. L1-L3, vol. 57.

Toda, Takako et al., "Enhancement of the Electroreduction of Oxygen on Pt Alloys with Fe, Ni, and Co", Journal of the Electrochemical Society, (1999), pp. 3750-3756, vol. 146:10.

Torrens, M. A., "Mossbauer Studies on Oxo-Bridged Iron (III) Porphines", Journal of the American Chemical Society, (1972), pp. 4160-4162, vol. 94:12.

van Dillen, A.J. et al., Synthesis of Supported Catalysts by Impregnation and Drying Using Aqueous Chelated Metal Complexes, Journal of Catalysis, (2003), pp. 257-264, vol. 216.

van Veen, J. A. R. et al., "On the Effect of a Heat Treatment on the Structure of Carbon-Supported Metalloporphyrins and Phthalocyanines", Electrochimica Acta, (1988), pp. 801-804, vol. 33:6, Pergamon Press plc., Great Britain.

van Veen, J. A. R. et al., "Effect of Heat Treatment on the Performance of Carbon-supported Transition-metal Chelates in the Electrochemical Reduction of Oxygen", J. Chem Soc., Faraday Trans. 1, (1981), pp. 2827-2843, vol. 77, The Royal Society of Chemistry, United Kingdom.

Van Der Putten, A. et al., "Oxygen Reduction on Pyrolysed Carbon-Supported Transition Metal Chelates,"Journal of Electroanalytical Chemistry and Interfacial Electrochemistry, (1986), pp. 233-244, vol. 205, Elsevier Sequoia S.A. Lausanne, The Netherlands.

Wang, H. et al., "Effect of the Pre-Treatment of Carbon Black Supports on the Activity of Fe-Based Electocatalysts for the Reduction of Oxygen," Journal of Physical Chemistry B, (1999), pp. 2042-2049, vol. 103, American Chemical Society.

Weng, L. T. et al., "Characterization of Electrocatalysts for Oxygen Reduction by TOF SIMS," Secondary Ion Mass Spectrometry, Proceedings of the International Conference on Secondary Ion Mass Spectrometry, 9th, Yokohama, (1994), pp. 442-445, Wiley, Chichester, United Kingdom.

Weng, L.T. et al., "Surface Characterization by Time-of-Flight SIMS of a Catalyst for Oxygen Electroreduction: Pyrolyzed Cobalt Phthalocyanine-On-Carbon Black," Applied Surface Science, (1995), pp. 9-21, vol. 84, Elsevier Science B.V.

White, M. et al., "Building a Better Catalyst", R&D Update, Process Industries Canada, (1991), p. 15.

Yap, N. et al., "Reactivity and Stability of Au in and on TS-1 for Epoxidation of Propylene with H₂ and O₂", Journal of Catalysis, (2004), pp. 156-170, vol. 226.

Office action issued in U.S. Appl. No. 10/919,028, dated Aug. 5, 2010, 9 pages.
Amendment H filed in U.S. Appl. No. 10/919,028, dated Oct. 26, 2010, in response to the Office action dated Aug. 5, 2010, 33 pages.
Issue Notification issued in U.S. Appl. No. 10/919,028, dated Apr. 6, 2011, 1 page.
Notice of Allowance issued in U.S. Appl. No. 10/919,028, dated Dec. 17, 2010, 20 pages.
Comments on Reasons for Allowance filed in U.S. Appl. No. 10/919,028, on Mar. 16, 2011, 2 pages.
Non-final Office action dated May 14, 2004 in connection with U.S. Appl. No. 10/366,947.
Amendment B submitted Oct. 14, 2004 in connection with U.S. Appl. No. 10/366,947 in response to the Office action dated May 14, 2004.
Final Office action dated Jan. 24, 2005 in connection with U.S. Appl. No. 10/366,947.
Amendment C submitted May 24, 2005 in connection with U.S. Appl. No. 10/366,947 in response to the Office action dated Jan. 24, 2005.
Non-Final Office Action dated Jun. 25, 2007 in connection with U.S. Appl. No. 10/923,416.
Amendment B submitted Nov. 29, 2007 in connection with U.S. Appl. No. 10/923,416 in response to the Office action dated Jun. 25, 2007.
International Search Report issued in connection with PCT/US03/04578, dated Jun. 30, 2003, 3 pages.
Written Opinion issued in connection with PCT/US03/04578, 9 pages, dated Apr. 12, 2003.
International Preliminary Examination Report issued in connection with PCT/US03/04578, 18 pages, dated Mar. 19, 2004.
International Search Report/Written Opinion issued in connection with PCT/US2004/026550, 31 pages, dated Aug. 16, 2005.
International Preliminary Report on Patentability issued in connection with PCT/US2004/026550, 21 pages, dated Nov. 18, 2005.
Fifth Supplemental Information Disclosure Statement reported in U.S. Appl. No. 10/923,416, dated Nov. 29, 2007, 22 pages.
Sixth Supplemental Information Disclosure Statement reported in U.S. Appl. No. 10/919,028, dated Nov. 29, 2007, 18 pages.
Final Office action dated May 12, 2009 in connection with U.S. Appl. No. 11/274,555.

1● 2ı 3- 4▲ 5○ 6□

1● 2□ 3▲ 4□

1∘ 2▫ 3▵ 4 -

1∘ 2▫ 3▵ 4▫

TRANSITION METAL-CONTAINING CATALYSTS AND CATALYST COMBINATIONS INCLUDING TRANSITION METAL-CONTAINING CATALYSTS AND PROCESSES FOR THEIR PREPARATION AND USE AS OXIDATION CATALYSTS

REFERENCE TO RELATED APPLICATIONS

This application claims the benefit of U.S. Provisional Application Ser. No. 60/654,085, filed Feb. 17, 2005, Ser. No. 60/654,086, filed Feb. 17, 2005, and Ser. No. 60/656,153, filed Feb. 24, 2005, the entire contents of which are incorporated herein by reference.

FIELD OF INVENTION

This invention relates to the field of heterogeneous catalysis, and more particularly to catalysts including carbon supports having compositions which comprise one or more transition metals in combination with nitrogen and/or carbon formed on or over the surface of the carbon support. The invention also relates to catalysts including carbon supports having compositions which comprise one or more primary transition metals with the catalyst further comprising an additional (i.e., secondary) metallic element. The secondary metallic element may be incorporated into the composition comprising the primary transition metal or metals or the catalyst may comprise a secondary catalytic composition comprising the secondary metallic element on or over the surface of the carbon support and/or the primary transition metal composition. The present invention further relates to catalyst combinations comprising catalysts including carbon supports having compositions which comprise one or more transition metals in combination with nitrogen and/or carbon formed on or over the surface of a carbon support and a secondary catalyst or, co-catalyst, including a secondary transition metal. The invention also relates to the field of catalytic oxidation reactions, including the preparation of secondary amines by the catalytic oxidation of tertiary amines.

BACKGROUND OF INVENTION

Investigations to discover alternative materials for use in catalysis concerning various types of reactions have included evaluation of the suitability of carbide and nitride materials. Generally, carbide and nitride materials have been considered as possible alternatives for use in various types of catalysis since they exhibit "metal-like" properties (e.g., high melting points, hardness and strength). Levy & Boudart report that carbide and nitride materials exhibit catalytic properties similar to those of noble metals. See *Platinum-Like Behavior of Tungsten Carbide in Surface Catalysis* (Science, 181 (1973), 547-549).

Supported carbide and nitride catalysts have been described generally and reported as suitable for use in various types of reactions. Slaugh et al. describe a supported molybdenum carbide composition prepared by impregnating hexamolybdenum dodecachloride onto a porous aluminous (e.g., $Al_2O_3$), siliceous or carbonaceous (e.g., active carbon) support which is then heated in a carbiding atmosphere at a temperature of about 650° C. to about 750° C. See U.S. Pat. No. 4,325,842.

Leclercq et al. report a catalytic reforming process employing catalysts based on tungsten and molybdenum carbides supported on alumina and active carbon. See U.S. Pat. No. 4,522,708. These catalysts are prepared by successive impregnations of active carbon using ammonium molybdate and ammonium tungstate solutions which are evaporated to dryness in air, calcined in a nitrogen atmosphere which is followed by reduction of the tungsten and molybdenum oxides formed during calcination under a hydrogen atmosphere. These compounds are then heated under hydrogen to allow the active phase compounds to react with the carbon support to produce mixed carbides of tungsten and molybdenum.

Sherif et al. report carbon-supported Group VIB metal (e.g., Cr, Mo, W) carbide-containing catalysts formed by calcining a carbon support (e.g., activated carbon and acid washed activated carbon) which has been impregnated with a water-soluble precursor for the metal carbide. See International Publication No. WO 95/32150.

Oyama reports interstitial alloys formed by the incorporation of carbon, nitrogen, and oxygen into the lattices of early transition metals to produce a class of compounds with metallic character. See *Preparation and Catalytic Properties of Transition Metal Carbides and Nitrides* (Catalysis Today, 15, 179-200. 1992).

Iwai et al. report carbonitrides consisting of a carbide and nitride of the metals of Groups IV, V, and VI prepared by calcining a precursor obtained by reacting polyphenol with the reaction product of ammonia and the halide of a Group IV, V, or VI metal. The precursor may also be obtained by reacting the reaction product of polyphenol and the halide of a Group IV, V, or VI metal with ammonia. See U.S. Pat. No. 4,333,916.

Faubert et al. report on methods for preparing iron-containing catalysts containing iron carbide particles prepared by activation of a precursor consisting of Fe hydroxide adsorbed on carbon black by hydrogen reduction and pyrolysis in the presence of acetonitrile. See *Activation and characterization of Fe-based catalysts for the reduction of oxygen in polymer electrolyte fuel cells* (Electrochimica Acta, Vol. 43, Nos. 14-15, pp. 1969-1984, 1998)

Cote et al. report on methods for preparation of non-noble metal based catalysts prepared by pyrolysis of a transition metal hydroxide (e.g., vanadium, chromium, iron, cobalt hydroxide) on carbon black including reduction in the presence of hydrogen and heating in the presence of acetonitrile. See *Non-noble metal-based catalysts for the reduction of oxygen in polymer electrolyte fuel cells* (Journal of New Materials for Electrochemical Systems, 1, 7-16, 1998).

Catalysts containing carbides or nitrides may be advantageous in certain instances due to the absence of a costly noble metal. One reaction in which an active catalyst which does not require the presence of a noble metal may be advantageous is the oxidation of a tertiary amine (e.g., N-(phosphonomethyl)iminodiacetic acid) to produce a secondary amine (e.g., N-(phosphonomethyl)glycine). N-(phosphonomethyl)glycine (known in the agricultural chemical industry as "glyphosate") is described in Franz, U.S. Pat. No. 3,799,758. N-(phosphonomethyl)glycine and its salts are conveniently applied as a post-emergent herbicide in an aqueous formulation. It is a highly effective and commercially important broad-spectrum herbicide useful in killing or controlling the growth of a wide variety of plants, including germinating seeds, emerging seedlings, maturing and established woody and herbaceous vegetation, and aquatic plants.

Various methods for making N-(phosphonomethyl)glycine are known in the art. Franz (U.S. Pat. No. 3,950,402) teaches that N-(phosphonomethyl)glycine may be prepared by the liquid phase oxidative cleavage of N-(phosphonomethyl)iminodiacetic acid (sometimes referred to as "PMIDA") with oxygen in the presence of a catalyst comprising a noble metal deposited on the surface of an activated carbon support:

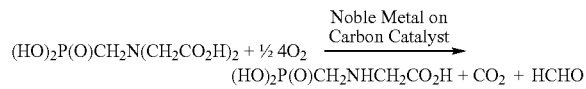

Other by-products also may form, such as formic acid, which is formed by the oxidation of the formaldehyde by-product; and aminomethylphosphonic acid ("AMPA"), which is formed by the oxidation of N-(phosphonomethyl) glycine. Even though the Franz method produces an acceptable yield and purity of N-(phosphonomethyl)glycine, high losses of the costly noble metal into the reaction solution (i.e., "leaching") result because under the oxidation conditions of the reaction, some of the noble metal is oxidized into a more soluble form and both PMIDA and N-(phosphonomethyl) glycine act as ligands which solubilize the noble metal.

In U.S. Pat. No. 3,969,398, Hershman teaches that activated carbon alone, without the presence of a noble metal, may be used to effect the oxidative cleavage of PMIDA to form N-(phosphonomethyl)glycine. In U.S. Pat. Nos. 4,624,937 and 4,696,772, Chou teaches that the activity of the carbon catalyst taught by Hershman may be increased by removing the oxides from the surface of the carbon catalyst before using it in the oxidation reaction. U.S. Pat. Nos. 4,624,937 and 4,696,772 provide a discussion regarding increasing the activity of the carbon catalyst by removing oxides from the surface of the carbon catalyst. Although the processes which use these catalysts obviously do not suffer from noble metal leaching, they do tend to produce greater concentrations of formaldehyde by-product when used to effect the oxidative cleavage of N-(phosphonomethyl)iminodiacetic acid. This formaldehyde by-product is undesirable because it reacts with N-(phosphonomethyl)glycine to produce unwanted by-products (mainly N-methyl-N-(phosphonomethyl)glycine, sometimes referred to as "NMG") which reduce the N-(phosphonomethyl)glycine yield. In addition, the formaldehyde by-product itself is undesirable because of its potential toxicity. See Smith, U.S. Pat. No. 5,606,107.

It has been suggested that the formaldehyde be simultaneously oxidized to carbon dioxide and water as the PMIDA is oxidized to N-(phosphonomethyl)glycine in a single reactor, thus giving the following reaction:

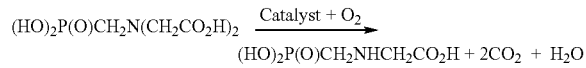

Previous attempts to develop a stable catalyst for such an oxidation process, however, have not been entirely satisfactory.

Like Franz, Ramon et al. (U.S. Pat. No. 5,179,228) teach using a noble metal deposited on the surface of a carbon support. To reduce the problem of leaching (which Ramon et al. report to be as great as 30% noble metal loss per cycle), however, Ramon et al. teach flushing the reaction mixture with nitrogen under pressure after the oxidation reaction is completed to cause re-deposition of the noble metal onto the surface of the carbon support. According to Ramon et al., nitrogen flushing reduces the noble metal loss to less than 1%. Still, the amount of noble metal loss incurred with this method is unacceptable. In addition, re-depositing the noble metal can lead to loss of noble metal surface area which, in turn, decreases the activity of the catalyst.

Using a different approach, Felthouse (U.S. Pat. No. 4,582,650) teaches using two catalysts: (i) an activated carbon to effect the oxidation of PMIDA into N-(phosphonomethyl) glycine, and (ii) a co-catalyst to concurrently effect the oxidation of formaldehyde into carbon dioxide and water. The co-catalyst consists of an aluminosilicate support having a noble metal located within its pores. The pores are sized to exclude N-(phosphonomethyl)glycine and thereby prevent the noble metal of the co-catalyst from being poisoned by N-(phosphonomethyl)glycine. According to Felthouse, use of these two catalysts together allows for the simultaneous oxidation of PMIDA to N-(phosphonomethyl)glycine and of formaldehyde to carbon dioxide and water. This approach, however, suffers from several disadvantages: (1) it is difficult to recover the costly noble metal from the aluminosilicate support for re-use; (2) it is difficult to design the two catalysts so that the rates between them are matched; and (3) the carbon support, which has no noble metal deposited on its surface, tends to deactivate at a rate which can exceed 10% per cycle.

Ebner et al., in U.S. Pat. No. 6,417,133, describe a deeply reduced noble metal on carbon catalyst which is characterized by a CO desorption of less than 1.2 mmole/g, preferably less than 0.5 mmole/g, when a dry sample of the catalyst, after being heated at a temperature of about 500° C. for about 1 hour in a hydrogen atmosphere and before being exposed to an oxidant following the heating in the hydrogen atmosphere, is heated in a helium atmosphere from about 20° to about 900° C. at a rate of about 10° C. per minute, and then at about 900° C. for about 30 minutes. The catalyst is additionally or alternatively characterized as having a ratio of carbon atoms to oxygen atoms of at least about 20:1, preferably at least about 30:1, at the surface as measured by x-ray photoelectron spectroscopy after the catalyst is heated at a temperature of about 500° C. for about 1 hour in a hydrogen atmosphere and before the catalyst is exposed to an oxidant following the heating in the hydrogen atmosphere.

The catalysts of U.S. Pat. No. 6,417,133 have proven to be highly advantageous and effective catalysts for the oxidation of N-(phosphonomethyl)iminodiacetic acid to N-(phosphonomethyl)glycine, and for the further oxidation of by-product formaldehyde and formic acid, and without excessive leaching of noble metal from the carbon support. It has further been discovered that these catalysts are effective in the operation of a continuous process for the production of N-(phosphonomethyl)glycine by oxidation of N-(phosphonomethyl)iminodiacetic acid.

Carbon and noble metal sites on the catalysts of U.S. Pat. No. 6,417,133 are highly effective for transfer of electrons in the oxidation of N-(phosphonomethyl)iminodiacetic acid, and the noble metal sites are especially effective for this purpose in the oxidation of formaldehyde and formic acid. However, it would be advantageous to have a multi-reaction catalyst and reaction process which oxidizes PMIDA to N-(phosphonomethyl)glycine while simultaneously exhibiting desired oxidation of formaldehyde to carbon dioxide and water (i.e., increased formaldehyde activity), and which does not require the presence of a noble metal. Additionally or alternatively, it would likewise be advantageous to have such a multi-reaction catalyst and reaction process which does not require costly noble metal, or which functions effectively with a reduced noble metal content relative to catalysts currently available for commercial manufacture of N-(phosphonomethyl)glycine or other secondary amines.

Titanium-containing catalysts (e.g., synthetic zeolites and molecular sieves containing titanium) have been discovered to be useful in catalysis of various oxidation reactions, particularly in conjunction with hydrogen peroxide as an oxidant. For example, titanium-containing zeolites have been reported as effective for the oxidation of alkanes (P. A. Jacobs et al, Nature, 345, 240-242 (1990)), oxidation of primary alcohols to aldehydes and secondary alcohols to ketones (U.S. Pat. No. 4,480,135), epoxidation of olefins (EP Patent No. 100,119), hydroxylation of aromatic compounds (Great Britain Patent No. 2,116,974 and Tangaraj et al., Appl. Catal. 57 (1990) L1), and oxidation of aniline (Tuel et al., Appl. Catal., A: 118(2) 173-186 (1994)) in the presence of hydrogen peroxide as an oxidant. Titanium-containing zeolites are generally prepared by isomorphous substitution of titanium into the framework of a zeolite. Molecular sieves and synthetic zeolites are described, for example, in *Kirk-Othmer Encyclopedia of Chemical Technology;* 4th Edition, John Wiley & Sons, New York, p. 1330-1333, 1999. Various titanium-containing zeolites are prepared by replacing silicon atoms of "silicalite" with titanium atoms. "Silicalite" is a zeolite structure constituted by pure crystalline $SiO_2$ and has been described, for example, by Flanigen E. M. (Nature 271, 512 (1978)). Titanium-containing silicates of differing crystal structures are known in the art. These include, for example, TS-1 which has a MFI crystal structure (i.e., ZSM-5 zeolite) and TS-2 which has a MEL crystal structure (i.e., ZSM-11 zeolite). MFI (ZSM-5) and MEL (ZSM-11) zeolite structures are well-known in the art. TS-1 has been found to be effective in the oxidation of various organic compounds using aqueous hydrogen peroxide as an oxidant including, for example, oxidation of alkanes, oxidation of primary alcohols to aldehydes and oxidation of secondary alcohols to ketones. TS-1, TS-2 and other titanium-containing zeolites are described, for example, in U.S. Pat. No. 3,702,886 to Argauer et al., U.S. Pat. No. 4,410,501 to Taramasso et al., U.S. Pat. No. 4,526,878 to Takegami et al., U.S. Pat. No. 5,098,684 to Kresge et al., U.S. Pat. No. 5,500,199 to Takegami et al., U.S. Pat. No. 5,525,563 to Thiele et al., U.S. Pat. No. 5,977,009 to Faraj, U.S. Pat. No. 6,106,803 to Hasenzahl et al., U.S. Pat. No. 6,391,278 to Pinnavaia et al., U.S. Pat. No. 6,403,514 to Mantegazza et al., U.S. Pat. No. 6,667,023 to Ludvig, U.S. Pat. No. 6,841,144 to Hasenzahl et al. In addition to TS-1 and TS-2, titanium-containing zeolites described in the above-referenced patents include, for example, EUROTS-1 (also described, for example, in J. A. Martens et al., Applied Catalysis A: General, 99 (1993) 71-84) and a titanium substituted analog of β-zeolite (also described, for example, in Corma et al., J. Chem. Soc. Chem. Commun., 589-590 (1992)), and titanium-substituted MCM-41 (described, for example, in U.S. Pat. No. 6,391,278 to Pinnavaia et al. and U.S. Pat. No. 5,098,684 to Kresge et al.).

SUMMARY OF THE INVENTION

This invention provides catalysts and catalyst combinations and methods for preparing catalysts and catalyst combinations that are useful in various heterogeneous oxidation reactions, including the preparation of secondary amines by the catalytic oxidation of tertiary amines. The catalysts include supports, particularly carbon supports, having compositions which comprise one or more transition metals and/or a secondary metallic element in combination with nitrogen and/or carbon formed on or over the surface of a carbon support. The catalyst combinations of the present invention likewise include a primary transition metal and a secondary metallic element, optionally incorporated into one or more active phases comprising the primary transition metal, or the secondary metallic element or both. An active phase comprising the primary transition metal is typically on a carbonaceous or other support. This active phase may also comprise the secondary metallic element. Optionally, the secondary metallic element may be contained in a second active phase which may be on the same support as the first active phase or may be comprised by a second catalyst.

The catalysts and catalyst combinations disclosed herein are particularly useful in the oxidative cleavage of PMIDA reagents such as N-(phosphonomethyl)iminodiacetic acid to form an N-(phosphonomethyl)glycine product. In such reactions, the catalysts and catalyst combinations of the present invention have proven to be effective in catalyzing the further oxidation of the formaldehyde and/or formic acid by-products. In particular, transition metals and/or a metal composition or active phase comprised thereby are effective for the catalytic oxidation of PMIDA reagents such as N-(phosphonomethyl)iminodiacetic acid to form an N-(phosphonomethyl)glycine product.

Briefly, therefore, the present invention is directed to catalysts comprising a carbon support having formed thereon a transition metal composition comprising a transition metal and nitrogen. In one such embodiment the carbon support is activated and the transition metal constitutes at least 1.6% by weight of the catalyst. In a further embodiment, the carbon support has a Langmuir surface area of from about 500 $m^2/g$ to about 2100 $m^2/g$ and the transition metal constitutes at least 1.6% by weight of the catalyst.

The present invention is further directed to catalysts comprising a carbon support having formed thereon a transition metal composition comprising a transition metal (M) and nitrogen wherein the catalyst is characterized as generating ions corresponding to the formula $MN_xC_y^+$ when the catalyst is analyzed by Time-of-Flight Secondary Ion Mass Spectrometry (ToF SIMS) as described in Protocol A.

In one such embodiment, the weighted molar average value of x is from about 0.5 to about 2.0 and the weighted molar average value of y is from about 0.5 to about 8.0. In a further embodiment, the transition metal constitutes at least 0.5% by weight of the catalyst and the weighted molar average value of x is from about 0.5 to about 2.10 and the weighted molar average value of y is from about 0.5 to about 8.0. In another such embodiment, the weighted molar average valuye of x is from about 0.5 to about 8.0 and the weighted molar average value of y is from about 0.5 to about 2.6.

In a further such embodiment, the weighted molar average value of x is from about 0.5 to about 8.0 and the weighted molar average value of y is from about 0.5 to about 8.0 and the catalyst is characterized by its effectiveness for catalyzing the oxidation of formaldehyde such that when a representative aqueous solution having a pH of about 1.5 and containing 0.8% by weight formaldehyde and 0.11% by weight of the catalyst is agitated and sparged with molecular oxygen at a rate of 0.75 $cm^3$ oxygen/minute/gram aqueous mixture at a temperature of about 100° C. and pressure of about 60 psig, at least about 5% of the formaldehyde is converted to formic acid, carbon dioxide and/or water. In a still further such embodiment, the the weighted molar average value of x is from about 0.5 to about 8.0 and the weighted molar average value of y is from about 0.5 to about 8.0 and the catalyst is characterized by its effectiveness for catalyzing the oxidation of formaldehyde such that when a representative aqueous solution having a pH of about 1.5 and containing 0.8% by weight formaldehyde, 5.74% by weight N-(phosphonomethyl)iminodiacetic acid, and 0.11% by weight of the catalyst is agitated and sparged with molecular oxygen at a rate of 0.75 cm³ oxygen/minute/gram aqueous mixture at a temperature of about 100° C. and pressure of about 60 psig, at least about 50% of the formaldehyde is converted to formic acid, carbon dioxide and/or water.

In a further embodiment, the transition metal is selected from the group consisting of copper, silver, vanadium, chromium, molybdenum, tungsten, manganese, cobalt, nickel, cerium, and combinations thereof and the weighted molar average value of x is from about 0.5 to about 3.0 and the weighted molar average value of y is from about 0.5 to about 8.0. In another embodiment, the transition metal is selected from the group consisting of copper, silver, vanadium, chromium, molybdenum, tungsten, manganese, cobalt, nickel, cerium, and combinations thereof and the weighted molar average value of x is from about 0.5 to about 8.0 and the weighted molar average value of y is from about 0.5 to about 5.0.

In another embodiment, the weighted molar average value of x is from about 0.5 to about 8.0, the weighted molar average of y is from about 0.5 to about 8.0, and $MN_xC_y^+$ ions in which the weighted molar average value of x is from 4 to about 8 constitute no more than about 60 mole percent of the $MN_xC_y^+$ of the $MN_xC_y^+$ ions detected during ToFSIMS analysis.

In a still further embodiment, the transition metal constitutes greater than 2% by weight of the catalyst and the weighted molar average value of x is from about 0.5 to about 8 and the weighted molar average value of y is from about 0.5 to about 8. In another embodiment, the transition metal constitutes greater than 2% by weight of the catalyst and the weighted molar average value of x is from about 0.5 to 2.2 and the weighted molar average value of y is from about 0.5 to about 8.

In a still further embodiment, the transition metal is selected from the group consisting of copper, silver, vanadium, chromium, molybdenum, tungsten, manganese, cobalt, nickel, cerium, and combinations thereof and the relative abundance of ions in which x is 1 is at least 20%.

The present invention is further directed to a catalyst comprising a carbon support having formed thereon a transition metal composition comprising cobalt and nitrogen, the catalyst being characterized such that the catalyst exhibits at least about $2.50 \times 10^{25}$ spins/mole cobalt when the catalyst is analyzed by Electron Paramagnetic Resonance (EPR) Spectroscopy as described in Protocol C.

The present invention is further directed to catalyst comprising a carbon support having formed thereon a transition metal composition comprising a transition metal and nitrogen, wherein the micropore Langmuir surface area of the catalyst is at least about 70% of the micropore Langmuir surface area of the carbon support prior to formation of the transition metal composition thereon.

The present invention is also directed a to catalyst comprising a carbon support having formed thereon a transition metal composition comprising a transition metal and nitrogen, wherein the transition metal constitutes at least about 2% by weight of the catalyst, and the micropore Langmuir surface area of the catalyst is from about 60% to less than 80% of the micropore Langmuir surface area of the carbon support prior to formation of the transition metal composition thereon.

In still further embodiments, the present invention is directed to a catalyst comprising a carbon support having formed thereon a transition metal composition comprising a transition metal and nitrogen wherein the transition metal constitutes from about 2% to less than 5% by weight of the catalyst, and the micropore Langmuir surface area of the catalyst is at least about 60% of the total Langmuir surface area of the carbon support prior to formation of the transition metal composition thereon.

In still further embodiments, the present invention is directed to a catalyst comprising a carbon support having formed thereon a transition metal composition comprising a transition metal and nitrogen in which the transition metal being selected from the group consisting of copper, silver, vanadium, chromium, molybdenum, tungsten, manganese, cobalt, nickel, cerium, and combinations thereof. In one such embodiment the transition metal constitutes at least about 2% by weight of the catalyst, and the total Langmuir surface area of the catalyst is at least about 60% of the total Langmuir surface area of the carbon support prior to formation of the transition metal composition thereon. In a further such embodiment, the total Langmuir surface area of the catalyst is less than about 2000 m²/g and the total Langmuie surface area of the catalyst is at least about 75% of the total Langmuir surface area of the carbon support prior to formation of the transition metal composition thereon. In another such embodiment, the transition metal constitutes at least about 2% by weight of the catalyst, the total Langmuir surface area of the catalyst is less than about 2000 m²/g, and the total Langmuir surface area of the catalyst is at least about 60% of the total Langmuir surface area of the carbon support prior to formation of the transition metal composition thereon.

The present invention is also directed to a catalyst comprising a carbon support having formed thereon a transition metal composition comprising a transition metal and nitrogen, wherein the catalyst is characterized such that when an aqueous mixture containing 0.15% by weight of the catalyst and about 5.75% by weight N-(phosphonomethyl)iminodiacetic is agitated and sparged with molecular oxygen at a rate of 0.875 cm³ oxygen/minute/gram aqueous mixture and sparged with nitrogen at a rate of 0.875 cm³ nitrogen/minute/gram aqueous mixture at a temperature of about 100° C. and a pressure of about 60 psig for from 30 to 35 minutes for a first reaction cycle, the catalyst exhibits a leaching/activity ratio during the first reaction cycle of less than about 0.25. The leaching/activity ratio is the ratio of the proportion of transition metal removed from the catalyst during the first reaction cycle (% by weight) to the N-(phosphonomethyl)iminodiacetic acid content of the mixture upon completion of the first reaction cycle (% by weight). The present invention is also directed to a a catalyst comprising a carbon support having formed thereon a transition metal composition comprising a transition metal and nitrogen wherein the catalyst is characterized such that when an aqueous mixture containing 0.15% by weight of the catalyst and about 5.75% by weight N-(phosphonomethyl)iminodiacetic is agitated and sparged with molecular oxygen at a rate of 0.875 cm³ oxygen/minute/gram aqueous mixture and sparged with nitrogen at a rate of 0.875 cm³ nitrogen/minute/gram aqueous mixture at a temperature of about 100° C. and a pressure of about 60 psig for from 30 to 35 minutes for a first reaction cycle and at least one subsequent reaction cycle, the catalyst exhibits a leaching/activity ratio during the at least one subsequent reaction cycle of less than 0.018.

The present invention is further directed to a catalyst comprising a carbon support having formed thereon a transition metal composition comprising cobalt and nitrogen, wherein when the catalyst is analyzed by X-Ray Photoelectron Spectroscopy (XPS) the C 1s spectra includes a component having a binding energy of from about 284.6 eV to about 285 eV, the N 1s spectra includes a component having a binding energy of from about 398.4 eV to about 398.8 eV, the Co 2p spectra includes a component having a binding energy of from about 778.4 eV to about 778.8 eV, and/or the O 1s spectra includes a component having a binding energy of from about 532.5 eV to about 533.7 eV.

The present invention is further directed to processes for the oxidation of an organic substrate using the various embodiments of the catalysts described above and elsewhere herein. In such processes, the organic substrate is contacted with an oxidizing agent in the presence of the catalyst.

The present invention is further directed to various processes for preparing a catalyst comprising a transition metal composition comprising a transition metal and nitrogen on a carbon support.

In one embodiment, the process comprises contacting the carbon support with a source of a transition metal and a liquid medium comprising a coordinating solvent capable of forming a coordination bond with the transition metal that is more stable than the coordination bond between the transition metal and water.

In another embodiment, the process comprises contacting the carbon support with a source of the transition metal and a liquid medium comprising a coordinating solvent selected from the group consisting of ethylenediamine, tetramethylenediamine, hexamethylenediamine, N,N,N',N',N" pentamethyldiethylenetriamine, diethylene glycol diethyl ether, dipropylene glycol methyl ether, diethylene glycol ethyl ether acetate, monoglyme, ethyl glyme, triglyme, tetraglyme, polyglyme, diglyme, ethyl diglyme, butyl diglyme, 1,4,7,10-tetraoxacyclododecane (12-crown-4), 1,4,7,10,13,16-hexaoxacyclooctadecane (18-crown-6), polyethylene glycol, polypropylene glycol, tetraethylene glycol, and combinations thereof.

In a further embodiment, the process comprises contacting the carbon support with a source of a transition metal and a coordination compound comprising a coordinating solvent bonded to the transition metal by one or more coordination bonds.

In a still further embodiment, the process comprises contacting the carbon support with a source of the transition metal and a non-polar solvent, a solvent having a dielectric constant at 20° C. of from about 2 to less than 80, or a solvent having a surface tension at 20° C. of from about 2 dynes/cm to less than 70 dynes/cm.

In a further embodiment, the process comprises contacting the carbon support with a source of a transition metal and a liquid medium comprising a carbon support having a boiling point of at least 100° C.

In another embodiment, the process comprises contacting the carbon support with a source of a transition metal and a liquid medium comprising a coordinating agent capable of forming a coordination bond with the transition metal that is more stable than the coordination bond between the transition metal and water.

The present invention is further directed to various processes for preparing a catalyst comprising a primary transition metal composition and a secondary metallic element over a carbon support, wherein the primary transition metal composition comprises a primary transition metal and nitrogen and the oxidation sate of the secondary metallic element is greater than or equal to zero.

In one embodiment, the process comprises contacting the carbon support with a source of the primary transition metal and a coordinating solvent capable of forming a coordination bond with the transition metal that is more stable than the coordination bond between the transition metal and water, thereby forming a primary precursor composition comprising the primary transition metal at a surface of the carbon support; heating the carbon support having the primary precursor composition thereon in the presence of a nitrogen-containing compound to form the primary transition metal composition over the carbon support; and contacting the carbon support with a source of the secondary metallic element.

In another embodiment, the process comprises contacting the carbon support with a source of the primary transition metal and a coordinating solvent selected from the group consisting of ethylenediamine, tetramethylenediamine, hexamethylenediamine, N,N,N',N',N" pentamethyldiethylenetriamine, diethylene glycol diethyl ether, dipropylene glycol methyl ether, diethylene glycol ethyl ether acetate, monoglyme, ethyl glyme, triglyme, tetraglyme, polyglyme, diglyme, ethyl diglyme, butyl diglyme, 1,4,7,10-tetraoxacyclododecane (12-crown-4), 1,4,7,10,13,16-hexaoxacyclooctadecane (18-crown-6), polyethylene glycol, polypropylene glycol, tetraethylene glycol, and combinations thereof, thereby forming a primary precursor composition comprising the primary transition metal at a surface of the carbon support; heating the carbon support having the primary precursor composition thereon in the presence of a nitrogen-containing compound to form the primary transition metal composition over the carbon support; and contacting the carbon support with a source of the secondary metallic element.

In a still further embodiment, the process comprises contacting the carbon support with a source of the primary transition metal and a coordination compound comprising a coordinating solvent bonded to the transition metal by one or more coordination bonds, thereby forming a primary precursor composition comprising the primary transition metal at a surface of the carbon support; heating the carbon support having the primary precursor composition thereon in the presence of a nitrogen-containing compound to form the primary transition metal composition over the carbon support; and contacting the carbon support with a source of the secondary metallic element.

In another embodiment, the process comprises contacting the carbon support with a source of the primary transition metal and a non-polar solvent, thereby forming a primary precursor composition comprising the primary transition metal at a surface of the carbon support; heating the carbon support having the primary precursor composition thereon in the presence of a nitrogen-containing compound to form the primary transition metal composition over the carbon support; and contacting the carbon support with a source of the secondary metallic element.

In a still further embodiment, the process comprises contacting the carbon support with a source of the primary transition metal and a solvent having a dielectric constant at 20° C. of from about 2 to less than 80, thereby forming a primary precursor composition comprising the primary transition metal at a surface of the carbon support; heating the carbon support having the primary precursor composition thereon in the presence of a nitrogen-containing compound to form the primary transition metal composition over the carbon support; and contacting the carbon support with a source of the secondary metallic element.

In another embodiment, the process comprises contacting the carbon support with a source of the primary transition metal and a solvent having a surface tension at 20° C. of from about 2 dynes/cm to less than 70 dynes/cm, thereby forming a primary precursor composition comprising the primary transition metal at a surface of the carbon support; heating the carbon support having the primary precursor composition thereon in the presence of a nitrogen-containing compound to form the primary transition metal composition over the carbon support; and contacting the carbon support with a source of the secondary metallic element.

The present invention is further directed to processes for the oxidation of an organic substrate using catalysts prepared in accordance with the processes described herein.

Other objects and features of this invention will be in part apparent and in part pointed out hereinafter.

DETAILED DESCRIPTION OF THE PREFERRED EMBODIMENTS

Figure 1:
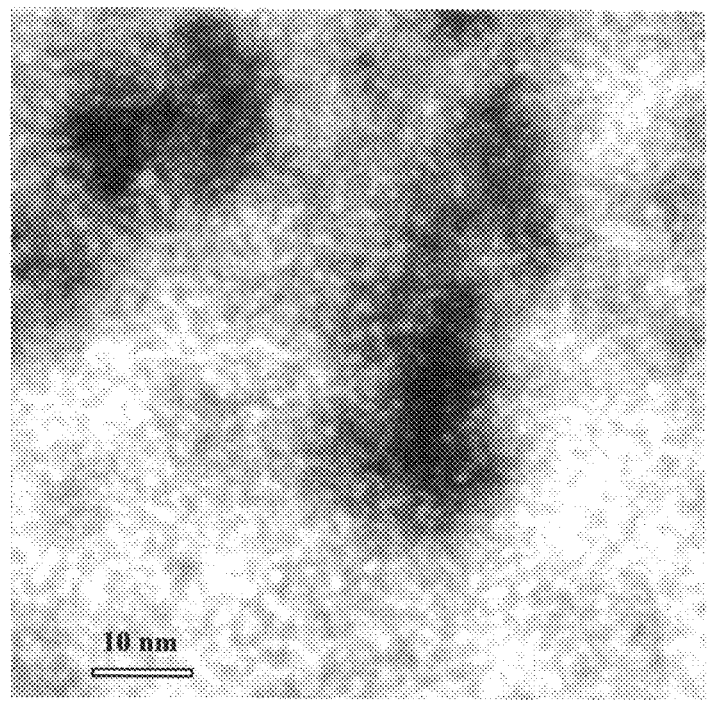
FIG. 1 is a High Resolution Transmission Electron Microscopy (HRTEM) image of a carbon-supported molybdenum carbide.

Described herein are catalysts including a transition metal composition comprising one or more transition metals, nitrogen and/or carbon formed on or over the surface of a carbon support. In various embodiments the catalyst comprises a primary transition metal composition comprising one or more primary transition metals and the catalyst further comprises an additional (i.e., secondary) metallic element. The secondary metallic element may be incorporated into the composition comprising the primary transition metal or metals or the catalyst may comprise a secondary catalytic composition comprising the secondary metallic element on or over the surface of the carbon support and/or the primary transition metal composition.

Catalysts of the present invention generally comprise one or more active phases which are effective for catalyzing the oxidation of a substrate. In various embodiments, the catalyst comprises an active phase comprising a transition metal composition comprising one or more transition metals, nitrogen and/or carbon. Advantageously, in various such embodiments, such an active phase is effective for catalyzing the oxidation of both a first substrate and a second substrate. For example, in the preparation of glyphosate from PMIDA, the first substrate may typically comprise PMIDA and the second substrate may comprise formaldehyde or formic acid, which are by-products of the PMIDA oxidation. In these and other embodiments, the catalyst may comprise an active phase comprising a transition metal composition comprising both a primary transition metal and a secondary metallic element, and such active phase is effective for catalyzing the oxidation of both a first substrate and an additional substrate different from the first substrate. In various other embodiments, the catalyst comprises a first active phase comprising a primary transition metal composition and a second active phase comprising a secondary catalytic composition. The first active phase is generally formed on or over the surface of the carbon support while the second active phase is formed on or over the surface of the carbon support and/or formed on or over the surface of the first active phase or primary transition metal composition. Additionally or alternatively, a first active comprising a primary transition metal composition may be formed on or over the surface of a second active phase comprising a secondary catalytic composition. Advantageously, in various such embodiments, the first active phase is effective for catalyzing the oxidation of a first substrate (e.g., PMIDA) and the second active phase is effective for catalyzing the oxidation of a substrate which may the same as or different from the first substrate (e.g., formaldehyde or formic acid by-products of PMIDA oxidation).

In the case of catalysts comprising a primary transition metal composition and a secondary metallic element, typically activity for the catalytic oxidation of the first substrate is imparted predominantly by the primary transition metal composition. As described in detail herein, the primary transition metal composition may also comprise carbon, and typically comprises a carbide, nitride or carbide-nitride of the primary transition metal. Activity for the oxidation of the second substrate is imparted predominantly by the presence of the secondary metallic element and/or by a secondary catalytic composition comprising a compound or complex of the secondary metallic element on or over a common carbon support, or optionally formed on a separate support which may be carbon, silica, alumina or zeolite. Such compound or complex may, for example, comprise a carbide, nitride, carbide-nitride, or oxide of the secondary metallic element.

Regardless of the presence of a secondary metallic element or secondary catalytic composition comprised thereby, active sites effective for the oxidation of the first substrate are believed to catalyze either two electron or four electron reduction of oxygen. Two electron reduction of oxygen results in the formation of hydrogen peroxide or other peroxides which can potentially react to cause oxidation of the first or second substrate, but the active sites effective for the oxidation of the first substrate by four electron transfer may not always be effective for catalyzing the oxidation of the second substrate. In particular, they may not be effective to catalyze oxidation by reaction of the substrate with a peroxide compound. However, active sites afforded by a secondary metallic element are believed to catalyze oxidation of the second substrate by reaction with hydrogen peroxide or other peroxide compound. Experimental results have indicated that oxidation of second substrates such as formaldehyde is promoted by the secondary metallic element, and that such oxidation may comprise reaction with hydrogen peroxide. Thus, the combination of the first active sites and other active sites provide benefits in enhanced oxidation of the two substrates, and more particularly the second substrate.

In certain embodiments of the invention, both the primary transition metal composition and the secondary metallic element may be present in a single active phase which presents sites active for contact with and oxidation of both types of substrates. In other embodiments, the primary transition metal composition may be contained in one active phase which presents the sites active for oxidation of the first substrate, and the secondary metallic element or secondary catalytic composition may be present in a second active phase which presents sites active for oxidation of the second substrate. Where the catalyst comprises separate active phases, the first active phase may be deposited on the carbon support and the second active phase may be formed on the support or on the first active phase, or over both. Alternatively, the second active phase may be deposited on the support and the first active phase formed on the support or on the second active phase or over both.

Also described herein are catalyst combinations, or catalyst systems, including a primary catalyst comprising a primary transition metal combined with a secondary catalyst comprising a secondary metallic element. In various embodiments, the primary catalyst comprises a primary transition metal composition formed on or over the surface of a carbon support. In other embodiments, the primary catalyst comprises a carbon support having a noble metal and/or promoter at a surface thereof and, in still other embodiments, the primary catalyst comprises an activated carbon catalyst. The secondary catalyst (i.e., co-catalyst), may include a catalytic composition comprising a secondary metallic element and formed on or over the surface of a carbon support. The secondary catalyst may also comprise a microporous crystalline material having a transition metal incorporated into its lattice including, for example, titanium-containing zeolites.

The catalysts and catalyst combinations of the invention comprise at least one transition metal composition. In various embodiments, the catalysts and catalyst combinations of the present invention comprise a primary transition metal composition, a secondary metallic element and a carbon support. The primary transition metal composition comprises a primary transition metal composition and nitrogen. The secondary metallic element can be incorporated as part of the primary transition metal composition; or it may form or be comprised by a secondary catalytic composition, which may optionally be formed on a separate support. The catalyst is understood to have sites that are active for the oxidation of a first substrate and sites that are active for the second substrate, which may be the same as or different from the first substrate.

As further discussed herein the catalyst may comprise a combination of a first catalyst comprising the first active phase and a second catalyst comprising the second active phase. In these embodiments, the first active phase may comprise noble metal active sites provided by a noble metal on carbon catalyst of the type described by U.S. Pat. No. 6,417,133 to Ebner et al.; or alternatively, the first active phase may be comprised by the surface of an active carbon that has been treated in the manner described in U.S. Pat. Nos. 4,624,937 and 4,696,772 to Chou.

Transition metal and catalytic compositions formed on or over the surface of a carbon support in accordance with the catalysts and catalyst combinations of the present invention generally comprise a transition metal or metallic element and nitrogen (e.g., a transition metal nitride); a transition metal or metallic element and carbon (e.g., a transition metal carbide); or a transition metal or metallic element, nitrogen, and carbon (e.g., a transition metal carbide-nitride).

Catalysts and catalyst combinations of the present invention may be used to catalyze liquid phase (e.g., in an aqueous solution or an organic solvent) oxidation reactions and, in particular, the oxidation of a tertiary amine (e.g., N-(phosphonomethyl)iminodiacetic acid) to produce a secondary amine (e.g., N-(phosphonomethyl)glycine). Advantageously, the catalysts and catalyst combinations of the present invention also catalyze oxidation of the formaldehyde and/or formic acid by-products that are formed in the oxidation of N-(phosphonomethyl)iminodiacetic acid to N-(phosphonomethyl)glycine. It has been observed that catalysts of the present invention comprising a transition metal composition comprising one or more transition metals, nitrogen and/or carbon formed on or over the surface of a carbon support comprise an active phase effective to catalyze the oxidation of N-(phosphonomethyl)iminodiacetic acid to N-(phosphonomethyl)glycine and the oxidation of formaldehyde and/or formic acid byproducts. In addition, various catalysts of the present invention include a first active phase and/or a primary transition metal composition as described herein that is effective to catalyze the oxidation of N-(phosphonomethyl)iminodiacetic acid to N-(phosphonomethyl)glycine and a second active phase and/or secondary catalytic composition effective to catalyze the oxidation of formaldehyde and/or formic acid byproducts. Similarly, various catalyst combinations of the present invention include a primary catalyst effective to catalyze the oxidation of N-(phosphonomethyl)iminodiacetic acid to N-(phosphonomethyl)glycine and a secondary catalyst effective to catalyze the oxidation of formaldehyde and/or formic acid byproducts.

Reference to the catalytic activity of a particular active phase (e.g., first active phase) for oxidation of a particular substrate should not be taken as exclusive of catalytic activity for oxidation of another substrate. For example, a secondary metallic element, secondary catalytic composition or secondary catalyst may exhibit catalytic activity for the oxidation of N-(phosphonomethyl)iminodiacetic acid to N-(phosphonomethyl)glycine. In addition, reference to the catalytic activity of an active phase or transition metal composition or catalytic composition formed on a carbon support or primary or secondary catalyst incorporating such a composition should not be taken as exclusive of the catalytic activity of the carbon support itself. For example, the carbon support alone is known to catalyze the oxidation of tertiary amines to secondary amines.

By evaluating experimental data for a particular substrate and process, applying standard economic principles, those skilled in the art can weigh the advantages of using a single catalyst comprising a primary transition metal and a secondary metallic element or using a catalyst combination including a primary transition metal and a secondary metallic element.

Further described herein are processes for preparing transition metal compositions and catalytic compositions comprising a transition metal or metallic element and nitrogen; a transition metal or metallic element and carbon; or a transition metal or metallic element, nitrogen, and carbon on or over the surface of a carbon support.

Supporting Structure

Generally, the supporting structure may comprise any material suitable for formation of a transition metal composition or catalytic composition thereon. Preferably, the supporting structure is in the form of a carbon support.

In general, the carbon supports used in the present invention are well known in the art. Activated, non-graphitized carbon supports are preferred. These supports are characterized by high adsorptive capacity for gases, vapors, and colloidal solids and relatively high specific surface areas. The support suitably may be a carbon, char, or charcoal produced by means known in the art, for example, by destructive distillation of wood, peat, lignite, coal, nut shells, bones, vegetable, or other natural or synthetic carbonaceous matter, but preferably is "activated" to develop adsorptive power. Activation usually is achieved by heating to high temperatures (800-900° C.) with steam or with carbon dioxide which brings about a porous particle structure and increased specific surface area. In some cases, hygroscopic substances, such as zinc chloride and/or phosphoric acid or sodium sulfate, are added before the destructive distillation or activation, to increase adsorptive capacity. Preferably, the carbon content of the carbon support ranges from about 10% for bone charcoal to about 98% for some wood chars and nearly 100% for activated carbons derived from organic polymers. The non-carbonaceous matter in commercially available activated carbon materials normally will vary depending on such factors as precursor origin, processing, and activation method. Many commercially available carbon supports contain small amounts of metals. In certain embodiments, carbon supports having the fewest oxygen-containing functional groups at their surfaces are most preferred.

The form of the carbon support is not critical. In certain embodiments, the support is a monolithic support. Suitable monolithic supports may have a wide variety of shapes. Such a support may be, for example, in the form of a screen or honeycomb. Such a support may also, for example, be in the form of a reactor impeller.

In a particularly preferred embodiment, the support is in the form of particulates. Because particulate supports are especially preferred, most of the following discussion focuses on embodiments which use a particulate support. It should be recognized, however, that this invention is not limited to the use of particulate supports.

Suitable particulate supports may have a wide variety of shapes. For example, such supports may be in the form of granules. Even more preferably, the support is in the form of a powder. These particulate supports may be used in a reactor system as free particles, or, alternatively, may be bound to a structure in the reactor system, such as a screen or an impeller.

Typically, a support which is in particulate form comprises a broad size distribution of particles. For powders, preferably at least about 95% of the particles are from about 2 to about 300 μm in their largest dimension, more preferably at least about 98% of the particles are from about 2 to about 200 μm in their largest dimension, and most preferably about 99% of the particles are from about 2 to about 150 μm in their largest dimension with about 95% of the particles being from about 3 to about 100 μm in their largest dimension. Particles being greater than about 200 μm in their largest dimension tend to fracture into super-fine particles (i.e., less than 2 μm in their largest dimension), which are difficult to recover.

In the following discussion, specific surface areas of carbon supports and the oxidation catalysts of the present invention are provided in terms of the well-known Langmuir method using $N_2$. However, such values generally correspond to those measured by the also well-known Brunauer-Emmett-Teller (B.E.T.) method using $N_2$.

The specific surface area of the carbon support, typically measured by the Langmuir method using $N_2$, is preferably from about 10 to about 3,000 $m^2/g$ (surface area of carbon support per gram of carbon support), more preferably from about 500 to about 2,100 $m^2/g$, and still more preferably from about 750 to about 2,100 $m^2/g$. In some embodiments, the most preferred specific area is from about 750 to about 1,750 $m^2/g$. In other embodiments, typically the particulate carbon support has a Langmuir surface area of at least about 1000 $m^2/g$ prior to formation of a transition metal composition on the carbon support, more typically at least about 1200 $m^2/g$ and, still more typically, at least about 1400 $m^2/g$. Preferably, the Langmuir surface area of the carbon support prior to formation of a transition metal composition on the carbon support is from about 1000 to about 1600 $m^2/g$ and, more preferably, from about 1000 to about 1500 $m^2/g$ prior to formation of a transition metal composition on the carbon support.

The Langmuir micropore surface area of the support (i.e., surface area of the support attributed to pores having a diameter less than 20 Å) is typically at least about 300 $m^2/g$, more typically at least about 600 m²/g. Preferably, the Langmuir micropore surface area is from about 300 to about 1500 m²/g and, more preferably, from about 600 to about 1400 m²/g. The Langmuir combined mesopore and macropore surface area of the support (i.e., surface area of the support attributed to pores having a diameter greater than 20 Å) is typically at least about 100 m²/g, more typically at least about 150 m²/g. Preferably, the combined Langmuir mesopore and macropore surface area is from about 100 to about 400 m²/g, more preferably from about 100 to about 300 m²/g and, still more preferably, from about 150 to about 250 m²/g.

For certain applications (e.g., hydrogenation, petroleum hydrotreating, and isomerization), non-carbon supports may be used with a catalyst containing a transition metal composition or catalytic composition formed on the support as described herein. For example, silica and alumina supports having Langmuir surface areas of at least about 50 m²/g. Typically, these supports will have Langmuir surface areas of from about 50 to about 300 m²/g. Such supports are also effective for use in oxidation catalysts as described herein.

Generally, supports having high surface areas are preferred because they tend to produce a finished catalyst having a high surface area.

Finished catalysts exhibiting sufficient pore volume are desired so that reactants are able to penetrate the pores of the finished catalyst. The pore volume of the support may vary widely. Generally, the pore volume of the support is at least about 0.1 cm³/g (pore volume per gram of support) and, typically, at least about 0.5 cm³/g. Typically, the pore volume is from about 0.1 to about 2.5 cm³/g and, more typically, from about 1.0 to about 2.0 cm³/g. Preferably, the pore volume of the support is from about 0.2 to about 2.0 cm³/g, more preferably from about 0.4 to about 1.7 cm³/g and, still more preferably, from about 0.5 to about 1.7 cm³/g. Catalysts comprising supports with pore volumes greater than about 2.5 cm³/g tend to fracture easily. On the other hand, catalysts comprising supports having pore volumes less than 0.1 cm³/g tend to have small surface areas and therefore low activity.

Penetration of reactants into the pores of the finished catalysts is also affected by the pore size distribution of the support. Typically, at least about 60% of the pore volume of the support is made up of pores having a diameter of at least about 20 Å. Preferably, from about 60 to about 75% of the pore volume of the support is made up of pores having a diameter of at least about 20 Å.

Typically, at least about 20% of the pore volume of the support is made up of pores having a diameter of between about 20 and about 40 Å. Preferably, from about 20 to about 35% of the pore volume of the support is made of pores having a diameter of between about 20 and about 40 Å. Typically, at least about 25% of the pore volume of the support is made up of pores having a diameter of at least about 40 Å. Preferably, from about 25 to about 60% of the pore volume of the support is made up of pores having a diameter of at least about 40 Å. Typically, at least about 5% of the pore volume of the support is made up of pores having a diameter of between about 40 and about 60 Å. Preferably, from about 5 to about 20% of the pore volume of the support is made up of pores having a diameter of between about 40 and about 60 Å.

Carbon supports for use in the present invention are commercially available from a number of sources. The following is a listing of some of the activated carbons which may be used with this invention: Darco G-60 Spec and Darco X (ICI-America, Wilmington, Del.); Norit SG Extra, Norit EN4, Norit EXW, Norit A, Norit Ultra-C, Norit ACX, and Norit 4×14 mesh (Amer. Norit Co., Inc., Jacksonville, Fla.); G1-9615, VG-8408, VG-8590, NB-9377, XZ, NW, and JV (Barnebey-Cheney, Columbus, Ohio); BL Pulv., PWA Pulv., Calgon C 450, and PCB Fines (Pittsburgh Activated Carbon, Div. of Calgon Corporation, Pittsburgh, Pa.); P-100 (No. Amer. Carbon, Inc., Columbus, Ohio); Nuchar CN, Nuchar C-1000 N, Nuchar C-190 A, Nuchar C-115 A, and Nuchar SA-30 (Westvaco Corp., Carbon Department, Covington, Va.); Code 1551 (Baker and Adamson, Division of Allied Amer. Norit Co., Inc., Jacksonville, Fla.); Grade 235, Grade 337, Grade 517, and Grade 256 (Witco Chemical Corp., Activated Carbon Div., New York, N.Y.); and Columbia SXAC (Union Carbide New York, N.Y.).

Transition Metal Compositions and Catalytic Compositions

Transition metal compositions (e.g., primary transition metal compositions) formed on or over the surface of a carbon support generally comprise a transition metal and nitrogen; a transition metal and carbon; or a transition metal, nitrogen, and carbon. Similarly, catalytic compositions (e.g., secondary catalytic compositions) formed on or over the surface of a carbon support and/or formed on or over the surface of a primary transition metal composition generally comprise a metallic element (e.g., a secondary metallic element which may be denoted as M(II)) and nitrogen; a metallic element and carbon; or a metallic element, nitrogen, and carbon.

In various embodiments, catalysts of the present invention comprise a transition metal composition at a surface of a carbon support. The transition metal compositions typically comprise a transition metal (e.g., a primary transition metal) selected from the group consisting of Group IB, Group VB, Group VIB, Group VIIB, iron, cobalt, nickel, lanthanide series metals, and combinations thereof. Groups of elements as referred to herein are with reference to the Chemical Abstracts Registry (CAS) system for numbering the elements of the Periodic Table (e.g., Group VIII includes iron, cobalt, and nickel). In particular, the primary transition metal is typically selected from the group consisting of copper (Cu), silver (Ag), vanadium (V), chromium (Cr), molybdenum (Mo), tungsten (W), manganese (Mn), iron (Fe), cobalt (Co), nickel (Ni), cerium (Ce), and combinations thereof. In certain embodiments, the primary transition metal is typically selected from the group consisting of copper, silver, vanadium, chromium, molybdenum, tungsten, manganese, cobalt, nickel, cerium, and combinations thereof. In various preferred embodiments the transition metal is cobalt. In certain other embodiments, the primary transition metal composition includes a plurality of primary transition metals (e.g., cobalt and cerium).

In various embodiments, catalysts of the present invention further comprise a secondary catalytic composition comprising a secondary metallic element which can be formed on or over the surface of a carbon support and/or formed on or over the surface of a primary transition metal composition formed on the carbon support. Additionally or alternatively, the secondary metallic element can be incorporated into a transition metal composition further comprising a primary transition metal. The secondary metallic element is typically selected from the group consisting of Group IIB, Group IVB, Group VB, Group VIB, Group VIIB, Group IIA, Group VIA, nickel, copper, and combinations thereof. Thus, the secondary metallic element is typically selected from the group consisting of zinc (Zn), titanium (Ti), vanadium, molybdenum, manganese, barium (Ba), calcium (Ca), magnesium (Mg), tellurium (Te), selenium (Se), nickel, copper, and combinations thereof. Although selenium and tellurium are generally classified as non-metals, they exist in allotropic forms that are lustrous and sometimes referred to as "metallic," and can function as semiconductors. They are, thus, referred to herein as "metallic elements," though not as "metals." In various preferred embodiments, the secondary metallic element is a transition metal (i.e., secondary transition metal) selected from the group consisting of zinc, titanium, vanadium, molybdenum, manganese, barium, magnesium, nickel, copper, and combinations thereof. Thus, in these embodiments, the secondary catalytic composition may properly be referred to as a secondary transition metal composition.

It is recognized that, depending on the context, any of several different transition metals may qualify as either a primary transition metal or a secondary metallic element. Thus, where two or more of such transition metals are present, they may in some instances function as plural primary transition metals and in other instances one or more of them may function as secondary metallic elements. The criteria for classification in this regard include the nature of the composition(s) in which each metal is present, and the relative effectiveness of the metals and the compositions within which they are included for oxidation of different substrates. More particularly, it will be understood that, to qualify as a primary transition metal, the metal must be comprised by a composition that also contains nitrogen. Otherwise the metal can qualify only as a secondary metallic element. It will be further understood that, where a composition comprising a given transition metal and nitrogen, for example, a nitride or carbide-nitride thereof, is less effective on a unit gram-atom metal basis than a composition or active phase comprising another transition metal and nitrogen for oxidation of a first substrate but more effective than the composition comprising the another metal for oxidation of a second substrate that is formed as a by-product of the oxidation of the first substrate, the another metal qualifies as a primary transition metal and the given metal qualifies as a secondary metallic element. For example, a primary transition metal composition is effective for catalyzing the oxidation of a first substrate (e.g., N-(phosphonomethyl)iminodiacetic acid) while a secondary metallic element or secondary catalytic composition comprising such element is less effective than the primary transition metal for oxidation of N-(phosphonomethyl)iminodiacetic acid. However, in various preferred embodiments, the secondary metallic element or second catalytic composition is more effective than (or enhances the effectiveness of) the primary transition metal composition for catalyzing the oxidation of formaldehyde and/or formic acid byproducts formed in the oxidation of N-(phosphonomethyl)iminodiacetic acid catalyzed by a primary transition metal.

Without being held to a particular theory, it is believed that the secondary metallic element or secondary catalytic composition may enhance the effectiveness of the catalyst as a whole for catalyzing the oxidation of the second substrate by reaction with hydrogen peroxide formed in the reduction of oxygen as catalyzed by either the primary transition metal composition, the secondary metallic element or the secondary catalytic composition. Aside from other criteria, any transition metal which has such enhancing effect may be considered a secondary metallic element for purposes of the present invention.

It is recognized that the same element may qualify as a primary transition metal with regard to one process and the first and second substrates oxidized therein, but qualify as a secondary metallic element for another combination of first and second substrates. But the functional definitions set out above may be applied for classification of a given metal in a given context. It will, in any event, be understood that the present invention contemplates bi-metallic catalysts including both combinations of plural primary transition metals and combinations of primary transition metal compositions and secondary metallic elements. Elements which may function as either primary transition metals or secondary metallic elements include, for example, copper, nickel, vanadium, manganese, or molybdenum. Specific combinations which may constitute plural primary transition metals in one context and a combination of primary transition metal and secondary metallic element in another include Co/Cu, Co/Ni, Co/V, Co/Mn, Co/Mo, Fe/Cu, Fe/Ni, Fe/V, Fe/Mn, Fe/Mo, Mo/Cu, Mo/Ni, Mo/V, Mo/Mn, Mo/Mo, W/Cu, W/Ni, W/V, W/Mn, W/Mo, Cu/Cu, Cu/Ni, Cu/V, Cu/Mn, Cu/Mo, Ag/Cu, Ag/Ni, Ag/V, Ag/Mn, Ag/Mo, V/Cu, V/Ni, V/V, V/Mn, V/Mo, Cr/Cu, Cr/Ni, Cr/V, Cr/Mn, Cr/Mo, Mn/Cu, Mn/Ni, Mn/V, Mn/Mn, Mn/Mo, Ni/Cu, Ni/Ni, Ni/V, Ni/Mn, Ni/Mo, Ce/Cu, Ce/Ni, Ce/V, Ce/Mn, and Ce/Mo.

Generally, transition metal compositions of the present invention (e.g., primary transition metal compositions) include the transition metal in a non-metallic form (i.e., in a non-zero oxidation state) combined with nitrogen, carbon, or carbon and nitrogen in form of a transition metal nitride, carbide, or carbide-nitride, respectively. The transition metal compositions may further comprise free transition metal in its metallic form (i.e., in an oxidation state of zero). Similarly, catalytic compositions of the present invention (e.g., secondary catalytic compositions) include the metallic element in a non-metallic or in the case of selenium and tellurium "non-elemental" form (i.e., in a non-zero oxidation state) combined with nitrogen, carbon, or carbon and nitrogen in form of a metallic nitride, carbide, or carbide-nitride, respectively. The catalytic compositions may further comprise free metallic element (i.e., in an oxidation state of zero). The transition metal compositions and catalytic compositions may also include carbide-nitride compositions having an empirical formula of $CN_x$ wherein x is from about 0.01 to about 0.7.

Typically, at least about 5% by weight of the transition metal or metallic element is present in a non-zero oxidation state (e.g., as part of a transition metal nitride, transition metal carbide, or transition metal carbide-nitride), more typically at least about 20%, still more typically at least about 30% and, even more typically, at least about 40%. Preferably, at least about 50% of the transition metal or metallic element is present in a non-zero oxidation state, more preferably at least about 60%, still more preferably at least about 75% and, even more preferably, at least about 90%. In various preferred embodiments, all or substantially all (e.g., greater than 95% or even greater than 99%) of the transition metal or metallic element is present in a non-zero oxidation state. In various embodiments, from about 5 to about 50% by weight of the transition metal or metallic element is in a non-zero oxidation state, in others from about 20 to about 40% by weight and, in still others, from about 30 to about 40% by weight of the transition metal or metallic element is in a non-zero oxidation state.

For catalysts including one or more metal compositions formed on or over the surface of a carbon support (e.g., a transition metal nitride), generally either or each composition constitutes at least about 0.1% by weight of the catalyst and, typically, at least about 0.5% by weight of the catalyst. More particularly, a transition metal composition formed on a carbon support typically constitutes from about 0.1 to about 20% by weight of the catalyst, more typically from about 0.5 to about 15% by weight of the catalyst, more typically from about 0.5 to about 10% by weight of the catalyst, still more typically from about 1 to about 12% by weight of the catalyst, and, even more typically, from about 1.5 to about 7.5% or from about 2% to about 5% by weight of the catalyst.

Generally, a transition metal constitutes at least about 0.01% by weight of the catalyst, at least about 0.1% by weight of the catalyst, at least about 0.2% by weight of the catalyst, at least about 0.5% by weight of the catalyst, at least about 1% by weight of the catalyst, at least about 1.5% by weight of the catalyst, or at least about 1.6% by weight of the catalyst. Typically, the transition metal constitutes at least about 1.8% by weight of the catalyst and, more typically, at least about 2.0% by weight of the catalyst. In accordance with these and other embodiments, the transition metal generally constitutes less than about 10% by weight of the catalyst or less than about 5% by weight of the catalyst. In certain embodiments, the transition metal typically constitutes from about 0.5% to about 3%, more typically from about 1% to about 3% or from about 1.5% to about 3% by weight of the catalyst. In various other embodiments, the transition metal constitutes between 1.6% and 5% or between 2% and 5% by weight of the catalyst.

The nitrogen component of the metal compositions (e.g., primary or secondary transition metal compositions) is generally present in a proportion of at least about 0.01% by weight of the catalyst, more generally at least about 0.1% by weight of the catalyst and, still more generally, at least about 0.5% or at least about 1% by weight of the catalyst. Typically, the nitrogen constitutes at least about 1.0%, at least about 1.5%, at least about 1.6%, at least about 1.8%, or at least about 2.0% by weight of the catalyst. More typically, the nitrogen component is present in a proportion of from about 0.1 to about 20% by weight of the catalyst, from about 0.5% to about 15 by weight of the catalyst, from about 1% to about 12% by weight of the catalyst, from about 1.5% to about 7.5% by weight of the catalyst, or from about 2% to about 5% by weight of the catalyst. It has been observed that catalyst activity and/or stability may decrease as nitrogen content of the catalyst increases. Increasing the proportion of nitrogen in the catalyst may be due to a variety of factors including, for example, use of a nitrogen-containing source of transition metal.

The secondary metallic element of a secondary catalytic composition is generally present in a proportion of at least about 0.01% by weight of the catalyst, more generally at least about 0.1% by weight of the catalyst or at least about 0.2% by weight of the catalyst. Typically, the secondary metallic element is present in a proportion of at least about 0.5% by weight of the catalyst and, more typically, at least about 1% by weight of the catalyst. Preferably, the secondary metallic element is present in a proportion of from about 0.1 to about 20% by weight of the catalyst, more preferably from about 0.5 to about 10% by weight of the catalyst, still more preferably from about 0.5 to about 2% by weight of the catalyst and, even more preferably, from about 0.5 to about 1.5% by weight of the catalyst.

For example, in various such embodiments, titanium is present in a proportion of about 1% by weight of the catalyst. In various embodiments, titanium is preferably present in a proportion of from about 0.5 to about 10% by weight of the catalyst, more preferably from about 0.5 to about 2% by weight of the catalyst and, even more preferably, from about 0.5 to about 1.5% by weight of the catalyst. In other embodiments, titanium is preferably present in a proportion of from about 0.1 to about 5% by weight of the catalyst, more preferably from about 0.1 to about 3% by weight of the catalyst and, even more preferably, from about 0.2 to about 1.5% by weight of the catalyst. Often, titanium is present in a proportion of about 1% by weight of the catalyst.

Nitrides

In various embodiments a transition metal composition comprising a transition metal and nitrogen comprises a transition metal nitride. For example, a transition metal/nitrogen composition comprising cobalt and nitrogen typically comprises cobalt nitride. Such cobalt nitride typically has an empirical formula of, for example, $CoN_x$ wherein x is typically from about 0.25 to about 4, more typically from about 0.25 to about 2 and, still more typically, from about 0.25 to about 1. Typically, the total proportion of at least one cobalt nitride having such an empirical formula (e.g., $Co_2N$) is at least about 0.01% by weight of the catalyst. Typically, the total proportion of all cobalt nitrides having such an empirical formula is at least about 0.1% by weight of the catalyst and, more typically, from about 0.1 to about 0.5% by weight of the catalyst. In such embodiments, cobalt may typically be present in a proportion of at least about 0.1% by weight of the catalyst, more typically at least about 0.5% by weight of the catalyst and, even more typically, at least about 1% by weight of the catalyst. By way of further example, a transition metal/nitrogen composition comprising iron and nitrogen typically comprises iron nitride. Such iron nitride typically has an empirical formula of, for example, $FeN_x$ wherein x is typically from about 0.25 to about 4, more typically from about 0.25 to about 2 and, still more typically, from about 0.25 to about 1. Typically, the total proportion of at least one iron nitride having such an empirical formula (e.g., FeN) is present in a proportion of at least about 0.01% by weight of the catalyst. Typically, the total proportion of all iron nitrides having such an empirical formula is at least about 0.1% by weight of the catalyst. In such embodiments, iron may typically be present in a proportion of at least about 0.01% by weight of the catalyst, more typically at least about 0.1% by weight of the catalyst, more typically at least about 0.2% by weight of the catalyst, even more typically at least about 0.5% by weight of the catalyst and, still more typically, at least about 1% by weight of the catalyst.

In further embodiments, a transition metal/nitrogen composition comprises molybdenum and nitrogen and, in a preferred embodiment, comprises molybdenum nitride. Typically, any molybdenum nitride formed on the carbon support as part of a transition metal composition comprises a compound having a stoichiometric formula of $Mo_2N$. In addition, transition metal/nitrogen compositions formed on the carbon support may comprise tungsten and nitrogen and, more particularly, comprise tungsten nitride. Typically, any tungsten nitride formed on the carbon support as part of the transition metal composition comprises a compound having a stoichiometric formula of $W_2N$.

In certain embodiments in which a transition metal composition comprises a primary transition metal (e.g., cobalt or iron) and nitrogen, the transition metal composition further comprises a secondary transition metal (e.g., titanium) or other secondary metallic element (e.g., magnesium, selenium, or tellurium). The primary transition metal and nitrogen are typically present in these embodiments in the proportions set forth above concerning transition metal compositions generally. In the case of titanium as the secondary transition metal, the transition metal composition typically includes titanium cobalt nitride or titanium iron nitride and, in particular, titanium cobalt nitride or titanium iron nitride having an empirical formula of $TiCo_yN_x$ or $TiFe_yN_x$, respectively, wherein each of x and y is typically from about 0.25 to about 4, more typically from about 0.25 to about 2 and, still more typically, from about 0.25 to about 1. In various other embodiments a metal composition (e.g., a primary transition metal composition or secondary catalytic composition) comprises a compound or complex of a secondary metallic element and nitrogen, e.g., a secondary transition metal nitride such as titanium nitride. More particularly, these compositions typically comprise titanium nitride which has an empirical formula of, for example, $TiN_x$ wherein x is typically from about 0.25 to about 4, more typically from about 0.25 to about 2 and, still more typically, from about 0.25 to about 1. Typically, the total proportion of at least one titanium cobalt nitride (e.g., $TiCoN_2$), titanium iron nitride (e.g., $TiFeN_2$), and/or titanium nitride (e.g., TiN) having such an empirical formula is at least about 0.01% by weight of the catalyst. Typically, the total proportion of all titanium cobalt nitrides, titanium iron nitrides, and/or titanium nitrides having such an empirical formula is at least about 0.1% by weight of the catalyst.

Carbides

In various embodiments a transition metal composition comprising a transition metal and carbon comprises a transition metal carbide. For example, a transition metal/carbon composition comprising cobalt and carbon typically comprises cobalt carbide. Such cobalt carbide typically has an empirical formula of, for example, $CoC_X$ wherein x is typically from about 0.25 to about 4, more typically from about 0.25 to about 2 and, still more typically, from about 0.25 to about 1. Typically, the total proportion of at least one cobalt carbide having such an empirical formula (e.g., $Co_2C$) is at least about 0.01% by weight of the catalyst. Typically, the total proportion of all cobalt carbide(s) having such an empirical formula is at least about 0.1% by weight of the catalyst and, more typically, from about 0.1 to about 0.5% by weight of the catalyst. In such embodiments, cobalt may generally be present in a proportion of at least about 0.1% by weight of the catalyst, at least about 0.5% by weight of the catalyst, or at least about 1% by weight of the catalyst. Typically, cobalt may be present in a proportion of from about 0.5 to about 10% by weight of the catalyst, more typically from about 1 to about 2% by weight of the catalyst and, still more typically, from about 1 to about 1.5% by weight of the catalyst. In certain embodiments, cobalt may be present in a proportion of from about 0.1 to about 3% by weight of the catalyst. By way of further example, a transition metal/carbon composition comprising iron and carbon typically comprises iron carbide. Such iron carbide typically has an empirical formula of, for example, $FeC_x$ wherein x is typically from about 0.25 to about 4, more typically from about 0.25 to about 2 and, still more typically, from about 0.25 to about 1. Typically, the total proportion of at least one iron carbide having such an empirical formula (e.g., $Fe_3C$) is at least about 0.01% by weight of the catalyst. Typically, the total proportion of all iron carbide(s) having such an empirical formula is at least about 0.1% by weight of the catalyst. In such embodiments, iron is generally present in a proportion of at least about 0.01% by weight of the catalyst or at least about 0.1% by weight of the catalyst. Typically, iron is present in a proportion of from about 0.1% to about 5% by weight of the catalyst, more typically from about 0.2% to about 1.5% by weight of the catalyst and, still more typically, from about 0.5 to about 1% by weight of the catalyst.

In further embodiments, a transition metal/carbon composition comprises molybdenum and carbon and, in a preferred embodiment, comprises molybdenum carbide. Typically, molybdenum carbide formed on the carbon support as part of a transition metal composition comprises a compound having a stoichiometric formula of $Mo_2C$. In other embodiments, a transition metal/carbon composition comprises tungsten and carbon and, in a preferred embodiment, comprises tungsten carbide. Typically, tungsten carbide formed on the carbon support as part of the primary transition metal composition comprises a compound having a stoichiometric formula of WC or $W_2C$.

In certain embodiments in which a transition metal composition comprises a primary transition metal (e.g., cobalt or iron) and carbon, the transition metal composition further comprises a secondary transition metal (e.g., titanium) or other secondary metallic element (e.g., magnesium, selenium or tellurium). The primary transition metal is typically present in these embodiments in the proportions set forth above concerning transition metal compositions generally. In the case of titanium as a secondary transition metal, the transition metal composition typically includes titanium cobalt carbide or titanium iron carbide and, in particular, titanium cobalt carbide or titanium iron carbide having an empirical formula of $TiCo_yC_x$ or $TiFe_yC_x$, respectively, wherein each of x and y is typically from about 0.25 to about 4, more typically from about 0.25 to about 2 and, still more typically, from about 0.25 to about 1. In various other embodiments the transition metal composition comprises a compound or complex of the secondary metal and carbon, e.g., a secondary transition metal carbide such as titanium carbide. More particularly, these compositions typically comprise titanium carbide which has an empirical formula of, for example, $TiC_x$ wherein x is typically from about 0.25 to about 4, more typically from about 0.25 to about 2 and, still more typically, from about 0.25 to about 1. Typically, the total proportion of at least one titanium cobalt carbide (e.g., $TiCoC_2$), titanium iron carbide (e.g., $TiFeC_2$), or titanium carbide (e.g., TiC) having such an empirical formula is at least about 0.01% by weight of the catalyst. Typically, the total proportion of all titanium cobalt carbide or titanium iron nitride having such an empirical formula is at least about 0.1% by weight of the catalyst.

Titanium is generally present in such embodiments in a proportion of at least about 0.01% by weight of the catalyst, typically at least about 0.1% by weight of the catalyst, more typically at least about 0.2% by weight of the catalyst, still more typically at least about 0.5% by weight of the catalyst and, even more typically, at least about 1% by weight of the catalyst.

In various embodiments (e.g., titanium cobalt carbide or titanium carbide), titanium is preferably present in a proportion of from about 0.5 to about 10% by weight of the catalyst, more preferably from about 0.5 to about 2 by weight of the catalyst, still more preferably from about 0.5 to about 1.5% by weight of the catalyst and, even more preferably, from about 0.5 to about 1.0% by weight of the catalyst. In other embodiments (e.g., titanium iron carbide or titanium carbide), titanium is preferably present in a proportion of from about 0.1 to about 5% by weight of the catalyst, more preferably from about 0.1 to about 3% by weight of the catalyst, more preferably from about 0.2 to about 1.5% by weight of the catalyst and, still more preferably, from about 0.5 to about 1.5% by weight of the catalyst.

Carbide and Nitride and Carbide-Nitrides

In various embodiments a transition metal composition comprises a transition metal, nitrogen, and carbon and, in such embodiments, may comprise a transition metal nitride and/or a transition metal carbide. For example, a transition metal composition comprising cobalt, carbon, and nitrogen may comprise cobalt carbide and cobalt nitride having empirical formulae as set forth above specifically describing cobalt carbide and/or cobalt nitride. Similarly, either or each of cobalt carbide and cobalt nitride, cobalt, and nitrogen are typically present in the proportions in terms of percent by weight of the catalyst set forth above specifically describing cobalt carbide and/or cobalt nitride. By way of further example, a transition metal composition comprising iron, carbon, and nitrogen may comprise iron carbide and iron nitride having empirical formulae as set forth above specifically describing iron carbide and/or iron nitride. Similarly, either or each of iron carbide and iron nitride, iron, and nitrogen are typically present in the proportions in terms of percent by weight of the catalyst set forth above specifically describing iron carbide and/or iron nitride.

Additionally or alternatively, a transition metal composition comprising a transition metal, nitrogen and carbon may comprise a transition metal carbide-nitride. For example, a transition metal composition comprising cobalt, carbon, and nitrogen may include cobalt carbide-nitride having an empirical formula of $CoC_yN_x$, where x and y are typically from about 0.25 to about 4, more typically from about 0.25 to about 2 and, still more typically, from about 0.25 to about 1. For example, CoCN or $CoC_2N$ may be present. Typically, a cobalt carbide-nitride having such an empirical formula is present in a proportion of at least about 0.01% by weight of the catalyst and, more typically, from about 0.1 to about 0.5% by weight of the catalyst. Typically, the total proportion of all cobalt carbide-nitrides of such empirical formula is at least about 0.1% by weight of the catalyst. In such embodiments, cobalt is typically present in the proportions set forth above specifically describing cobalt nitride and/or cobalt carbide. Likewise, nitrogen is typically present in such embodiments in the proportions set forth above specifically describing cobalt nitride. By way of further example, a transition metal composition comprising iron, carbon, and nitrogen may include iron carbide-nitride having an empirical formula of $FeC_yN_x$, where x and y are typically from about 0.25 to about 4, more typically from about 0.25 to about 2 and, still more typically, from about 0.25 to about 1. For example, FeCN or $FeC_2N$ may be present. Typically, an iron carbide-nitride having such an empirical formula is present in a proportion of at least about 0.01% by weight of the catalyst and, more typically, from about 0.1 to about 0.5% by weight of the catalyst. Typically, the total proportion of all iron carbide-nitrides of such empirical formula is at least about 0.1% by weight of the catalyst. In such embodiments, iron is typically present in the proportions set forth above specifically describing iron nitride and/or iron carbide. Likewise, nitrogen is typically present in such embodiments in the proportions set forth above specifically describing iron nitride.

In various embodiments in which the transition metal composition comprises a transition metal, nitrogen and carbon, the transition metal composition comprises a transition metal carbide, a transition metal nitride and a transition metal carbide-nitride. For example, catalysts of the present invention may comprise cobalt carbide, cobalt nitride, and cobalt carbide-nitride. In such embodiments, typically the total proportion of such carbide(s), nitride(s), and carbide-nitride(s) is at least about 0.1% by weight of the catalyst and, still more typically, from about 0.1 to about 20% by weight of the catalyst. By way of further example, catalysts of the present invention may comprise iron carbide, iron nitride, and iron carbide-nitride. In such embodiments, typically the total proportion of such carbide(s), nitride(s), and carbide-nitride(s) is at least about 0.1% by weight of the catalyst and, still more typically, from about 0.1 to about 20% by weight of the catalyst.

In certain embodiments in which a transition metal composition comprises a primary transition metal (e.g., cobalt or iron), nitrogen, and carbon, the transition metal composition further comprises a secondary metallic element (e.g., a secondary transition metal such as titanium). Thus, the transition metal composition may include, for example, titanium cobalt carbide and/or titanium cobalt nitride. In particular, the transition metal composition may comprise titanium cobalt carbide and/or titanium cobalt nitride having empirical formulae as set forth above specifically describing titanium cobalt carbide and/or titanium cobalt nitride. Similarly, either or each of titanium cobalt carbide and titanium cobalt nitride are present in the proportions in terms of percent by weight of the catalyst set forth above specifically describing titanium cobalt carbide and/or titanium cobalt nitride. Cobalt, titanium, and nitrogen are typically present in these embodiments in the proportions set forth above concerning transition metal/nitrogen/carbon compositions generally comprising cobalt, titanium, nitrogen and/or carbon. Additionally or alternatively, the transition metal composition may include titanium cobalt carbide-nitride including, for example, titanium cobalt carbide-nitride having an empirical formula of $TiCo_zC_yN_x$, wherein each of x, y and z is typically from about 0.25 to about 4, more typically from about 0.25 to about 2 and, still more typically, from about 0.25 to about 1. For example, TiCoCN may be present. Typically, a titanium cobalt carbide-nitride having such an empirical formula is present in a proportion of at least about 0.01% by weight of the catalyst and, more typically, from about 0.1 to about 0.5% by weight of the catalyst. Typically, the total proportion of all titanium cobalt carbide-nitrides of such empirical formula is at least about 0.1% by weight of the catalyst. Cobalt, titanium, and nitrogen are typically present in these embodiments in the proportions set forth above concerning transition metal/nitrogen/carbon compositions generally comprising cobalt, titanium, nitrogen and/or carbon.

In various embodiments, the catalyst may comprise titanium cobalt carbide, titanium cobalt nitride, and titanium cobalt carbide-nitride. In such embodiments, typically the total proportion of such carbide(s), nitride(s), and carbide-nitride(s) is at least about 0.1% by weight of the catalyst and, still more typically, from about 0.1 to about 20% by weight of the catalyst.

Transition metal compositions comprising iron, nitrogen, and carbon may also further comprise titanium. In these embodiments, the transition metal composition includes, for example, titanium iron carbide and/or titanium iron nitride. In particular, the transition metal composition may comprise titanium iron carbide and titanium iron nitride having empirical formula as set forth above specifically describing titanium iron carbide and/or titanium iron nitride. Similarly, either or each of titanium iron carbide and titanium iron nitride are present in the proportions in terms of percent by weight of the catalyst set forth above specifically describing titanium iron carbide and/or titanium iron nitride. Iron, titanium, and nitrogen are typically present in these embodiments in the proportions set forth above concerning transition metal/nitrogen/carbon compositions generally comprising iron, titanium, nitrogen and/or carbon.

In various other embodiments a transition metal composition comprising titanium, iron, carbon, and nitrogen may include titanium iron carbide-nitride having an empirical formula of $TiFe_zC_yN_x$, where x, y and z are typically from about 0.25 to about 4, more typically from about 0.25 to about 2 and, still more typically, from about 0.25 to about 1. For example, TiFeCN may be present. Typically, a titanium iron carbide-nitride having such an empirical formula is present in a proportion of at least about 0.01% by weight of the catalyst and, more typically, from about 0.1 to about 0.5% by weight of the catalyst. Typically, the total proportion of all titanium iron carbide-nitrides of such empirical formula is at least about 0.1% by weight of the catalyst.

Iron, titanium, and nitrogen are typically present in these embodiments in the proportions set forth above concerning transition metal/nitrogen/carbon compositions generally comprising iron, titanium, nitrogen and/or carbon.

In various embodiments, the catalyst may comprise titanium iron carbide, titanium iron nitride, and titanium iron carbide-nitride. In such embodiments, typically the total proportion of such carbide(s), nitride(s), and carbide-nitride(s) is at least about 0.1% by weight of the catalyst and, still more typically, from about 0.1 to about 20% by weight of the catalyst.

In various other embodiments, a secondary metallic element composition (e.g., a secondary catalytic composition) comprises, for example, tellurium or a transition metal such as titanium. Thus, in certain embodiments the secondary catalytic composition comprises titanium, carbon and nitrogen. More particularly, in these embodiments the secondary catalytic composition may comprise titanium carbide (e.g., TiC) and/or titanium nitride (e.g., TiN) having empirical formula as set forth above specifically describing titanium carbide and/or titanium nitride. Similarly, either or each of titanium carbide and titanium nitride, titanium, and nitrogen, are typically present in the proportions in terms of percent by weight of the catalyst set forth above specifically describing titanium carbide and/or titanium nitride.

In various other embodiments a transition metal composition comprising titanium, cobalt, carbon, and nitrogen may include titanium carbide-nitride having an empirical formula of $TiC_yN_x$, where x and y are typically from about 0.25 to about 4, more typically from about 0.25 to about 2 and, still more typically, from about 0.25 to about 1. For example, TiCN may be present. Typically, a titanium carbide-nitride having such an empirical formula is present in a proportion of at least about 0.01% by weight of the catalyst and, more typically, from about 0.1 to about 0.5% by weight of the catalyst. Typically, the total proportion of all titanium carbide-nitrides of such empirical formula is at least about 0.1% by weight of the catalyst. Titanium and nitrogen are typically present in these embodiments in the proportions in terms of percent by weight of the catalyst set forth above specifically describing titanium carbide and/or titanium nitride. Similarly, cobalt is typically present in these embodiments in the proportions set forth above describing cobalt carbide and/or cobalt nitride.

In various embodiments, the catalyst may comprise titanium cobalt carbide, titanium cobalt nitride, and titanium cobalt carbide-nitride. In such embodiments, typically the total proportion of such carbide(s), nitride(s), and carbide-nitride(s) is at least about 0.1% by weight of the catalyst and, still more typically, from about 0.1 to about 20% by weight of the catalyst.

Further in accordance with the present invention, a transition metal composition (e.g., a primary transition metal composition) may include a plurality of transition metals selected from the group consisting of Group IB, Group VB, Group VIB, Group VIIB, iron, cobalt, nickel, lanthanide series metals, and combinations thereof. In particular, the primary transition metal composition may include a plurality of transition metals selected from the group consisting of copper, silver, vanadium, chromium, molybdenum, tungsten, manganese, iron, cobalt, nickel, ruthenium and cerium. For example, the transition metal composition may comprise cobalt cerium nitride, cobalt cerium carbide, cobalt cerium carbide-nitride, nickel cobalt nitride, vanadium cobalt nitride, chromium cobalt nitride, manganese cobalt nitride, copper cobalt nitride.

Other bi-metallic carbide-nitrides present in transition metal compositions in accordance with the present invention may be in the form of cobalt iron carbide-nitride or cobalt copper carbide-nitride. One of such bi-transition metal compositions (e.g., a bi-transition metal nitride) may be present in a total proportion of at least about 0.1% by weight and, more typically, in a proportion of from about 0.1 to about 20% by weight of the catalyst. One or more of such bi-transition metal compositions (e.g., nitride, carbide, and/or carbide-nitride) may be present in a total proportion of at least about 0.1% by weight and, more typically, in a proportion of from about 0.1 to about 20% by weight of the catalyst. Bi-primary transition metal compositions may further comprise a secondary transition metal (e.g., titanium) in accordance with the discussion set forth above.

In certain embodiments, a transition metal composition formed on the carbon support generally comprises either or both of a composition comprising a transition metal and carbon (i.e., a transition metal/carbon composition) or a composition comprising a transition metal and nitrogen (i.e., a transition metal/nitrogen composition) in which the transition metal is selected from molybdenum and tungsten.

In various embodiments including a transition metal composition comprising either or both of a transition metal/carbon composition or a transition metal/nitrogen composition in which the transition metal is selected from molybdenum and tungsten, generally the transition metal composition constitutes at least about 5% by weight of a catalyst including a transition metal composition formed on a carbon. Typically, the transition metal composition comprises from about 5% to about 20% by weight of the catalyst, more typically from about 10% to about 15% by weight of the catalyst, and, still more typically, from about 10% to about 12% by weight of the catalyst. Generally, the transition metal component of the transition metal composition (i.e., molybdenum or tungsten and nitrogen and/or carbon) comprises at least about 5% by weight of the catalyst. Preferably, the transition metal component of the transition metal composition comprises from about 8% to about 15% by weight of the catalyst.

Processes for Preparation of the Oxidation Catalyst

As noted, catalysts of the present invention include at least one transition metal composition comprising one or more transition metals, nitrogen, and/or carbon formed on or over the surface of a carbon support. The transition metal composition may comprise a single compound or a mixture of compounds including, for example, transition metal nitrides, transition metal carbides, and transition metal carbide-nitrides. Generally, the transition metal composition is present in the form of discrete particles and/or a film (e.g., an amorphous or crystalline film). Regardless of the precise chemical structure of the transition metal composition, in various embodiments a substantial portion of the transition metal and nitrogen of the transition metal composition are believed to be present in either an amorphous film or in discrete particles. In the case of a transition metal composition comprising discrete particles, preferably a substantial portion of the transition metal and nitrogen of the transition metal composition are present in discrete particles.

The transition metal composition is formed on a carbon support by heating the carbon support having a precursor composition thereon, typically in the presence of a nitrogen-containing environment. Two competing events are believed to be occurring during heat treatment of the precursor composition, although, depending on the conditions, one can prevail substantially to the exclusion of the other. One of these processes comprises formation of elemental metal, e.g., metallic cobalt, which tends to aggregate into relatively large metallic particles. The other is the generation of a form of a metal nitride that develops in a physical form comprising relatively fine crystallites, a crystalline film, and/or an amorphous film. Without being bound to a particular theory, there is evidence that the transition metal/nitrogen composition comprises a crystalline or quasi-crystalline metal lattice wherein the metal atoms are ionized to a substantial degree, e.g., in the case of cobalt, a substantial fraction of the cobalt is present as $Co^{+2}$. Nitrogen is believed to be dispersed in the interstices of the metal lattice, apparently in the form of nitride ions and/or as nitrogen co-ordinated to the metal or metal ions. In this regard, the dispersion of nitrogen in the transition metal composition may be comparable to, or in any event analogized to, the dispersion of carbon or carbide in Fe structure of steel, although the nitrogen content of the transition metal composition may likely be somewhat greater than the carbon content of steel. The exact structure of the transition metal/nitrogen composition is complex and difficult to precisely characterize, but evidence consistent with the structural characteristics described above is consistent with X-Ray Photoelectron Spectroscopy (XPS), Electron Paramagnetic Resonance (EPR) Spectroscopy, and particle size data obtained on the catalysts.

The incidence of relatively large particles generally increases as the proportion of metal ions of the precursor composition in close proximity at the surface of the carbon support increases; a substantial portion of relatively large particles is preferably avoided due to the attendant reduction in catalytic surface area, and further because the larger particles are believed to be largely constituted of catalytically inactive elemental metal. Formation of the transition metal composition is generally promoted in preference to formation of relatively large metal particles by relatively sparse precursor composition dispersion that allows access of the nitrogen-containing environment to the metal particles. Thus, the size distribution of particles comprising the transition metal composition, and/or the distribution of such composition between discrete particles and an amorphous film is currently believed to be a function of the dispersion of metal ions of the precursor composition. In accordance with the present invention, various novel processes have been discovered for the preparation of active oxidation catalysts. These preparation processes are believed to contribute to advantageous (i.e., relatively sparse) dispersion of metal ions of the precursor composition at a given metal loading and, consequently, minimize, and preferably substantially eliminate, formation of a substantial portion of relatively large particles (e.g., particles of a size greater than 20 nm, 30 nm, or 40 nm in their largest dimension) while promoting formation of the transition metal composition (e.g., a transition metal nitride). These processes include, for example, selection of certain preferred compounds as the source of transition metal, contacting the carbon support with solvents such as a coordinating solvent, a solvent having a polarity less than that of water and/or a solvent having a surface tension less than that of water, and treatment of the carbon support.

Formation of a substantial portion of relatively large metal particles generally increases with metal loading and the detrimental effect of such particles on catalytic activity thus tends to increase as metal loading increases. Where the precursor composition is deposited from a liquid medium consisting only of water, increases in metal loading beyond a threshold level may result in formation of a substantial portion of relatively large particles and, thus, negate any appreciable gain in catalytic activity that might otherwise result from the presence of a larger concentration of metal. Advantageously, the techniques described herein allow the use of higher metal loadings (e.g., greater than 1.6%, greater than 1.8%, greater than 2.0%, up to about 2.5%, or even up to about 3%, by weight of the catalyst, or greater) while avoiding formation of a substantial portion of relatively large particles and the attendant reduction in catalytic surface area.

Formation of Transition Metal Composition Precursor

In processes for forming a transition metal composition (e.g., forming a transition metal composition or secondary catalytic composition on or over the surface of a carbon support and/or on or over the surface of a metal composition), generally a precursor of the transition metal composition is formed on the carbon support by contacting the carbon support with a source of the transition metal and a liquid medium, typically in a mixture that comprises the liquid medium. During precursor formation, transition metal source compound is typically dispersed and/or dissolved in a liquid medium (e.g., an aqueous medium such as water) and transition metal ions are solvated in the liquid medium (i.e., transition metal ions are bound to one or more molecules of the liquid medium). The precursor composition may typically comprise solvated ions which may be deposited on and/or bound to the carbon support (i.e., the precursor composition may comprise a metal ion bonded to the carbon support and/or molecules of a liquid medium). The pre-treated carbon support is then subjected to further treatment (e.g., elevated temperature) to provide a transition metal composition and/or discrete particles on the carbon support.

Transition Metal Sources

The dispersion of metal ions of the precursor composition on the carbon support and, likewise, the size of discrete particles formed upon treatment of the precursor composition, may be affected by the structure of the source compound (e.g., transition metal salt), in particular the amount of space occupied by the structure of the transition metal salt (i.e., its relative bulk). The distribution of the transition metal composition between discrete particles and an amorphous film formed upon treatment of the precursor composition may also be affected by the structure of the source compound. For example, transition metal salts containing relatively large anions (e.g., an octanoate as compared to a halide salt) are believed to conduce to more sparse dispersion of metal centers of the precursor composition.

Generally, the source compound comprises a salt of the transition metal. Typically, the source compound is in the form of a water-soluble transition metal salt comprising a metal cation and an anion such as, for example, carbonate, halide, sulfate, nitrate, acetlyacetonate, phosphate, formate, orthoformate, carboxylate, and combinations thereof, or an anion comprising a transition metal and a cation such as ammonium or alkali metal. In various embodiments, the transition metal source comprises a transition metal carboxylate salt such as an acetate, formate, octanoate, or combinations thereof. The source compound is also preferably soluble in a polar organic solvent such as a lower alcohol and/or in a coordinating (e.g., chelating) solvent such as glyme, diglyme, or other coordinating solvents described below, or at least in aqueous mixtures comprising such polar organic solvents and/or coordinating solvents.

In the case of a transition metal source comprising iron, the transition metal salt is typically an iron halide (e.g., $FeCl_2$ or $FeCl_3$), iron sulfate (e.g., $FeSO_4$), iron acetate, ferrocyanide (e.g., ammonium ferrocyanide, $(NH_4)_4Fe(CN)_6$), ferricyanide, or combinations thereof.

In the case of a transition metal source comprising cobalt, the transition metal salt may typically be a cobalt halide (e.g., $CoCl_2$), a cobalt sulfate (e.g., $CoSO_4$), cobalt nitrate (i.e., $Co(NO_3)_2$), cobalt acetate, cobalt acetylacetonate (e.g., $CoC_{10}H_{14}O_4$), cobalt octanoate, a cobalt formate, a cobalt orthoformate, or combinations thereof.

By way of further example, to produce a transition metal composition comprising titanium, the source compound may typically comprise a titanium sulfate (e.g., $Ti_2(SO_4)_3$), titanium oxysulfate (TiO(SO$_4$)), a titanium halide (e.g., TiCl$_4$), a titanium alkoxide, or a combination thereof.

In the case of transition metal compositions comprising tungsten or molybdenum, the source compound may conveniently be a salt that comprises an anion containing highly oxidized molybdenum or tungsten, for example, a molybdate or tungstate salt. Heteromolybdates and heterotungstates, such as phosphomolybdates and phosphotungstates are also suitable, as are molybdophosphoric acid and tungstophosphoric acid. In most of these, the molybdenum or tungsten is hexavalent. Where a salt is used, it is preferably selected from among those that are water-soluble or those soluble in a polar organic solvent such as a lower alcohol and/or in a coordinating (e.g., chelating) solvent, so that the cation is most typically sodium, potassium or ammonium. Salts comprising molybdenum or tungsten cations may also be used, but the molybdates and tungstates are generally the more convenient sources.

Other types of transition metal-containing compounds including, for example, carbonates (e.g., CoCO$_3$) or oxides of the transition metal (e.g., CoO) may be used in processes for depositing the transition metal. While these types of compounds are generally less soluble in deposition liquid media suitable for use in the processes detailed herein than the sources previously detailed, they may be acidified by reaction with, for example, hydrochloric acid to provide a source of transition metal that is more soluble in the deposition liquid medium (e.g., CoCl$_2$). Operation in this manner may be advantageous in commercial preparation of the catalyst due to the relatively low cost and availability of these types of cobalt-containing compounds, particularly cobalt carbonate. It should be understood that reference to a "source" of transition metal throughout the present specification and claims thus encompasses these types of transition metal-containing compounds.

It is currently believed that sulfates, nitrates, ammonium salts, octanoates, and acetyloctanoates are "bulkier" than halide salts. Thus, in various preferred embodiments the source of transition metal is selected from the group consisting of sulfates, nitrates, ammonium salts, octanoates, acetyloctanoates and combinations thereof. However, it should be understood that using source compounds comprising halide salts provides active catalysts as well.

A mixture comprising a source of the transition metal (i.e., a source compound) and a liquid medium, optionally comprising one or more solvents, may be contacted with a carbon support. Advantageously, this may be accomplished by preparing a slurry of a particulate carbon support in a liquid medium (e.g., water), and adding to the slurry a mixture containing a source of the transition metal (e.g., a transition metal salt). Alternatively, an aqueous slurry containing a particulate carbon support can be added to a mixture containing a transition metal salt and a liquid medium, the liquid medium optionally, but preferably comprising one or more solvents. A further alternative involves adding the carbon support (e.g., neat carbon support) to a mixture containing a transition metal salt and a liquid medium, the liquid medium optionally comprising one or more solvents.

The relative proportions of source compound contacted with the carbon support, or present in a mixture or slurry contacted with the carbon support, are not narrowly critical. Overall, a suitable amount of source compound should be added to any slurry or mixture containing the carbon support to provide sufficient transition metal deposition.

Typically, the source compound is present in a mixture or slurry containing the source compound and a liquid medium in a proportion of at least about 0.01 g/liter and, more typically, from about 0.1 to about 10 g/liter. The carbon support is typically present in the suspension of slurry in a proportion of at least about 1 g/liter and, more typically, from about 1 g/liter to about 50 g/liter. Additionally or alternatively, the liquid medium generally contains the source of transition metal at a concentration of at least about 0.1% by weight, at least about 0.2% by weight, or at least about 0.5% by weight. Typically, the metal is present in the liquid medium at a concentration of from about 0.1% to about 8% by weight, more typically from about 0.2% to about 5% by weight and, still more typically, at a concentration of from about 0.5% to about 3% by weight.

Preferably, the source compound and carbon support are present in the suspension or slurry at a weight ratio of transition metal/carbon in the range of from about 0.1 to about 20 and, more preferably, from about 0.5 to about 10.

The rate of addition of a transition metal source (e.g., a transition metal-containing salt, typically a salt solution having a concentration of approximately 0.1 molar(M)) to a slurry containing the carbon support is not narrowly critical but, typically, the source compound is added to the carbon support mixture at a rate of at least about 0.05 millimoles (mmoles)/minute/liter and, more typically, at a rate of from about 0.05 to about 0.5 mmoles/minute/liter. Generally, at least about 0.05 L/hour per L slurry (0.05 gal./hour per gal. of slurry) of salt solution is added to the slurry, preferably from about 0.05 L/hour per L slurry (0.05 gal./hour per gal. of slurry) to about 0.4 L/hour per L slurry (0.4 gal./hour per gal. of slurry) and, more preferably, from about 0.1 L/hour per L of slurry (0.1 gal./hour per gal. of slurry) to about 0.2 L/hour per L of slurry (0.2 gal./hour per gal. of slurry) of salt solution is added to the slurry containing the carbon support.

In certain embodiments in which the transition metal composition formed on the carbon support includes either a composition comprising molybdenum or tungsten and carbon, or a composition comprising molybdenum or tungsten and nitrogen, or a composition comprising molybdenum or tungsten and both carbon and nitrogen, the method of precursor formation generally proceeds in accordance with the above discussion. Generally, an aqueous solution of a salt containing molybdenum or tungsten is added to an aqueous slurry of a particulate carbon support. Typically, the salt is present in a suspension or slurry containing the salt and a liquid medium in a proportion of at least about 0.1 g/liter and, more typically, from about 0.1 g/liter to about 5 g/liter. The carbon support is typically present in the suspension or slurry in a proportion of at least about 1 g/liter and, more typically, from about 5 to about 20 g/liter. Preferably, the molybdenum or tungsten-containing salt and carbon support are present in the suspension or slurry at a weight ratio of molybdenum/carbon or tungsten/carbon in the range of from about 0.1 to about 20 and, more preferably, at a weight ratio of molybdenum/carbon or tungsten/carbon in the range of from about 1 to about 10. The salt and carbon support are typically present in the aqueous medium in such relative concentrations at the outset of precursor deposition.

The rate of addition of the molybdenum or tungsten-containing salt solution to the slurry in such embodiments is not narrowly critical but, typically, the salt is added to the carbon support slurry at a rate of at least about 0.05 mmoles/minute/L and, more typically, at a rate of from about 0.05 to about 0.5 mmoles/minute/L. Generally, at least about 0.001 L of the molybdenum or tungsten-containing salt solution per gram of carbon support are added to the slurry. Preferably, from about 0.001 L to about 0.05 L transition metal-containing salt solution per gram of carbon support are added to the slurry. Generally, at least about 0.05 L/hour per L slurry (0.05 gal./hour per gal. of slurry) of salt solution is added to the slurry.

Preferably, from about 0.05 L/hour per L slurry (0.05 gal./hour per gal. of slurry) to about 0.4 L/hour per L slurry (0.4 gal./hour per gal. of slurry) and, more preferably, from about 0.1 L/hour per L of slurry (0.1 gal./hour per gal. of slurry) to about 0.2 L/hour per L of slurry (0.2 gal./hour per gal. of slurry) of salt solution is added to the slurry.

It is believed that the pH of the transition metal salt and carbon support mixture relative to the zero charge point of carbon (i.e., in mixtures having a pH of 3, for example, carbon exhibits a charge of zero whereas in mixtures having a pH greater than 3 or less than 3 carbon exhibits a negative charge or positive charge, respectively) may affect transition metal-containing precursor formation. For example, in the case of ammonium molybdate, the majority of the molybdenum exists as $MoO_4^{2-}$, regardless of pH. Thus, when the carbon in the slurry has a zero charge point at pH 3, a greater proportion of $MoO_4^{2-}$ is adsorbed on the carbon in a slurry having a pH 2 than in a slurry having a pH of 5. In the case of ammonium tungstate or ammonium molybdate in a slurry having a pH of from about 2 to about 3, substantially all of the transition metal is adsorbed on the carbon support (i.e., less than about 0.001% of the transition metal remains in the salt solution). Thus, the pH of the slurry comprising source compound and carbon support and, accordingly, the charge of the carbon support, may be controlled to promote deposition of the metal depending on whether the transition metal component is present as the cation or anion of the source compound. Accordingly, when the transition metal is present as the cation of the source compound the pH of the slurry is preferably maintained above 3 to promote adsorption of transition metal on the carbon support surface. In certain embodiments, the pH of the liquid medium is maintained at 7.5 or above. The pH of the slurry may be controlled by addition of an acid or base either concurrently with the transition metal salt or after addition of the transition metal salt to the slurry is complete.

In various embodiments, transition metal is present in the source compound as the cation (e.g., $FeCl_3$, $CoCl_2$, or $Co(NO_3)_2$). As the pH of the liquid medium increases, the transition metal cation of the source compound becomes at least partially hydrolyzed. For example, in the case of $FeCl_3$, iron hydroxide ions such as $Fe(OH)_2^{+1}$ or $Fe(OH)^{+2}$ may form and, in the case of $CoCl_2$ or $Co(NO_3)_2$, cobalt hydroxide ions such as $Co(OH)^{+1}$ may form.

Such ions are adsorbed onto the negatively charged carbon support surface. Preferably, the ions diffuse into the pores and are adsorbed and dispersed throughout the surface of the carbon support, including the surfaces within the pores. However, if the pH of the liquid medium is increased too rapidly, a metal hydroxide may precipitate in the liquid medium. Conversion of the transition metal ions to neutral metal hydroxide removes the electrostatic attraction between transition metal and the carbon support surface, and thus reduces deposition of metal on the support surface. Precipitation of hydroxide into the liquid medium may also impede dispersion of metal ions throughout the pores of the carbon support surface. Thus, preferably the pH of the liquid medium is controlled to avoid rapid precipitation of transition metal hydroxides before the occurrence of sufficient deposition of transition metal onto the carbon support surface by virtue of the electrostatic attraction between transition metal ions and the carbon support surface. After sufficient deposition of transition metal onto the carbon support surface, the pH of the liquid medium may be increased at a greater rate since a reduced proportion of transition metal remains in the bulk liquid phase.

The temperature of the liquid medium also affects the rate of precipitation of transition metal, and the attendant deposition of transition metal onto the carbon support. Generally, the rate of precipitation increases as the temperature of the medium increases. Typically, the temperature of the liquid medium during introduction of the source compound is maintained in a range from about 10° C. to about 30° C. and, more typically, from about 20° C. to about 25° C.

The initial pH and temperature levels of the liquid medium when metal begins to deposit onto the carbon support and levels to which they are increased generally depend on the transition metal cation. For example, in certain embodiments in which the transition metal is cobalt, the pH of the liquid medium is initially generally from about 7.5 to about 8.0 and typically increased to at least about 8.5, in others to at least about 9.0 and, in still other embodiments, to at least about 9.0. Further in accordance with such embodiments, the temperature of the liquid medium is initially generally about 25° C. and typically increased to at least about 40° C., more generally to at least about 45° C. and, still more generally, to at least about 50° C. Typically, the temperature is increased at a rate of from about 0.5 to about 10° C./min and, more typically, from about 1 to about 5° C./min. After an increase of the temperature and/or pH of the liquid medium, typically the medium is maintained under these conditions for a suitable period of time to allow for sufficient deposition of transition metal onto the carbon support surface. Typically, the liquid medium is maintained at such conditions for at least about 2 minutes, more typically at least about 5 minutes and, still more typically, at least about 10 minutes. In particular, in such embodiments, the temperature of the liquid medium is typically initially about 25° C. and the pH of the liquid medium is maintained at from about 7.5 to about 8.0 during addition of the source compound. After addition of the source compound is complete, the liquid medium is agitated by stirring for from about 25 to about 35 minutes while its pH is preferably maintained at from about 7.5 to about 8.5. The temperature of the liquid medium is then preferably increased to a temperature of from about 40° C. to about 50° C. at a rate of from about 1 to about 5° C./min while the pH of the liquid medium is maintained at from about 7.5 to about 8.5. The medium may then be agitated by stirring for from about 15 to about 25 minutes while the temperature of the liquid medium is maintained at from about 40° C. to about 50° C. and the pH at from about 7.5 to about 8.0. The slurry may then be heated to a temperature of from about 50° C. to about 55° C. and its pH adjusted to from about 8.5 to about 9.0, with these conditions being maintained for approximately 15 to 25 minutes. Finally, the slurry may be heated to a temperature of from about 55° C. to about 65° C. and its pH adjusted to from about 9.0 to about 9.5, with these conditions maintained for approximately 10 minutes.

Regardless of the presence of a primary transition metal, secondary transition metal, or other secondary metallic element in the source compound as an anion or cation, in order to promote contact of the support with the transition metal source compound, and mass transfer from the liquid phase, the slurry may be agitated concurrently with additions of source compound to the slurry or after addition of the transition metal salt to the slurry is complete. The liquid medium may likewise be agitated prior to, during, or after operations directed to increasing its temperature and/or pH. Suitable means for agitation include, for example, by stirring or shaking the slurry.

For transition metal compositions comprising a plurality of metals (e.g., a transition metal composition comprising a plurality of primary transition metals or a transition metal composition comprising a primary transition metal and a secondary metallic element), typically a single source compound comprising all of the metals, or a plurality of source compounds each containing at least one of the metals or other metallic elements is contacted with the carbon support in accordance with the preceding discussion. Formation of precursors of the transition metal(s) or other metallic element(s) may be carried out concurrently (i.e., contacting the carbon support with a plurality of source compounds, each containing the desired element for formation of a precursor) or sequentially (formation of one precursor followed by formation of one or more additional precursors) in accordance with the above discussion.

After the source of the transition metal or other secondary element has contacted the support for a time sufficient to ensure sufficient deposition of the source compound(s) and/or formation of its(their) derivative(s), the slurry is filtered, the support is washed with an aqueous solution and allowed to dry. Typically, the source contacts a porous support for at least about 0.5 hours and, more typically, from about 0.5 to about 5 hours, so that the support becomes substantially impregnated with a solution of the source compound. Generally, the impregnated support is allowed to dry for at least about 2 hours. Preferably, the impregnated support is allowed to dry for from about 5 to about 12 hours. Drying may be accelerated by contacting the impregnated carbon support with air at temperatures generally from about 80° C. to about 150° C.

After deposition of the precursor and solids/liquid separation to recover the carbon support having the precursor thereon, the resulting filtrate or centrate, which comprises undeposited source compound, may be recovered and recycled for use in subsequent catalyst preparation protocols. For example, the transition metal content of the recovered filtrate or centrate may typically be replenished with additional transition metal source prior to use in subsequent catalyst preparation. Additionally or alternatively, the filtrate/centrate may be combined with fresh transition metal source-containing liquid medium for use in subsequent catalyst preparation.

Generally, it has been observed that deposition of transition metal in accordance with the methods detailed herein results in a relatively high proportion of the transition metal contacted with the carbon support being deposited thereon (e.g., at least about 75% by weight, at least about 90% by weight, at least about 95% by weight, or even at least about 99% by weight). In those embodiments in which the liquid medium contacted with the carbon support includes a coordinating solvent the proportion of transition metal deposited on the carbon support generally varies with the strength of the coordination bonds formed between the transition metal and solvent-derived ligands. That is, the stronger the bonds, the lower proportion of transition metal deposited. Any such reduction in metal deposition is generally believed to be slight and, in any event, does not detract from the advantages associated with the presence of the solvent detailed elsewhere herein to any significant degree. However, in certain embodiments in which the liquid medium contacted with the carbon support includes a coordinating solvent, lesser proportions of the transition metal may deposit onto the carbon support (e.g., less than about 60% or less than about 50%) due, at least in part, to the coordinating power of the solvent. Thus, recycle and/or regeneration of the filtrate or centrate is generally more preferred in these embodiments than those in which a relatively high proportion of transition metal deposits onto the carbon support.

One consideration that may affect deposition of transition metal of the precursor composition in the "filtration" method is the partition coefficient of the transition metal between solvation in the liquid medium and adsorption on the carbon support surface to form the precursor composition. That is, deposition of transition metal over the surface of the carbon support may rely on the affinity of the transition metal ion, coordinated transition metal ion, or a hydrolysis product thereof, toward adsorption on the carbon surface relative to the solvating power of the liquid medium. If the partition coefficient between the liquid phase and the carbon surface is unfavorable, the filtration method may require a high ratio of source compound to carbon surface area in the deposition slurry, which in turn may require a relatively high concentration of source compound, a relatively large volume of liquid medium, or both. In any case, deposition of a sufficient quantity of source compound on the carbon surface may require a substantial excess of source compound, so that the filtrate or centrate comprises a relatively large quantity of source compound that has not deposited on the carbon but instead has been retained in the liquid medium at the equilibrium defined by the prevailing partition coefficient. Such can represent a significant yield penalty unless the filtrate can be recycled and used in depositing the precursor on fresh carbon.

Incipient Wetness Impregnation

Metal composition precursor can be deposited on the carbon support by a method using a significantly lesser proportion of liquid medium than that used in the method in which the impregnated carbon support is separated from the liquid medium by filtration or centrifugation. In particular, this alternative process preferably comprises combining the carbon support with a relative amount of liquid medium that is approximately equal to or slightly greater than the pore volume of the carbon support. In this manner, deposition of the transition metal over a large portion, preferably substantially all, of the external and internal surface of the carbon support is promoted while minimizing the excess of liquid medium. This method for deposition of metal onto a carbon support is generally referred to as incipient wetness impregnation. In accordance with this method, a carbon support having a pore volume of X is typically contacted with a volume of liquid medium that is from about 0.50x to less than about 1.25x, more typically from about 0.90x to about 1.10x and, still more typically, a volume of liquid medium of about X. Incipient wetness impregnation generally avoids the need for separating the impregnated carbon support from the liquid medium and generates significantly less waste that must be disposed of or replenished and/or recycled for use in further catalyst preparation than in catalyst preparations utilizing higher proportions of liquid medium. Use of these lower proportions of liquid medium generally necessitates incorporating the source compound into the liquid medium at a greater concentration than in the "filtration" method. Thus, a liquid medium suitable for incipient wetness impregnation generally contains the source of transition metal at a concentration sufficient to provide a transition metal concentration therein of at least about 0.1% by weight, at least about 0.2% by weight, or at least about 0.5% by weight. Typically, an incipient wetness impregnation liquid medium contains the source of transition metal at a concentration of from about 0.1% to about 10% by weight, more typically from about 0.5% to about 7% by weight and, still more typically, at a concentration of from about 1% to about 5% by weight. One consideration that may affect deposition of transition metal of the precursor composition in the incipient wetness method is the affinity of the metal ion or coordinated metal ion for sites on the carbon support.

Solvents

Incorporation of certain polar organic solvents into a mixture or liquid medium that contacts the carbon support for deposition of the precursor composition is currently believed to provide a more sparse dispersion of metal ions than has been observed with a mixture that does not contain such a solvent (e.g., a mixture comprising a liquid medium consisting solely of water).

Coordinating Solvents

Certain polar organic solvents that have been found to provide a relatively sparse metal ion dispersion are characterized as "coordinating solvents" because they are capable of forming co-ordination compounds with various metals and metal ions, including transition metals such as cobalt, iron, etc. Thus, where the liquid medium comprises a coordinating solvent, particles or film of precursor composition deposited on the carbon support may comprise such a coordination compound. Without limiting the disclosure to a particular theory, it is believed that a coordinating solvent in fact forms a coordination compound with the metal or metal ion of the metal salt, and also binds to the carbon support, thereby promoting deposition of the precursor composition.

Coordination Compounds

Generally, a coordination compound includes an association or bond between the metal ion and one or more binding sites of one or more ligands. The coordination number of a metal ion of a coordination compound is the number of other ligand atoms linked thereto. Typically, ligands are attached to the central metal ion by one or more coordinate covalent bonds in which the electrons involved in the covalent bonds are provided by the ligands (i.e., the central metal ion can be regarded as an electron acceptor and the ligand can be regarded as an electron donor). The typical donor atoms of the ligand include, for example, oxygen, nitrogen, and sulfur. The solvent-derived ligands can provide one or more potential binding sites; ligands offering two, three, four, etc., potential binding sites are termed bidentate, tridentate, tetradentate, etc., respectively. Just as one central atom can coordinate with more than one ligand, a ligand with multiple donor atoms can bind with more than one central atom. Coordinating compounds including a metal ion bonded to two or more binding sites of a particular ligand are typically referred to as chelates.

The stability of a coordination compound or, complex, is typically expressed in terms of its equilibrium constant for the formation of the coordination compound from the solvated metal ion and the ligand. The equilibrium constant, K, is termed the formation or, stability, constant:

$x$ metal center+$y$ ligand------->complex $K$=[complex]/[metal center]$^x$*[ligand]$^y$

[ ]=concentration (moles/liter)

Values for equilibrium constants reported in the literature are typically determined in an aqueous medium. Coordination compounds derived in accordance with the process of the present invention typically comprise a metal ion coordinated with one or more ligands, typically solvent-derived ligands. In various embodiments of the present invention, the coordination compound includes one or more bonds between the metal or metal ion of the transition metal source and one or more molecules of the coordinating solvent. In various such embodiments the metal or metal ion of the transition metal source is attached to the solvent-derived ligand by two bonds; thus, it may be said that the metal or metal ion is "chelated." Accordingly, in such embodiments, the coordinating solvent is properly termed a "chelating solvent." For example, in the case of a chelating solvent comprising diglyme, the metal ion is typically associated or bonded with two diglyme oxygen atoms. In various other embodiments, there may exist a bond or association between the metal ion and greater than two binding sites of a solvent-derived ligand (i.e., the coordination compound may include a tri- or tetradentate ligand such as, for example, N,N,N',N',N'' pentamethyldiethylenetriamine, tartrate, and ethylene diamine diacetic acid). In addition, metal ions of coordination compounds derived in accordance with the present invention may be associated with or bonded to a plurality of ligands. The coordination numbers of metal ions of coordination compounds derived in accordance with the present invention are not narrowly critical and may vary widely depending on the number and type of ligands (e.g., bidentate, tridentate, etc.) associated with or bonded to the metal ion.

In the embodiments wherein such a coordination compound is formed and deposited on the carbon support, such compound provides all or part of the precursor composition from which the nitride or carbide-nitride catalyst is ultimately derived. Eventually the bonds of the coordination compounds typically are broken to provide metal ions available for formation of transition metal composition by, for example, nitridation. However, the precise chemical structure of the ultimate transition metal/nitrogen composition is not known, so that the possible presence of co-ordination bonds between the metal or metal ion and carbon, oxygen, and/or nitrogen in the catalyst active phase cannot be positively excluded, and is likely. One method for breaking the coordination bonds comprises hydrolyzing the coordination complex by adjusting the pH of the liquid medium as detailed elsewhere herein concerning precursor composition deposition generally. Hydrolysis of the coordination complex (i.e., combining a metal cation with hydroxyl ions) in response to adjustments in pH of the liquid medium may generally be represented by the following:

$[ML_n]^{x+} + yOH^- \rightarrow [M(OH)_yL_{n-y}]^{(x-y)+} + yL$

However, it will be understood that the hydroxyl ion may not necessarily displace a ligand, but instead may exchange with another counteranion, e.g., chloride, to form the hydroxide of the co-ordinated metal ion, and such hydroxide is typically of lower solubility than the chloride so that it may precipitate on the carbon support. Alternatively, a metal/hydroxide/ligand complex as formed, for example, in accordance with the equation set out above (and shown on the right side of the equation), may rearrange to the hydroxide of the co-ordinated metal ion. In any case, a metal oxide bond may typically be formed in deposition of the precursor composition onto the support.

As previously noted, the precursor composition generally comprises metal ions solvated by a solvent present in a liquid medium in which or in combination with which the source compound is contacted with the carbon support. In various embodiments the metal ions are solvated with water. Thus, in these embodiments, solvated metal ions are essentially separated from surrounding metal ions by at least two layers of water molecules (i.e., solvated metal ions are separated by water molecules bound thereto and water molecules bound to adjacent solvated metal ions). When a coordinating solvent (e.g., diglyme) is present in the liquid medium, the metal ions are understood to be separated from surrounding metal ions by at least two layers of coordinating solvent molecules. Diglyme molecules, and those of other coordinating solvents that may be used in accordance with the present invention, generally occupy greater space (i.e., are generally bulkier) than water molecules. The bulkier nature of these coordination compounds as compared to water-solvated metal ions is generally due to the larger structure of the coordinating solvent molecule as compared to a water molecule. The solvent molecules thus provide a larger barrier between metal ions, and thus between precipitated metal ions or coordinated metal ions, than is provided by water molecules, such that deposited metal ions bonded to solvent molecules are more sparsely dispersed on the carbon support. A greater bond distance between metal and solvent-derived ligands of the initial coordination compound than between metal and water molecules of water-solvated ions may also contribute to a relatively sparse dispersion of metal ions. However, the effect on dispersion arising from the use of a solvent such as diglyme is believed to be due primarily to the larger structure of the coordinating solvent molecule as compared to a water molecule.

The effectiveness of any coordinating solvent that contacts the carbon support to contribute to relatively sparse precursor composition dispersion may be influenced by various features of the coordinating solvent and/or a coordination compound including a solvent-derived ligand. Where the liquid medium from which the precursor composition is deposited contains other solvents, e.g., water or a primary alcohol, one contributing feature of the coordinating solvent is its solubility in the liquid medium as a whole. Generally, coordinating solvents used in accordance with the present invention are soluble in water and/or in an aqueous medium comprising a water-soluble organic solvent (e.g., ethanol or acetone). In particular, it is preferred for the solvent and/or compound to exhibit at least a certain degree of solubility. For example, if the coordinating solvent is not soluble in the liquid medium any coordination compound formed tends to precipitate from the liquid medium and form a physical mixture with the carbon support without sufficient deposition of the coordination compound and/or transition metal at the surface of the carbon support. Furthermore, as detailed elsewhere herein, it is preferred for the precursor composition to be deposited over a substantial portion of the porous carbon support surface, particularly the interior regions of the porous carbon substrate. If the coordination compound is not soluble to a sufficient degree to promote ingress of the coordination compound and/or transition metal into the pores of the carbon support in preference to precipitation of the metal or metal-ligand complex, a substantial portion of the coordination compound and/or transition metal may be deposited at the outer edges of the porous carbon support. Accordingly, the desired relatively sparse dispersion of precursor composition may not be achieved to a sufficient degree. However, the desired relatively sparse dispersion of precursor composition may likewise not be achieved to a sufficient degree if the coordinating solvent and/or coordination compound are soluble in the liquid medium to a degree such that the coordination compound and/or coordinated metal ion does not precipitate onto the carbon support, even in response to adjustments to the liquid medium including, for example, adjusting its pH. Accordingly, the solubility of the coordination compound and/or coordinated metal is preferably of a degree such that each of these considerations is addressed.

The strength of coordination between the coordinating solvent and transition metal also influences the effectiveness of the coordinating solvent for promoting relatively sparse precursor composition dispersion. Unless the chelating power reaches a minimum threshold, the effect of the solvent on dispersion will not be noticeable to any significant degree and the degree of coordination that prevails in the liquid medium will essentially mimic water salvation. However, if the chelating power of the coordinating solvent is too strong and does not allow coordination bonds to be broken, uncoordinated ions available for formation of the transition metal composition will not be present at the surface of the carbon support and/or hydrolysis of the metal complex may be impeded to such a degree that the coordination complex and/or metal ions do not deposit onto the carbon support.

It is currently believed that at least a portion of the coordinating solvent is present on the carbon support at the outset of treatment of the precursor composition. Thus, the boiling point of the coordinating solvent may affect the ability of solvent molecules on the surface of the carbon support to promote an advantageous particle size distribution. That is, if all solvent molecules are removed from the carbon support at or near the outset of heating of the precursor composition, aggregation of metal particles to form relatively large metal particles may proceed in preference to formation of the transition metal composition. Thus, it is generally preferred for the boiling point of the solvent to be such that solvent molecules remain on the surface of the carbon support during at least a portion of the period of heating the precursor composition and thereby inhibit aggregation of metal particles during formation of the transition metal composition. Generally, the boiling point of the coordinating solvent is at least 100° C., at least about 150° C., at least about 200° C., or at least about 250° C.

Generally, the coordinating solvent utilized in the process of the present invention comprises an amine, an ether (e.g., a crown ether, glycol ether) or a salt thereof, an alcohol, an amino acid or a salt thereof, a hydroxyacid, or a combination thereof.

In various embodiments, the coordinating solvent comprises an amine selected from the group consisting of ethylenediamine, tetramethylenediamine, hexamethylenediamine, N,N,N',N',N" pentamethyldiethylenetriamine, and combinations thereof.

In other embodiments, the coordinating solvent comprises an ether such as, for example, crown ethers, glycol ethers, and combinations thereof. In particular, the coordinating solvent may comprise a glycol ether such as glyme, ethyl glyme, triglyme, tetraglyme, polyglyme, diglyme, ethyl diglyme, butyl diglyme, diethylene glycol diethyl ether (i.e., ethyl diglyme), dipropylene glycol methyl ether, diethylene glycol ethyl ether acetate, and combinations thereof. The coordinating solvent may also comprise a crown ether such as 1,4,7,10-tetraoxacyclododecane (12-crown-4), 1,4,7,10,13,16-hexaoxacyclooctadecane (18-crown-6), or a combination thereof. In still other embodiments, the coordinating solvent may comprise an alcohol or polyol, such as polyethylene glycol, polypropylene glycol, and combinations thereof.

In still further embodiments, the liquid medium contacting the carbon may include a coordinating agent such as an amino acid or a salt thereof. In particular, the coordinating agent may typically comprise iminodiacetic acid, a salt of iminodiacetic acid, N-(phosphonomethyl)iminodiacetic acid, a salt of N-(phosphonomethyl)iminodiacetic acid, ethylenediaminetetraacetic acid (EDTA), or a combination thereof.

In other such embodiments, the coordinating agent may comprise a hydroxyacid such as oxalic acid, citric acid, lactic acid, malic acid, and combinations thereof.

In certain embodiments, the coordinating solvent may be selected in view of the source of transition metal. For example, in the case of a transition metal composition comprising cobalt, use of a source of transition metal comprising cobalt nitrate along with a coordinating solvent comprising diglyme has produced active catalysts, though it will be understood that other coordinating solvents can be used with cobalt nitrate, and multiple other combinations of cobalt salt and coordinating solvent can be used.

Solvents Less Polar than Water and Low Surface Tension Solvents

Other solvents may constitute or be incorporated in a mixture or liquid medium that contacts the carbon support for deposition of the precursor composition. At least certain of these other solvents are believed to provide a relatively sparse dispersion of metal ions on the basis of a greater affinity than water for wetting the carbon surface. This affinity of the solvent for the carbon surface is currently believed to conduce to distribution and deposition of solvated metal ions over a greater portion of the carbon surface than observed with water-solvated metal ions.

Since the surface of the carbon support is generally non-polar (though limited polarity may be imparted by atmospheric oxidation of the carbon surface, or oxidation incident to precursor deposition), solvents that have a polarity less than water are believed to more effectively wet the surface of the carbon support than water, due to the reduced difference in polarity between the solvent and support. One measure of the polarity of a liquid is its dielectric constant. Water generally exhibits a dielectric constant of approximately 80 (at 20° C.). Thus, solvents suitable for use in accordance with the present invention typically exhibit a dielectric constant (at 20° C.) of less than 80, less than 70, less than 60, less than about 50, or less than about 40. However, solvents that are less polar than water to such a degree that the affinity of the solvent for wetting the carbon surface predominates over its ability to provide a relatively sparse dispersion of metal ions over the surface of the carbon support are undesired. Thus, the solvent preferably exhibits a certain minimum threshold of polarity. Accordingly, solvents suitable for use in the present invention typically exhibit a dielectric constant (at 20° C.) of at least about 2, at least about 5, at least about 10, at least about 20, or at least about 30 and up to any one of the previously stated maxima. Thus, solvents used in the present invention typically exhibit a dielectric constant (at 20° C.) of from about 2 to less than 80, more typically from about 5 to about 70, still more typically from about 10 to about 60, and, even more typically, from about 20 to about 50 or from about 30 to about 40. Depending on, for example, the solvent and the desired characteristics of the finished catalyst, in various embodiments the solvent may exhibit a dielectric constant near the lower or upper bounds of these generally broad ranges. Accordingly, in various embodiments, the solvent typically exhibits a dielectric constant (at 20° C.) of from about 5 to about 40, more typically from about 10 to about 30 and, still more typically, from about 15 to about 25. In various other embodiments, the solvent typically exhibits a dielectric constant (at 20° C.) of from about 40 to less than 80, more typically from about 50 to about 70 and, still more typically, from about 55 to about 65.

Additionally or alternatively, the affinity of a solvent for wetting the carbon surface may also be expressed in terms of the interfacial tension between the carbon support and the solvent; that is, the lower the interfacial tension between the solvent and carbon support surface the greater the effectiveness of the solvent for wetting the carbon surface. The surface tension of a solvent is generally proportional to the interfacial tension it will provide with a surface. Thus, the affinity of a solvent for wetting the carbon surface may also be expressed in terms of the solvent's surface tension; that is, a solvent having a surface tension less than that of water is believed to more effectively wet the carbon surface than water. Water typically exhibits a surface tension (at 20° C.) of 70 dynes/cm. Solvents for use in accordance with the present invention on the basis of their affinity for wetting the carbon surface exhibit a surface tension of less than 70 dynes/cm, typically less than about 60 dynes/cm, less than about 50 dynes/cm, or less than about 40 dynes/cm. However, as with polarity, a minimum threshold of surface tension is preferred so that the affinity of the solvent for wetting the carbon surface does not predominate over its ability to provide solvated metal ions to a degree that substantially impedes precursor composition formation. Accordingly, solvents suitable for use in the present invention typically exhibit a surface tension (at 20° C.) of at least about 2 dynes/cm, at least about 5 dynes/cm, at least about 10 dynes/cm, at least about 15 dynes/cm, or at least about 20 dynes/cm and up to one of the previously stated maxima. In various embodiments the solvent exhibits a surface tension near the lower or upper bounds of these generally broad ranges. Accordingly, in various embodiments, the solvent typically exhibits a surface tension (at 20° C.) of from about 5 to about 40 dynes/cm, more typically from about 10 to about 30 dynes/cm and, still more typically, from about 15 to about 25 dynes/cm. In various other embodiments, the solvent exhibits a surface tension (at 20° C.) of from about 40 to less than 70 dynes/cm and, more typically, from about 50 to about 60 dynes/cm.

Coordinating solvents also may contribute to advantageous (i.e., relatively sparse) dispersion of metal ions or coordinated metal salt ions due to affinity of the solvent for the carbon surface, effectively wetting the surface. Coordinating (e.g., chelating) solvents generally exhibit both non-polar and polar characteristics; non-polar portions bond to the non-polar carbon support and polar portions bond to the polar metal. Non-polar portions of the solvent are less polar than water; thus, the difference in polarity between the support and solvent is less than that between the support and water, so that the solvent is more likely to wet the surface of the carbon support.

Although there is a general preference for solvents that meet the dielectric constant and/or surface tension parameters outlined above, certain relatively more polar solvents such as dimethyl sulfoxide or dimethyl formamide are also considered to be suitable for use in depositing a precursor composition onto a carbon support. In commercial implementation of the processes of the invention for preparation of catalysts of the invention, those skilled in the art may choose to consider any of a variety of readily available solvents, some of which are strongly co-ordinating, such as glyme, diglyme, tetraglyme, polyglyme, etc., some of which are moderately polar but not typically classified as strongly co-ordinating, such as methanol, ethanol, propanol, butanol, ethylene glycol, propylene glycol, acetic acid, lactic acid, gluconic acid, diethyl ether, ethylene carbonate, and others of which are considered rather strongly polar, such as dimethyl sulfoxide or dimethyl formamide. Various combinations of such solvents may conveniently be used to tailor the properties of the solvent for optimum dispersion of the precursor composition on the carbon support.

In various embodiments, inclusion of a solvent may have a greater effect on the size of discrete particles formed on the support than selection of the metal salt. Thus, selection of a "bulky" salt in accordance with the preceding discussion is not required to achieve advantageous precursor composition dispersion where the salt is deposited from a mixture or liquid medium comprising a solvent which effectively promotes dispersion. However, in various preferred embodiments, a transition metal salt selected in accordance with the preceding discussion is incorporated into an aqueous medium comprising a solvent.

The carbon support may be contacted with the source compound and a liquid medium comprising a coordinating solvent, non-polar solvent, and/or low surface tension solvent either concurrently or sequentially.

Preferably, the carbon support is concurrently contacted with the source compound and solvent(s), and is typically contacted with the source compound in a liquid medium comprising the source compound dissolved or dispersed in solvent(s). Preferably, the carbon support is contacted with a mixture comprising the transition metal source and a liquid medium comprising a coordinating, non-polar, and/or low surface tension solvent. Optionally, such medium may also be aqueous.

In the case of sequential contact of the carbon support with the source compound and solvent(s), the order of contact is not critical. In various such embodiments, the carbon support is first contacted with the source compound and then contacted with a liquid medium comprising the solvent(s). In other embodiments the carbon support is first contacted with a liquid medium comprising the solvent(s) followed by contact with the source compound.

In accordance with any of the embodiments described above, the liquid medium may be aqueous. In still other embodiments, the liquid medium may consist essentially of a coordinating solvent, non-polar solvent, low surface tension solvent, or a combination thereof.

Preferably the liquid medium comprises at least about 5 wt. % of polar organic solvent(s) that have a polarity and/or surface tension less than water or that provide a lower interfacial tension between the solvent and the carbon support than between water and the support. More preferably, the liquid medium comprises at least about 15 wt. %, at least about 25 wt. %, at least about 35 wt. %, at least about 45 wt. %, at least about 55 wt. % of such polar organic solvent(s), at least about 70 wt. %, at least about 80 wt. % or at least about 90 wt. % of such as solvent(s). Typically, the polar organic solvent(s) may constitute between about 5% to about 95%, more typically between about 15% and about 85%, still more typically between about 25% and about 75%, even more typically from about 35% to about 65%, an in many cases between about 45% and about 55%, by weight polar organic solvent. The fraction of the liquid medium constituted by polar solvents can be constituted either entirely of coordinating solvent(s), by a mixture of coordinating solvent and another polar organic solvent, or entirely of such other organic solvent. In the embodiments wherein the non-aqueous solvent component is exclusively constituted of coordinating solvent(s), the above stated preferences for minimum polar organic solvent content and ranges of polar organic solvent content apply to the chelating or other coordinating solvent, and where the non-aqueous solvent is exclusively constituted of other polar organic solvent(s), such as, for example, lower primary alcohol(s), the above stated minimums and ranges apply to such other polar organic solvent(s).

It should further be understood that the liquid medium can contain some fraction, ordinarily a minor fraction of a non-polar solvent such as, e.g., hexane, heptane, octane or decane. Such non-polar solvents might be used to adjust the surface tension or dielectric constant of the liquid medium, or to adjust the interfacial tension between the liquid medium and the carbon support. In such case the above stated preferences for minimum and ranges of organic solvent content apply to the sum of all organic solvents, polar and non-polar.

Consistently with the above stated preferred minimums and ranges, the weight ratio of polar organic solvent or mixture of polar organic solvents to water is generally at least about 0.05:1, at least about 0.5:1, at least about 1:1, at least about 5:1, or at least about 10:1. Typically, the weight ratio of a solvent or mixture of polar organic solvent(s) to water in such embodiments is from about 0.05:1 to about 15:1, more typically from about 0.5:1 to about 10:1 and, still more typically, from about 1:1 to about 5:1.

Vapor Deposition

A source compound or derivative may also be formed on the carbon support by vapor deposition methods in which the carbon support is contacted with a mixture comprising a vapor phase source of a transition metal or secondary metallic element. In chemical vapor deposition the carbon support is contacted with a volatile metallic compound generally selected from the group consisting of halides, carbonyls, and organometallic compounds which decomposes to produce a transition metal suitable for formation on the carbon support. Examples of suitable metal carbonyl compounds include $Mo(CO)_6$, $W(CO)_6$, $Fe(CO)_5$, and $CO(CO)_4$.

Decomposition of the compound generally occurs by subjecting the compound to light or heat. In the case of decomposition using heat, temperatures of at least about 100° C. are typically required for the decomposition.

It should be understood that the precursor compound formed on the carbon support and heated to form a transition metal composition may be the same as the source compound, or it may differ as a result of chemical transformation occurring during the process of deposition and/or otherwise prior to contact with a nitrogen-containing compound, carbon-containing compound (e.g., a hydrocarbon), nitrogen and carbon-containing compound, and/or a non-oxidizing atmosphere. For example, where a porous carbon support is impregnated with an aqueous solution of a source compound comprising ammonium molybdate, the precursor is ordinarily the same as the source compound. But where vapor deposition techniques are used with a source compound such as a molybdenum halide, the precursor formed may be metallic molybdenum or molybdenum oxide.

Heat Treatment of the Carbon Support

Regardless of the method for formation of the source compound or its derivative (e.g., precursor of a transition metal composition) on the carbon support, in certain embodiments the pretreated support is then subjected to further treatment (e.g., temperature programmed treatment) to form a transition metal composition or compositions comprising a transition metal and nitrogen, a transition metal and carbon, or a transition metal, nitrogen, and carbon on or over the surface of the carbon support. Generally, the pretreated carbon support is contacted with a nitrogen-containing, carbon-containing, or nitrogen and carbon-containing compound under certain, ordinarily relatively severe, conditions (e.g., elevated temperature). Generally, a fixed or fluidized bed comprising carbon support having the precursor deposited and/or formed thereon is contacted with a nitrogen- and/or carbon-containing compound. Preferably, the carbon support is established in a fixed bed reactor and a vapor-phase nitrogen-containing, carbon-containing, or nitrogen and carbon-containing compound is contacted with the support by passage over and/or through the bed of carbon support.

In the case of catalysts comprising a composition comprising a primary transition metal composition and a secondary metallic element, a composition comprising both precursor compositions may be formed on the carbon support followed by treatment at elevated temperatures. Precursor compositions can be formed concurrently or sequentially in accordance with the preceding discussion. Such a method for preparing a catalyst comprising two transition metal compositions utilizing a single treatment at elevated temperatures is hereinafter referred to as the "one step" method. Alternatively, catalysts comprising more than one transition metal composition, or a transition metal and a secondary metallic element, can be prepared by forming a single precursor on the carbon support, treating the support and precursor at elevated temperatures to produce a transition metal composition, forming a second precursor over the carbon support, and treating the support having the second precursor thereover at elevated temperatures. Such a method for preparing a catalyst comprising two transition metal compositions, or a primary transition metal composition and a secondary catalytic composition, utilizing two treatments at elevated temperatures is hereinafter referred to as the "two step" method.

In various embodiments when a transition metal composition(s) comprising a transition metal and nitrogen is(are) desired, typically the pretreated carbon support is contacted with any of a variety of nitrogen-containing compounds which may include ammonia, an amine, a nitrile, a nitrogen-containing heterocyclic compound, or combinations thereof. Exemplary nitrogen-containing compounds useful for this purpose include ammonia, dimethylamine, ethylenediamine, isopropylamine, butylamine, melamine, acetonitrile, propionitrile, picolonitrile, pyridine, pyrrole, and combinations thereof.

Typically, the carbon support having at least one precursor of a transition metal composition formed or deposited thereon is contacted with a nitriding atmosphere which comprises a vapor phase nitrogen-containing compound as set forth above. In a preferred embodiment, the nitrogen-containing compound comprises acetonitrile. Typically, the nitriding atmosphere comprises at least about 5% by volume of nitrogen-containing compound and, more typically, from about 5 to about 20% by volume of the nitrogen-containing compound. Generally, the carbon support is contacted with at least about 100 liters of nitrogen-containing compound per kg of carbon per hour (at least about 3.50 ft$^3$ of nitrogen-containing compound per lb of carbon per hour). Preferably, the carbon support is contacted with from about 200 to about 500 liters of nitrogen-containing compound per kg of carbon per hour (from about 7.0 to about 17.7 ft$^3$ of nitrogen-containing compound per lb of carbon per hour).

The nitriding atmosphere optionally includes additional components selected from the group consisting of hydrogen and inert gases such as argon. Hydrogen, where present, generally may be present in a proportion of at least about 1% by volume hydrogen or, more generally, from about 1 to about 10% by volume hydrogen. Additionally or alternatively, the nitriding atmosphere typically comprises at least about 75% by volume argon and, more typically, from about 75 to about 95% by volume argon or other inert gas. In certain embodiments, the nitriding atmosphere comprises at least about 10 liters of hydrogen per kg of carbon support per hour (at least about 0.35 ft$^3$ of hydrogen per lb of carbon support). Preferably, such a nitriding atmosphere comprises from about 30 to about 50 liters of hydrogen per kg of carbon support per hour (from about 1.05 to about 1.8 ft$^3$ of hydrogen per lb of carbon support per hour). In various other embodiments, the nitriding atmosphere comprises at least about 900 liters of argon or other inert gas per kg of carbon support per hour (at least about 31.5 ft$^3$ of argon per lb of carbon support). Preferably, such a nitriding atmosphere comprises from about 1800 to about 4500 liters of argon per kg of carbon support per hour (from about 63 to about 160 ft$^3$ of argon per lb of carbon support per hour). In further embodiments, the nitriding atmosphere comprises at least about 10 liters of hydrogen per kg of carbon support per hour (at least about 0.35 ft$^3$ of hydrogen per lb of carbon support) and at least about 900 liters of argon per kg of carbon support per hour (at least about 31.5 ft$^3$ of argon per lb of carbon support).

The carbon support having at least one precursor of a transition metal composition thereon is typically contacted with the nitrogen-containing compound in a nitride reaction zone under a total pressure of no greater than about 15 psig. Typically, the nitride reaction zone is under a pressure of from about 2 to about 15 psig. The nitrogen-containing compound partial pressure of the nitride reaction zone is typically no greater than about 2 psig and, more typically, from about 1 to about 2 psig. The partial pressure of any hydrogen present in the nitriding zone is typically less than about 1 psig and, more typically, from about 0.1 to about 1 psig. However, if equipment constructed of high temperature alloys is used for contacting the carbon support with a nitrogen-containing compound, higher pressures may be employed.

When a transition metal composition comprising a transition metal and carbon is desired, typically the pretreated carbon support is contacted with a carbiding atmosphere containing a carbon-containing compound including, for example, hydrocarbons such as methane, ethane, propane, butane, and pentane.

Typically, the carbon support having a precursor of the transition metal composition formed or deposited thereon is contacted with a carbiding atmosphere which comprises a vapor phase carbon-containing compound. In a preferred embodiment, the carbon-containing compound comprises methane. Typically, the carbiding atmosphere comprises at least about 5% by volume of carbon-containing compound and, more typically, from about 5 to about 50% by volume of the carbon-containing compound. Generally, at least about 100 liters of carbon-containing compound per kg of carbon per hour (at least about 3.50 ft$^3$ of carbon-containing compound per lb of carbon per hour) are contacted with the carbon support. Preferably, from about 200 to about 500 liters of carbon-containing compound per kg of carbon per hour (from about 7.0 to about 17.7 ft$^3$ of carbon-containing compound per lb of carbon per hour) are contacted with the carbon support.

The carbiding atmosphere optionally includes additional components selected from the group consisting of hydrogen and inert gases such as argon and nitrogen. Hydrogen, where present, generally is present in a proportion of at least about 1% by volume or, more generally, from about 1 to about 50% by volume. In certain embodiments, the carbiding atmosphere comprises at least about 10 liters of hydrogen per kg of carbon support per hour (at least about 0.35 ft$^3$ of hydrogen per lb of carbon support). Preferably, such a carbiding atmosphere comprises from about 30 to about 50 liters of hydrogen per kg of carbon support per hour (from about 1.05 to about 1.8 ft$^3$ of hydrogen per lb of carbon support per hour).

In various other embodiments, the carbiding atmosphere comprises at least about 900 liters of argon per kg of carbon support per hour (at least about 31.5 ft$^3$ of argon per lb of carbon support). Preferably, such a carbiding atmosphere comprises from about 1800 to about 4500 liters of argon per kg of carbon support per hour (from about 63 to about 160 ft$^3$ of argon per lb of carbon support per hour).

In further embodiments, the carbiding atmosphere comprises at least about 10 liters of hydrogen per kg of carbon support per hour (at least about 0.35 ft$^3$ of hydrogen per lb of carbon support) and at least about 900 liters of argon per kg of carbon support per hour (at least about 31.5 ft$^3$ of argon per lb of carbon support).

In various other embodiments, the carbiding atmosphere comprises at least about 900 liters of carbon per kg of carbon support per hour (at least about 31.5 ft$^3$ of carbon per lb of carbon support). Preferably, such a carbiding atmosphere comprises from about 1800 to about 4500 liters of carbon per kg of carbon support per hour (from about 63 to about 160 ft$^3$ of carbon per lb of carbon support per hour).

The carbon support having a precursor of the transition metal composition thereon is typically contacted with the carbon-containing compound in a carbide reaction zone under a total pressure of no greater than about 15 psig. Typically, the carbide reaction zone is under a pressure of from about 2 to about 15 psig. The carbon-containing compound partial pressure of the carbide reaction zone is typically no greater than about 2 psig and, more typically, from about 1 to about 2 psig. The partial pressure of any hydrogen present in the carbide reaction zone is typically less than about 2 psig and, more typically, from about 0.1 to about 2 psig. As with a nitriding atmosphere, if equipment constructed of high temperature alloys is used for contacting the carbon support with a carbon-containing compound, higher pressures may be employed.

In certain embodiments, the pretreated carbon support, having a precursor transition metal compound thereon, may be treated to form a transition metal composition comprising both carbon and nitrogen and the transition metal on the carbon support. In such embodiments, the precursor compound on the support may be contacted with a "carbiding-nitriding atmosphere." One method involves contacting the pretreated carbon support with a carbon and nitrogen-containing compound. Suitable carbon and nitrogen-containing compounds include amines, nitriles, nitrogen-containing heterocyclic compounds, or combinations thereof. Such carbon and nitrogen-containing compounds are generally selected from the group consisting of dimethylamine, ethylenediamine, isopropylamine, butylamine, melamine, acetonitrile, propionitrile, picolonitrile, pyridine, pyrrole, and combinations thereof.

Typically, the carbon support having a precursor of the transition metal composition deposited or formed thereon is contacted with a carbiding-nitriding atmosphere which comprises a vapor phase carbon and nitrogen-containing compound. Typically, the carbiding-nitriding atmosphere comprises at least about 5% by volume of carbon and nitrogen-containing compound and, more typically, from about 5 to about 20% by volume of the carbon and nitrogen-containing compound. Generally, at least about 100 liters of carbon and nitrogen-containing compound per kg of carbon per hour (at least about 3.50 ft$^3$ of carbon and nitrogen-containing compound per lb of carbon per hour) are contacted with the carbon support. Preferably, from about 200 to about 500 liters of carbon and nitrogen-containing compound per kg of carbon per hour (from about 7.0 to about 17.7 ft$^3$ of carbon and nitrogen-containing compound per lb of carbon per hour) are contacted with the carbon support.

The carbiding-nitriding atmosphere optionally includes additional components selected from the group consisting of hydrogen and inert gases such as argon. Hydrogen, where present, is generally present in a proportion of at least about 1% by volume or, more generally, from about 1 to about 5% by volume. In certain embodiments, the carbiding-nitriding atmosphere comprises at least about 10 liters of hydrogen per kg of carbon support per hour (at least about 0.35 ft$^3$ of hydrogen per lb of carbon support). Preferably, such a carbiding-nitriding atmosphere comprises from about 30 to about 50 liters of hydrogen per kg of carbon support per hour (from about 1.05 to about 1.8 ft$^3$ of hydrogen per lb of carbon support per hour).

In various other embodiments, the carbiding-nitriding atmosphere comprises at least about 900 liters of argon per kg of carbon support per hour (at least about 31.5 ft$^3$ of argon per lb of carbon support). Preferably, such a carbiding-nitriding atmosphere comprises from about 1800 to about 4500 liters of argon per kg of carbon support per hour (from about 63 to about 160 ft$^3$ of argon per lb of carbon support per hour).

In further embodiments, the carbiding-nitriding atmosphere comprises at least about 10 liters of hydrogen per kg of carbon support per hour (at least about 0.35 ft$^3$ of hydrogen per lb of carbon support) and at least about 900 liters of argon per kg of carbon support per hour (at least about 31.5 ft$^3$ of argon per lb of carbon support).

The carbon support having a precursor of the transition metal composition thereon is typically contacted with the carbon and nitrogen-containing compound in a carbide-nitride reaction zone under a total pressure of no greater than about 15 psig. Typically, the carbide-nitride reaction zone is under a pressure of from about 2 to about 15 psig. The carbon and nitrogen-containing compound partial pressure of the carbide-nitride reaction zone is typically no greater than about 2 psig and, more typically, from about 1 to about 2 psig. The partial pressure of any hydrogen present in the carbide-nitride reaction zone is typically less than about 1 psig and, more typically, from about 0.1 to about 1 psig. As with nitriding and carbiding atmospheres, if equipment constructed of high temperature alloys is used for contacting the carbon support with a carbon and nitrogen-containing compound, higher pressures may be employed.

Additionally or alternatively, a transition metal composition comprising a transition metal, carbon, and nitrogen may be formed by contacting the support and precursor with a nitrogen-containing compound as described above with the carbon of the transition metal composition derived from the supporting structure.

In further embodiments, the support and precursor of the transition metal composition may be contacted with a nitrogen-containing compound (e.g., ammonia) and a carbon-containing compound (e.g., methane) as set forth above to form a transition metal composition comprising a transition metal, carbon, and nitrogen on and/or over the carbon support.

In still further embodiments the carbon support is contacted with a compound comprising a transition metal, nitrogen, and carbon to form a precursor of the transition metal composition thereon (i.e., the source compound and carbon and nitrogen-containing compound are provided by one composition) and heated in accordance with the following description to form a transition metal composition comprising a transition metal, nitrogen, and carbon on a carbon support. Typically, such compositions comprise a co-ordination complex comprising nitrogen-containing organic ligands including, for example, nitrogen-containing organic ligands including five or six membered heterocyclic rings comprising nitrogen. Generally, such ligands are selected from the group consisting of porphyrins, porphyrin derivatives, polyacrylonitrile, phthalocyanines, pyrrole, substituted pyrroles, polypyrroles, pyridine, substituted pyridines, bipyridyls, phthalocyanines, imidazole, substituted imidazoles, pyrimidine, substituted pyrimidines, acetonitrile, o-phenylenediamines, bipyridines, salen ligands, p-phenylenediamines, cyclams, and combinations thereof. In certain embodiments, the co-ordination complex comprises phthalocyanine (e.g., a transition metal phthalocyanine) or a phthalocyanine derivative. Certain of these co-ordination complexes are also described in International Publication No. WO 03/068387 A1 and U.S. Application Publication No. 2004/0010160 A1, the entire disclosures of which are hereby incorporated by reference.

To deposit and/or form the transition metal composition precursor in such embodiments, typically a suspension is prepared comprising the carbon support and the co-ordination complex which is agitated for a time sufficient for adsorption of the co-ordination compound on the carbon support. Typically, the suspension contains the carbon support in a proportion of from about 5 to about 20 g/liter and the co-ordination compound in a proportion of from about 2 to about 5. Preferably, the carbon support and co-ordination compound are present in a weight ratio of from about 2 to about 5 and, more preferably, from about 3 to about 4.

Formation of a transition metal composition on the carbon support proceeds by heating the support and precursor in the presence of an atmosphere described above (i.e., in the presence of a nitrogen-containing, carbon-containing, or nitrogen and carbon-containing compound). Typically, the carbon support having the precursor thereon is heated using any of a variety of means known in the art including, for example, an electrical resistance furnace or an induction furnace.

Generally, the transition metal composition precursor may contain a transition metal salt, partially hydrolyzed transition metal, and/or a transition metal oxide. For example, in the case of iron, the precursor may comprise $FeCl_3$, $Fe(OH)_3$, $Fe(OH)_2^{+1}$, $Fe(OH)^{+2}$, and/or $Fe_2O_3$. Generally, heating the carbon support having a precursor of the transition metal composition thereon forms the transition metal composition by providing the energy necessary to replace the bond between the transition metal and the other component of the precursor composition(s) with a bond between the transition metal and nitrogen, carbon, or carbon and nitrogen. Additionally or alternatively, the transition metal composition may be formed by reduction of transition metal oxide to transition metal which combines with the carbon and/or nitrogen of the composition present in the nitriding, carbiding, or carbiding-nitriding atmosphere with which the carbon support is contacted to form the transition metal composition.

Typically, the support (i.e., carbon support having a precursor of a transition metal composition thereon) is heated to a temperature of at least about 600° C., more typically to a temperature of at least about 700° C., still more typically to a temperature of at least about 800° C. and, even more typically, to a temperature of at least about 850° C. to produce the transition metal composition.

The maximum temperature to which the support is heated is generally sufficient to produce a transition metal nitride, transition metal carbide, or transition metal carbide-nitride. The support can be heated to temperatures greater than 1000° C., greater than 1250° C., or up to about 1500° C. It has been observed, however, that graphitization of the carbon support may occur if the support is heated to temperatures above 1000° C. or above 1100° C. Graphitization may have a detrimental effect on the activity of the catalyst. Thus, preferably, the support is heated to a temperature of no greater than about 1000° C. However, active catalysts can be prepared by heating the support and precursor to temperatures in excess of 1000° C., regardless of any graphitization which may occur. Preferably, the support is heated to a temperature of from about 600° C. to about 1000° C., more preferably, from about 600 to about 975° C., more preferably from about 700 to about 975° C., even more preferably from about 800 to about 975° C., still more preferably from about 850 to about 975° C. and especially to a temperature of from about 850° C. to about 950° C.

In the case of a carbiding atmosphere comprising a hydrocarbon (e.g., methane), it has been observed that heating the carbon support to temperatures above 700° C. may cause polymeric carbon to form on the carbon support. Thus, in certain embodiments in which a transition metal composition comprising a transition metal and carbon is desired, it may be preferable to form such a composition by heating the support to temperatures of from about 600 to about 700° C. However, it should be understood that formation of a transition metal composition comprising a transition metal and carbon proceeds at temperatures above 700° C. and such a method produces suitable catalysts for use in accordance with the present invention provided $T_{max}$ is sufficient for carbide formation (e.g., at least 500° C. or at least 600° C.).

The rate of heating is not narrowly critical. Typically, the support having a precursor deposited or formed thereon is heated at a rate of at least about 2° C./minute, more typically at least about 5° C./minute, still more typically at least about 10° C./minute and, even more typically, at a rate of at least about 12° C./minute. Generally, the support having a precursor thereon is heated at a rate of from about 2 to about 15° C./minute and, more generally, at a rate of from about 5 to about 15° C./minute.

Likewise, the time at which the catalyst is maintained at the maximum temperature (i.e., the holding time) is not narrowly critical. Typically, the catalyst is maintained at the maximum temperature for at least about 30 minutes, more typically at least about 1 hour and, still more typically, still from about 1 to about 3 hours. In various embodiments, the catalyst is maintained at the maximum temperature for about 2 hours.

Typically, the catalyst is prepared in a batch process (e.g., in a fluid or fixed bed reaction chamber) over a cycle time (i.e., the period of time which includes heating the support and precursor to its maximum temperature and maintaining at the maximum temperature) of at least about 1 hour, more typically at least about 2 hours and, still more typically, at least about 3 hours. In various embodiments, the cycle time for catalyst preparation is about 4 hours.

Catalyst may also be prepared by heating the support and precursor in a continuous fashion using, for example, a kiln through which a heat treatment atmosphere is passed. Various types of kilns may be used including, for example, rotary kilns and tunnel kilns. Typically, the residence time of the catalyst in the kiln is at least about 30 minutes, more typically at least about 1 hour and, still more typically, at least about 2 hours. In various such embodiments, the residence time of the catalyst in the kiln is from about 1 to about 3 hours and, in others, the residence time of the catalyst in the kiln is from about 2 to about 3 hours.

In certain embodiments of the present invention it may be desired to form a transition metal composition comprising carbon or nitrogen (i.e., a transition metal carbide or nitride). For example, the desired composition may comprise molybdenum (i.e., molybdenum carbide or molybdenum nitride) or tungsten (i.e., tungsten carbide or tungsten nitride). One method for forming such carbides and nitrides involves temperature programmed reduction (TPR) which includes contacting the support and the transition metal precursor with a carbiding (i.e., carbon-containing) or nitriding (i.e., nitrogen-containing) atmosphere under the conditions described below. It should be understood that the following discussion regarding forming carbon or nitrogen-containing transition metal compositions does not limit the discussion set forth above regarding forming catalytically active transition metal compositions comprising carbon and/or nitrogen.

In embodiments in which a transition metal carbide is desired, typically, a carbiding atmosphere comprises a hydrocarbon having from 1 to 5 carbons. In a preferred embodiment, the carbon-containing compound comprises methane. Typically, the carbiding atmosphere comprises at least about 5% by volume of carbon-containing compound and, more typically, from about 5 to about 50% by volume of the carbon-containing compound. Generally, at least about 100 liters of carbon-containing compound per kg of carbon per hour (at least about 3.50 ft³ of carbon-containing compound per lb of carbon per hour) are contacted with the carbon support. Preferably, from about 200 to about 500 liters of carbon-containing compound per kg of carbon per hour (from about 7.0 to about 17.7 ft³ of carbon-containing compound per lb of carbon per hour) are contacted with the carbon support.

The carbiding atmosphere optionally includes additional components selected from the group consisting of hydrogen and inert gases such as argon or nitrogen. Hydrogen, where present, is generally present in a proportion of at least about 1% by volume hydrogen or, more generally, from about 1 to about 50% by volume hydrogen. In one such embodiment, the carbiding atmosphere comprises at least about 10 liters of hydrogen per kg of carbon support per hour (at least about 0.35 ft³ of hydrogen per lb of carbon support per hour). Preferably, such a carbiding atmosphere comprises from about 30 to about 50 liters of hydrogen per kg of carbon support per hour (from about 1.05 to about 1.8 ft³ of hydrogen per lb of carbon support per hour).

In such embodiments in which a transition metal nitride is desired, a nitriding atmosphere generally comprises a nitrogen-containing compound such as ammonia and may also include inert gases such as argon and nitrogen. Typically, the nitriding atmosphere comprises at least about 5% by volume of nitrogen-containing compound and, more typically, from about 5 to about 20% by volume of the nitrogen-containing compound. Generally, at least about 100 liters of nitrogen-containing compound per kg of carbon per hour (at least about 3.50 ft³ of nitrogen-containing compound per lb of carbon) are contacted with the carbon support. Preferably, from about 200 to about 500 liters of nitrogen-containing compound per kg of carbon per hour (from about 7.1 to about 17.7 ft³ of nitrogen-containing compound per lb of carbon per hour) are contacted with the carbon support. Hydrogen, where present, generally is present in a proportion of at least about 1% by volume hydrogen or, more generally, from about 1 to about 5% by volume hydrogen.

In various embodiments in which a transition metal carbide or nitride is desired, the temperature of the atmosphere is increased to a temperature $T_1$ having a value of at least about 250° C., more typically 300° C., over a period of time, $t_1$. Preferably, the temperature of the atmosphere is increased to from about 250 to about 350° C. and, more preferably, increased to from about 275 to about 325° C. during $t_1$. This period of time ($t_1$) necessary for increasing the temperature from $T_0$ to $T_1$ is generally at least about 5 minutes. Typically, $t_1$ is from about 5 to about 30 minutes and, more typically, from about 10 to about 15 minutes. The rate of temperature increase during $t_1$ is not narrowly critical and generally is less than 150° C./min. Typically, the rate of temperature increase during $t_1$ is from about 10 to about 100° C./min and, more typically, from about 20 to about 50° C.

During $t_1$ the source compound or derivative transition metal carbide or nitride may be transformed (e.g., by calcination) to an intermediate oxide formed on the surface of the support. The intermediate oxides formed during $t_1$ generally have an empirical formula of $A_xO_y$, wherein A is the transition metal (e.g., molybdenum or tungsten), depending on the desired make-up of the transition metal composition. Typically, the ratio of x to y is at least about 0.33:1 and preferably from about 0.33:1 to about 1:1. It is desired to convert as great a proportion of any transition metal oxide formed during a carbiding or nitriding operation as possible. Typically, at least about 80% and, more typically, from about 80% to about 95% of the transition metal oxide is converted to the transition metal composition. Preferably, no more than about 5% by weight of the oxide precursor remains unconverted, more preferably, no more than about 3% by weight of the oxide precursor remains unconverted and, still more preferably, no more than about 1% by weight of the oxide precursor remains unconverted.

Considerations concerning the initial temperature ($T_0$), rate of increase from $T_0$ to $T_1$ ($t_1$), the value of $T_1$, and precursor formation are generally the same regarding formation of carbides and nitrides from the precursor or intermediate oxide. However, the remainder of the temperature programmed reduction method differs in certain important respects based on whether a carbide or nitride is desired.

After the initial period of temperature increase, $t_1$, which typically results in formation of transition metal oxide precursor, the temperature of a carbiding (i.e., carburization) atmosphere is elevated from $T_1$ to a maximum temperature ($T_{max}$) during which time a transition metal carbide (e.g., molybdenum carbide or tungsten carbide) is formed on the surface of the carbon support by reduction of the transition metal oxide precursor.

Typically, $T_{max}$ is at least about 500° C., more typically at least about 600° C., still more typically at least about 700° C. and, even more typically, at least about 800° C. or at least about 850° C. Preferably, $T_{max}$ is from about 600° C. to about 1000° C. and, more preferably, from about 850° C. to about 950° C.

In the case of a carbiding atmosphere comprising a hydrocarbon (e.g., methane), it has been observed that heating the carbon support to temperatures above 700° C. may cause polymeric carbon to form on the carbon support. Thus, in certain embodiments in which a transition metal composition comprising a transition metal and carbon is desired, it may be preferable to form such a composition by heating the support to temperatures of from about 600 to about 700° C. However, it should be understood that formation of a transition metal composition comprising a transition metal and carbon proceeds at temperatures above 700° C. and such a method produces suitable catalysts for use in accordance with the present invention provided $T_{max}$ is sufficient for carbide formation (e.g., at least 500° C. or at least 600° C.).

In certain embodiments for carbiding atmospheres comprising, for example, methane, the precursor is heated to 650° C. at a rate of at least about 2° C./min. While not narrowly critical, typically the precursor is heated to $T_{max}$ over a period of time ($t_2$) of at least about 10 minutes and, more typically, from about 15 to about 150 minutes and, still more typically, from about 30 to about 60 minutes. The rate at which the temperature increases from $T_1$ to $T_{max}$ is not narrowly critical but generally is at least about 2° C./min. Typically, this rate is from about 2 to about 40° C./min and, more typically, from about 5 to about 10° C./min.

After the atmosphere contacting the oxide-containing precursor reaches $T_{max}$, the temperature of the atmosphere is generally maintained at $T_{max}$ for a time sufficient to ensure the desired reduction of the transition metal oxide to form the transition metal carbide. Typically, this holding time at $T_{max}$, $t_3$, during which time the temperature remains at $T_{max}$ is at least about 1 hour and may be from about 1 to about 8 hours; however, care is preferably taken to ensure that $t_3$ is not of a duration such that polymeric carbon forms on the carbon support in amounts that adversely affect catalyst activity. Preferably, $t_3$ is from about 1 to about 4 hours and, more preferably, from about 2 to about 3 hours.

Generally, the intermediate transition metal oxide is contacted with the hydrocarbon under conditions which substantially avoid the production of polymeric carbon on the surface of the transition metal carbide.

The transition metal oxide is typically contacted with the hydrocarbon in a carbide reaction zone under a total pressure of no greater than about 15 psig. Typically, the carbide reaction zone is under a pressure of from about 2 to about 15 psig. The hydrocarbon partial pressure of the carbide reaction zone is typically no greater than about 2 psig and, more typically, from about 1 to about 2 psig. However, if equipment constructed of high temperature alloys is used for contacting the carbon support with a carbon-containing compound, higher pressures may be employed.

Both $T_{max}$ and the holding time at $T_{max}$, $t_3$, directly affect carbide formation with each condition being controlled in order to provide sufficient carbide formation. However, ensuring that both conditions are within a preferred range provides even more preferred conditions for carbide formation. Thus, in a particularly preferred embodiment, $T_{max}$ is from about 625 to about 675° C. while $t_3$ is from about 2 to about 3 hours.

After the initial period of temperature increase, $t_1$, which typically results in formation of a transition metal oxide, the temperature of a nitriding (i.e., nitridation) atmosphere is elevated from $T_1$ to a maximum temperature ($T_{max}$) in order to form the transition metal nitride (e.g., molybdenum nitride or tungsten nitride). In contrast to the method described above for carbide formation, the temperature of a nitriding atmosphere is then elevated from $T_1$ to a maximum temperature ($T_{max}$) of at least about 700° C. to produce the nitride since it has been observed that at temperatures below 700° C. the nitride formation is not substantially complete. However, as the nitriding atmosphere approaches temperatures of from about 900° C. and above the metal nitride may be reduced by hydrogen produced by decomposition of the nitriding gas. Thus, $T_{max}$ is preferably from about 700 to about 900° C., more preferably from about 700 to about 850° C. and, still more preferably, from about 725 to about 800° C. While not narrowly critical, typically the oxide-containing precursor is heated to $T_{max}$ over a period of time ($t_2$) of at least about 15 minutes, more typically from about 15 to about 250 minutes and, still more typically, from about 30 to about 60 minutes. The rate at which the temperature increases from $T_1$ to $T_{max}$ is not narrowly critical but generally is at least about 2° C./min. Typically, this rate is from about 2 to about 40° C./min and, more typically, from about 5 to about 10° C./min.

After the atmosphere contacting the oxide-containing precursor reaches $T_{max}$, the temperature of the atmosphere is generally maintained at $T_{max}$ for a time sufficient to ensure the desired reduction of the transition metal oxide to a transition metal nitride. Typically, this period of time, $t_3$, during which the temperature remains at $T_{max}$ is at least about 1 hour. Preferably, $t_3$ is preferably from about 1 to about 5 hours and, more preferably, from about 3 to about 4 hours.

As with carbide formation, both $T_{max}$ and the holding time at $T_{max}$, $t_3$, directly affect nitride formation with each condition being controlled in order to provide sufficient nitride formation. However, ensuring that both conditions are within a preferred range provides even more preferred conditions for nitride formation. Thus, in a particularly preferred embodiment, $T_{max}$ is from about 725 to about 800° C. while $t_3$ is from about 1 to about 5 hours.

It has been observed that during temperature programmed reduction used to produce a transition metal nitride in which the nitrogen-containing atmosphere comprises ammonia, the transition metal nitride thus formed (e.g., molybdenum nitride) may be reduced to form free transition metal.

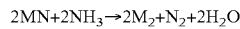

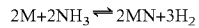

This reaction typically occurs when the nitridation reaction is complete (i.e., substantially all of the oxide precursor has been reduced to the nitride) and is likely to occur when $T_{max}$ reaches higher temperatures (i.e., above 900° C.). Even though these reactions may result in producing the desired transition metal nitride by the forward reaction between free transition metal and ammonia, the conditions for direct ammonia nitridation of free transition metal are preferably avoided because of the possibility of the reverse reduction of the nitride by hydrogen. This is typically controlled by maintaining $T_{max}$ during nitridation below that which accelerates decomposition of ammonia to form hydrogen, thereby preventing the reverse formation of free transition metal by the reduction of the nitride by hydrogen.

The contact of either a carbiding or nitriding atmosphere with the support may occur via a gas phase flow within a fluid bed reaction chamber at a space velocity of at least about 0.01 sec$^{-1}$. The gas phase flow of the carbiding or nitriding atmosphere within a fluid bed reaction chamber is not narrowly critical and may typically exhibit a space velocity of from about 0.01 to about 0.50 sec$^{-1}$. While carbide and nitride formation proceeds readily over a wide range of gas phase flow rates, the flow rate may be increased to initially increase diffusion of the source compound into the pores of the support to accelerate formation of the carbide or nitride and reduce the time necessary to hold the temperature at $T_{max}$ to ensure sufficient carbide or nitride formation.

In addition to temperature programmed reduction, other methods for producing a transition metal carbide (e.g., molybdenum carbide or tungsten carbide) may be used. For example, a carbon support having a precursor formed on its surface in accordance with the above description may be contacted with an inert gas at temperatures ranging from about 500 to about 1400° C. It is believed that the precursor is reduced by the carbon support under the high temperature conditions and the precursor reacts with the carbon support to form a carbide on the surface of the support. The inert gas may be selected from the group consisting of argon, nitrogen, and helium.

Another method includes contacting a volatile metal compound and a carbon support at temperatures ranging from about 500 to about 1400° C. to reduce the volatile metal compound which then reacts with the carbon support to form a carbide. The volatile metal compound is generally an organometallic compound.

A carbon support having a precursor formed on its surface may also be contacted with hydrogen at a temperature of from about 500 to about 1200° C. (typically, about 800° C.) to reduce the precursor which reacts with the carbon support to form a carbide on the surface of the carbon support.

The time to reach the maximum temperature, the maximum temperature itself or time for holding the temperature at the maximum are not narrowly critical and may vary widely in accordance with either of these methods.

It has been observed that the yield and stability (e.g., resistance to leaching under reaction conditions) of a carbide produced using the alternatives to temperature programmed reduction described above are reduced as compared to carbides produced using temperature programmed reduction. Thus, temperature programmed reduction is the preferred method for carbide formation.

Formation of a transition metal (e.g., molybdenum or tungsten) carbide and nitride on the surface of a carbon support may proceed generally in accordance with the above discussion. An exemplary preparation is formation of a transition metal (i.e., molybdenum or tungsten) carbide and nitride on the surface of a carbon support having a molybdenum or tungsten-containing precursor deposited thereon as described above. One such method involves subjecting a carbon support to high temperatures (e.g., from about 600 to about 1000° C.) in the presence of an organic ligand containing carbon and nitrogen to form both a carbide and nitride on the support surface. Possible ligands include, for example, a transition metal porphyrin or a nitrogen-containing molybdenum organometallic compound (e.g., a molybdenum pyridine compound).

In a further alternative process for preparing a catalyst comprising a transition metal carbide and a transition metal nitride, a transition metal-containing (e.g., molybdenum or tungsten-containing) nitride is formed according to any of the process schemes described above for that purpose, after which the nitride is contacted with a hydrocarbon or a mixture comprising a hydrocarbon and hydrogen. Thus, a composition containing both a carbide and a nitride is formed on the surface of the carbon support by virtue of the conversion of only a certain portion of the nitride. Remainder of a portion of the nitride is assured by maintaining conditions under which conversion of nitride to carbide is incomplete, for example, by limiting $T_{max}$ or limiting the hold time at $T_{max}$.

In the transition metal/nitrogen composition, or transition metal/nitrogen/carbon composition, it is believed that the transition metal is bonded to nitrogen atoms by co-ordination bonds. In at least certain embodiments of the process for preparing the catalyst, a nitrogen-containing compound may be reacted with the carbon substrate, and the product of this reaction further reacted with a transition metal source compound or precursor compound to produce a transition metal composition in which the metal is coordinated to the nitrogen. Reaction of the nitrogen-containing compound with the carbon substrate is believed to be incident to many if not most embodiments of the process for preparing the transition metal composition, but can be assured by initially contacting a carbon substrate with the nitrogen-containing compound under pyrolysis conditions in the absence of the transition metal or source thereof, and thereafter cooling the pyrolyzed nitrogen-containing carbon, impregnating the cooled nitrogen-containing carbon with a transition metal precursor compound, and pyrolyzing again. According to this alternative process, during the first pyrolysis step the carbon may be contacted with a nitrogen-containing gas such as ammonia or acetonitrile at greater than 700° C., typically about 900° C. The second pyrolysis step may be conducted in the presence of an inert or reducing gas (e.g., hydrogen and/or additional nitrogen-containing compound) under the temperature conditions described herein for preparation of a transition metal/nitrogen composition or transition metal/nitrogen/carbon composition on a carbon support. Conveniently, both pyrolysis steps may be conducted by passing a gas of appropriate composition through a fixed or fluid bed comprising a particulate carbon substrate.

Where nitrogen is combined with the carbon substrate, the nitrogen atoms on the carbon support are understood to be typically of the pyridinic-type wherein nitrogen contributes one $\pi$ electron to carbon of the support, e.g., to the graphene plane of the carbon, leaving an unshared electron pair for co-ordination to the transition metal. It is further preferred that the concentration of transition metal on the support be not substantially greater than that required to saturate the nitrogen atom co-ordination sites on the carbon. Increasing the transition metal concentration beyond that level may result in the formation of zero valence (metallic form) of the transition metal, which is believed to be catalytically inactive for at least certain reactions. The formation of zero valence transition metal particles on the surface may also induce graphitization around the metal particles. Although the graphite may itself possess catalytic activity for certain reactions, graphitization reduces effective surface area, an effect that, if excessive, may compromise the activity of the catalyst.

In various embodiments, a secondary metallic element is deposited on or over a carbon support having a primary transition metal composition formed thereon using a variation of the "two step" method described above. In this variation, the second treatment is not necessarily performed in the presence of a nitrogen-containing compound and/or nitrogen and carbon-containing compound but, rather, is carried out in the presence of a non-oxidizing environment which generally consists essentially of inert gases such as $N_2$, noble gases (e.g., argon, helium) or mixtures thereof. In certain embodiments the secondary metallic element in elemental or metallic form is deposited on or over the surface of the carbon support and/or on or over the surface of a primary transition metal composition (i.e., a secondary catalytic composition comprising nitrogen and/or carbon is not required). In such embodiments, the non-oxidizing environment comprises a reducing environment and includes a gas-phase reducing agent, for example, hydrogen, carbon monoxide or combinations thereof. The concentration of hydrogen in a reducing environment may vary, although a hydrogen content of less than 1% by volume is less preferred when reduction of the catalyst surface is desired as such concentrations require a longer time to reduce the catalyst surface. Typically, hydrogen is present in the heat treatment atmosphere at a concentration of from about 1 to about 10% by volume and, more typically, from about 2 to about 5% by volume. The remainder of the gas may consist essentially of a non-oxidizing gas such as nitrogen, argon, or helium. Such non-oxidizing gases may be present in the reducing environment at a concentration of at least about 90% by volume, from about 90 to about 99% by volume, still more typically, from about 95 to about 98% by volume.

Catalysts

Generally, it is preferred for the catalysts of the present invention and the catalysts of catalyst combinations of the present invention to have a high surface area. Formation of a transition metal/nitrogen, transition metal/carbon and/or transition metal/carbon/nitrogen composition on a carbon support typically is associated with some reduction in Langmuir surface area. Loss of surface area may be a result of coating of the carbon surface with a transition metal composition of relatively lower surface area, e.g., in the form of an amorphous film and/or relatively large particles of the transition metal composition. Amorphous transition metal composition may be in the form of either amorphous particles or an amorphous film. Preferably, the sacrifice in surface area is not greater than about 40%. Where the transition metal composition is formed under the preferred conditions described above, the loss in total Langmuir surface area is typically between about 20 and about 40%. Thus, generally, the surface area of a catalyst (i.e., carbon support having one or more transition metal compositions formed thereon) is at least about 60% of the surface area of the carbon support prior to formation of the transition metal composition(s) thereon and, more generally, from about 60 to about 80%. In various embodiments, the surface area of a catslyst is at least about 75% of the surface area of the carbon support prior to formation of the transition metal composition(s) thereon.

Typically, the catalyst has a total Langmuir surface area of at least about 500 $m^2/g$, more typically at least about 600 $m^2/g$. Preferably, the total Langmuir surface area of the catalyst is at least about 800 $m^2/g$, more preferably at least about 900 $m^2/g$. It is generally preferred that the total Langmuir surface area of the catalyst remains at a value of at least about 1000 m²/g, more preferably at least about 1100 m²/g, even more preferably at least about 1200 m²/g, after a transition metal composition has been formed on a carbon support. Generally, the catalyst has a total Langmuir surface area of less than about 2000 m²/g, from about 600 to about 1500 m²/g, typically from about 600 to about 1400 m²/g. In certain embodiments, the catalyst has a total Langmuir surface area of from about 800 to about 1200 m²/g. Preferably, the catalyst has a total Langmuir surface area of from about 1000 to about 1400 m²/g, more preferably from about 1100 to about 1400 m²/g and, even more preferably, from about 1200 to about 1400 m²/g.

The Langmuir surface area of an oxidation catalyst of the present invention attributed to pores having a diameter of less than 20 Å (i.e., micropores) is typically at least about 750 m²/g, more typically at least 800 m²/g, still more typically at least about 800 m²/g and, even more typically, at least about 900 m²/g. Preferably, the micropore Langmuir surface area of the oxidation catalyst is from about 750 to about 1100 m²/g and, more preferably, from about 750 to about 1000 m²/g.

The Langmuir surface area of an oxidation catalyst of the present invention attributed to pores having a diameter of from about 20-40 Å (i.e., mesopores) and pores having a diameter greater than 40 Å (i.e., macropores) is generally at least about 175 m²/g and, more generally, at least about 200 m²/g. Preferably, the combined mesopore and macropore Langmuir surface area of the oxidation catalyst is from about 175 to about 300 m²/g and, more preferably, from about 200 to about 300 m²/g. In certain embodiments, the combined mesopore and macropore surface area is from about 175 to about 250 m²/g.

Additionally or alternatively, it is preferred that the micropore Langmuir surface area of the catalyst remain at a value of at least about 750 m²/g, more preferably at least about 800 m²/g, and the combined mesopore and macropore Langmuir surface area of the catalyst remain at a value of at least about 175 m²/g, more preferably at least about 200 m²/g, after the transition metal composition has been formed.

It is further preferred that, as compared to the carbon support, the micropore Langmuir surface area be reduced by not more than 45%, more preferably not more than about 40%. Thus, the micropore Langmuir surface area of the oxidation catalyst is generally at least about 55% of the micropore Langmuir surface area of the carbon support prior to formation of the transition metal composition thereon, more generally at least about 60% or at least about 70%, and, still more generally, at least about 80%. Typically, the micropore Langmuir surface area of the catalyst is from about 55 to about 80% of the micropore Langmuir surface area of the carbon support prior to formation of the transition metal composition thereon, more typically from about 60 to about 80% and, still more typically, from about 70 to about 80%.

In addition to the preferred limitation on the extent to which the micropore surface area is reduced, it is further generally preferred that the combined mesopore and macropore Langmuir surface area be reduced by not more than about 30%, more preferably not more than about 20%, as a result of the formation of the transition metal composition on the carbon support. Thus, generally, the combined mesopore and macropore Langmuir surface area of the oxidation catalyst is generally at least about 70% of the combined mesopore and macropore Langmuir surface area of the carbon support prior to formation of the transition metal composition thereon and, more generally, at least about 80%. Typically, the combined mesopore and macropore Langmuir surface area of the catalyst is from about 70 to about 90% of the combined mesopore and macropore Langmuir surface area of the carbon support prior to formation of the transition metal composition thereon.

A further advantageous feature of the oxidation catalysts of the present invention is a pore volume sufficient to allow for diffusion of reactants into the pores of the catalyst. Thus, preferably, catalysts of the present invention including a transition metal composition formed on a carbon support typically have a pore volume of at least about 0.1 cm³/g, more typically at least about 0.3 cm³/g and, still more typically at least about 0.5 cm³/g. Generally, the catalyst has a pore volume of from about 0.1 to about 2 cm³/g, more generally from about 0.50 to about 2.0 cm³/g and, still more generally, from about 0.5 to about 1.5 cm³/g.

In addition to overall pore volume, the pore volume distribution of the oxidation catalysts of the present invention preferably conduces to diffusion of reactants into the pores of the finished catalyst. Preferably, pores having a diameter of less than about 20 Å make up no more than about 45% of the overall pore volume of the catalyst and, more preferably, no more than about 30% of the overall pore volume. Pores having a diameter of greater than about 20 Å preferably make up at least about 60% of the overall pore volume of the catalyst and, more preferably, at least about 65% of the overall pore volume.

It has been observed that "mesopores" (i.e., pores having a diameter of from about 20 to about 40 Å) allow suitable diffusion of reactants into the pores of the catalyst. Thus, preferably mesopores make up at least about 25% of the overall pore volume and, more preferably, at least about 30% of the overall pore volume. Macro pores (i.e., pores having a diameter larger than about 40 Å) also allow suitable diffusion of reactants into the pores of the catalyst. Thus, preferably, these pores make up at least about 5% of the overall pore volume and, more preferably, at least about 10% of the overall pore volume of the catalyst.

Catalysts prepared in accordance with the process of the present invention comprising a transition metal composition comprising molybdenum or tungsten likewise preferably exhibit pore volumes sufficient to allow for diffusion of reactants into the pores of the finished catalyst. Thus, preferably a catalyst comprising such a transition metal/carbon composition (e.g., a molybdenum or tungsten carbide) has a total pore volume of at least about 0.50 cm³/g and, more preferably, a pore volume of at least about 0.60 cm³/g.

In addition to overall pore volume, the pore volume distribution of these catalysts of the present invention preferably conduces to diffusion of reactants into the pores of the finished catalyst. Preferably, pores having a diameter of less than about 20 Å make up no more than about 45% of the overall pore volume of the catalyst and, more preferably, no more than about 30% of the overall pore volume. Pores having a diameter of greater than about 20 Å preferably make up at least about 60% of the overall pore volume of the catalyst and, more preferably, at least about 65% of the overall pore volume.

Generally, pore having a diameter greater than 20 Å make up at least about 10% or from about 10% to about 405 of the total pore volume of the catalyst.

It has been observed that "mesopores" (i.e., pores having a diameter of from about 20 to about 40 Å) allow suitable diffusion of reactants into the pores of a catalyst. Thus, preferably mesopores make up at least about 25% of the overall pore volume of these catalysts and, more preferably, at least about 30% of the overall pore volume. Macropores (i.e., pores having a diameter larger than about 40 Å) also allow suitable diffusion of reactants into the pores of the catalyst. Thus, preferably, these pores make up at least about 5% of the overall pore volume and, more preferably, at least about 10% of the overall pore volume of the catalyst. Generally, such pore constitute from about 5% to about 20% of the total pore volume of the catalyst.

It is generally preferred for the transition metal composition (e.g., the transition metal carbide or transition metal nitride) to be distributed over the surface of the pores of the carbon particle (e.g., the surface of the pore walls and interstitial passages of the catalyst particles). Thus, generally it is preferred that the transition metal composition be distributed over all surfaces accessible to fluid with which the catalyst is contacted. More particularly, it is preferred for the transition metal composition to be substantially uniformly distributed over the surface of the pores of the carbon particle.

Particle size of the transition metal composition, as determined, for example, by X-ray diffraction, affects such uniform distribution and it has been observed that the smaller the size of the particulate crystals of the transition metal composition, the more uniform its deposition. Where a transition metal composition is formed on a carbon support in accordance with a preferred method, in accordance with various embodiments, it is believed that the composition comprises a substantial fraction of very fine particles, e.g., wherein at least about 20 wt. % of the transition metal is in amorphous form or in the form of particles of less than 15 nm, more typically less than 5 nm, more typically 2 nm, as determined by X-ray diffraction.

In various particularly preferred embodiments of the invention, X-ray diffraction analysis at a detection limit of 1 nm does not detect any significant portion of transition metal composition particles. Thus, it is currently believed that the transition metal composition particles are present on the surface of the carbon support in the form of discrete particles having a particle size of less than 1 nm or are present on the surface of the carbon support in the form of an amorphous film. However, based on the decrease in surface area after formation of the transition metal composition on the carbon support, it is reasonable to infer the transition metal composition may be present at least in part as an amorphous film since an increase in surface area would be expected in the case of deposition of crystallites having a particle size below 1 nm.

In various embodiments of catalysts of the present invention, generally at least about 95% by weight of the transition metal composition particles formed on a carbon support have a particle size, in their largest dimension, of less than about 1000 nm. Typically, at least about 80% by weight of the transition metal composition particles have a particle size, in their largest dimension, of less than about 250 nm. More typically, at least about 70% by weight of the transition metal composition particles have a particle size, in their largest dimension, of less than about 200 nm. Still more typically, at least about 60% by weight of the transition metal composition particles have a particle size, in their largest dimension, of less than about 18 nm. Even more typically, at least about 20% by weight, preferably at least about 55% by weight of the transition metal composition particles have a particle size, in their largest dimension, of less than about 15 nm. Preferably, at least about 20% by weight of the transition metal composition particles have a particle size, in their largest dimension, of less than about 5 nm, more preferably, less than about 2 nm, and even more preferably, less than about 1 nm. More preferably, from about 20 to about 95% by weight of the transition metal composition particles have a particle size, in their largest dimension, of less than about 1 nm and, more preferably, from about 20 to about 100% by weight.

Generally, at least about 75%, on a number basis, of the transition metal composition particles have a particle size, in their largest dimension, of less than about 1000 nm. Typically, at least about 60%, on a number basis, of the transition metal composition particles have a particle size, in their largest dimension, of less than about 250 nm. More typically, at least about 50%, on a number basis, of the transition metal composition particles have a particle size, in their largest dimension, of less than about 200 nm. Still more typically, at least about 40%, on a number basis, of the transition metal composition particles have a particle size, in their largest dimension, of less than about 18 nm. Even more typically, at least about 35%, on a number basis, of the transition metal composition particles have a particle size, in their largest dimension, of less than about 15 nm.

For oxidation catalysts comprising a carbon support having a transition metal composition comprising molybdenum or tungsten formed thereon, typically at least about 99% of the particles of the molybdenum or tungsten-containing transition metal composition formed on the carbon support exhibit a particle size of less than about 100 nm, thereby contributing to uniform distribution of the transition metal composition throughout the carbon support since it has been observed that a greater proportion of particles of such a size provide a uniform coating of transition metal composition on the carbon support. More preferably, at least about 95% of the particles of the carbide or nitride formed on the carbon support exhibit a particle size of from about 5 nm to about 50 nm.

It has been observed that uniform distribution of the transition metal composition on the carbon support (i.e., reduced clustering of the transition metal and/or suitable distribution of the transition metal composition throughout the pores of the carbon support) may improve catalytic activity of catalysts including a transition metal composition deposited on a carbon support and/or may allow for improved coating of a secondary metal or secondary transition metal composition on the carbon support having a transition metal composition formed on and/or over its surface.

FIG. 1 is a High Resolution Transmission Electron Microscopy (HRTEM) image of a carbon-supported molybdenum carbide prepared in accordance with the above methods in which molybdenum carbide is present in a proportion of 15% by weight. As shown, a carbon support having molybdenum carbide formed thereon prepared in accordance with the methods described above exhibits uniform dispersion of molybdenum carbide throughout the carbon support.

Figure 2:
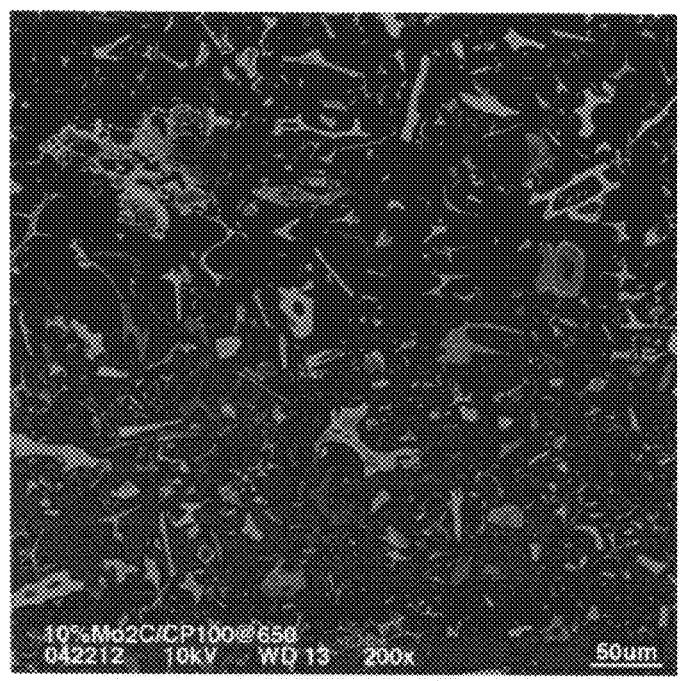
FIG. 2 is a SEM image of a carbon supported molybdenum carbide.
Figure 3:
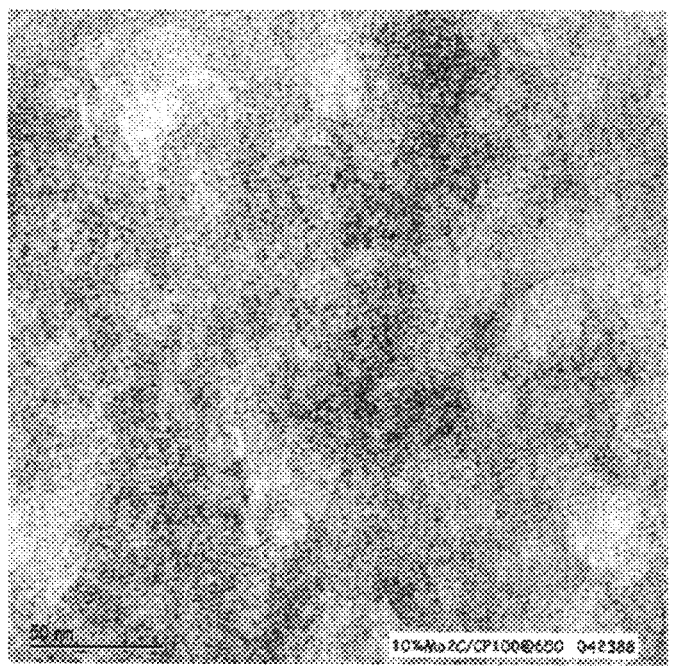
FIG. 3 is a TEM image of a carbon supported molybdenum carbide.

FIG. 2 is a Scanning Electron Microscopy (SEM) image of a carbon supported molybdenum carbide prepared in accordance with the above methods in which the carbide is present in a proportion of 10% by weight. As shown, a carbon support having molybdenum carbide formed thereon in a proportion of 10% by weight of the catalyst in accordance with the methods described above exhibits uniform distribution of molybdenum throughout the carbon support. FIG. 3 is a Transmission Electron Microscopy (TEM) image of a carbon supported molybdenum carbide prepared in accordance with the above methods in which the carbide is present in a proportion of 10% by weight. As shown, a carbon support having molybdenum carbide formed thereon in a proportion of 10% by weight of the catalyst in accordance with the above methods exhibits uniformity of molybdenum carbide distribution throughout believed to be due, at least in part, to the particle size distribution of molybdenum carbide.

In certain embodiments (e.g., transition metal compositions including molybdenum carbide or nitride or tungsten carbide or nitride prepared using a carbon or nitrogen-containing atmosphere), a suitable portion of the surface area of the carbon support is coated with transition metal composition. The percentage of surface area of the carbon support covered with the transition metal composition generally indicates uniform distribution of the transition metal composition. Generally, at least about 20% and, more generally, at least about 50% of the surface area of the carbon support is coated with a transition metal composition (e.g., a transition metal carbide or nitride). Typically, from about 20 to about 80% and, more typically, from about 50% to about 80% of the surface area of the carbon support is coated with a transition metal composition (e.g., a transition metal carbide or nitride).

Transition metal (M), carbon and nitrogen containing ions corresponding to the formula $MN_xC_y^+$ are generated and detected when catalysts of the present invention (e.g., primary catalysts) are analyzed by Time-of-Flight Secondary Ion Mass Spectrometry (ToF SIMS) as described in Protocol A in Example 46.

In various embodiments, the weighted molar average value of x (determined from the relative intensitites of the various ion families detected by ToFSIMS analysis) is generally from about 0.5 to about 8.0, more generally from about 1.0 to about 8.0 and, still more generally, from about 0.5 to about 3.5. Typically, the weighted molar average value of x is from about 0.5 to about 3.0, from about 0.5 to about 2.6, from about 0.5 to about 2.2, from about 0.5 to about 2.1, or from about 0.5 to about 2.0. In various embodiments, the weighted molar average value of x is generally from 1.0 to about 8.0. Typically, the weighted molar average value of x is from 1.0 to about 5.0, more typically from 1.0 to about 3.0, more typically from 1.0 to about 2.10 and, still more typically, from about 1.0 to about 2.0 or from about 1.5 to about 2.0.

The weight molar average value of y is generally from about 0.5 to about 8.0 or from about 1.0 to about 8.0, more generally from about 0.5 to about 5.0 or from about 1.0 to about 5.0. In various embodiments, the weighted molar average value of y is from about 0.5 to about 2.6, more typically from 1.0 to about 2.6, still more typically from 1.5 to about 2.6 and, still more typically, from about 2.0 to about 2.6.

In particular, ions corresponding to the formula $CoN_xC_y^+$ are generated when cobalt-containing catalysts of the present invention are analyzed by ToF SIMS as described in Protocol A in Example 46. Generally, in such embodiments, the weighed molar average value of x is from about 0.5 to about 8.0 or from about 1.0 to about 8.0. Typically, the weighted molar average value of x is from about 0.5 to about 5.0 or from about 1.0 to about 5.0, more typically from about 0.5 to about 3.5, still more typically from about 0.5 to about 3.0 or from about 1.0 to about 3.0, even more typically from about 0.5 to about 2.2. The weighted molar average value of x in such embodiments may also typically be from 1.0 to about 2.1 and, more typically, from 1.0 to about 2.0 or from about 1.5 to about 2.0.

Further in accordance with embodiments in which the transition metal composition comprises cobalt, the weighted molar average value of y is generally from about 0.5 to about 8.0 or from about 1.0 to about 8.0. Typically, the weighted molar average value of y is from about 1.0 to about 5.0, more typically from 1.0 to about 4.0, still more typically from 1.0 to about 3.0 and, even more typically, from 1.0 to about 2.6 or from 1.0 to about 2.0.

It is believed that ions corresponding to the formula $MN_xC_y^+$ in which x is less than 4 provide a greater contribution to the activity of the catalyst than those ions in which x is 4 or greater. Additionally or alternatively, ions in which x is 4 or greater may detract from the activity of the catalyst. Thus, preferably, $MN_xC_y^+$ ions in which the weighted molar average value of x is from 4.0 to about 8.0 constitute no more than about 25 mole percent, more preferably no more than about 20 mole percent, still more preferably no more than about 15 mole percent, and, even more preferably, no more than about 10 mole percent of $MN_xC_y^+$ ions generated during the ToF SIMS analysis. The effect of ions of formulae in which x is greater than 4 is likewise observed in the case of ions corresponding to the formula $CoN_xC_y^+$. Thus, typically preferably $CoN_xC_y^+$ ions in which the weighted molar average value of x is from 4 to about 8 constitute no more than about 60 mole percent, more typically no more than about 50 mole percent and, still more typically, no more than about 40 mole percent of the $CoN_xC_y^+$ ions generated during ToF SIMS analysis. Preferably, $CoN_xC_y^+$ ions in which the weighted molar average value of x is from 4 to about 8 constitute no more than about 30 mole percent, more preferably no more than about 20 mole percent, still more preferably no more than about 15 mole percent and, even more preferably, no more than about 10 mole percent of the $CoN_xC_y^+$ ions generated during ToF SIMS analysis.

More particularly, it is believed that ions corresponding to the formula $MN_xC_y^+$ in which x is 1 provide a greater contribution to the activity of the catalyst than those ions in which x is 2 or greater. Thus, in various preferred embodiments, the relative abundance of ions in which x is 1 is typically at least about 20%, more typically at least about 25%, still more typically at least about 30%, even more typically at least about 35% and, even more typically, at least about 42% or at least about 45%. Further in accordance with such embodiments, ions corresponding to the formula $MN_xC_y^+$ in which x and y are each 1 may provide a greater contribution to the activity of the catalyst than those ions in which either x or y are 2 or greater. Thus, in accordance with certain embodiments, the relative abundance of $MN_xC_y^+$ ions in which both x and y are 1 may typically be at last about 10%, at least about 15%, at least about 20%, at least about 25%, at least about 30%, or at least about 35%. Further in accordance with such embodiments, the relative abundance of ions in which both x and y are 1 is generally from about 10% to about 40%, from about 15% to about 35%, or from about 20% to about 30%.

The total exposed metal surface area of catalysts of the present invention may be determined using static carbon monoxide chemisorption analysis, in particular, using the method described in Example 48 (Protocol B). The carbon monoxide chemisorption analysis described in Example 48 includes first and second cycles. Catalysts of the present invention subjected to such analysis are characterized as chemisorbing less than about 2.5 mmoles of carbon monoxide per gram of catalyst, typically less than about 2 µmoles of carbon monoxide per gram of catalyst and, more typically, less than about 1 µmole during the second cycle which is indicative of the total exposed metal (e.g., Co) at the surface of the carbon support.

Exposed metal surface area ($m^2$ per gram catalyst) may be determined from the volume of CO chemisorbed using the following equation:

$$\text{Metal surface area (m}^2\text{/g catalyst)} = 6.023 \times 10^{23} * V / 2 * SF * A / 22,414, \text{ where:}$$

V=volume of CO chemisorbed ($cm^3$/g STP) (Volume of one mole of gas is 22,414 cm3 STP, i.e., the volume of one µmole of CO is 0.022414 $cm^3$)

SF=stoichiometry factor (assumed to be equal to 1, i.e., one CO molecule per exposed metal atom)

A=effective area of one exposed metal atom ($m^2$/atom) ($8 \times 10^{-20}$ $m^2$/atom of metal)

Thus, catalysts of the present invention typically exhibit exposed metal surface area of less than about 0.06 m$^2$/g, more typically less than about 0.048 m$^2$/g and, still more typically, less than about 0.024 m$^2$/g.

It has been discovered that cobalt-containing catalysts prepared in accordance with the present invention exhibit strong Electron Paramagnetic Resonance (EPR) spectra, in particular strong EPR spectra when analyzed in accordance with Protocol C detailed in Example 58. EPR spectroscopy is a well-known technique for measuring the properties of unpaired electrons in solids and liquids and is described in, for example, Drago, Russell S., "Physical Methods in Chemistry," *Saunders Golden Sunburst Series*, Chapter 9, W. B. Saunders Company.

Figure 109A:
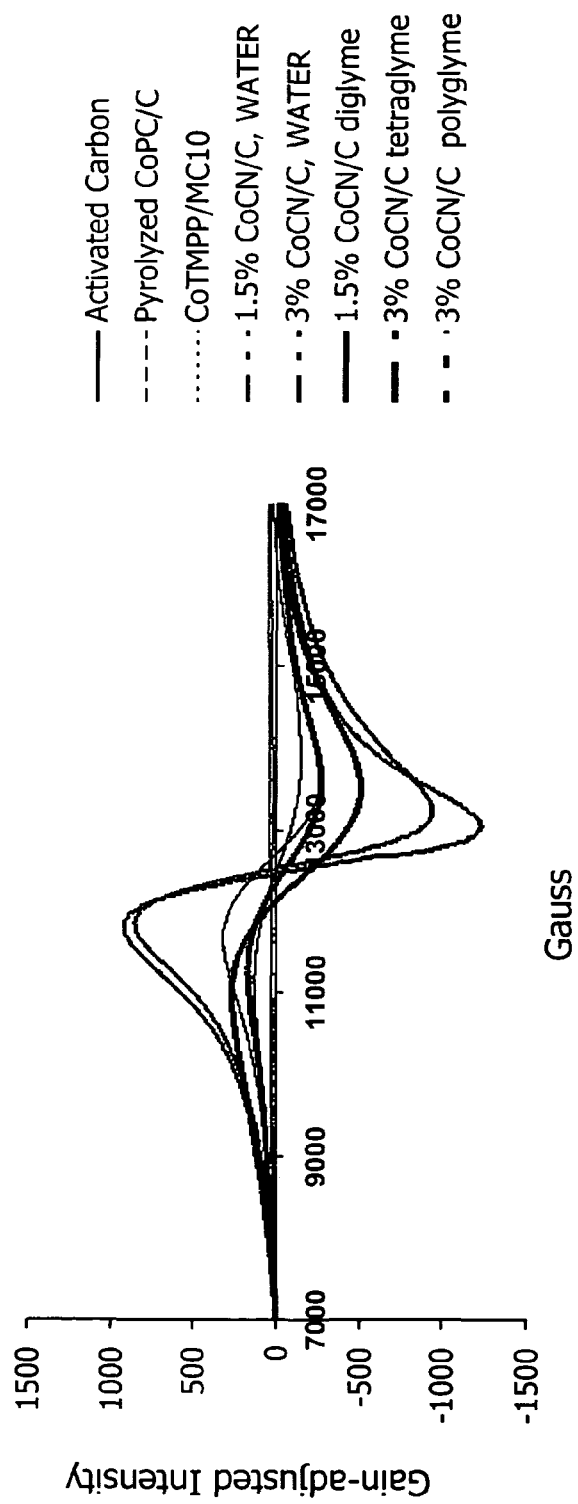
FIGS. 109A and 109B show spectra obtained by Electron Paramagnetic Resonance (EPR) Spectroscopy as described in Example 58.
Figure 109B:
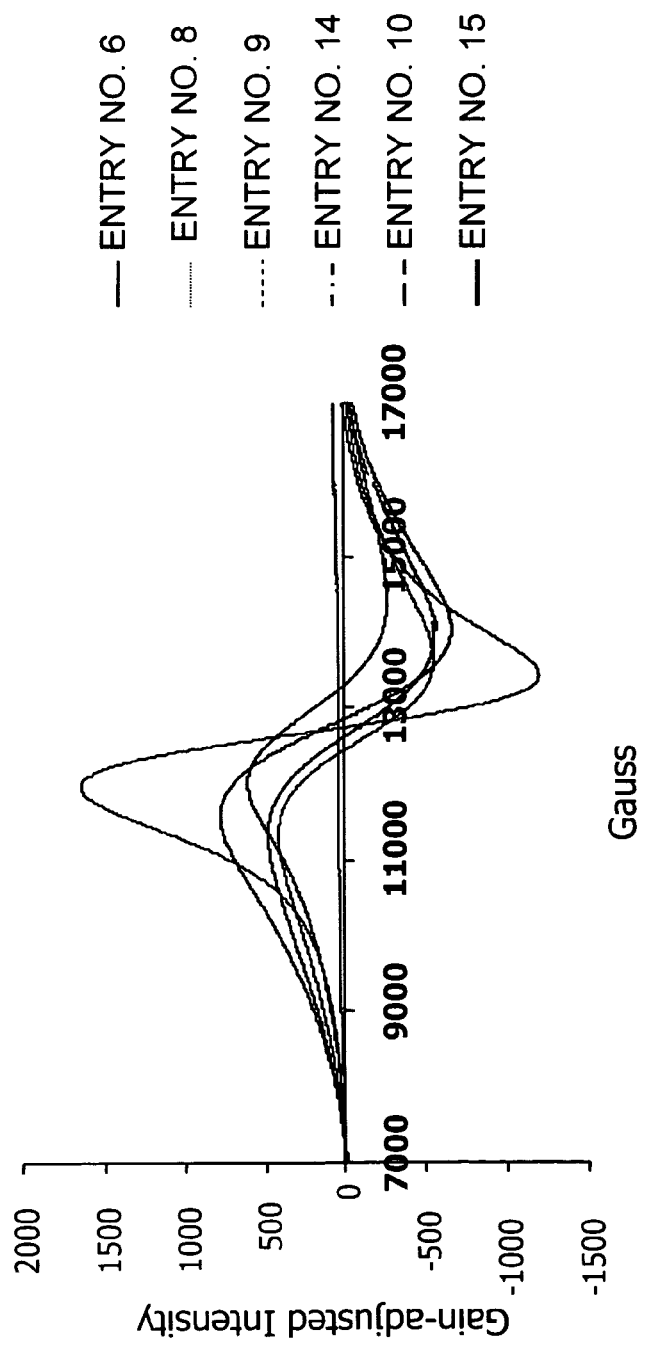

A sample of the cobalt-containing catalyst is placed in a microwave cavity of fixed frequency (e.g., X-band frequency of approximately 9500 MHz, or Q-band frequency of approximately 35 GHz) between the poles of the magnet. The magnetic field is swept through a range chosen to achieve a resonance between the energy required to reverse the electron spin and the microwave frequency of the cavity. The analyses detailed in the present specification and Example 58 used a microwave cavity having a Q-band frequency. The spectra obtained represent the microwave absorption versus the applied magnetic field. To provide a sharper response, these curves are generally presented in terms of the derivative of the microwave absorption versus the applied field. FIGS. 109A and 109B represent EPR spectra (of varying spectral windows) obtained for cobalt-containing catalysts of the present invention. The spectra have been adjusted for the setting of the amplifier so that the relative intensity of the spectra are proportional to the EPR responses of the samples.

It is currently believed that the EPR spectra of the catalysts of the present invention demonstrate that the cobalt is present in the form of a nitride, carbide-nitride, or a combination thereof. As previously noted, EPR is used to analyze substances with unpaired electrons. Thus, the EPR signals are not attributable to any metallic cobalt (i.e., Co$^0$) present in the catalysts. Accordingly, the observation of an EPR signal is strong evidence that divalent cobalt (i.e., Co$^{+2}$) is present in the samples since Co$^{+3}$ does not provide an EPR response. Thus, the identification of Co$^{+2}$ indicates that the catalyst may contain cobalt oxide, cobalt nitride, or cobalt carbide-nitride.

However, the nature of the spectra observed is currently believed to rule out the possibility that they are attributable to any cobalt oxide present in the catalyst since the spectra of the cobalt-containing catalysts of the present invention are remarkable in two respects. In particular, the linewidths of the spectra are exceptionally broad, with a peak-to-peak linewidth of over 1000 Gauss in the Q-band spectra, centered near g=2, with a mixed Gaussian-Lorentzian lineshape. At resonance the microwave energy (hv) is proportional to the applied field, B, but also to a factor, conventionally denoted as g*β, where β is the Bohr magneton. For a description of the g value, and EPR spectroscopy generally, see *Transition Ion Electron Paramagnetic Resonance* by J. R. Pilbrow, Clarendon Press, Oxford, 1990, pgs 3-7.

It has been discovered that the spectra linewidths decrease with increasing temperature, a behavior that is known to be characteristic of relatively small ferromagnetic particles (typically less than 10 nm in diameter in their largest dimension) dispersed in a diamagnetic matrix, which exhibit a type of magnetic behavior known as superparamagetism. In this case, activated carbon is the diamagnetic matrix. This phenomenon is described by J. Kliava and R. Berger in the *Journal of Magnetism and Magnetic Materials*, 1999, 205, 328-42. The narrowing of linewidth with temperature is also described by R. Berger, J. Kliava, J.-C. Bissey, and V Baietto in *J. Appl. Phys.*, 2000, 87, 7389-96. Cobalt oxide is not ferromagnetic. Thus, the observation of superparamagnetism rules out assignment of the EPR spectra to cobalt oxide. Accordingly, it is currently believed that the Co$^{+2}$ ions are present in a metallic cobalt matrix, which indicates that the counterion, in this case interstitial nitrogen or carbon is present in the metallic matrix too. The second remarkable feature of the EPR spectra of the cobalt-containing catalysts of the present invention is the fact that the observed apparent number of spins per mole of cobalt exceeds Avogadro's number, further proof that the EPR spectra are not attributable to cobalt oxide. In particular, a standard paramagnetic material, Co$_3$O$_4$, was analyzed by Protocol C and found to exhibit spins/mole cobalt generally in accordance with the expected value. This standard has one mole of Co$^{2+}$ and two moles Co$^{3+}$ ions per mole of material, but only the Co$^{2+}$ ions give an EPR signal; thus, in theory, one expects 2.01E23 (0.333*6.022E23) spins/mole cobalt with this standard. The standard was found to exhibit approximately 1.64E23 spins per mole cobalt that generally agrees with the spins/mole cobalt expected based on stoichiometry. As shown in Table 43, the intensity of the spectra for the catalysts of the present invention analyzed by Protocol C far exceed this value, providing further proof that the EPR spectra are not attributable to cobalt oxide and, moreover, that the cobalt is present in the form of a cobalt nitride, carbide-nitride, or a combination thereof.

Furthermore, the fact that the catalysts exhibit more spins than would be predicted based on stoichiometry is evidence that the spins are polarized in a superparamagnetic matrix of a cobalt nitride or carbide-nitride particle since superparamagetism is associated with ferromagnetic materials, which cobalt oxide is not.

As an overall standard, copper sulfate pentahydrate (CuSO$_4$.5H$_2$O, MW: 249.69 g/mol) was analyzed in Protocol C. The molecular weight of the CuSO$_4$.5H$_2$O sample corresponds to approximately $2.41*10^{21}$ spins per gram catalyst. The spins/gram of this strong pitch (i.e., a solid solution of char in KCl) was measured by Protocol C to be $2.30*10^{21}$ spins per gram catalyst, indicating reliability of the results for the cobalt-containing catalysts analyzed and the conclusions drawn from these results.

Generally, therefore, catalysts of the present invention typically exhibit at least about $2.50 \times 10^{25}$ spins/mole cobalt, at least about $3.00 \times 10^{25}$ spins/mole cobalt, at least about $3.50 \times 10^{25}$ spins/mole cobalt, at least about $4.50 \times 10^{25}$ spins/mole cobalt, at least about $5.50 \times 10^{25}$ spins/mole cobalt, at least about $6.50 \times 10^{25}$ spins/mole cobalt, at least about $7.50 \times 10^{25}$ spins/mole cobalt, at least about $8.50 \times 10^{25}$ spins/mole cobalt, or at least about $9.50 \times 10^{25}$ spins/mole cobalt when the catalyst is analyzed by Electron Paramagnetic Resonance (EPR) Spectroscopy as described in Protocol C. In various embodiments, catalysts of the present invention exhibit at least about $1.0 \times 10^{26}$ spins/mole cobalt, at least about $1.25 \times 10^{26}$ spins/mole cobalt, at least about $1.50 \times 10^{26}$ spins/mole cobalt, at least about $1.75 \times 10^{26}$ spins/mole cobalt, at least about $2.0 \times 10^{26}$ spins/mole cobalt, at least about $2.25 \times 10^{26}$ spins/mole cobalt, or at least about $2.50 \times 10^{26}$ spins/mole cobalt when the catalyst is analyzed by Electron Paramagnetic Resonance (EPR) Spectroscopy as described in Protocol C. In accordance with any such embodiments, the catalysts of the present invention may be characterized such that the catalyst exhibits less than about $1.0 \times 10^{27}$ spins/mole cobalt, less than about $7.5 \times 10^{26}$ spins/mole cobalt, or less than about $5.0 \times 10^{26}$ spins/mole cobalt when the catalyst is analyzed by EPR Spectroscopy as described in Protocol C.

Oxidation catalysts of the present invention may exhibit one or more properties described in Ebner et al., U.S. Pat. No. 6,417,133, the entire disclosure of which is hereby incorporated by reference. Such characteristics may be found, for example, at column 3, line 6 to column 7, line 23; column 8, line 27 to column 9, line 24; column 10, lines 53-57; column 11, line 49 to column 14, line 18; column 14, line 50 to column 16, line 3; column 17, line 14 to column 21, line 2; column 26 (Example 2); column 27, lines 21-34 (Example 4); and column 30, line 21 to column 40, line 61 (Examples 7 to 19).

Oxidation catalysts of the present invention may include carbon nanotubes on the surface of the carbon support which may contain a certain proportion of the transition metal contained in the catalyst. Additionally or alternatively, the carbon nanotubes may contain a portion of the nitrogen of the transition metal composition. Typically, any such transition metal is present at the root or the tip of the nanotube, however, transition metal may also be present along the length of the nanotube. The carbon nanotubes typically have a diameter of at least about 0.01 μm and, more typically, have a diameter of at least about 0.1 μm. In certain embodiments, the carbon nanotubes have a diameter of less than about 1 μm and, in other embodiments, have a diameter of less than about 0.5 μm.

Oxidation Reactions

Generally, catalysts and catalyst combinations of the present invention are suitable for use in reactions which may be catalyzed by a noble metal-containing catalyst due to the similarity between the electronic nature of the transition metal composition (e.g., cobalt nitride) and noble metals. More particularly, catalysts and catalyst combinations of the present invention may be used for liquid phase oxidation reactions. Examples of such reactions include the oxidation of alcohols and polyols to form aldehydes, ketones, and acids (e.g., the oxidation of 2-propanol to form acetone, and the oxidation of glycerol to form glyceraldehyde, dihydroxyacetone, or glyceric acid); the oxidation of aldehydes to form acids (e.g., the oxidation of formaldehyde to form formic acid, and the oxidation of furfural to form 2-furan carboxylic acid); the oxidation of tertiary amines to form secondary amines (e.g., the oxidation of nitrilotriacetic acid ("NTA") to form iminodiacetic acid ("IDA")); the oxidation of secondary amines to form primary amines (e.g., the oxidation of IDA to form glycine); and the oxidation of various acids (e.g., formic acid or acetic acid) to form carbon dioxide and water.

The oxidation catalysts and catalyst combinations disclosed herein are particularly suited for catalyzing the liquid phase oxidation of a tertiary amine to a secondary amine, for example in the preparation of glyphosate and related compounds and derivatives. For example, the tertiary amine substrate may correspond to a compound of Formula I having the structure:

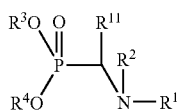

[Formula I]

wherein $R^1$ is selected from the group consisting of $R^5OC(O)CH_2$— and $R^5OCH_2CH_2$—, $R^2$ is selected from the group consisting of $R^5OC(O)CH_2$—, $R^5OCH_2CH_2$—, hydrocarbyl, substituted hydrocarbyl, acyl, —$CHR^6PO_3R^7R^8$, and —$CHR^9SO_3R^{11}$, $R^6$, $R^9$ and $R^{11}$ are selected from the group consisting of hydrogen, alkyl, halogen and —$NO_2$, and $R^3$, $R^4$, $R^5$, $R^7$, $R^8$ and $R^{10}$ are independently selected from the group consisting of hydrogen, hydrocarbyl, substituted hydrocarbyl and a metal ion. Preferably, $R^1$ comprises $R^5OC(O)CH_2$—, $R^{11}$ is hydrogen, $R^5$ is selected from hydrogen and an agronomically acceptable cation and $R^2$ is selected from the group consisting of $R^5OC(O)CH_2$—, acyl, hydrocarbyl and substituted hydrocarbyl. As noted above, the oxidation catalyst of the present invention is particularly suited for catalyzing the oxidative cleavage of a PMIDA substrate such as N-(phosphonomethyl)iminodiacetic acid or a salt thereof to form N-(phosphonomethyl)glycine or a salt thereof. In such an embodiment, the catalyst is effective for oxidation of byproduct formaldehyde to formic acid, carbon dioxide and/or water.

For example, in various embodiments, catalysts of the present invention are characterized by their effectiveness for catalyzing the oxidation of formaldehyde such that a representative aqueous solution having a pH of about 1.5 and containing 0.8% by weight formaldehyde and 0.11% by weight of a catalyst of the present invention is agitated and sparged with molecular oxygen at a rate of 0.75 cm³ oxygen/minute/gram aqueous mixture at a temperature of about 100° C. and pressure of about 60 psig, typically at least about 5%, more typically at least about 10%, still more typically at least about 15% and, even more typically, at least about 20% or at least about 30% of the formaldehyde is converted to formic acid, carbon dioxide and/or water. Catalysts of the present invention are characterized in various embodiments by their effectiveness for oxidation of formaldehyde in the presence of N-(phosphonomethyl)iminodiacetic acid. For example, when a representative aqueous solution having a pH of about 1.5 and containing 0.8% by weight formaldehyde, 5.74% by weight N-(phosphonomethyl)iminodiacetic acid, and 0.11% by weight of a catalyst of the present invention is agitated and sparged with molecular oxygen at a rate of 0.75 cm³ oxygen/minute/gram aqueous mixture at a temperature of about 100° C. and pressure of about 60 psig, typically at least about 50%, more typically at least about 60%, still more typically at least about 70%, and, even more typically at least about 80% or at least about 90% of the formaldehyde is converted to formic acid, carbon dioxide and/or water.

More particularly, it is believed that transition metal-containing catalysts and catalyst combinations of the present invention provide improved oxidation of formaldehyde and/or formic acid byproducts produced during PMIDA oxidation. In particular, it is believed that peroxides can be generated in the course of catalytic reduction of molecular oxygen during the oxidation of PMIDA to N-(phosphonomethyl)glycine utilizing certain transition metal-containing catalysts. These peroxides include, for example, hydrogen peroxide and may further include peroxide derivatives such as peracids. Oxidation of PMIDA to glyphosate comprises a four electron transfer in the catalytic reduction of oxygen. However, a portion of molecular oxygen introduced into the reaction medium may undergo only a two electron transfer yielding hydrogen peroxide or other peroxides. Four electron and two electron reduction of molecular oxygen are shown in the following equations, respectively.

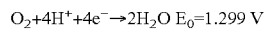
$O_2 + 4H^+ + 4e^- \rightarrow 2H_2O \quad E_0 = 1.299 \text{ V}$

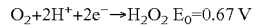
$O_2 + 2H^+ + 2e^- \rightarrow H_2O_2 \quad E_0 = 0.67 \text{ V}$

Formation of hydrogen peroxide is generally undesired as it may be reduced to yield hydrogen, an undesired byproduct. Titanium-based catalysts are effective for the oxidation of various substrates, particularly in the presence of hydrogen peroxide as an oxidant. These various substrates include, for example, primary alcohols and aldehydes. Thus, in various preferred embodiments of the present invention, titanium is incorporated as a secondary transition metal into the oxidation catalyst or a secondary catalyst including titanium is used in order to utilize the hydrogen peroxide as an oxidant for oxidation of formaldehyde and/or formic acid byproducts to produce carbon dioxide and/or water. Additionally or alternatively, oxidation of formaldehyde in the presence of hydrogen peroxide may proceed via intermediate formation of performic acid which may also function as an oxidant for formaldehyde oxidation. Advantageously, operation in this manner reduces formaldehyde and formic acid byproduct formation and hydrogen generation.

Catalysts of the present invention have been observed to combine activity for oxidation of an organic substrate with retention of the metal component of the catalyst throughout one or more reaction cycles. This combination of the activity for oxidation with resistance to leaching is defined herein as the ratio of the proportion of transition metal removed from the catalyst during a first or subsequent reaction cycle(s) to the substrate content of the reaction mixture upon completion of a first or subsequent reaction cycle(s) (i.e., the leaching/activity ratio). For example, catalysts of the present invention may be characterized such that when an aqueous mixture containing 0.15% by weight of the catalyst and about 5.75% by weight N-(phosphonomethyl)iminodiacetic is agitated and sparged with molecular oxygen at a rate of 0.875 $cm^3$ oxygen/minute/gram aqueous mixture and sparged with nitrogen at a rate of 0.875 $cm^3$ nitrogen/minute/gram aqueous mixture at a temperature of about 100° C. and a pressure of about 60 psig for from 30 to 35 minutes for a first reaction cycle, the catalyst exhibits a leaching/activity ratio during the first reaction cycle of generally less than about 1, less than about 0.75, less than about 0.50, less than about 0.25, or less than about 0.225. Typically, catalysts of the present invention exhibit a leaching/activity ratio under such conditions of less than about 0.2, more typically less than about 0.175, still more typically less than about 0.15 or less than about 0.125, even more typically less than about 0.1 or less than about 0.075. In various embodiments, catalysts of the present invention exhibit a leaching/activity ratio under such conditions of less than about 0.050, less than about 0.025, less than about 0.015, less than about 0.010, or less than about 0.08. Further in accordance with such embodiments, catalyst of the present invention may generally exhibit a leaching/activity ratio during one or more reaction cycles subsequent a first reaction cycle of less than about 0.5, less than about 0.4, less than about 0.3, less than about 0.2, or less than about 0.1. Typically, catalysts of the present invention exhibit a leaching/activity ratio during one or more reaction cycles subsequent a first reaction cycle of less than about 0.075, more typically less than about 0.05, still more typically less than about 0.018 or less than about 0.015 and, even more typically, less than about 0.010 or less than about 0.008.

Catalyst Combinations

In various embodiments, the present invention is directed to catalyst combinations comprising a secondary transition metal-containing catalyst and a primary transition metal-containing catalyst comprising a transition metal composition (e.g., cobalt nitride) formed on a carbon support, prepared generally in accordance with the above discussion and also described in U.S. patent application Ser. No. 10/919,028, filed Aug. 16, 2004, the entire disclosure of which is hereby incorporated by reference. Generally, these combinations are advantageous since the primary catalyst is effective for oxidizing PMIDA, formaldehyde, and formic acid, while not requiring the presence of a costly noble metal, and the secondary catalyst enhances the oxidation of formaldehyde and/or formic acid by products, and is believed to help control the undesired formation of hydrogen. More particularly it is believed that the secondary catalyst is effective to promote oxidation of formaldehyde and formic acid by hydrogen peroxide formed in the reduction of molecular oxygen catalyzed by the primary catalyst. Thus, such a catalyst combination may potentially provide a more economical process.

In accordance with certain embodiments in which the primary catalyst includes a primary active phase comprising a transition metal composition prepared generally in accordance with the above discussion and described in U.S. Ser. No. 10/919,028, the secondary catalyst includes a secondary active phase comprising a secondary catalytic composition formed on a carbon support in accordance with the above discussion. In various particularly preferred embodiments, the secondary transition metal is titanium. Thus, the secondary active phase comprises a secondary transition metal composition which may include any or all of titanium nitride, titanium carbide, or titanium carbide-nitride, in accordance with the discussion set forth above.

Typically, such a catalyst combination comprises at least about 10% by weight of a secondary catalyst described herein, more typically at least about 20% by weight and, most typically from about 20 to about 50% by weight, basis the catalyst combination as a whole. Additionally, the catalyst combination comprises at least about 10% by weight of the primary catalyst of the present invention, more typically at least about 20% by weight and, most typically, from about 20 to about 50% by weight of the primary catalyst.

In accordance with various other embodiments of catalyst combinations in which the primary catalyst includes a transition metal composition prepared generally in accordance with the above discussion and described in U.S. Ser. No. 10/919,028, the secondary catalyst comprises a titanium-containing zeolite. Typically, such a catalyst combination comprises at least about 10% by weight of a secondary catalyst described herein, more typically at least about 20% by weight and, most typically from about 20 to about 50% by weight, basis the catalyst combination as a whole. Additionally, the catalyst combination comprises at least about 10% by weight of the primary catalyst of the present invention, more typically at least about 20% by weight and, most typically, from about 20 to about 50% by weight of the primary catalyst.

Generally in such catalysts titanium is incorporated into the lattice or, molecular structure, of a silicon-containing zeolite by replacing silicon atoms of the lattice by isomorphous substitution. Titanium atoms contained in a secondary active phase may be subject to formation of coordination compounds (i.e., chelation) with either N-(phosphonomethyl)iminodiacetic acid or N-(phosphonomethyl)glycine present in the reaction medium. In particular, titanium atoms present for example, as $TiO_2$ on a support, and also titanium atoms substituted in the lattice at the exterior of a zeolite particle are believed to be susceptible to chelation and leaching from the lattice. However, titanium substituted in the lattice in the interior of the zeolite particle is generally less subject to leaching than titanium at the exterior, especially where the pore size of the zeolite is within the preferred ranges described hereinbelow. Thus, preferably, the zeolite lattice comprises substantial substitution with titanium atoms in regions of the zeolite lattice located within the interior of the catalyst particle.

Preferably, the pores of the titanium-containing zeolite are of a size sufficient to permit access of formaldehyde, formic acid and hydrogen peroxide while also allowing egress of carbon dioxide produced by the oxidation of formaldehyde and/or formic acid from the pores. However, the pores are preferably not so large as to permit access of N-(phosphonomethyl)iminodiacetic acid or N-(phosphonomethyl)glycine. Preventing access of these compounds to the interior of the catalyst particle avoids chelation of titanium atoms present in the interior lattice. As a result, leaching of titanium is minimized, but titanium contained within the particle interior remains available and effective for oxidizing low molecular weight compounds such as formaldehyde and formic acid. Preferably, the pores of the titanium-containing zeolite have a pore diameter of less than about 100 Å, more preferably less than about 50 Å, still more preferably less than about 25 Å and, even more preferably, less than about 10 Å.

In certain embodiments, to promote ease of handling the catalyst (e.g., filtering), it is preferred for the zeolite particles to have a size distribution similar to that of the carbon support particles. Typically, at least about 95% of the zeolite particles are from about 10 to about 500 nm in their largest dimension, more typically at least about 95% of the zeolite particles are from about 10 to about 200 nm in their largest dimension and, still more typically, at least about 95% of the zeolite particles are from about 10 to about 100 nm in their largest dimension.

Suitable titanium-containing zeolites may comprise any of a variety of crystal structures including, for example, MFI (ZSM-5), MEL (ZSM-11) and beta ($\beta$) crystal structures. One suitable titanium-containing zeolite is known in the art as TS-1 which includes titanium silicalite having a formula of $xTiO_2.(1-x)SiO_2$ with x generally being from about 0.0001 to about 0.04. TS-1 has an MFI crystal structure. Other titanium-containing zeolites known in the art include TS-2 (titanium silicalite having an MEL crystal structure) and MCM-41. These and other titanium containing zeolites are described, for example, in U.S. Pat. No. 3,702,886 to Argauer et al., U.S. Pat. No. 4,410,501 to Taramasso et al., U.S. Pat. No. 4,526,878 to Takegami et al., U.S. Pat. No. 5,098,684 to Kresge et al., U.S. Pat. No. 5,500,199 to Takegami et al., U.S. Pat. No. 5,525,563 to Thiele et al., U.S. Pat. No. 5,977,009 to Faraj, U.S. Pat. No. 6,106,803 to Hasenzahl et al., U.S. Pat. No. 6,391,278 to Pinnavaia et al., U.S. Pat. No. 6,403,514 to Mantegazza et al., U.S. Pat. No. 6,667,023 to Ludvig, U.S. Pat. Nos. 6,841,144 and 6,849,570 to Hasenzahl et al., the entire disclosures of which are hereby incorporated by reference. Suitable secondary catalysts containing titanium silicalite (i.e., TS-1) may be prepared generally in accordance with the procedures described in Yap, N., et al., "Reactivity and Stability of Au in and on TS-1 for Epoxidation of Propylene with $H_2$ and $O_2$," Journal of Catalysis, 2004, Pages 156-170, Volume 226, Elsevier Inc. including, for example, TS-1 catalysts of varying Si/Ti ratios and/or crystallite size. In various embodiments, TS-1 catalysts prepared in this manner may have a Si/Ti ratio of at least about 10, at least about 15, at least about 20, or at least about 30. In various such embodiments the Si/Ti ratio of the TS-1 containing catalyst is from about 10 to about 40 or from about 15 to about 30. Additionally or alternatively, TS-1 containing catalysts prepared in this manner may have a crystallite size of about 300×400 nm.

The present invention is further directed to catalyst combinations comprising a secondary catalyst (e.g., a catalyst comprising titanium nitride formed on a carbon support or a titanium-containing zeolite) and a noble-metal containing bifunctional catalyst (i.e., a catalyst effective both for oxidation of PMIDA and oxidation of formaldehyde and formic acid byproducts) as described in U.S. Pat. No. 6,417,133 to Ebner et al., the entire disclosure of which is incorporated by reference as stated above. The catalysts described by Ebner et al. have been proven to be highly advantageous and effective for PMIDA oxidation and the further oxidation of by-product formaldehyde and/or formic acid. Secondary catalysts described herein are also effective for oxidation of by-product formaldehyde and/or formic acid. Thus, combination of the catalysts described by Ebner et al. with a secondary catalyst described herein may be advantageous, particularly in the event hydrogen peroxide is generated in PMIDA oxidation catalyzed by a catalyst described by Ebner et al. Typically, such a catalyst combination comprises at least about 10% by weight of a bifunctional catalyst as described in U.S. Pat. No. 6,417,133, more typically at least about 20% by weight and, most typically from about 10 to about 50% by weight, basis the catalyst combination as a whole. Additionally, the catalyst combination comprises at least about 10% by weight of a secondary transition metal-containing catalyst of the present invention, more typically at least about 20% by weight and, most typically, from about 20 to about 50% by weight of a secondary transition metal-containing catalyst of the present invention.

The present invention is also directed to catalyst combinations comprising a secondary transition metal-containing catalyst (e.g., a catalyst comprising titanium nitride formed on a carbon support or a titanium-containing zeolite) and an activated carbon catalyst as described in U.S. Pat. Nos. 4,264,776 and 4,696,772 to Chou, the entire disclosures of which are hereby incorporated by reference. Generally, the catalysts described in U.S. Pat. Nos. 4,264,776 and 4,696,772 comprise activated carbon treated to remove oxides from the surface thereof. Oxides removed include carbon functional groups containing oxygen and hetero atom functional groups containing oxygen. The procedure for removing oxides from particulate activated carbon is typically commenced by contacting the carbon surface with an oxidizing agent selected from the group consisting of liquid nitric acid, nitrogen dioxide, $CrO_3$, air, oxygen, $H_2O_2$, hypochlorite, a mixture of gases obtained by vaporizing nitric acid, or combinations thereof to produce labile oxides at the carbon surface. The oxidized carbon is then heated while in contact with an atmosphere comprising nitrogen, steam, carbon dioxide, or combinations thereof. In various embodiments oxides are removed from the surface of the activated carbon catalyst in one step which includes heating the catalyst while in contact with an atmosphere comprising oxygen and a nitrogen-containing compound including, for example, an atmosphere which contains ammonia and water vapor.

The activated carbon catalyst described by Chou is effective to oxidize PMIDA while the secondary catalyst provides oxidation of formaldehyde and formic acid byproducts, while not requiring the presence of costly noble metal. Thus, combination of the catalysts described by Chou with a secondary catalyst described herein may be advantageous, particularly in the event hydrogen peroxide is generated in PMIDA oxidation catalyzed by a catalyst described by Chou.

Typically, such a catalyst combination comprises at least about 10% by weight of a catalyst as described in U.S. Pat. Nos. 4,264,776 and 4,696,772, more typically at least about 20% by weight and, most typically from about 20 to about 50% by weight, basis the catalyst combination as a whole. Additionally, the catalyst combination comprises at least about 10% by weight of a secondary transition metal-containing catalyst of the present invention, more typically at least about 20% by weight and, most typically, from about 20 to about 50% by weight of a secondary transition metal-containing catalyst of the present invention.

Reaction Conditions

The above-described catalysts and catalyst combinations are especially useful in liquid phase oxidation reactions at pH levels less than 7, and in particular, at pH levels less than 3. One such reaction is the oxidation of PMIDA or a salt thereof to form N-(phosphonomethyl)glycine or a salt thereof in an environment having pH levels in the range of from about 1 to about 2. This reaction is often carried out in the presence of solvents which solubilize noble metals and, in addition, the reactants, intermediates, or products often solubilize noble metals. Various catalysts (and combinations) of the present invention avoid these problems due to the absence of a noble metal.

The description below discloses with particularity the use of catalysts described above containing at least one transition metal composition (e.g., a transition metal nitride, transition metal carbide or transition metal carbide-nitride) or containing a single transition metal composition comprising a plurality of transition metal compositions. The description below likewise applies to the use of catalyst combinations of the present invention including a primary catalyst containing a transition metal composition combined with a secondary catalyst. It should be understood that reference to "catalyst" in the description below refers to catalysts, catalyst combinations, and individual catalysts of the catalyst combinations of the present invention. It should be recognized, however, that the principles disclosed below are generally applicable to other liquid phase oxidative reactions, especially those at pH levels less than 7 and those involving solvents, reactants, intermediates, or products which solubilize noble metals.

To begin the PMIDA oxidation reaction, it is preferable to charge the reactor with the PMIDA reagent (i.e., PMIDA or a salt thereof), catalyst, and a solvent in the presence of oxygen. The solvent is most preferably water, although other solvents (e.g., glacial acetic acid) are suitable as well.

The reaction may be carried out in a wide variety of batch, semi-batch, and continuous reactor systems. The configuration of the reactor is not critical. Suitable conventional reactor configurations include, for example, stirred tank reactors, fixed bed reactors, trickle bed reactors, fluidized bed reactors, bubble flow reactors, plug flow reactors, and parallel flow reactors.

When conducted in a continuous reactor system, the residence time in the reaction zone can vary widely depending on the specific catalyst and conditions employed. Typically, the residence time can vary over the range of from about 3 to about 120 minutes. Preferably, the residence time is from about 5 to about 90 minutes, and more preferably from about 5 to about 60 minutes. When conducted in a batch reactor, the reaction time typically varies over the range of from about 15 to about 120 minutes. Preferably, the reaction time is from about 20 to about 90 minutes, and more preferably from about 30 to about 60 minutes.

In a broad sense, the oxidation reaction may be practiced in accordance with the present invention at a wide range of temperatures, and at pressures ranging from sub-atmospheric to super-atmospheric. Use of mild conditions (e.g., room temperature and atmospheric pressure) have obvious commercial advantages in that less expensive equipment may be used. However, operating at higher temperatures and super-atmospheric pressures, while increasing capital requirements, tends to improve phase transfer between the liquid and gas phase and increase the PMIDA oxidation reaction rate.

Preferably, the PMIDA reaction is conducted at a temperature of from about 20 to about 180° C., more preferably from about 50 to about 140° C., and most preferably from about 80 to about 110° C. At temperatures greater than about 180° C., the raw materials tend to begin to slowly decompose.

The pressure used during the PMIDA oxidation generally depends on the temperature used. Preferably, the pressure is sufficient to prevent the reaction mixture from boiling. If an oxygen-containing gas is used as the oxygen source, the pressure also preferably is adequate to cause the oxygen to dissolve into the reaction mixture at a rate sufficient such that the PMIDA oxidation is not limited due to an inadequate oxygen supply. The pressure preferably is at least equal to atmospheric pressure. More preferably, the pressure is from about 30 to about 500 psig, and most preferably from about 30 to about 130 psig.

The catalyst concentration typically is from about 0.1 to about 10 wt. % ([mass of catalyst÷total reaction mass]× 100%). More typically, the catalyst concentration is from about 0.1 to about 5 wt. %, still more typically from about 0.1 to about 3.0 wt. % and, most typically, from about 0.1 to about 1.5 wt. %. Concentrations greater than about 10 wt. % are difficult to filter. On the other hand, concentrations less than about 0.1 wt. % tend to produce unacceptably low reaction rates.

The concentration of PMIDA reagent in the feed stream is not critical. Use of a saturated solution of PMIDA reagent in water is preferred, although for ease of operation, the process is also operable at lesser or greater PMIDA reagent concentrations in the feed stream. If catalyst is present in the reaction mixture in a finely divided form, it is preferred to use a concentration of reactants such that all reactants and the N-(phosphonomethyl)glycine product remain in solution so that the catalyst can be recovered for re-use, for example, by filtration. On the other hand, greater concentrations tend to increase reactor through-put. Alternatively, if the catalyst is present as a stationary phase through which the reaction medium and oxygen source are passed, it may be possible to use greater concentrations of reactants such that a portion of the N-(phosphonomethyl)glycine product precipitates.

It should be recognized that, relative to many commonly-practiced commercial processes, this invention allows for greater temperatures and PMIDA reagent concentrations to be used to prepare N-(phosphonomethyl)glycine while minimizing by-product formation. In commercial processes using a carbon-only catalyst, it is economically beneficial to minimize the formation of the NMG by-product, which is formed by the reaction of N-(phosphonomethyl)glycine with the formaldehyde by-product. In processes based on carbon catalysts, temperatures are typically maintained from about 60 to 90° C., and PMIDA reagent concentrations are typically maintained below about 9.0 wt. % ([mass of PMIDA reagent÷total reaction mass]×100%) to achieve cost effective yields and to minimize the generation of waste. At such temperatures, the maximum N-(phosphonomethyl)glycine solubility typically is less than 6.5%. However, with the oxidation catalysts, catalyst combinations and reaction process of this invention, formaldehyde is effectively oxidized, thereby allowing for reaction temperatures as high as 180° C. or greater with PMIDA reagent solutions and slurries of the PMIDA reagent. The use of higher temperatures and reactor concentrations permits reactor throughput to be increased, reduces the amount of water that must be removed before isolation of the solid N-(phosphonomethyl)glycine, and reduces the cost of manufacturing N-(phosphonomethyl)glycine. This invention thus provides economic benefits over many commonly-practiced commercial processes.

Normally, a PMIDA reagent concentration of up to about 50 wt. % ([mass of PMIDA reagent÷total reaction mass]× 100%) may be used (especially at a reaction temperature of from about 20 to about 180° C.). Preferably, a PMIDA reagent concentration of up to about 25 wt. % is used (particularly at a reaction temperature of from about 60 to about 150° C.). More preferably, a PMIDA reagent concentration of from about 12 to about 18 wt. % is used (particularly at a reaction temperature of from about 100 to about 130° C.). PMIDA reagent concentrations below 12 wt. % may be used, but are less economical because a relatively low payload of N-(phosphonomethyl)glycine product is produced in each reactor cycle and more water must be removed and energy used per unit of N-(phosphonomethyl)glycine product produced. Relatively low reaction temperatures (i.e., temperatures less than 100° C.) often tend to be less advantageous because the solubility of the PMIDA reagent and N-(phosphonomethyl)glycine product are both relatively low at such temperatures.

The oxygen source for the PMIDA oxidation reaction may be any oxygen-containing gas or a liquid comprising dissolved oxygen. Preferably, the oxygen source is an oxygen-containing gas. As used herein, an "oxygen-containing gas" is any gaseous mixture comprising molecular oxygen which optionally may comprise one or more diluents which are non-reactive with the oxygen or with the reactant or product under the reaction conditions.

Examples of such gases are air, pure molecular oxygen, or molecular oxygen diluted with helium, argon, nitrogen, or other non-oxidizing gases. For economic reasons, the oxygen source most preferably is air, oxygen-enriched air, or pure molecular oxygen.

Oxygen may be introduced by any conventional means into the reaction medium in a manner which maintains the dissolved oxygen concentration in the reaction mixture at a desired level. If an oxygen-containing gas is used, it preferably is introduced into the reaction medium in a manner which maximizes the contact of the gas with the reaction solution. Such contact may be obtained, for example, by dispersing the gas through a diffuser such as a porous frit or by stirring, shaking, or other methods known to those skilled in the art.

The oxygen feed rate preferably is such that the PMIDA oxidation reaction rate is not limited by oxygen supply. Generally, it is preferred to use an oxygen feed rate such that at least about 40% of the oxygen is utilized. More preferably, the oxygen feed rate is such that at least about 60% of the oxygen is utilized. Even more preferably, the oxygen feed rate is such that at least about 80% of the oxygen is utilized. Most preferably, the rate is such that at least about 90% of the oxygen is utilized. As used herein, the percentage of oxygen utilized equals: (the total oxygen consumption rate÷oxygen feed rate)×100%. The term "total oxygen consumption rate" means the sum of: (i) the oxygen consumption rate ("$R_i$") of the oxidation reaction of the PMIDA reagent to form the N-(phosphonomethyl)glycine product and formaldehyde, (ii) the oxygen consumption rate ("$R_{ii}$") of the oxidation reaction of formaldehyde to form formic acid, and (iii) the oxygen consumption rate ("$R_{iii}$") of the oxidation reaction of formic acid to form carbon dioxide and water.

In various embodiments of this invention, oxygen is fed into the reactor as described above until the bulk of PMIDA reagent has been oxidized, and then a reduced oxygen feed rate is used. This reduced feed rate preferably is used after about 75% of the PMIDA reagent has been consumed. More preferably, the reduced feed rate is used after about 80% of the PMIDA reagent has been consumed. Where oxygen is supplied as pure oxygen or oxygen-enriched air, a reduced feed rate may be achieved by purging the reactor with (non-enriched) air, preferably at a volumetric feed rate which is no greater than the volumetric rate at which the pure molecular oxygen or oxygen-enriched air was fed before the air purge. The reduced oxygen feed rate preferably is maintained for from about 2 to about 40 minutes, more preferably from about 5 to about 20 minutes, and most preferably from about 5 to about 15 minutes. While the oxygen is being fed at the reduced rate, the temperature preferably is maintained at the same temperature or at a temperature less than the temperature at which the reaction was conducted before the air purge. Likewise, the pressure is maintained at the same or at a pressure less than the pressure at which the reaction was conducted before the air purge. Use of a reduced oxygen feed rate near the end of the PMIDA reaction allows the amount of residual formaldehyde present in the reaction solution to be reduced without producing detrimental amounts of AMPA by oxidizing the N-(phosphonomethyl)glycine product.

In embodiments in which a catalyst combination comprising a noble metal on carbon catalyst is used, reduced losses of noble metal may be observed with this invention if a sacrificial reducing agent is maintained or introduced into the reaction solution. Suitable reducing agents include formaldehyde, formic acid, and acetaldehyde. Most preferably, formic acid, formaldehyde, or mixtures thereof are used. Experiments conducted in accordance with this invention indicate that if small amounts of formic acid, formaldehyde, or a combination thereof are added to the reaction solution, the catalyst will preferentially effect the oxidation of the formic acid or formaldehyde before it effects the oxidation of the PMIDA reagent, and subsequently will be more active in effecting the oxidation of formic acid and formaldehyde during the PMIDA oxidation. Preferably from about 0.01 to about 5.0 wt. % ([mass of formic acid, formaldehyde, or a combination thereof÷total reaction mass]×100%) of sacrificial reducing agent is added, more preferably from about 0.01 to about 3.0 wt. % of sacrificial reducing agent is added, and most preferably from about 0.01 to about 1.0 wt. % of sacrificial reducing agent is added.

In certain embodiments, unreacted formaldehyde and formic acid are recycled back into the reaction mixture for use in subsequent cycles. In this instance, an aqueous recycle stream comprising formaldehyde and/or formic acid also may be used to solubilize the PMIDA reagent in the subsequent cycles. Such a recycle stream may be generated by evaporation of water, formaldehyde, and formic acid from the oxidation reaction mixture in order to concentrate and/or crystallize product N-(phosphonomethyl)glycine. Overheads condensate containing formaldehyde and formic acid may be suitable for recycle.

As noted above, various oxidation catalysts of the present invention comprising one or more metal compositions (e.g., a primary transition metal nitride and/or a secondary metal nitride) are effective for the oxidation of formaldehyde to formic acid, carbon dioxide and water. In particular, oxidation catalysts of the present invention are effective for the oxidation of byproduct formaldehyde produced in the oxidation of N-(phosphonomethyl)iminodiacetic acid. More particularly, such catalysts are characterized by their effectiveness for catalyzing the oxidation of formaldehyde such that when a representative aqueous solution containing about 0.8% by weight formaldehyde and having a pH of about 1.5 is contacted with an oxidizing agent in the presence of the catalyst at a temperature of about 100° C., at least about 5%, preferably at least about 10%, more preferably at least about 15%, even more preferably at least about 20% or even at least about 30% by weight of said formaldehyde is converted to formic acid, carbon dioxide and/or water.

Oxidation catalysts of the present invention are particularly effective in catalyzing the liquid phase oxidation of formaldehyde to formic acid, carbon dioxide and/or water in the presence of a PMIDA reagent such as N-(phosphonomethyl) iminodiacetic acid. More particularly, such catalyst is characterized by its effectiveness for catalyzing the oxidation of formaldehyde such that when a representative aqueous solution containing about 0.8% by weight formaldehyde and about 6% by weight of N-(phosphonomethyl)iminodiacetic acid and having a pH of about 1.5 is contacted with an oxidizing agent in the presence of the catalyst at a temperature of about 100° C., at least about 50%, preferably at least about 60%, more preferably at least about 70%, even more preferably at least about 80%, and especially at least about 90% by weight of said formaldehyde is converted to formic acid, carbon dioxide and/or water.

Typically, the concentration of N-(phosphonomethyl)glycine in the product mixture may be as great as 40% by weight, or greater. Preferably, the N-(phosphonomethyl)glycine concentration is from about 5 to about 40%, more preferably from about 8 to about 30%, and still more preferably from about 9 to about 15%. Concentrations of formaldehyde in the product mixture are typically less than about 0.5% by weight, more preferably less than about 0.3%, and still more preferably less than about 0.15%.

Hydrogen Generation

In addition to incorporating titanium as a secondary metal or use of a secondary catalyst comprising titanium, modest hydrogen generation associated with use of transition metal-containing catalysts of the present invention can be effectively dealt with using one or more approaches. Hydrogen formation and/or concentration in the reactor is preferably minimized due to its highly flammable and explosive nature. For example, any adverse effect of hydrogen generation can be minimized by dilution of the reactor headspace with nitrogen or carbon dioxide. Alternatives for this purpose include using compressed air as a portion of the oxygen-containing gas introduced as the oxidant for oxidation of the organic substrate, dilution of the headspace with carbon dioxide formed in the oxidation reaction, and recycle into the reactor headspace carbon dioxide formed in a downstream operation, for example, by oxidation of formic acid that has been separated from an oxidation product mixture produced by the catalytic oxidation of PMIDA to glyphosate. Introduction of nitrogen and/or carbon dioxide to the reactor headspace reduces the headspace concentration of hydrogen and oxygen. Use of compressed air as the oxygen-containing gas provides a source of nitrogen which dilutes both the hydrogen and oxygen concentration in the headspace.

Following the oxidation, the catalyst preferably is subsequently separated by filtration. The N-(phosphonomethyl) glycine product may then be isolated by precipitation, for example, by evaporation of a portion of the water and cooling. In certain embodiments, it should be recognized that the catalyst of this invention has the ability to be reused over several cycles. N-(phosphonomethyl)glycine prepared in accordance with the present invention may be further processed in accordance with many well-known methods in the art to produce agronomically acceptable salts of N-(phosphonomethyl)glycine commonly used in herbicidal glyphosate compositions. As used herein, an "agronomically acceptable salt" is defined as a salt which contains a cation(s) that allows agriculturally and economically useful herbicidal activity of an N-(phosphonomethyl)glycine anion. Such a cation may be, for example, an alkali metal cation (e.g., a sodium or potassium ion), an ammonium ion, an isopropyl ammonium ion, a tetra-alkylammonium ion, a trialkyl sulfonium ion, a protonated primary amine, a protonated secondary amine, or a protonated tertiary amine. A concentrate comprising a salt of N-(phosphonomethyl)glycine in a concentration of, for example, at least 240 gpl, a.e may be prepared. The concentrate may include a surfactant such as, for example, an alkoxylated alkylamine or an alkoxylated etheramine.

The present invention is illustrated by the following examples which are merely for the purpose of illustration and not to be regarded as limiting the scope of the invention or the manner in which it may be practiced.

EXAMPLE 1

This example details the preparation of a precursor for use in preparing carbon-supported molybdenum carbides and nitrides.

A carbon support (20.0 g) having a B.E.T. surface area of 1067 $m^2/g$ commercially available from Degussa Corp. was added to a 1 liter beaker containing deionized water (300 ml) and a magnetic stirring bar to form a carbon support slurry.

A solution (60 ml) of ammonium molybdate (($NH_4$)$_2$ $MoO_4$) (4.236 g) (Aldrich Chemical Co., Milwaukee, Wis.) in deionized water was added to the carbon support slurry using a MasterFlex® meter pump (MasterFlex® L/S®) manufactured by Cole-Parmer Instrument Company (Vernon Hills, Ill.) at a rate of 2.0 ml/min over the course of about 30-40 minutes. The carbon support slurry was agitated using a mechanical stirrer while the molybdenum solution was added to the carbon support slurry. Also, during addition of the molybdenum solution to the carbon slurry, the pH of the resulting mixture was maintained at approximately 4.0 by co-addition of diluted nitric acid (approximately 5-10 ml) (Aldrich Chemical Co., Milwaukee, Wis.).

After addition of the molybdenum solution to the carbon support slurry was complete, the resulting mixture was agitated using a mechanical stirrer for approximately 30 minutes. The pH of the mixture was then adjusted to approximately 3.0 by addition of diluted nitric acid (2-5 ml) (Aldrich Chemical Co., Milwaukee, Wis.) and once again agitated for approximately 30 minutes.

The resulting mixture was filtered and washed with approximately 800 ml of deionized water and the wet cake was dried in a nitrogen purged vacuum oven at approximately 120° C. overnight. The resulting precursor contained ammonium ($NH_4$)$_2$$MoO_4$ deposited on the carbon support.

EXAMPLE 2

This example details preparation of a carbon-supported molybdenum carbide catalyst using a catalyst precursor prepared as described in Example 1.

The precursor (8.0 g) was charged into a Hastelloy C tube reactor packed with high temperature insulation material. The reactor was purged by introducing argon to the reactor at approximately 100 $cm^3/min$ and approximately 20° C. for approximately 15 minutes. A thermocouple was inserted into the center of the reactor for charging of the precursor.

After the precursor was introduced to the reactor, the temperature of the reactor atmosphere was increased to approximately 300° C. over the course of 30 minutes during which time a 50%/50% (v/v) mixture of methane and hydrogen (Airgas Co., St. Louis, Mo.) was introduced to the reactor at a rate of about 100 $cm^3/min$.

The temperature of the reactor atmosphere was increased to approximately 650° C. at a rate of approximately 2° C./min; the reactor atmosphere was maintained at approximately 650° C. for approximately 4 hours. During this time a 50%/50% (v/v) mixture of methane and hydrogen (Airgas Co., St. Louis, Mo.) was introduced to the reactor at a rate of approximately 100 $cm^3/minute$.

The resulting carbon-supported catalyst contained approximately 15% by weight molybdenum carbide (15% $Mo_2C/C$) and was cleaned by contact with a 20%/80% (v/v) flow of a mixture of hydrogen and argon introduced to the reactor at a rate of about 100 $cm^3$/min. The temperature of the reactor was maintained at about 650° C. for approximately another 30 minutes after which time the reactor was cooled to approximately 20° C. over the course of 90 minutes under a flow of argon at 100 $cm^3$/min.

EXAMPLE 3

This example details preparation of a carbon-supported molybdenum nitride catalyst using a catalyst precursor prepared as described in Example 1.

The precursor (10.0 g) was charged into a Hastelloy C tube reactor packed with high temperature insulation material. The reactor was purged by introducing argon to the reactor at approximately 100 $cm^3$/min and approximately 20° C. for approximately 15 minutes. A thermocouple was inserted into the center of the reactor for charging of the precursor.

The temperature of the reactor was then raised to about 300° C. over the course of 30 minutes during which time ammonia (Airgas Co., St. Louis, Mo.) was introduced to the reactor at a rate of about 100 $cm^3$/min.

After the precursor was introduced to the reactor, the temperature of the reactor atmosphere was increased to approximately 800° C. at a rate of approximately 2° C./min. The reactor atmosphere was maintained at approximately 800° C. for approximately 4 hours. During this period of constant temperature, the reactor was maintained under flow of ammonia introduced to the reactor at a rate of about 100 $cm^3$/min. The reactor was cooled to approximately 20° C. over the course of 90 minutes under a flow of 100 $cm^3$/min of argon.

The resulting carbon-supported catalyst contained approximately 15% by weight molybdenum nitride (15% $Mo_2N/C$).

EXAMPLE 4

This example details use of molybdenum carbide as a catalyst in the oxidation of N-(phosphonomethyl)iminodiacetic acid (PMIDA).

An 8.2% by weight solution of PMIDA (11.48 g) in water (127.8 ml) was charged to a 1 liter Parr reactor together with molybdenum carbide at a loading of 1.3% (1.84 g). Prior to being charged to the reactor the molybdenum carbide was subjected to a helium atmosphere at a temperature of approximately 800° C. for approximately 1 hour.

The reactor was pressurized to 60 psig in the presence of a nitrogen atmosphere and the reaction mixture was heated to 100° C. The reaction was allowed to proceed for approximately 1 hour under a flow of 100 cc/min of pure oxygen.

Samples of the reaction product were removed from the reactor and analyzed to determine the conversion of N-(phosphonomethyl)iminodiacetic acid. HPLC analysis indicated a conversion of PMIDA to N-(phosphonomethyl)glycine of approximately 18.2% and a conversion of formaldehyde to formic acid of approximately 33.9%.

EXAMPLE 5

This example details preparation of a carbon-supported molybdenum catalyst.

Activated carbon (10.2 g) was added to water (160 ml) at a temperature of approximately 20° C. over the course of approximately 40 minutes to form a carbon support slurry.

Phosphomolybdic acid ($H_3Mo_{12}O_{40}P$) (0.317 g) was dissolved in water (30 ml) to form a solution that was added to the carbon support slurry. The resulting mixture was stirred for approximately 30 minutes after which time the carbon support having molybdenum at its surface was isolated by filtration, washed with deionized water and dried in a vacuum at approximately 120° C. for approximately 8 hours.

The dried carbon support having molybdenum at its surface was then subjected to a reduction operation in a 5% hydrogen in helium atmosphere at a temperature of from about 8000 to about 900° C.

EXAMPLE 6

This example details use of a catalyst prepared as described in Example 5 in PMIDA oxidation.

A 4.1% by weight solution of PMIDA (5.74 g) in water (133.8 g) was charged to a 1 liter Parr reactor together with the carbon-supported molybdenum catalyst at a loading of 0.309% (0.432 g). The reactor was pressurized to 60 psig in a nitrogen atmosphere and the reaction mixture was heated to approximately 100° C.

The reaction was allowed to proceed for approximately 80 minutes under a flow of 100 $cm^3$/min of oxygen. Four reaction cycles were performed and the catalyst from the previous cycle was used in each of the final 3 cycles.

Samples from the reaction mixtures produced during the third and fourth reaction cycles were analyzed by HPLC. The analyses indicated conversions of PMIDA to N-(phosphonomethyl)glycine during the third and fourth cycles were approximately 86.2% and 86.9%, respectively. The conversions of formaldehyde to formic acid during the third and fourth cycles were approximately 30.0% and 34.4%, respectively.

EXAMPLE 7

This example details use of a catalyst prepared as described in Example 5 in PMIDA oxidation.

A 4.11% by weight solution of PMIDA (5.74 g) in water (133.8 g) was charged to a 1 liter Parr reactor together with the carbon-supported molybdenum catalyst at a loading of 0.155% (0.216 g).

The reactor was pressurized to 60 psig in a nitrogen atmosphere and the reaction mixture was heated to approximately 100° C. The reaction was allowed to proceed for approximately 15 minutes under a flow of 100 $cm^3$/min of oxygen.

A sample was removed from the reaction mixture and analyzed. HPLC analysis indicated a conversion of PMIDA to N-(phosphonomethyl)glycine of approximately 6.8% and a conversion of formaldehyde to formic acid of approximately 17.4%.

EXAMPLE 8

This example details the preparation of a carbon-supported iron-containing catalyst precursor.

A particulate carbon support (10.0 g) designated D1097 having a Langmuir surface area of approximately 1500 $m^2$/g was added to a 1 liter flask containing deionized water (400 ml) to form a carbon support slurry. The D1097 carbon support was supplied to Monsanto by Degussa. The pH of the slurry was approximately 8.0 and its temperature approximately 20° C.

Iron chloride ($FeCl_3.6H_2O$) (0.489 g) was added to a 100 ml beaker containing deionized water (30 ml) to form a solution. The iron solution was added to the carbon support at a rate of approximately 2 ml/minute over the course of approximately 15 minutes. The pH of the carbon support slurry was maintained at from about 4 to about 4.4 by co-addition of a 0.1% by weight solution of sodium hydroxide (Aldrich Chemical Co., Milwaukee, Wis.); approximately 5 ml of the 0.1% by weight sodium hydroxide solution was added to the carbon support slurry during addition of the iron solution. The pH of the slurry was monitored using a pH meter (Thermo Orion Model 290).

After addition of the iron solution to the carbon support slurry was complete, the resulting mixture was stirred for 30 minutes using a mechanical stirring rod (at 50% output) (IKA-Werke RW16 Basic); the pH of the mixture was monitored using the pH meter and maintained at approximately 4.4 by dropwise addition of 0.1% by weight sodium hydroxide or 0.1% by weight $HNO_3$.

The mixture was then heated under a nitrogen blanket to 70° C. at a rate of about 2° C. per minute while its pH was maintained at 4.4. Upon reaching 70° C., the pH of the mixture was slowly raised by addition of 0.1% by weight sodium hydroxide (5 ml) according to the following pH profile: the pH was maintained at approximately 5.0 for 10 minutes, increased to 5.5, maintained at 5.5 for approximately 20 minutes at pH 5.5, and stirred for approximately 20 minutes during which time a constant pH of 6.0 was reached.

The resulting mixture was filtered and washed with a plentiful amount of deionized water (approximately 500 ml) and the wet cake was dried for approximately 16 hours in a vacuum oven at approximately 120° C. The precursor contained approximately 1.0% by weight iron.

EXAMPLE 9

This example details the preparation of a carbon-supported iron-containing catalyst using a precursor prepared as described in Example 8.

Iron-containing precursor (5.0 g) was charged into a Hastelloy C tube reactor packed with high temperature insulation material. The reactor was purged with argon introduced to the reactor at a rate of approximately 100 $cm^3$/min at approximately 20° C. for approximately 15 minutes. A thermocouple was inserted into the center of the reactor for charging the precursor.

After introduction of the precursor was complete, the temperature of the reactor was increased to approximately 300° C. over the course of approximately 15 minutes during which time a 10%/90% (v/v) mixture of acetonitrile and argon (Airgas, Inc., Radnor, Pa.) was introduced to the reactor at a rate of approximately 100 $cm^3$/minute. The temperature of the reactor was then increased to approximately 950° C. over the course of 30 minutes during which time the 10%/90% (v/v) mixture of acetonitrile and argon flowed through the reactor at a rate of approximately 100 $cm^3$/minute. The reactor was maintained at approximately 950° C. for approximately 120 minutes. The reactor was cooled to approximately 20° C. over the course of approximately 90 minutes under a flow of argon at approximately 100 $cm^3$/minute.

The resulting catalyst contained approximately 1% by weight iron.

EXAMPLE 10

This example details the use of various noble metal-containing and non-noble metal-containing catalysts in the oxidation of PMIDA to N-(phosphonomethyl)glycine.

A 0.5% by weight iron-containing catalyst was prepared as described in Example 9. Its precursor was prepared in accordance with the procedure set forth in Example 8 ($FeCl_3 \cdot 6H_2O$) using a solution containing iron chloride ($FeCl_3 6H_2O$) (0.245 g) in deionized water (60 ml) that was contacted with the carbon support slurry.

Figure 4:
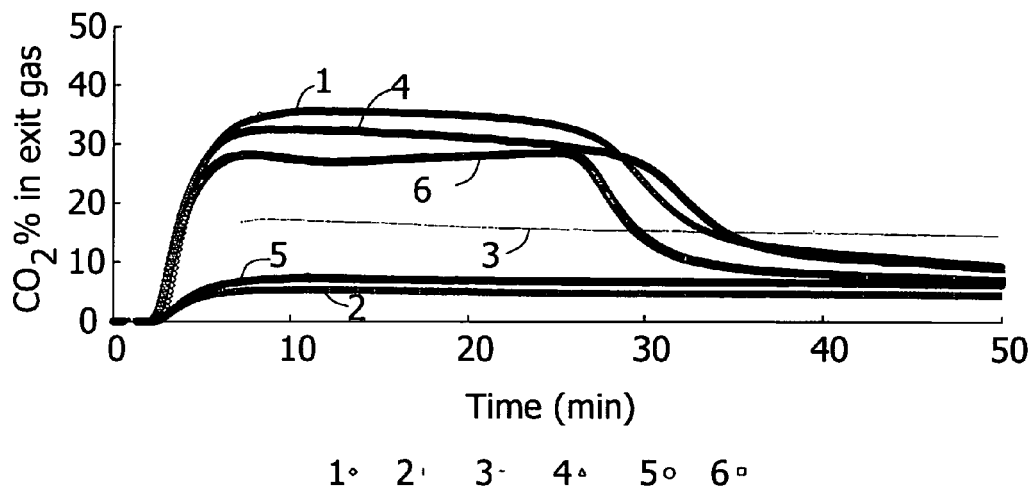
FIG. 4 shows the percentage of carbon dioxide in the exit gas produced during N-(phosphonomethyl)iminodiacetic acid (PMIDA) oxidation carried out using various catalysts as described in Example 10.

The 0.5% by weight iron catalyst was used to catalyze the oxidation of PMIDA to glyphosate (curve 6 of FIG. 4). Its performance was compared to: (1) 2 samples of a 5% platinum, 0.5% iron (5% Pt/0.5% Fe) particulate carbon catalyst prepared in accordance with Ebner et al., U.S. Pat. No. 6,417,133, Samples 1 and 2 (curves 1 and 4, respectively, of FIG. 4); (2) a particulate carbon catalyst prepared in accordance with Chou, U.S. Pat. No. 4,696,772 (4,696,772 catalyst) (curve 3 of FIG. 4); (3) a 1% Fe containing catalyst precursor prepared as described in Example 8 treated in accordance with the catalyst preparation procedure described in Example 9 using argon (Ar) in place of acetonitrile (AN) (curve 2 of FIG. 4); and (4) a particulate carbon support having a Langmuir surface area of approximately 1500 $m^2$/g that was treated with acetonitrile in accordance with the procedure set forth above in Example 9 used to prepare the 1% by weight iron catalyst (curve 5 of FIG. 4).

In each instance, the PMIDA oxidation was conducted in a 200 ml glass reactor containing a total reaction mass (200 g) that included 5.74% by weight PMIDA (11.48 g) and 0.11% catalyst (0.22 g). The oxidation was conducted at a temperature of approximately 100° C., a pressure of approximately 60 psig, a stir rate of approximately 100 revolutions per minute (rpm), and an oxygen flow rate of approximately 150 $cm^3$/minute for a run time of approximately 50 minutes.

The maximum $CO_2$ percentage in the exit gas and cumulative $CO_2$ generated were used as indicators of the degree of oxidation of PMIDA, formaldehyde, and formic acid.

FIG. 4 shows the percentage of $CO_2$ in the exit gas during a first reaction cycle using each of the six different catalysts. As shown in FIG. 4, the 0.5% by weight iron catalyst exhibited greater activity than the 4,696,772 catalyst and exhibited comparable activity as compared to 5% Pt/0.5% Fe catalysts. Also shown in FIG. 4, the acetonitrile-treated carbon support and argon-treated precursor showed little activity. Table 1 shows the $CO_2$ in the exit gas and cumulative $CO_2$ generated in the reaction cycle using each of the 6 catalyst samples.

TABLE 1

| Catalyst | Maximum $CO_2$ % in exit gas | Cumulative $CO_2$ ($cm^3$) |
|---|---|---|
| 5% Pt/0.5% Fe/C, Sample 1 | 41.45 | 2140 |
| 5% Pt/0.5% Fe/C, Sample 2 | 37.4 | 2021 |
| 4,696,772 catalyst | 20.02 | 1255 |
| Ar treated 1% Fe/C | 6.29 | 373 |
| $CH_3CN$ treated carbon | 8.79 | 533 |
| 0.5% FeCN/C | 33.34 | 1742 |

The designation MCN/C used throughout the present specification and examples does not require the presence of a particular transition metal composition. For example, this designation is not limited to compositions comprising molecular species including carbon. Rather, this designation is intended to encompass transition metal compositions including a transition metal and nitrogen (e.g., a transition metal nitride), a transition metal and carbon (e.g., a transition metal carbide), and/or a transition metal, nitrogen, and carbon (e.g., a transition metal carbide-nitride). It is currently believed that there is a high probability that molecular species containing both nitrogen and carbon are, in fact, present in catalysts prepared in accordance with the methods detailed in the present specification and examples. There is substantial experimental evidence of the presence of nitride(s) in the transition metal composition comprising cobalt and this evidence is believed to support the conclusion that nitride(s) are present in the transition metal compositions comprising other transition metals as well. With respect to carbon, the belief that carbide(s) are present is based, at least in part, on the presence of a carbon support, the high temperature treatments used to prepare the catalysts, and/or the use of certain carbon-containing heat treatment atmospheres.

EXAMPLE 11

The performance of iron-containing catalysts of varying iron loadings (0.5%, 0.75%, 1%, and 2% by weight iron) was tested in PMIDA oxidation.

The 0.5% by weight iron catalyst prepared as described in Example 10 and the 1% by weight iron catalyst prepared as described in Example 9 were tested along with a 0.75% by weight iron catalyst and 2% by weight iron catalyst.

The precursors of the 0.75% and 2% iron catalysts were prepared as described in Example 8 using varying amounts of iron chloride ($FeCl_3.6H_2O$), depending on the desired catalyst loading. For the catalyst containing 0.75% by weight iron, a solution containing iron chloride (0.366 g) in deionized water (60 ml) was prepared and contacted with the carbon support slurry.

For the catalyst containing 2.0% by weight iron, a solution containing iron chloride (0.988 g) in deionized water (60 ml) was prepared and contacted with the carbon support slurry.

Each of the catalysts was tested in PMIDA oxidation under the conditions set forth in Example 10.

Figure 5:
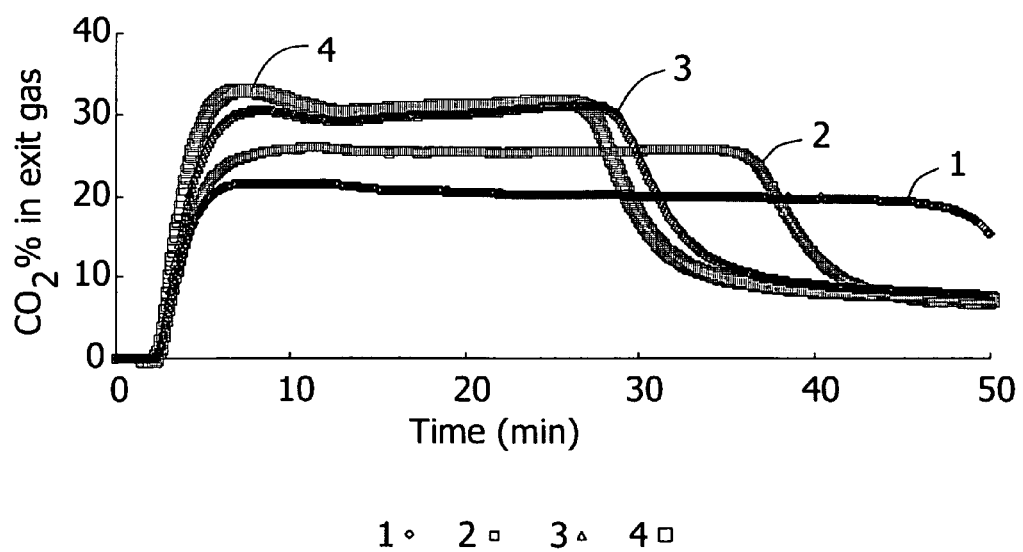
FIG. 5 shows carbon dioxide profiles of PMIDA oxidation carried out using various catalysts as described in Example 11.

FIG. 5 shows the first cycle $CO_2$ profiles for the various catalysts. Curve 1 of FIG. 5 corresponds to the first cycle using the 2% Fe catalyst, curve 2 of FIG. 5 corresponds to the first cycle using the 1% Fe catalyst, curve 3 of FIG. 5 corresponds to the first cycle using the 0.75% Fe catalyst, and curve 4 of FIG. 5 corresponds to the first cycle using the 0.5% Fe catalyst. As shown, the catalyst containing 0.5% by weight iron demonstrated the highest activity.

Table 2 shows HPLC results for the product mixtures of the reactions carried out using the 1% by weight iron catalyst prepared as in Example 9 and a 5% Pt/0.5% Fe catalyst prepared in accordance with Ebner et al., U.S. Pat. No. 6,417,133. The table shows the N-(phosphonomethyl)iminodiacetic acid (PMIDA), N-(phosphonomethyl)glycine (Gly), formaldehyde (FM), formic acid (FA), iminodiacetic acid (IDA), aminomethylphosphonic acid and methyl aminomethylphosphonic acid ((M)AMPA), N-methy-N-(phosphonomethyl) glycine (NMG), imino-bis-(methylene)-bis-phosphonic acid (iminobis), and phosphate ion ($PO_4$) content of the reaction mixture.

TABLE 2

|  | 5% Pt/0.5% Fe/C | 1% FeCN/C |
|---|---|---|
| PMIDA (%) | 0.0108 | ND |
| Gly (%) | 3.76 | 3.63 |
| FM (ppm) | 1427 | 6115 |
| FA (ppm) | 3030 | 2100 |
| IDA (%) | 0.0421 | 0.0058 |
| AMPA(M) (ppm) | 758 | 2231 |
| NMG (ppm) | 78 | 138 |
| Iminobis (ppm) | 230 | 256 |
| $PO_4$ (ppm) | 385 | 107 |

EXAMPLE 12

This example details preparation of a carbon-supported cobalt-containing catalyst precursor containing 1% by weight cobalt.

A particulate carbon support (10.0 g) having a Langmuir surface area of approximately 1500 $m^2/g$ was added to a 1 liter flask containing deionized water (400 ml) to form a slurry. The pH of the slurry was approximately 8.0 and the temperature approximately 20° C.

Cobalt chloride ($COCl_2.2H_2O$) (0.285 g) (Sigma-Aldrich, St. Louis, Mo.) was added to a 100 ml beaker containing deionized water (60 ml) to form a solution. The cobalt solution was added to the carbon slurry incrementally over the course of 30 minutes (i.e., at a rate of approximately 2 ml/minute). The pH of the carbon slurry was maintained at from about 7.5 to about 8.0 during addition of the cobalt solution by co-addition of a 0.1 wt % solution of sodium hydroxide (Aldrich Chemical Co., Milwaukee, Wis.). Approximately 1 ml of 0.1 wt. % sodium hydroxide solution was added to the carbon slurry during addition of the cobalt solution. The pH of the slurry was monitored using a pH meter (Thermo Orion, Model 290).

After addition of the cobalt solution to the carbon slurry was complete, the resulting mixture was stirred using a mechanical stirring rod operating at 50% of output (Model IKA-Werke RW16 Basic) for approximately 30 minutes; the pH of the mixture was monitored using the pH meter and maintained at about 8.0 by dropwise addition of 0.1 wt. % sodium hydroxide (1 ml) or 0.1 wt. % $HNO_3$ (1 ml). The mixture was then heated under a nitrogen blanket to approximately 45° C. at a rate of approximately 2° C. per minute while maintaining the pH at approximately 8.0 by dropwise addition of 0.1 wt. % sodium hydroxide (1 ml) or 0.1 wt. % $HNO_3$ (1 ml). Upon reaching 45° C., the mixture was stirred using the mechanical stirring bar described above for approximately 20 minutes at constant temperature of approximately 45° C. and a pH of approximately 8.0. The mixture was then heated to approximately 50° C. and its pH was adjusted to approximately 8.5 by addition of 0.1 wt. % sodium hydroxide solution (5 ml); the mixture was maintained at these conditions for approximately 20 minutes. The mixture was then heated to approximately 60° C., its pH adjusted to approximately 9.0 by addition of 0.1 wt. % sodium hydroxide solution (5 ml) and maintained at these conditions for approximately 10 minutes.

The resulting mixture was filtered and washed with deionized water (approximately 500 ml) and the wet cake was dried for approximately 16 hours in a vacuum oven at 120° C. The precursor contained approximately 1.0% by weight cobalt.

EXAMPLE 13

This example details preparation of a carbon-supported cobalt-containing catalyst using a precursor prepared as described in Example 12.

Catalyst precursor (5.0 g) was charged into a Hastelloy C tube reactor packed with high temperature insulation material. The reactor was purged with argon introduced to the reactor at a rate of approximately 100 $cm^3$/min at approximately 20° C. for approximately 15 minutes. A thermocouple was inserted into the center of the reactor for charging the precursor.

After the precursor was charged to the reactor, the temperature of the reactor was raised to approximately 700° C. during which time a 50%/50% (v/v) hydrogen/methane mixture (Airgas, Inc., Radnor, Pa.) was introduced to the reactor at a rate of approximately 20 cm$^3$/minute; a flow of argon at a rate of approximately 100 cm$^3$/min was also introduced to the reactor. The reactor was maintained at approximately 700° C. for approximately 120 minutes.

The reactor was cooled to approximately 20° C. over the course of 90 minutes under a flow of argon at approximately 100 cm$^3$/minute. The resulting catalyst contained approximately 1% by weight cobalt.

A 1% cobalt-containing catalyst from the precursor prepared as described in Example 12 was also prepared generally as described in Example 9 (i.e., using acetonitrile).

EXAMPLE 14

Catalysts of varying cobalt loadings (0.75%, 1%, 1.5%, and 2%) prepared generally as described above were tested in PMIDA oxidation.

Figure 6:
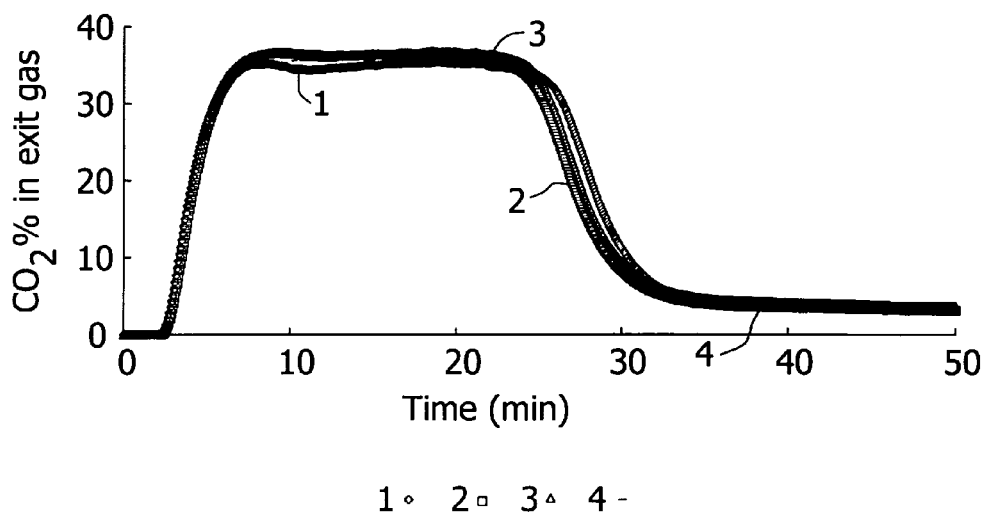
FIG. 6 shows carbon dioxide profiles of PMIDA oxidation carried out using various catalysts as described in Example 14.

As shown in FIG. 6, catalysts containing from 1-1.5% cobalt demonstrated the highest activity.

For comparison purposes, a catalyst containing 5% platinum and 0.5% iron on a carbon support (i.e., 5% Pt/0.5% Fe/C) prepared generally as described in Ebner et al., U.S. Pat. No. 6,417,133, was tested in PMIDA oxidation under the conditions described in Example 10.

The HPLC results for the product streams of the four PMIDA reaction cycles using the 1% cobalt catalyst are shown in Table 3. The HPLC results for the first, second, fourth, and sixth reaction cycles using the 5% Pt/0.5% Fe/C catalyst are summarized in Table 3. The table shows the N-(phosphonomethyl)iminodiacetic acid (GI), N-(phosphonomethyl)glycine (Gly), formaldehyde (FM), formic acid (FA), iminodiacetic acid (IDA), aminomethylphosphonic acid and methyl aminomethylphosphonic acid ((M)AMPA), N-methy-N-(phosphonomethyl)glycine (NMG), imino-bis-(methylene)-bis-phosphonic acid (iminobis), and phosphate ion (PO$_4$) content of the reaction mixture for the various cycles.

TABLE 3

|  | Cycle | PMIDA (%) | Gly (%) | FM (ppm) | FA (ppm) | IDA (%) | (M) AMPA (ppm) | NMG (ppm) | Iminobis (ppm) | PO$_4$ (ppm) |
|---|---|---|---|---|---|---|---|---|---|---|
| 5% Pt/ | 1 | 0.0108 | 3.76 | 1427 | 3030 | 0.0421 | 758 | 78 | 230 | 385 |
| 0.5% Fe/C | 2 | 0.0088 | 3.57 | 1554 | 3336 | 0.0261 | 643 | 128 | 228 | 258 |
|  | 4 | 0.0135 | 3.91 | 2094 | 4057 | 0.0133 | 632 | 259 | 227 | 171 |
|  | 6 | 0.0149 | 3.80 | 2257 | 3942 | 0.0099 | 510 | 313 | 240 | 150 |
| 1% CoCN/C | 1 | 0.0160 | 3.81 | 1551 | 8243 |  | 1245 | 167 | 236 | 294 |
|  | 2 | 0.0171 | 3.86 | 1316 | 8669 |  | 860 | 180 | 225 | 381 |
|  | 3 | 0.0205 | 4.03 | 1263 | 9174 |  | 737 | 174 | 230 | 444 |
|  | 4 | 0.0177 | 4.05 | 1239 | 9340 |  | 653 | 214 | 232 | 471 |

The 1% cobalt-containing catalyst was prepared as described in Example 13 using acetonitrile.

The precursors of the 0.5%, 0.75%, and 2% by weight cobalt catalysts were prepared in accordance with the procedure set forth above in Example 12 using varying amounts of cobalt chloride (COCl$_2$.2H$_2$O), depending on the desired catalyst loading. The catalysts were then prepared in accordance with the procedure described in Example 13 using acetonitrile.

For the catalyst containing 0.75% by weight cobalt, a solution containing cobalt chloride (0.214 g) in deionized water (60 ml) was prepared and contacted with the carbon support slurry.

For the catalyst containing 1.5% by weight cobalt, a solution containing cobalt chloride (0.428 g) in deionized water (60 ml) was prepared and contacted with the carbon support slurry.

For the catalyst containing 2.0% by weight cobalt, a solution containing cobalt chloride (0.570 g) was prepared and contacted with the carbon support slurry.

Each of the catalysts was tested in PMIDA oxidation under the conditions described in Example 10.

FIG. 6 shows the first cycle CO$_2$ profiles using the various catalysts. Curve 1 of FIG. 6 corresponds to the first cycle using the 0.75% Co catalyst, curve 2 of FIG. 6 corresponds to the first cycle using the 1% Co catalyst, curve 3 of FIG. 6 corresponds to the first cycle using the 1.50% Co catalyst, and curve 4 of FIG. 6 corresponds to the first cycle using the 2.0% Co catalyst.

EXAMPLE 15

This example compares the stability of a 1% iron catalyst prepared as described in Example 9, a 1% cobalt catalyst prepared as described in Example 13 using acetonitrile, a 5% Pt/0.5% Fe/C catalyst prepared generally in accordance with U.S. Pat. No. 6,417,133 to Ebner et al., and a particulate carbon catalyst prepared in accordance with U.S. Pat. No. 4,696,772 to Chou (4,696,772).

Each of the catalysts was tested in PMIDA oxidation under the conditions described in Example 10 for multiple reaction cycles.

Figure 7:
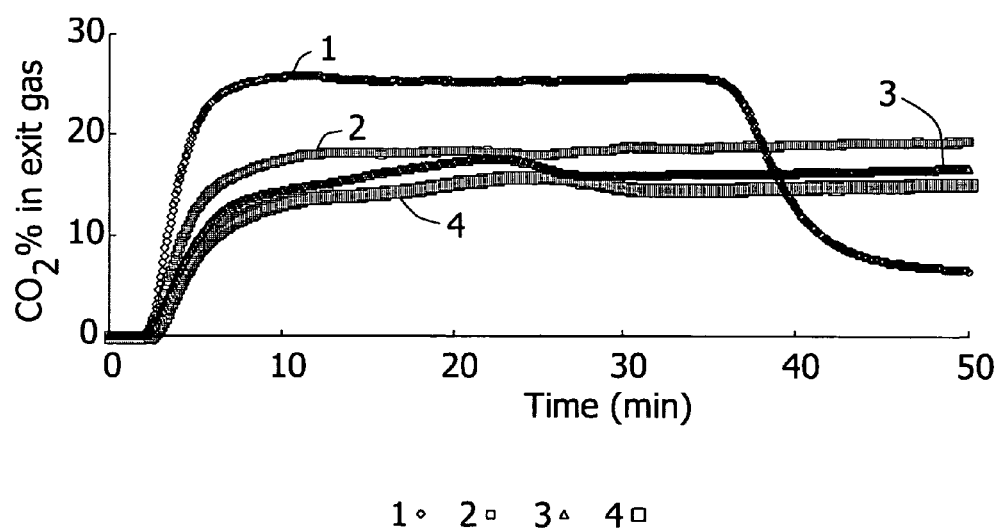
FIGS. 7-10 show the carbon dioxide percentage in the exit gas produced during PMIDA oxidation as described in Example 15.

FIG. 7 shows the CO$_2$ percentage in the exit gas during each of four reaction cycles (labeled accordingly) carried out using the 1% iron catalyst.

Figure 8:
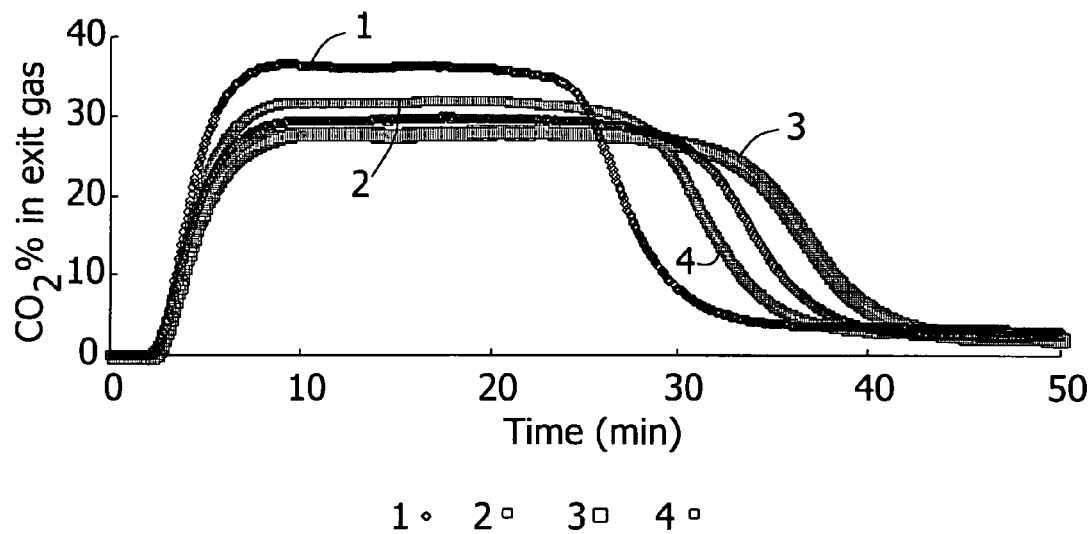

FIG. 8 shows the CO$_2$ percentage in the exit gas during each of four reaction cycles (labeled accordingly) carried out using the 1% cobalt catalyst.

Figure 9:
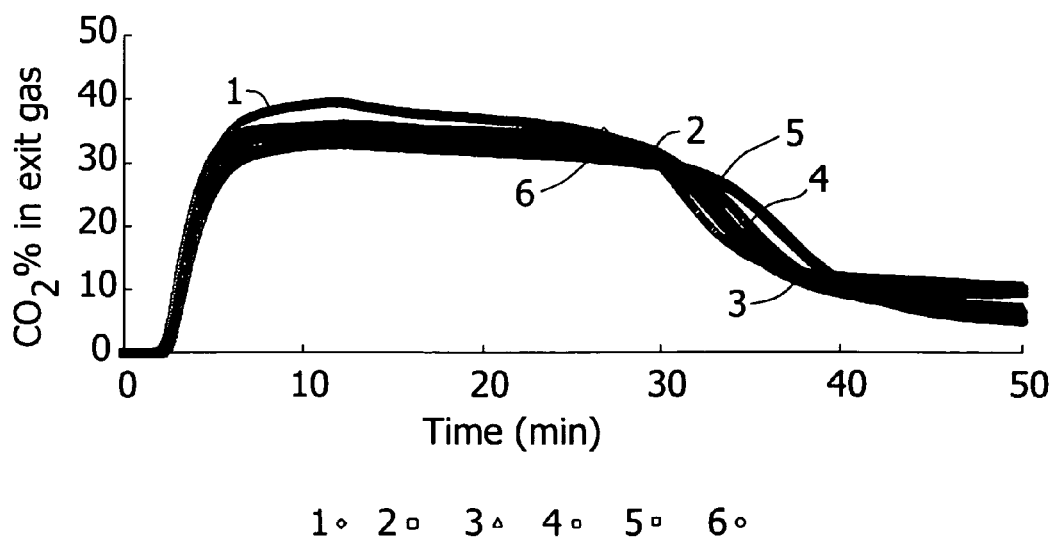

FIG. 9 shows the CO$_2$ percentage in the exit gas during each of six reaction cycles (labeled accordingly) carried out using the 5% Pt/0.5% Fe/C catalyst.

Figure 10:
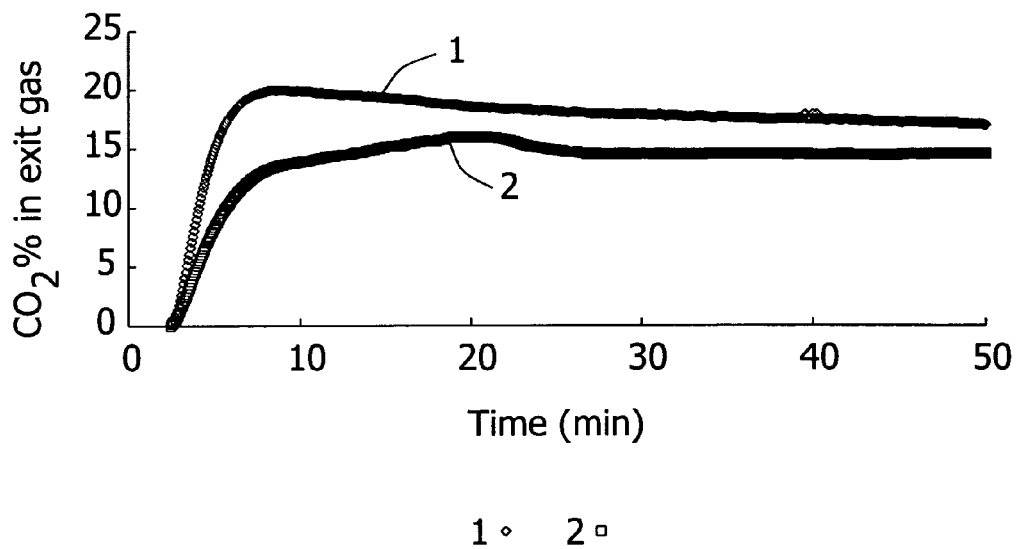

FIG. 10 shows the CO$_2$ percentage in the exit gas during each of two reaction cycles (labeled accordingly) carried out using the 4,696,772 catalyst.

The iron-containing catalyst exhibited a drop in activity after the first cycle, possibly due to overoxidation of the catalyst. Minor deactivations were observed in later cycles where the catalyst was not overoxidized. The 5% Pt/0.5% Fe/C was the most stable. The 1% cobalt catalyst showed similar stability to the 5% Pt/0.5% Fe/C catalyst. The 4,696, 772 catalyst exhibited the least stability, even in the absence of overoxidation of the catalyst.

EXAMPLE 16

This example details the preparation of various carbon-supported metal-containing catalysts.

Precursors containing vanadium, tellurium, molybdenum, tungsten, ruthenium, and cerium were prepared generally in accordance with Example 8 with variations in the pH and heating schedule depending the metal to be deposited (detailed below).

Preparation of vanadium precursor: $Na_3VO_4.10H_2O$ (0.721 g) was added to a 100 ml beaker containing deionized water (60 ml) to form a solution that was contacted with the carbon support slurry. During addition of the vanadium solution, the pH of the carbon support slurry was maintained at from about 3.4 to about 3.7 by co-addition of a 0.1 wt. % solution of nitric acid. Approximately 5 ml of nitric acid was added to the carbon support slurry during addition of the vanadium solution. After addition of the vanadium solution to the carbon support slurry was complete, the resulting mixture was stirred for 30 minutes using mechanical stirring rod operating at 50% of output (Model IKA-Werke RW16 Basic) with the pH of the mixture monitored using the pH meter described above and maintained at approximately 3.6 by addition of nitric acid (0.1 wt. % solution) (2 ml). The resulting mixture was filtered and washed with deionized water (approximately 500 ml) and the wet cake was dried for approximately 16 hours in a vacuum oven at approximately 120° C. The precursor contained approximately 1% by weight vanadium.

Preparation of tellurium precursor: $Te(OH)_6$ (0.092 g) was added to a 100 ml beaker containing deionized water (60 ml) to form a solution that was contacted with the carbon support slurry. During addition of the tellurium solution, the pH of the carbon support slurry was maintained at from about 6.5 to about 6.9 by co-addition of a 0.1 wt. % solution of sodium hydroxide. Approximately 2 ml of 0.1 wt. % sodium hydroxide solution was added to the carbon support slurry during addition of the tellurium solution. After addition of the tellurium solution to the carbon support slurry was complete, the resulting mixture was stirred for 30 minutes with the pH of the mixture monitored using the pH meter described above and maintained at approximately 6.7 by addition of 0.1 wt. % sodium hydroxide solution (1-2 ml). The pH of the mixture was maintained at pHs of 6.0, 5.0, 4.0, 3.0, 2.0, and 1.0 for 10 minutes each. The resulting mixture was filtered and washed with deionized water (approximately 500 ml) and the wet cake was dried for approximately 16 hours in a vacuum oven at approximately 120° C. The precursor contained approximately 1% by weight tellurium.

Preparation of molybdenum precursor: $(NH_4)_2MoO_4$ (0.207 g) was added to a 100 ml beaker containing deionized water (50 ml) to form a solution that was contacted with the carbon support slurry. During addition of the molybdenum solution, the pH of the carbon support slurry was maintained at from about 1.5 to about 2.0 by co-addition of a 0.1 wt. % solution of nitric acid. Approximately 5 ml of the 0.1 wt. % nitric acid solution was added to the carbon support slurry during addition of the molybdenum solution. After addition of the molybdenum solution to the carbon slurry was complete, the resulting mixture was stirred for approximately 30 minutes with pH of the slurry monitored using the pH meter and maintained at approximately 2.0 by addition of 0.1 wt. % nitric acid. The pH was then increased to approximately 3.0 by addition of 0.1 wt. % sodium hydroxide, maintained at approximately 3.0 for approximately 20 minutes, increased to approximately 4.0 by addition of 0.1 wt. % sodium hydroxide solution, and maintained at approximately 4.0 for approximately 20 minutes. The resulting mixture was filtered and washed with deionized water (approximately 500 ml) and the wet cake was dried for approximately 16 hours in a vacuum oven at approximately 120° C. The precursor contained approximately 1% by weight molybdenum.

Preparation of tungsten precursor: $(NH_4)_6W_{12}O_{39}.2H_2O$ (0.135 g) was added to a 100 ml beaker containing deionized water (60 ml) to form a solution that was contacted with the carbon support slurry. During addition of the tungsten solution, the pH of the carbon support slurry was maintained at from about 3.0 to about 3.2 by co-addition of a 0.1 wt. % solution of sodium hydroxide. Approximately 2 ml of nitric acid was added to the carbon support slurry during addition of the tungsten solution. After addition of the tungsten solution to the carbon support slurry, the resulting mixture was stirred for approximately 30 minutes with pH of the mixture monitored using the pH meter described above and maintained at approximately 3.0 by addition of 0.1 wt. % nitric acid solution. The pH of the mixture was then decreased to approximately 2.5 by addition of 0.1 wt. % nitric acid solution, maintained at approximately 2.5 for 10 minutes, decreased to approximately 2.0 by addition of 0.1 wt. % nitric acid solution, and maintained at approximately 2.0 for 10 minutes. The resulting mixture was filtered and washed with deionized water (approximately 500 ml) and the wet cake was dried for approximately 16 hours in a vacuum oven at approximately 120° C. The precursor contained approximately 1% by weight tungsten.

Preparation of ruthenium precursor: $RuCl_3.2H_2O$ (0.243 g) was added to a 100 ml beaker containing deionized water (50 ml) to form a solution that was contacted with the carbon support slurry. During addition of the ruthenium solution, the pH of the carbon support slurry was maintained at from about 3.0 to about 3.5 by co-addition of a 0.1 wt. % solution of sodium hydroxide. Approximately 1 ml of sodium hydroxide was added to the carbon support slurry during addition of the ruthenium solution. After addition of the ruthenium solution to the carbon support slurry was complete, the resulting mixture was stirred for approximately 30 minutes with the pH of the mixture monitored using the pH meter (described above) and maintained at approximately 3.5 by addition of 0.1 wt. % nitric acid solution. The pH of the mixture was then increased to approximately 4.2 by addition of 0.1 wt. % sodium hydroxide (1 ml), maintained at approximately 4.2 for approximately 10 minutes, increased to approximately 5.0 by addition of 0.1 wt. % sodium hydroxide solution (1 ml), maintained at approximately 5.0 for approximately 10 minutes, increased to approximately 5.7 by addition of 0.1 wt. % sodium hydroxide (1 ml), and maintained at approximately 5.7 for approximately 10 minutes. The resulting mixture was filtered and washed with deionized water (approximately 500 ml) and the wet cake was dried for approximately 16 hours in a vacuum oven at approximately 120° C. The precursor contained approximately 1% by weight ruthenium.

Preparation of cerium precursor: $Ce(NO_3)_3.6H_2O$ (0.117 g) was added to a 100 ml beaker containing deionized water (50 ml) to form a solution that was contacted with the carbon support slurry. During addition of the cerium solution, the pH of the carbon support slurry was maintained at from about 7.0 to about 7.5 by co-addition of a 0.1 wt. % solution of sodium hydroxide. Approximately 1 ml of sodium hydroxide was added to the carbon support slurry during addition of the cerium solution. After addition of the cerium solution to the carbon support slurry was complete, the resulting mixture was stirred for approximately 30 minutes with pH of the slurry monitored using the pH meter and maintained at approximately 7.5 by addition of 0.1 wt. % sodium hydroxide solution (1 ml). The pH was then increased to approximately 8.0 by addition of 0.1 wt. % sodium hydroxide (1 ml), maintained at approximately 8.0 for 20 minutes, increased to approximately 9.0 by addition of 0.1 wt. % sodium hydroxide (1 ml), maintained at approximately 9.0 for 20 minutes, increased to approximately 10.0 by addition of 0.1 wt. % sodium hydroxide solution (1 ml), and maintained at approximately 10.0 for 20 minutes. The resulting mixture was filtered and washed with deionized water (approximately 500 ml) and the wet cake was dried for approximately 16 hours in a vacuum oven at approximately 120° C. The precursor contained approximately 1% by weight cerium.

Precursors were also prepared for catalysts containing nickel, chromium, manganese, magnesium, copper, and silver generally in accordance with Example 12 detailing preparation of a cobalt-containing catalyst precursor with variations in the pH and heating schedule depending on the metal to be deposited (described below).

Preparation of nickel precursor: $NiCl_2.6H_2O$ (0.409 g) was added to a 100 ml beaker containing deionized water (60 ml) to form a solution that was contacted with the carbon support slurry. During addition of the nickel solution, the pH of the carbon support slurry was maintained at from about 7.5 to about 8.0 by co-addition of a 0.1 wt. % solution of sodium hydroxide. Approximately 2 ml of sodium hydroxide was added to the carbon support slurry during addition of the nickel solution. After addition of the nickel solution to the carbon support slurry, the resulting mixture was stirred for approximately 30 minutes with pH of the slurry monitored using the pH meter described above and maintained at approximately 8.0 by addition of 0.1 wt. % sodium hydroxide solution (1 ml). The mixture was then heated under a nitrogen blanket to approximately 40° C. at a rate of about 2° C. per minute while maintaining its pH at approximately 8.5 by addition of 0.1 wt. % sodium hydroxide solution. Upon reaching approximately 60° C., the mixture was stirred for approximately 20 minutes at constant temperature of approximately 40° C. and a pH of approximately 8.5. The mixture was then heated to approximately 50° C. and its pH was adjusted to approximately 9.0 by addition of sodium hydroxide solution (2 ml); the mixture was maintained at these conditions for approximately 20 minutes. The mixture was then heated to approximately 60° C., its pH adjusted to approximately 10.0 by addition of sodium hydroxide solution (2 ml) and maintained at these conditions for approximately 20 minutes. The resulting mixture was filtered and washed with deionized water (approximately 500 ml) and the wet cake was dried for approximately 16 hours in a vacuum oven at approximately 120° C. The precursor contained approximately 1% by weight nickel.

Preparation of chromium precursor: $CrCl_3.6H_2O$ (0.517 g) was added to a 100 ml beaker containing deionized water (50 ml) to form a solution which was contacted with the carbon support slurry. During addition of the chromium solution, the pH of the carbon support slurry was maintained at from about 7.0 to about 7.5 by co-addition of a 0.1 wt. % solution of sodium hydroxide. Approximately 1 ml of sodium hydroxide was added to the carbon support slurry during addition of the chromium solution. After addition of the chromium solution to the carbon support slurry was complete, the resulting mixture was stirred for approximately 30 minutes with pH of the mixture monitored using the pH meter described above and maintained at approximately 7.5 by addition of sodium hydroxide. The mixture was then heated under a nitrogen blanket to approximately 60° C. at a rate of about 2° C. per minute while maintaining its pH at approximately 8.0 by addition of 2 ml of 0.1 wt. % sodium hydroxide. The resulting mixture was filtered and washed with deionized water (approximately 500 ml) and the wet cake was dried for approximately 16 hours in a vacuum oven at approximately 120° C. The precursor contained approximately 1% by weight chromium.

Preparation of manganese precursor: $MnCl_2.4H_2O$ (0.363 g) was added to a 100 ml beaker containing deionized water (60 ml) to form a solution that was contacted with the carbon support slurry. During addition of the manganese solution, the pH of the carbon support slurry was maintained at from about 7.5 to about 8.0 by co-addition of a 0.1 wt. % solution of sodium hydroxide. Approximately 1 ml of sodium hydroxide solution was added to the carbon support slurry during addition of the manganese solution. After addition of the manganese solution to the carbon support slurry was complete, the resulting mixture was stirred for approximately 30 minutes with pH of the mixture monitored using the pH meter described above and maintained at approximately 7.4 by addition of sodium hydroxide. The mixture was then heated under a nitrogen blanket to approximately 45° C. at a rate of about 2° C. per minute while maintaining its pH at approximately 8.0 by addition of 2 ml of 0.1 wt. % sodium hydroxide solution. Upon reaching approximately 60° C., the mixture was stirred for approximately 20 minutes at constant temperature of approximately 50° C. and a pH of approximately 8.5. The mixture was then heated to approximately 55° C. and its pH was adjusted to approximately 9.0 by addition of sodium hydroxide solution (2 ml); the mixture was maintained at these conditions for approximately 20 minutes. The mixture was then heated to approximately 60° C., its pH adjusted to approximately 9.0 by addition of sodium hydroxide solution (1 ml) and maintained at these conditions for approximately 20 minutes. The resulting mixture was filtered and washed with deionized water (approximately 500 ml) and the wet cake was dried for approximately 16 hours in a vacuum oven at approximately 120° C. The precursor contained approximately 1% by weight manganese.

Preparation of magnesium precursor: $MgCl_2.6H_2O$ (0.420 g) was added to a 100 ml beaker containing deionized water (50 ml) to form a solution that was contacted with the carbon support slurry. During addition of the magnesium solution, the pH of the carbon support slurry was maintained at from about 8.5 to about 9.0 by co-addition of a 0.1 wt. % solution of sodium hydroxide. Approximately 5 ml of sodium hydroxide solution was added to the carbon support slurry during addition of the magnesium solution. After addition of the magnesium solution to the carbon slurry was complete, the resulting mixture was stirred for 30 minutes with pH of the mixture monitored using the pH meter and maintained at approximately 8.5 by addition of 0.1 wt. % sodium hydroxide solution (1 ml). The pH of the mixture was then increased to approximately 9.0 by addition of 0.1 wt. % sodium hydroxide solution (1 ml) and maintained at approximately 9.0 for approximately 30 minutes. The resulting mixture was filtered and washed with deionized water (approximately 500 ml) and the wet cake was dried for approximately 16 hours in a vacuum oven at 120° C. The precursor contained approximately 1% by weight magnesium.

Preparation of copper precursor: $CuCl_2$ (1.11 g) was added to a 100 ml beaker containing deionized water (60 ml) to form a solution that was contacted with the carbon support slurry. During addition of the copper solution, the pH of the carbon support slurry was maintained at from about 6.0 to about 6.5 by co-addition of a 0.1 wt. % solution of sodium hydroxide. Approximately 1 ml of sodium hydroxide was added to the carbon slurry during addition of the copper solution. After addition of the copper solution to the carbon slurry was complete, the slurry was stirred for approximately 30 minutes with pH of the slurry monitored using the pH meter and maintained at approximately 6.5 by addition of sodium hydroxide. The slurry was then heated under a nitrogen blanket to approximately 40° C. at a rate of about 2° C. per minute while maintaining its pH at approximately 7.0 by addition of 0.1 wt. % sodium hydroxide solution. Upon reaching approximately 40° C., the slurry was stirred for approximately 20 minutes at constant temperature of approximately 40° C. and a pH of approximately 7.0. The slurry was then heated to approximately 50° C. and its pH was adjusted to approximately 7.5 by addition of approximately 0.1 wt. % sodium hydroxide solution (1 ml); the slurry was maintained at these conditions for approximately 20 minutes. The resulting mixture was filtered and washed with deionized water (approximately 500 ml) and the wet cake was dried for approximately 16 hours in a vacuum oven at approximately 120° C. The precursor contained approximately 5% by weight copper.

Preparation of silver precursor: $AgNO_3$ (0.159 g) was added to a 100 ml beaker containing deionized water (60 ml) to form a solution that was contacted with the carbon support slurry. During addition of the silver solution, the pH of the carbon support slurry was maintained at from about 4.0 to about 4.5 by co-addition of a 0.1 wt. % solution of nitric acid. Approximately 2 ml of nitric acid solution was added to the carbon slurry during addition of the silver solution. After addition of the silver solution to the carbon support slurry was complete, the resulting mixture was stirred for approximately 30 minutes with pH of the mixture monitored using the pH meter and maintained at approximately 4.5 by addition of nitric acid solution (2 ml). The resulting mixture was filtered and washed with deionized water (approximately 500 ml) and the wet cake was dried for approximately 16 hours in a vacuum oven at approximately 120° C. The precursor contained approximately 1% by weight silver. Metal (M), nitrogen and carbon-containing catalysts (MCN/C) containing 1% by weight metal (in the case of copper, 5% by weight) were prepared from each of the catalyst precursors as described above in Example 9.

EXAMPLE 17

Each of the catalysts prepared as described in Example 16 was tested in PMIDA oxidation under the conditions described in Example 10.

The maximum $CO_2$ percent composition in the exit gas and the total $CO_2$ generated during the 50 minutes of reaction were used to measure the catalysts' activity. The results are shown in Table 4.

TABLE 4

First cycle reaction results for various MCN catalysts

| Catalyst | $CO_2$ max in offgas | Total $CO_2$ after 50 minutes (cm$^3$) |
|---|---|---|
| 1% FeCN/C | 25.93 | 1624 |
| 1% CoCN/C | 36.5 | 1571 |
| 1% NiCN/C | 7.36 | 343 |
| 1% VCN/C | 11.69 | 676 |
| 1% CrCN/C | 34.88 | 1809 |
| 1% MnCN/C | 22.22 | 1526 |
| 5% CuCN/C | 28.45 | 1571 |
| 1% MoCN/C | 10.92 | 753 |
| 1% WCN/C | 11.8 | 684 |

TABLE 4-continued

First cycle reaction results for various MCN catalysts

| Catalyst | $CO_2$ max in offgas | Total $CO_2$ after 50 minutes (cm$^3$) |
|---|---|---|
| 1% MgCN/C | 13.4 | 830 |
| 1% TeCN/C | 10.12 | 648 |
| 1% AgCN/C | 12.09 | 817 |
| 1% RuCN/C | 17.77 | 1041 |
| 1% CeCN/C | 16.54 | 1282 |

The carbon-supported cobalt-containing catalyst and chromium-containing catalysts showed the highest PMIDA oxidation activity.

EXAMPLE 18

This example details the effectiveness of various carbon-supported carbide-nitride containing catalysts for the oxidation of formaldehyde and formic acid during PMIDA oxidation under the conditions described in Example 10.

Figure 11:
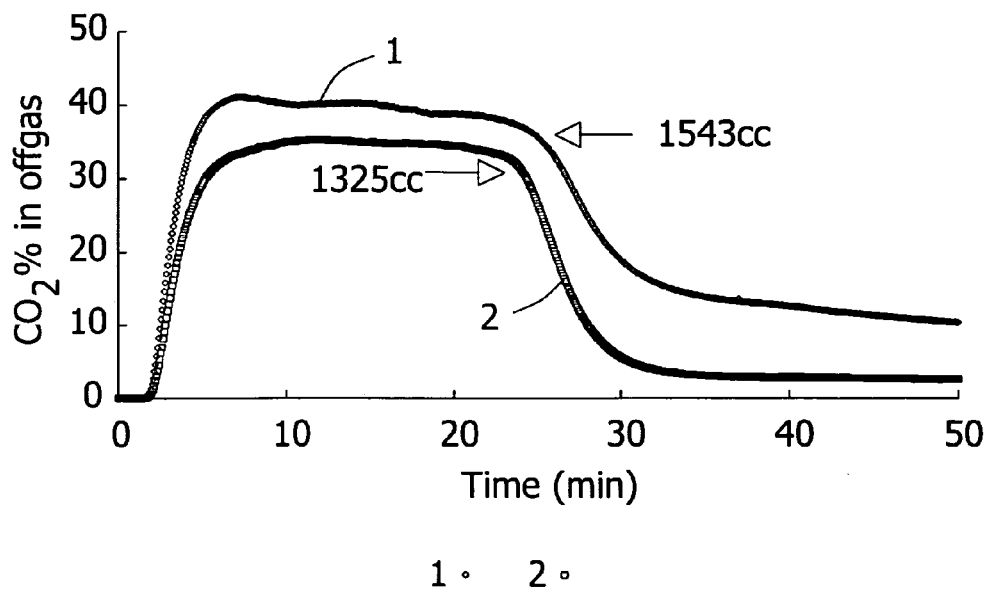
FIG. 11 shows the results of the carbon dioxide drop-point measurement comparison as described in Example 18.

Two methods were employed to evaluate the activity of various carbon-supported metal carbide-nitride catalysts in the oxidation of formaldehyde and formic acid: (1) HPLC analysis of the reaction product and (2) the $CO_2$ drop-point measurement. The drop-point measurement is the total amount of $CO_2$ that has passed through the exit gas at the moment a sudden reduction in exit gas $CO_2$ composition is observed. As shown in FIG. 11, a particulate carbon catalyst containing 5% Pt/1% Fe prepared in accordance with U.S. Pat. No. 6,417,133 to Ebner et al. produces a $CO_2$ drop-point around 1500-1600 cm$^3$ of total $CO_2$ under the PMIDA oxidation conditions of Example 10 (curve 1 of FIG. 11). Also shown in FIG. 11, a 1% cobalt-containing catalyst prepared as described above in Example 13 using acetonitrile, exhibits a $CO_2$ drop point around 1300 cm$^3$ under the PMIDA oxidation conditions of Example 10 (curve 2 of FIG. 11).

The approximately 200-300 cm$^3$ increase in total $CO_2$ generation associated with use of the 5% Pt/1% Fe catalyst prepared in accordance with U.S. Pat. No. 6,417,133 to Ebner et al. may be due to greater oxidation of formic acid as compared to the 1% cobalt catalyst.

Table 5 shows the HPLC results of the PMIDA oxidation product using various carbon-supported carbide-nitride catalysts prepared as described above in Example 17: 1% by weight cobalt, 1% by weight manganese, 5% by weight copper, 1% by weight magnesium, 1% by weight chromium, 1% by weight molybdenum, and 1% by weight tungsten. The carbon-supported cobalt carbide-nitride catalyst showed the highest formaldehyde oxidation activity.

TABLE 5

| Catalyst | Loading | Cycle | PMIDA (%) | Gly (%) | FM (ppm) | FA (ppm) |
|---|---|---|---|---|---|---|
| 1% CoCN/C | 0.21 g | 1 | 0.016 | 3.81 | 1551 | 8243 |
|  | 0.21 g | 2 | 0.017 | 3.86 | 1316 | 8669 |
| 1% MnCN/C | 0.42 g | 1 | 0.021 | 3.28 | 4496 | 3711 |
| 5% CuCN/C | 0.21 g | 1 | 0.018 | 3.15 | 3143 | 5750 |
| 1% MgCN/C | 0.63 g | 1 | 0.028 | 3.01 | 5503 | 2338 |
| 1% CrCN/C | 0.21 g | 1 | 0.044 | 3.20 | 5846 | 2287 |
| 1% MoCN/C | 0.63 g | 1 | 0.058 | 3.51 | 4281 | 3230 |
| 1% WCN/C | 0.21 g | 1 | 2.654 | 1.90 | 1905 | 2223 |

Catalyst mixtures (0.21 g) containing 50% by weight of the 1% by weight cobalt catalyst prepared as described in Example 13 using acetonitrile and 50% by weight of each of the 1% nickel, 1% vanadium, 1% magnesium, and 1% tellurium catalysts prepared in accordance with Example 17 were prepared and tested under the PMIDA oxidation conditions described in Example 10 to further test the activity toward oxidation of formaldehyde and formic acid. A drop point of approximately 1300 cm$^3$ was observed for each of the 4 catalyst mixtures.

EXAMPLE 19

This example details use of various promoters in combination with a 1% cobalt catalyst prepared as described above in Example 13 using acetonitrile in PMIDA oxidation under the conditions described in Example 10. The 1% cobalt catalyst loading was 0.021 g.

The promoters tested were: bismuth nitrate ($Bi(NO_3)_3$), bismuth oxide ($Bi_2O_3$), tellurium oxide ($TeO_2$), iron chloride ($FeCl_3$), nickel chloride ($NiCl_2$), copper sulfate ($CuSO_4$), ammonium molybdate (($NH_4$) $2MoO_4$), and ammonium tungstate (($NH_4)_{10}W_{12}O_{41}$). The promoters were introduced to the reaction mixture at the outset of the reaction cycle. The promoters were introduced to the reaction mixture at varying loadings as shown in Table 6.

The maximum $CO_2$ concentration in the exit gas stream and the cumulative $CO_2$ number were measured to determine the catalytic activity and the $CO_2$ drop-point measurement was recorded to determine the catalytic formic acid oxidation activity. Table 6 shows the maximum $CO_2$ in the exit gas and the total $CO_2$ generated during a first 50 minute reaction cycle. The $CO_2$ drop points when using each of the six promoters were between about 1300 and 1350 cm$^3$. It is recognized that certain of these promoters qualify as secondary catalysts as described above or, if not, may provide an auxiliary effect for oxidation of one or more substrates (e.g., PMIDA, formaldehyde and/or formic acid).

TABLE 6

| Promoter | $CO_2$ % max in offgas | Total $CO_2$ after 50 minutes (cm$^3$) |
| --- | --- | --- |
| None | 36.5 | 1571 |
| 20 mg $Bi(NO_3)_3$ | 35.58 | 1571 |
| 25 mg $Bi_2O_3$ | 33.4 | 1654 |
| 10 mg $TeO_2$ | 36.31 | 1496 |
| 20 mg $TeO_2$ | 35.39 | 1580 |
| 50 mg $TeO_2$ | 37.81 | 1491 |
| 1 mg $FeCl_3$ | 36.2 | 1636 |
| 5 mg $FeCl_3$ | 35.97 | 1646 |
| 5 mg $NiCl_2$ | 34.69 | 1669 |
| 5 mg $CuSO_4$ | 33.18 | 1594 |
| 5 mg $(NH_4)_2MoO_4$ | 30.66 | 1635 |
| 5 mg $(NH_4)_{10}W_{12}O_{41}$ | 31.04 | 1569 |

EXAMPLE 20

This example details preparation of bi-metallic carbon-supported carbide-nitride catalysts and their use in PMIDA oxidation.

A catalyst containing 1% by weight cobalt and 0.5% by weight iron was prepared in accordance with the process described above in Example 13 using acetonitrile. The precursor for the 1% cobalt and 0.5% iron catalyst was prepared by sequential deposition of each of the metals in accordance with the methods described above in Examples 12 and 8, respectively.

Similarly, a catalyst containing 1% cobalt and 0.5% cerium was prepared in accordance with the process described above in Example 13 using acetonitrile. The precursor for the 1% cobalt and 0.5% cerium catalyst was prepared by sequential deposition of each of the metals in accordance with the methods described above in Examples 12 and 16, respectively.

A catalyst containing 1% cobalt and 0.5% copper was prepared in accordance with the process described above in Example 13. The precursor for the 1% cobalt and 0.5% copper catalyst was prepared by sequential deposition of each of the metals in accordance with the methods described above in Examples 12 and 16, respectively.

Figure 12:
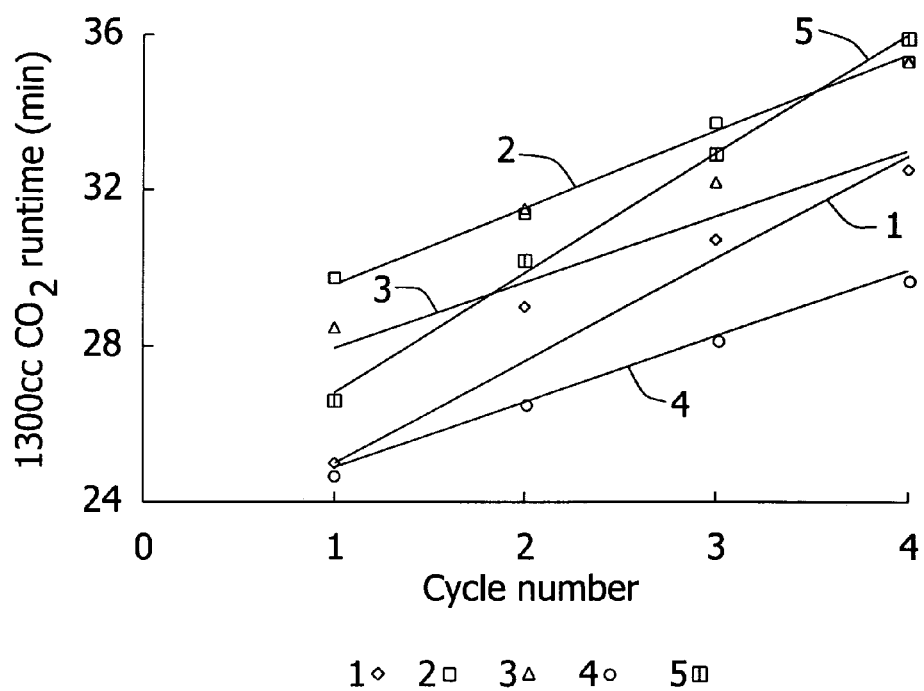
FIG. 12 shows carbon dioxide generation during PMIDA oxidation carried out as described in Example 20.

Each of the catalysts was tested in PMIDA oxidation under the conditions described in Example 10 over the course of four cycles. The time required to generate 1300 cm$^3$ of $CO_2$ was determined for each of the cycles using each of the catalysts. For comparison purposes, a 1% by weight cobalt and 1.5% by weight cobalt catalyst, each prepared as described in Example 14, were also tested in this manner. The results are shown in FIG. 12. As shown in FIG. 12, the 1.5% cobalt catalyst had lower activity than the 1% cobalt catalyst but exhibited greater stability. The cobalt-cerium catalyst exhibited improved stability as compared to each of the cobalt catalysts but lower activity. Overall, the results indicated that the cobalt, cobalt-iron, and cobalt-cerium catalysts had similar formaldehyde oxidation activity.

HPLC results for the product when using the 1.5% cobalt catalyst and 1.5% cobalt/0.5% copper catalyst at 50 minutes of reaction time are set forth in Table 7. The carbon-supported cobalt-copper catalyst converted more formaldehyde to formic acid than the carbon-supported cobalt carbide-nitride catalyst.

TABLE 7

| | Cycle | PMIDA (%) | Gly (%) | FM (ppm) | FA (ppm) | IDA (%) | (M) AMPA (ppm) | NMG (ppm) | Iminobis (ppm) | $PO_4$ (ppm) | NFG (ppm) | Glycine (ppm) |
| --- | --- | --- | --- | --- | --- | --- | --- | --- | --- | --- | --- | --- |
| 1.5% Co | 1 | 0.013 | 4.22 | 1683 | 8476 | 0.007 | 842 | 355 | 232 | 309 | 1758 | 128 |
| | 2 | 0.016 | 4.45 | 1634 | 9261 | 0.009 | 795 | 269 | 244 | 376 | 2254 | 161 |
| | 3 | 0.016 | 4.47 | 1569 | 9665 | 0.010 | 696 | 322 | 242 | 416 | 2240 | 180 |
| | 4 | 0.015 | 4.39 | 1495 | 9516 | 0.009 | 622 | 266 | 238 | 427 | 2248 | 187 |
| 1.5% Co/.5% Cu | 1 | 0.009 | 4.27 | 1729 | 8930 | 0.007 | 1232 | 236 | 249 | 284 | 2134 | 134 |
| | 2 | 0.014 | 4.36 | 1442 | 9774 | 0.008 | 898 | 237 | 241 | 381 | 2314 | 182 |
| | 3 | 0.016 | 4.35 | 1302 | 9975 | 0.009 | 750 | 201 | 234 | 444 | 2371 | 209 |
| | 4 | 0.014 | 4.25 | 1237 | 9661 | 0.010 | 626 | 214 | 231 | 469 | 2181 | 214 |

EXAMPLE 21

This example details use of a 1:1 mixture (0.21 g) of a 5% Pt/0.5% Fe catalyst prepared in accordance with U.S. Pat. No. 6,417,133 to Ebner et al. (0.105 g) and a carbon-supported catalyst containing 1% by weight cobalt prepared as described above in Example 13 using acetonitrile (0.105 g) in PMIDA oxidation. The catalyst mixture was tested in PMIDA oxidation under the conditions set forth in Example 10 over the course of six reaction cycles.

For comparison purposes, a 5% Pt/0.5% Fe catalyst prepared in accordance with U.S. Pat. No. 6,417,133 to Ebner et al. (0.21 g) was also tested in PMIDA oxidation under the conditions set forth in Example 10 over the course of six reaction cycles.

The maximum $CO_2$ proportion in the exit gas, total $CO_2$ generated during each of the reaction cycles, remaining formaldehyde content in the reaction mixture, formic acid content in the reaction mixture, and platinum leaching are summarized below in Table 8.

TABLE 8

| Catalyst | Cycle No. | $CO_2$ % Max in offgas | Total $CO_2$ after 50 min (cc) | FM (ppm) | FA (ppm) | Pt Leaching (ppm) |
|---|---|---|---|---|---|---|
| 6,417,133 catalyst (0.21 g) | 1 | 39.37 | 1987 | 2021 | 3341 | 0.01 |
|  | 2 | 35.58 | 1921 | 2016 | 3736 | 0.02 |
|  | 3 | 35.92 | 1897 |  |  |  |
|  | 4 | 34.72 | 1852 | 2357 | 4164 | 0.02 |
|  | 5 | 33.38 | 1836 |  |  |  |
|  | 6 | 32.94 | 1800 | 2485 | 4078 | 0.02 |
| 50/50 mixture (0.21 g) | 1 | 40.3 | 1736 | 1900 | 5986 | <0.01 |
|  | 2 | 37.36 | 1650 |  |  |  |
|  | 3 | 32.71 | 1538 | 1738 | 6985 | 0.01 |
|  | 4 | 27.59 | 1535 |  |  |  |
|  | 5 | 24.61 | 1499 | 1228 | 8280 | 0.01 |
|  | 6 | 22.65 | 1424 |  |  |  |

The catalyst mixture performed similarly to the 5% Pt/0.5% Fe catalyst in the first cycle except the catalyst mixture exhibited a lower cumulative $CO_2$ number, possibly due to less oxidation of formic acid. During the remaining cycles, the catalyst mixture performed in a similar manner to the 1% by weight cobalt catalyst (based on the results set forth in, for example, Example 14) and exhibited deactivation with the accumulation of formic acid. Metal analysis showed minimal Pt leaching, indicating the platinum had been deactivated.

EXAMPLE 22

Various carbon-supported cobalt carbide-nitride catalysts were prepared in accordance with the process described above in Example 13 generally by varying the atmosphere introduced to the reactor.

Methane/hydrogen reactor environment: A 1% by weight cobalt catalyst was prepared as described in Example 13 under a methane/hydrogen environment; catalyst precursor (5.0 g) was treated in the reactor using a flow of 100 cm³/minute of a 50%/50% (v/v) mixture of methane and hydrogen.

Ammonia reactor environment: A 1% by weight cobalt catalyst was prepared as described in Example 13 under an ammonia environment; catalyst precursor (5.0 g) was treated in the reactor using a flow of 50 cm³/minute $NH_3$ and 100 cm³/minute of argon.

Ammonia reactor environment: A 1% by weight cobalt catalyst was prepared as described in Example 13 under an ammonia environment; catalyst precursor (5.0 g) was treated in the reactor using a flow of 50 cm³/minute $NH_3$, 20 cm³/minute hydrogen, and 100 cm³/minute of argon.

Ammonia/methane reactor environment: A 1% by weight cobalt catalyst was prepared as described in Example 13 under an $NH_3/CH_4$ environment; catalyst precursor (5.0 g) was treated in the reactor using a flow of 25 cm³/minute $NH_3$, 25 cm³/minute of a 50%/50% (v/v) mixture of hydrogen/methane, and 100 cm³/minute of argon.

Acetonitrile reactor environment: A 1% by weight cobalt catalyst was prepared as described in Example 13 under an acetonitrile-containing environment; catalyst precursor (5.0 g) was treated in the reactor using a flow of 100 cm³/minute argon and approximately 10 cm³/minute of acetonitrile vapor.

Butylamine reactor environment: A 1% by weight cobalt catalyst was prepared as described in Example 13 under a butylamine-containing environment; catalyst precursor (5.0 g) was treated in the reactor using a flow of 100 cm³/minute argon and approximately 15 cm³/minute of butylamine vapor.

Pyridine reactor environment: A 1% by weight cobalt catalyst was prepared as described in Example 13 under a pyridine-containing environment; catalyst precursor (5.0 g) was treated in the reactor using a flow of 100 cm³/minute argon and approximately 3 cm³/minute of pyridine vapor.

Pyrrole reactor environment: A 1% by weight cobalt catalyst was prepared as described in Example 13 under a pyrrole-containing environment; catalyst precursor (5.0 g) was treated in the reactor using a flow of 100 cm³/minute argon and approximately 2 cm³/minute of pyrrole vapor.

Picolonitrile reactor environment: A 1% by weight cobalt catalyst was prepared as described in Example 13 under a picolonitrile-containing environment; catalyst precursor (5.0 g) and picolonitrile (3 g) were treated in the reactor using a flow of 100 cm³/minute argon.

Melamine reactor environment: A 1% by weight cobalt catalyst was prepared as described in Example 13 under a melamine-containing environment; catalyst precursor (5.0 g) and melamine (1 g) were treated in the reactor using a flow of 100 cm³/minute argon.

A carbon-supported cobalt containing catalyst was prepared using an organometallic compound (cobalt(II)phthalocyanine). A particulate carbon support (5.0 g) having a Langmuir surface area of approximately 1500 m²/g and acetone (200 ml) (Aldrich, Milwaukee, Wis.) were added to a 1 liter flask to form a slurry. Cobalt(II)phthalocyanine (0.490 g) was dissolved in acetone (200 ml) contained in a 1 liter flask. The cobalt-containing solution was added to the carbon support slurry over the course of approximately 30 to 40 minutes. The resulting mixture was stirred using a mechanical stirring rod at 50% output at approximately 20° C. for approximately 48 hours under a nitrogen blanket. The mixture was filtered and dried in a vacuum oven for approximately 16 hours at approximately 120° C. under a small nitrogen flow of approximately 20 cm³/minute. The resulting precursor contained approximately 1% by weight cobalt. Dried catalyst precursor (5.0 g) was charged to the Hastelloy C tube reactor described in Example 9 via a thermocouple inserted into the center of the reactor. The reactor was purged with argon introduced at a rate of approximately 100 cm³/minute at approximately 20° C. for approximately 15 minutes. After the precursor was charged to the reactor, the temperature of the reactor was increased to approximately 950° C. over the course of approximately 45 minutes under a flow of argon of 100 cc/min. The temperature of the reactor was maintained at approximately 950° C. for approximately 120 minutes. The resulting catalyst contained approximately 1% by weight cobalt.

EXAMPLE 23

This example details the results of PMIDA oxidations carried out under the conditions described in Example 10 using each of the catalysts prepared as described in Example 22. The results are shown in Table 9.

TABLE 9

| Catalyst | C and/or N sources | Cat. charge (g) | $CO_2$ % Max in offgas | Total $CO_2$ % after 50 min (cc) | PMIDA (%) | Gly (%) | FM (ppm) | FA (ppm) |
|---|---|---|---|---|---|---|---|---|
| 1% CoC/C | 50/50 $CH_4/H_2$ gas | 0.21 | 6.89 | 450 | | | | |
| | | 0.84 | 17.68 | 1246 | 0.962 | 3.19 | 1021 | 6180 |
| 1% CoCN/C | $NH_3$ | 0.21 | 10.38 | 689 | | | | |
| | | 0.84 | 29.33 | 1658 | 0.049 | 3.65 | 651 | 9119 |
| 1% CoCN/C | $NH_3 + H_2$ | 0.21 | 8.24 | 556 | | | | |
| | | 0.84 | 18.48 | 1389 | 0.607 | 3.23 | 530 | 7224 |
| 1% CoCN/C | $CH_4/H_2 + NH_3$ | 0.21 | 15.97 | 1231 | 1.116 | 2.72 | 1143 | 6139 |
| 1% CoCN/C | $CH_3CN$ | 0.21 | 34.6 | 1650 | 0.016 | 3.81 | 1551 | 8243 |
| 1% CoCN/C | Butylamine ($C_4H_{11}N$) | 0.21 | 28.96 | 1625 | 0.04 | 3.74 | 1035 | 8348 |
| 1% CoCN/C | Pyridine ($C_5H_5N$) | 0.21 | 28.9 | 1608 | 0 | 3.52 | 669 | 8783 |
| 1% CoCN/C | Pyrrole ($C_4H_5N$) | 0.21 | 25.39 | 1622 | 0 | 3.31 | 500 | 8971 |
| 1% CoCN/C | Picolinonitrile ($C_6H_4N_2$) | 0.21 | 38.03 | 1577 | 0.08 | 3.28 | 866 | 7715 |
| 1% CoCN/C | Melamine ($C_3H_6N_6$) | 0.21 | 44.69 | 1712 | 0.017 | 3.43 | 2557 | 6624 |
| 1% CoCN/C | Cobalt phthalocyanine ($C_{32}H_{16}N_8$)Co | 0.21 | 32.83 | 1620 | 0.054 | 3.78 | 895 | 8791 |

As shown in Table 9, catalysts prepared using $CH_4/H_2$, $NH_3$, $NH_3$ and $H_2$, and $CH_4/H_2$ and $NH_3$ exhibited lower activity as compared to catalysts made from $CH_3CN$, butylamine, pyridine, pyrrole, picolinonitrile, melamine, and cobalt phthalocyanine. Each cobalt catalyst exhibited formaldehyde oxidation activity when the reaction was driven to greater than 80% PMIDA conversion.

EXAMPLE 24

This example details preparation of cobalt-containing catalysts having varying metal loadings and their use in PMIDA oxidation.

Each catalyst was prepared using an acetonitrile environment in accordance with the procedure set forth above in Example 22 and tested in PMIDA oxidation under the conditions described in Example 10. The results are shown in Table 10.

TABLE 10

| Catalyst | Calcination Temp. (° C.) | Calcination time (hr) T | Cycle # | $CO_2$ % Max in offgas | Total $CO_2$ at 50 min (cc) | PMIDA (%) | Gly (%) | FM (ppm) | FA (ppm) |
|---|---|---|---|---|---|---|---|---|---|
| 1.0% CoCN/C | 950 | 2 | 1 | 36.59 | 1557 | 0.016 | 3.81 | 1551 | 8243 |
| | | | 2 | 31.9 | 1514 | 0.017 | 3.86 | 1316 | 8669 |
| | | | 3 | 29.8 | 1521 | 0.021 | 4.03 | 1263 | 9174 |
| | | | 4 | 28.18 | 1533 | 0.017 | 4.05 | 1239 | 9340 |
| 1.0% CoCN/C | 950 | 2 | 1 | 39.24 | 1678 | 0.046 | 3.46 | 1577 | 6908 |
| 1.5% CoCN/C | 950 | 2 | 1 | 38.45 | 1611 | 0.013 | 4.22 | 1683 | 8476 |
| | | | 2 | 33.63 | 1571 | 0.016 | 4.45 | 1634 | 9261 |
| | | | 3 | 31.97 | 1556 | 0.016 | 4.47 | 1569 | 9665 |
| | | | 4 | 30.97 | 1550 | 0.015 | 4.39 | 1495 | 9516 |
| 1.5% C0CN/C | 950 | 3 | 1 | 31.28 | 1544 | 0.013 | 4.08 | 2029 | 7825 |
| | | | 2 | 30.69 | 1509 | 0 | 4.14 | 1836 | 8487 |
| | | | 3 | 28.24 | 1490 | 0 | 4.11 | 1758 | 8595 |
| 2.0% CoCN/C | 950 | 2 | 1 | 36.89 | 1532 | 0.010 | 4.18 | 1628 | 8781 |
| | | | 2 | 32.41 | 1522 | 0.015 | 4.42 | 1361 | 9711 |
| 5.0% CoCN/C | 950 | 2 | 1 | 34.12 | 1627 | 0.017 | 3.49 | 1095 | 8232 |
| | | | 2 | 28.94 | 1606 | 0.018 | 3.85 | 1067 | 9234 |
| | | | 3 | 26.38 | 1595 | 0.017 | 3.79 | 1068 | 9142 |
| 5.0% CoCN/C | 950 | 4 | 1 | 34.22 | 1655 | 0.045 | 3.64 | 1315 | 7626 |
| 10% CoCN/C | 950 | 2 | 1 | 23.85 | 1615 | 0.066 | 3.58 | 1025 | 8200 |

As shown in Table 10, all carbon-supported cobalt carbide-nitride catalysts exhibited good PMIDA oxidation activity. The catalysts also demonstrated higher formaldehyde oxidation activity and much better stability compared to the carbon-supported iron carbide-nitride catalyst. The carbon-supported cobalt carbide-nitride catalyst containing 1-2% by weight cobalt exhibited the best overall reaction performance.

EXAMPLE 25

This example details the preparation of a carbon-supported iron-containing catalyst using iron tetraphenylporphyrin (FeTPP).

A carbon support (8.0 g) was added to a 1 liter flask and charged with 400 ml of acetone to form a slurry. A solution (200 ml) containing iron (III) tetraphenylporphyrin chloride (FeTPP) (2.0 g) in acetone was added drop wise to the carbon support slurry for approximately 30-40 minutes. The resulting mixture was then stirred at room temperature for approximately 48 hours under a nitrogen blanket. The mixture was then filtered and dried overnight in a vacuum oven at 120° C. under a small nitrogen flow. The resulting precursor was then heated in a continuous flow of argon at a temperature of approximately 800° C. for approximately 2 hours. The resulting catalyst contained approximately 1.1% by weight iron.

EXAMPLE 26

This example details testing of catalysts prepared in accordance Examples 9 and 25 in PMIDA oxidation under the conditions described in Example 10. Results are shown in Table 11.

All of the carbon-supported iron carbide-nitride catalysts suffered from catalyst deactivation. Both the maximum $CO_2$ concentration and the cumulative $CO_2$ decreased with subsequent reaction cycles. The catalyst synthesized from iron (III) tetraphenylporphyrin showed high PMIDA oxidation activity but lower activity toward the oxidation of formaldehyde and formic acid. The catalyst synthesized from $CH_3CN$ exhibited PMIDA oxidation activity and formaldehyde oxidation activity.

EXAMPLE 27

This examples details preparation of molybdenum and tungsten-containing catalysts in different carbiding environments and their use in PMIDA oxidation under the conditions described in Example 10.

Molybdenum and tungsten-containing catalysts of varying metal contents were prepared generally as described in Example 2 from precursors prepared as described in Example 1 using flows of various carbon and/or nitrogen sources of approximately 100 cm$^3$/min (including a 50%/50% (v/v) mixture of methane and hydrogen as described in Example 2). Each of the catalysts was tested in PMIDA oxidation under the conditions described in Example 10. The results are shown in Table 12.

TABLE 11

| Catalyst | C and N sources | Calcination Temp. (° C.) | Cycle | $CO_2$ % Max in offgas | Total $CO_2$ at 50 min (cc) | PMIDA (%) | Gly (%) | FM (ppm) | FA (ppm) |
| --- | --- | --- | --- | --- | --- | --- | --- | --- | --- |
| 0.5% FeCN/C | $CH_3CN$ | 850 | 1 | 33.24 | 1670 | 0.014 | 3.34 | 6281 | 1663 |
|  |  |  | 2 | 22.57 | 1515 |  |  |  |  |
| 0.5% FeCN/C | $CH_3CN$ | 950 | 1 | 33.34 | 1740 | 0.017 | 3.71 | 6169 | 1349 |
|  |  |  | 2 | 24.48 | 1555 |  |  |  |  |
| 0.75% FeCN/C | $CH_3CN$ | 850 | 1 | 31.15 | 1682 | 0.011 | 3.50 | 6162 | 1857 |
|  |  |  | 2 | 21.58 | 1477 |  |  |  |  |
| 1.0% FeCN/C | $CH_3CN$ | 850 | 1 | 25.93 | 1624 | 0 | 3.63 | 6115 | 1976 |
|  |  |  | 2 | 19.42 | 1344 | 0.355 | 3.50 | 4775 | 2156 |
|  |  |  | 3 | 17.68 | 1105 | 1.279 | 3.11 | 4285 | 1986 |
|  |  |  | 4 | 16.06 | 1005 | 1.721 | 2.92 | 3948 | 1925 |
| 2.0% FeCN/C | $CH_3CN$ | 850 | 1 | 21.56 | 1470 | 0.009 | 3.82 | 5010 | 2208 |
| 1.1% FeCN/C | FeTPP $Fe(C_{44}H_{28}N_4)Cl$ | 800 | 1 | 57.09 | 2150 | 0.014 | 2.98 | 7748 | 530 |
|  |  |  | 2 | 43.06 | 1708 | 0.017 | 3.07 | 7092 | 821 |
|  |  |  | 3 | 36.25 | 1597 | 0.018 | 3.38 | 6968 | 1028 |
|  |  |  | 4 | 31.84 | 1571 |  |  |  |  |

TABLE 12

| Catalyst | C (&N) source | Calcination Temp. (° C.) | Cat. charge (g) | $CO_2$ % Max in offgas | Total $CO_2$ at 50 min (cc) | PMIDA (%) | Gly (%) | FM (ppm) | FA (ppm) |
|---|---|---|---|---|---|---|---|---|---|
| 1% MoCN/C | $CH_3CN$ | 950 | 0.21 | 10.92 | 753 | | | | |
| | | | 0.63 | 22.53 | 1664 | 0.058 | 3.51 | 4281 | 3230 |
| 1% WCN/C | $CH_3CN$ | 950 | 0.21 | 11.8 | 684 | | | | |
| | | | 0.63 | 22.04 | 1638 | 0 | 3.52 | 3288 | 4534 |
| 10% $Mo_2C$/C | $CH_4 + H_2$ | 650 | 0.21 | 5.19 | 350 | | | | |
| | | | 1.05 | 12.51 | 870 | | | | |
| 10% $W_2C$/C | $CH_4 + H_2$ | 700 | 0.21 | 4.63 | 293 | | | | |
| | | | 1.05 | 15.07 | 1084 | 1.353 | 2.30 | 3100 | 1413 |
| 10% WC/C | $CH_4 + H_2$ | 850 | 0.21 | 4.21 | 284 | | | | |
| | | | 1.05 | 6.43 | 435 | 3.664 | 0.9 | 1271 | 561 |

The catalysts prepared using $CH_3CN$ treatment had superior PMIDA oxidation activity and formaldehyde oxidation activity as compared to the catalysts prepared by $CH_4/H_2$ treatment.

EXAMPLE 28

Various carbon-supported transition metal-containing catalysts and carbon supports were analyzed to determine their total Langmuir surface area, Langmuir surface area attributed to pores having a diameter less than 20 Å (i.e., micropores), and Langmuir surface area attributed to pores having a diameter greater than 20 Å (i.e., mesopores and micropores). The surface area and pore volume analyses were carried out using a Micromeritics 2010 Micropore analyzer with a one-torr transducer and a Micromeritics 2020 Accelerated Surface Area and Porosimetry System, also with a one-torr transducer. These analysis methods are described in, for example, Analytical Methods in fine Particle Technology, First Edition, 1997, Micromeritics Instrument Corp.; Atlanta, Ga. (USA); and Principles and Practice of Heterogeneous Catalysis, 1997, VCH Publishers, Inc; New York, N.Y. (USA).

Catalysts and supports analyzed included: the carbon support described above in Example 8 having a total Langmuir surface area of approximately 1500 m²/g, a 1% FeCN/C catalyst prepared in accordance with Example 9, a 1% CoCN/C catalyst prepared in accordance with Example 13, a carbon support having a total Langmuir surface area of approximately 1600 m²/g, and a 1.1% FeTPP/C catalyst prepared in accordance with Coleman et al., International Publication No. WO 03/068387 A1. The results are shown in Table 13.

TABLE 13

| Surface Area (SA) (m²/g) | Example 8 Support | 1% FeCN/C | 1% CoCN/C | Example 28 Support | 1.1% FeTPP/C |
|---|---|---|---|---|---|
| Overall SA | 1584 | 1142 | 1263 | 1623 | 888 |
| Micropore SA | 1329 | 937 | 1051 | 1365 | 717 |
| Meso- & Macropore SA | 256 | 205 | 212 | 258 | 171 |

Figure 13:
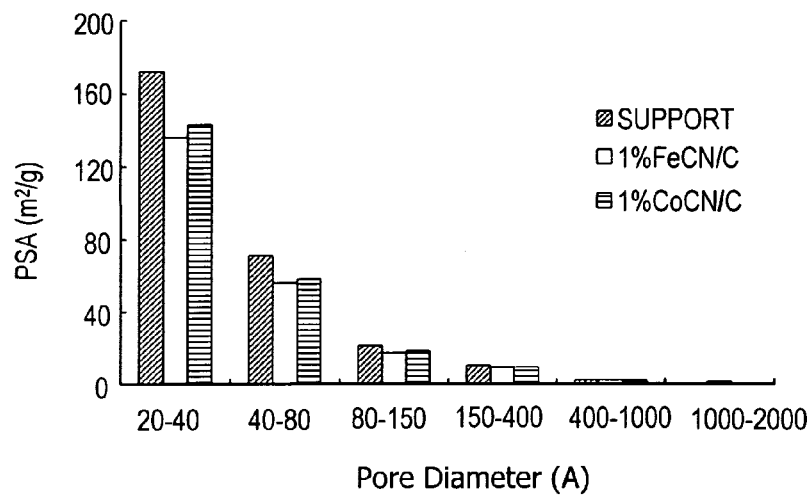
FIGS. 13-14 show a comparison of the pore surface area of various catalysts as described in Example 28.
Figure 14:
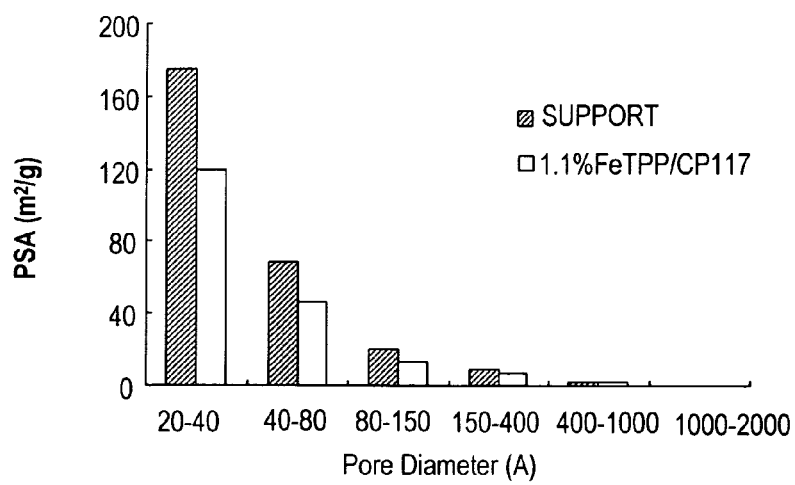
Figure 15:
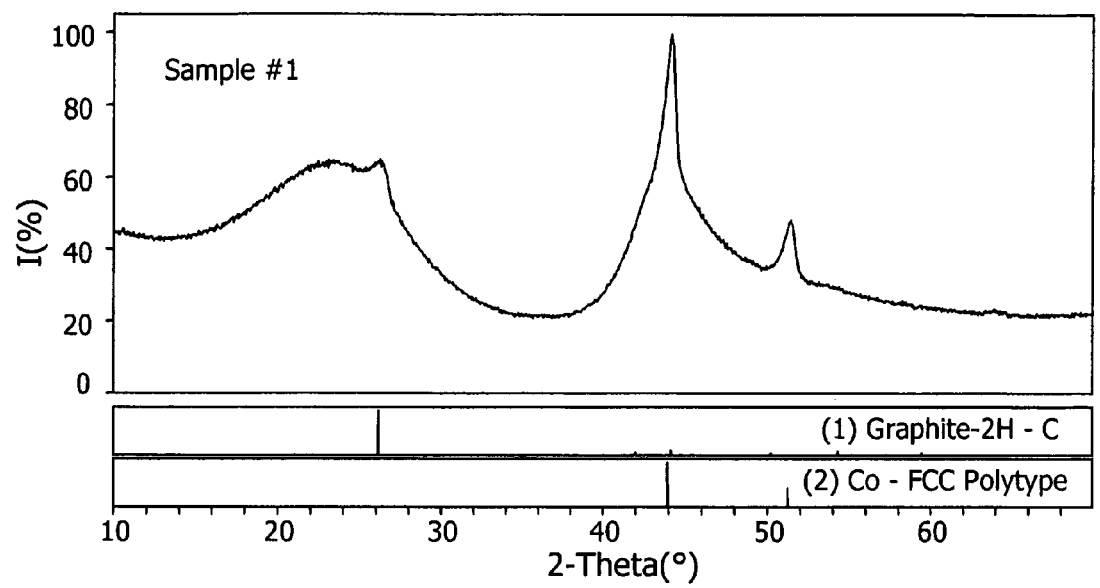
FIGS. 15-26 show X-ray diffraction (XRD) results for catalyst samples analyzed as described in Example 30.
Figure 16:
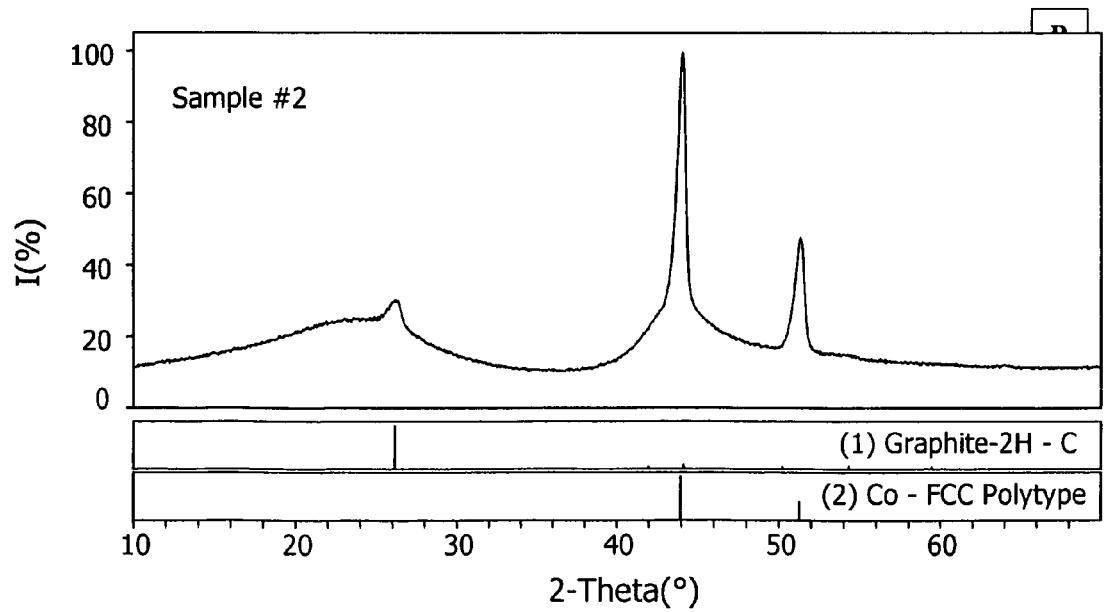
Figure 17:
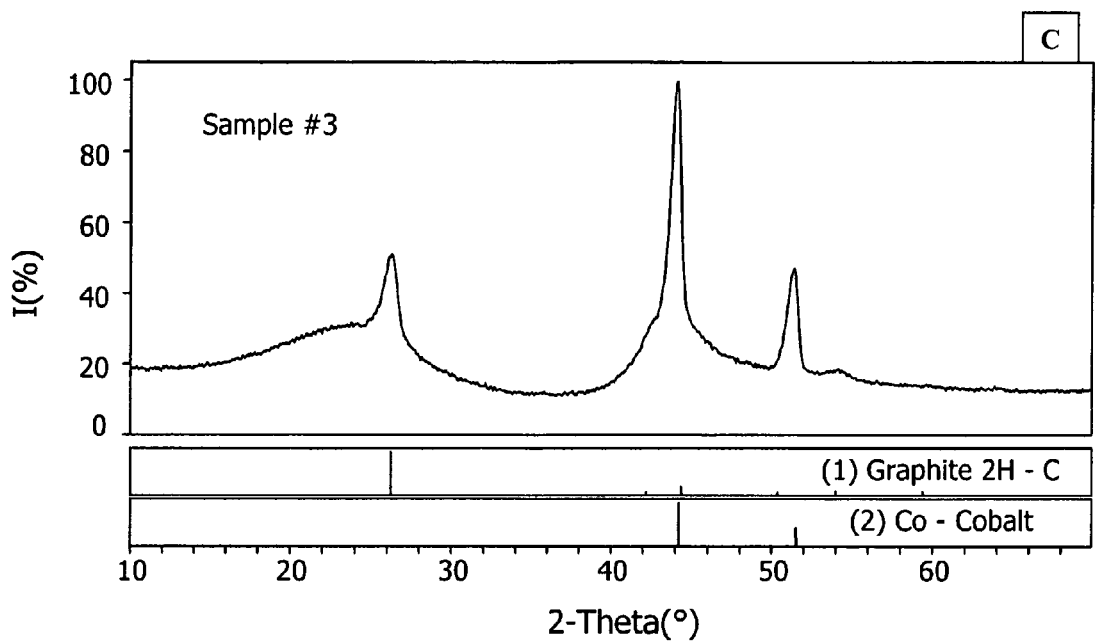
Figure 18:
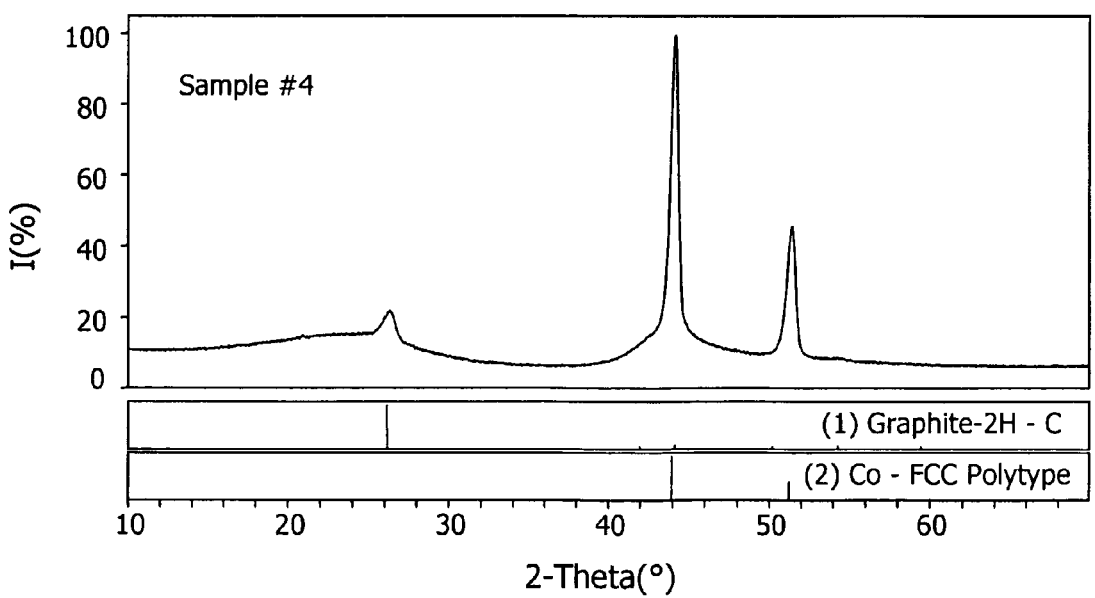
Figure 19:
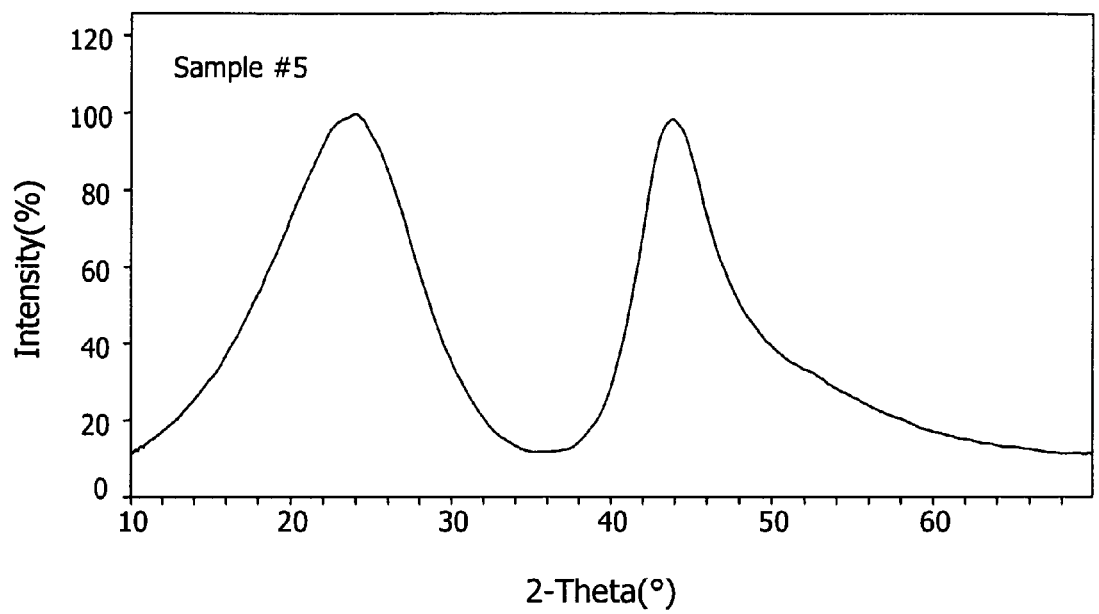
Figure 20:
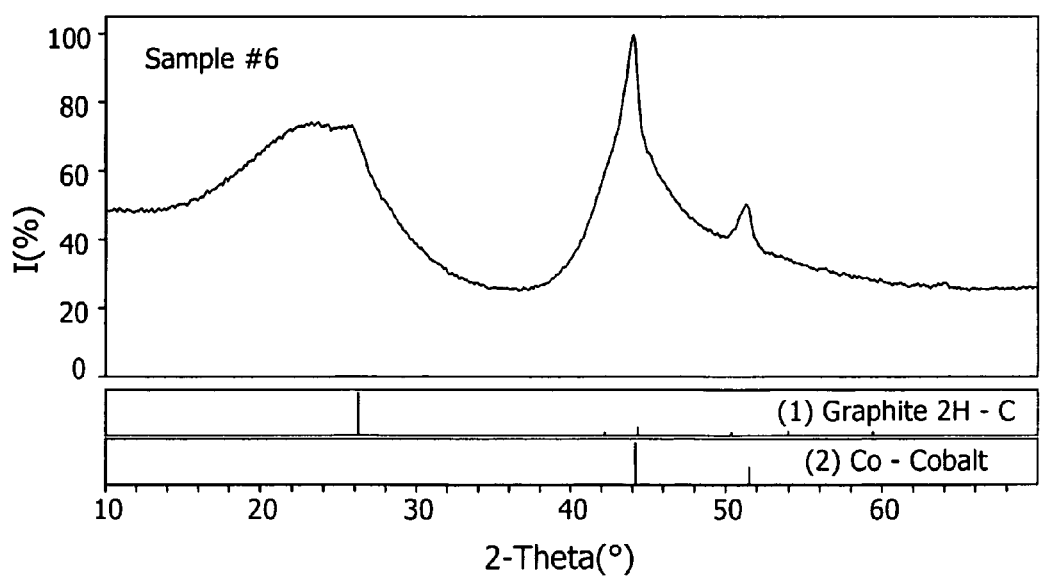
Figure 21:
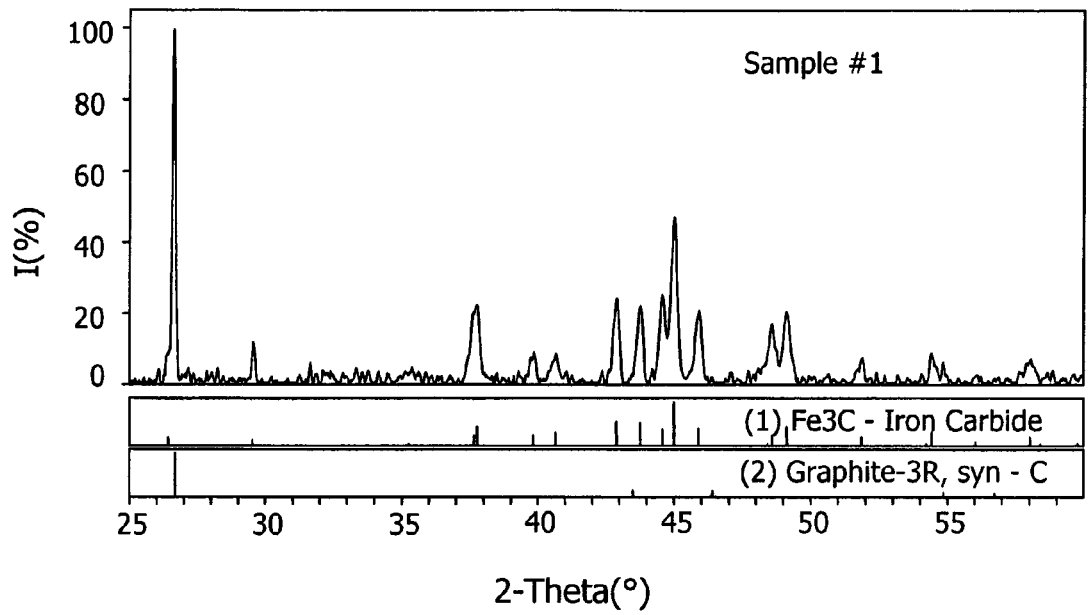
Figure 22:
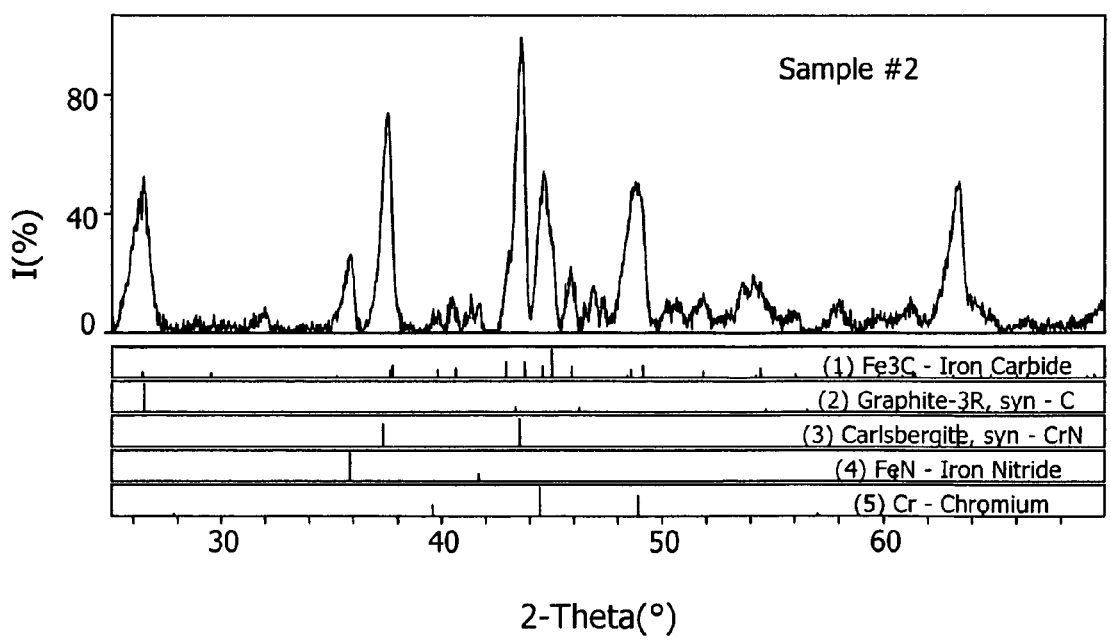

FIG. 13 shows a comparison of the pore surface area of the of the 1% Fe, 1% Co catalysts, and the carbon support. FIG. 14 compares the pore surface area of the 1.1% FeTPP catalyst and its carbon support. As shown in FIG. 13, the 1% Fe catalyst has a surface area approximately 80% the total surface area of its carbon support while the 1% Co catalyst has a surface area approximately 72% the total surface area of its carbon support. As shown in FIG. 14, the 1.1% FeTPP catalyst has a surface area approximately 55% of the total surface area of its carbon support.

EXAMPLE 29

1% CoCN/C and 1.5% CoCN/C catalysts prepared as described in Example 14 were analyzed by Inductively Coupled Plasma (ICP) analysis to determine their nitrogen and transition metal contents. The analysis was carried out using a Thermo Jarrell Ash (TJA), IRIS Advantage Duo View inductively coupled plasma optical emission spectrometer. The results are shown in Table 14.

TABLE 14

| | Co (wt. %) | N (wt. %) | C + O + H (wt. %) |
|---|---|---|---|
| Example 8 support | | <0.1% | |
| 1% CoCN/C | 1.0 | 1.4 | 97.6 |
| 1.5% CoCN/C | 1.5 | 1.7 | 96.8 |

EXAMPLE 30

This example details X-ray powder diffraction (XRD) analysis of various catalysts prepared under different conditions. The catalysts were generally prepared in accordance with the procedure set forth above in Example 9, 13, 22, or 25 above. The samples and conditions for their preparation are described below in Table 15.

TABLE 15

| Catalyst Sample | Processing conditions |
|---|---|
| 1) 1.5% CoCN/C | $CH_3CN$ treated at 950° C. for 2 hours |
| 2) 5% CoCN/C | $CH_3CN$ treated at 950° C. for 2 hours |
| 3) 5% CoCN/C | $CH_3CN$ treated at 950° C. for 4 hours |
| 4) 10% CoCN/C | $CH_3CN$ treated at 950° C. for 2 hours |
| 5) Example 8 support | $CH_3CN$ treated at 950° C. for 2 hours |
| 6) 1% Co-phthalocyanine (PLCN) CN/C | Argon treated at 950° C. for 2 hours |
| 7) 1.1% FeTPP/C | Argon treated at 800° C. for 2 hours |
| 8) 1% FeCN/C | $CH_3CN$ treated at 950° C. for 2 hours |

The powder samples were analyzed by placing them directly onto a zero background holder and then placing them directly into a Philips PW 1800 θ/θ diffractometer using Cu radiation at 40 KV/30 mA and equipped with a diffracted beam monochromator to remove the floursecent radiation from the cobalt.

The resulting diffraction patterns for samples 1-8 are shown in FIGS. 15-22, respectively. The diffraction patterns for samples 1-4, and 6 (FIGS. 15-18, and 20) detected graphite and the face centered cubic (FCC) form of cobalt. Particle size analysis of the cobalt and graphite phases was performed through broadening of the diffraction lines which is sensitive to particles in the 100 Å to 2000 Å range. The results are summarized below in Table 16.

TABLE 16

| Sample # | Particle Size (Å) | |
| --- | --- | --- |
| | FCC cobalt | Graphite |
| 1 | 122 | 101 |
| 2 | 145 | 100 |
| 3 | 125 | 83 |
| 4 | 153 | 110 |
| 6 | 120 | 77 |

The diffraction patterns for sample 7 (FIG. 21) detected graphite and iron carbide ($Fe_3C$). Particle size analysis provided a particle size of the graphite of >1000 Å and approximately 505 Å. The diffraction patterns for sample 8 (FIG. 22) detected graphite, chromium nitride (CrN), iron nitide (FeN), chromium, and iron carbide ($Fe_3C$). Particle size analysis provided a particle size of graphite of approximately 124 Å, chromium nitride of approximately 183 Å, and iron nitride of approximately 210 Å.

Figure 23:
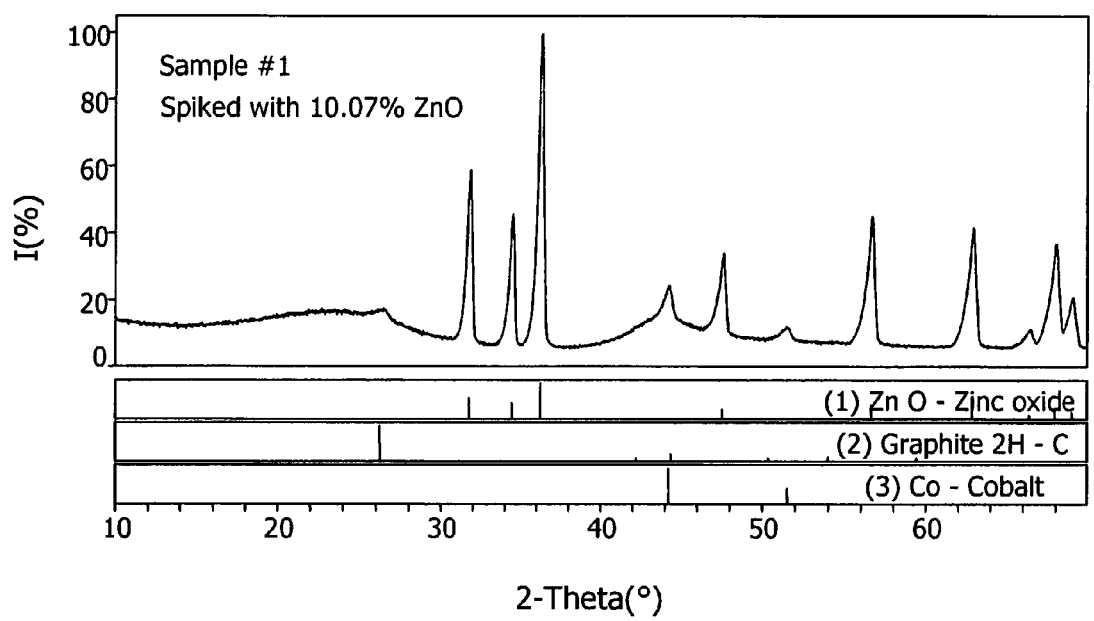
Figure 24:
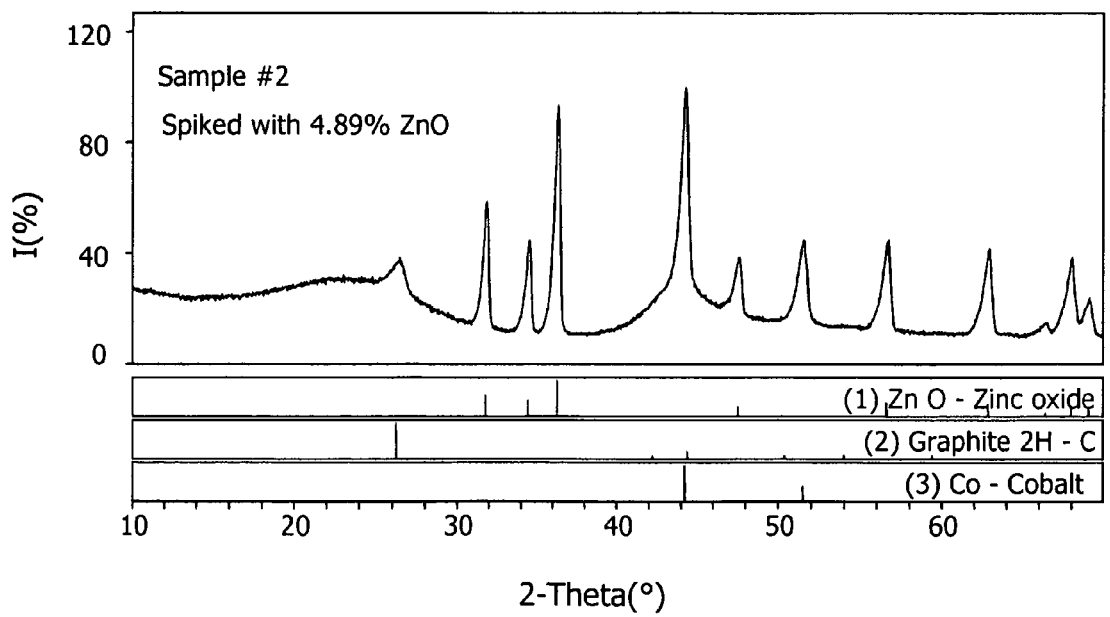

Quantitative analysis was carried out on Samples 1 and 2. The preferred internal standard was ZnO since it is well characterized and has no lines that overlap the peaks of interest. Approximately 100 mg of samples 1 and 2 were mixed with 10.7% ZnO (Sample 1) and 4.89% ZnO (Sample 2) and tested using the XRD procedure described above. The resulting diffraction for patterns for Samples 1 and 2 are provided in FIGS. 23 and 24, respectively.

Quantitative analysis was then carried out on Samples 1 and 2 using Rivetfeld refinement to determine the amount of each phase. The Rivetfeld refinement is a whole pattern-fitting program that computes a diffraction pattern based on first principles, compares it to the experimental pattern, computes an error between the two patterns, and then modifies the theoretical pattern until the residual error is minimized. In both cases, the Rivetfeld refinement gave low residual errors in the 5-7% range. The results of the Rivetfeld refinement are set forth below in Table 17.

TABLE 17

| Sample # | Weight Fractions (%) | |
| --- | --- | --- |
| | Cobalt (FCC) | Graphite |
| 1 | 1.2 +/− 0.2% | 4.2 +/− 0.3% |
| 2 | 3.7 +/− 0.3% | 4.6 +/− 0.2% |

An estimate of the weight fractions of Samples 3 and 6 are provided in Table 18.

TABLE 18

| Sample # | Weight Fractions (%) | |
| --- | --- | --- |
| | Cobalt (FCC) | Graphite |
| 3 | 3.0% | 12.0% |
| 6 | 0.5% | 1.4% |

Figure 25:
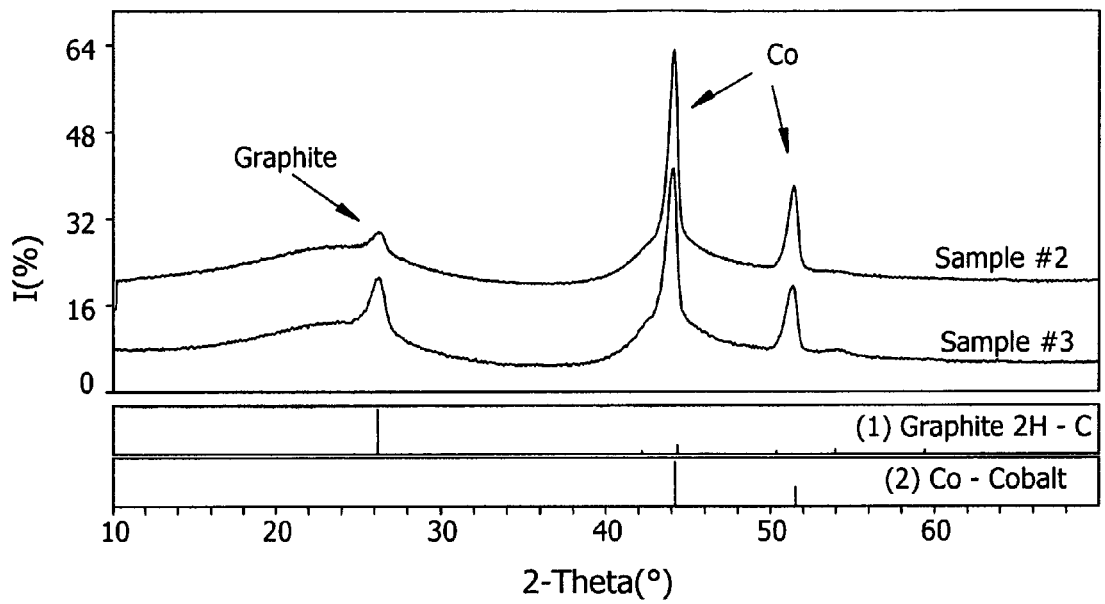
Figure 26:
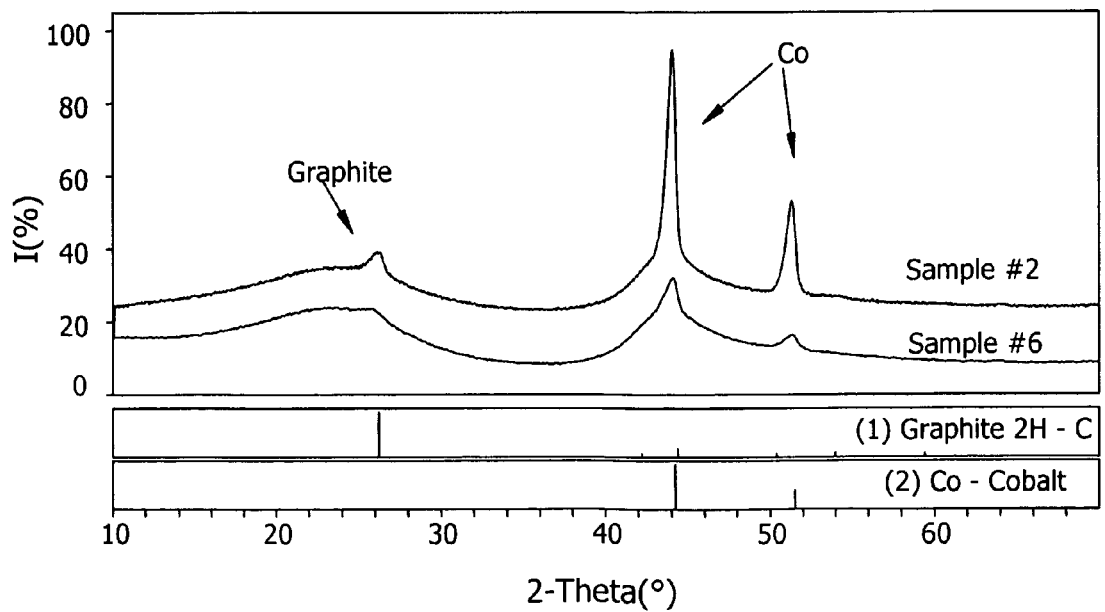

FIGS. 25 and 26 provide comparisons of the diffraction patterns of Samples 2 and 3, and Samples 3 and 6, respectively.

EXAMPLE 31

This example details scanning electron microscopy (SEM) and transmission electron microscopy (TEM) analysis of Samples 1, 2, 4, 7, and 8 described above in Example 30. The SEM analysis was performed using a JEOL (JEOL USA, Peabody, Mass.) JSM 6460LV scanning electron microscope operated at 30 kV. The TEM characterizations were carried out using a JEOL 1200 EX transmission electron microscope operated at 120 keV and/or JEOL 2000 EX TEM operated at 200 keV.

Figure 27:
FIGS. 27-37 are SEM images of catalyst samples analyzed as described in Example 31.
Figure 28:
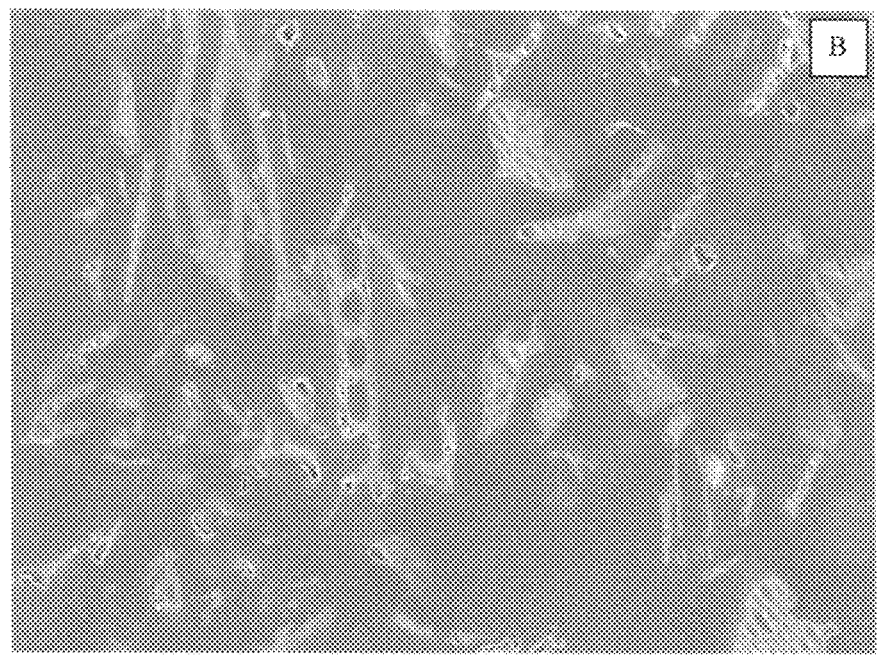
Figure 29:
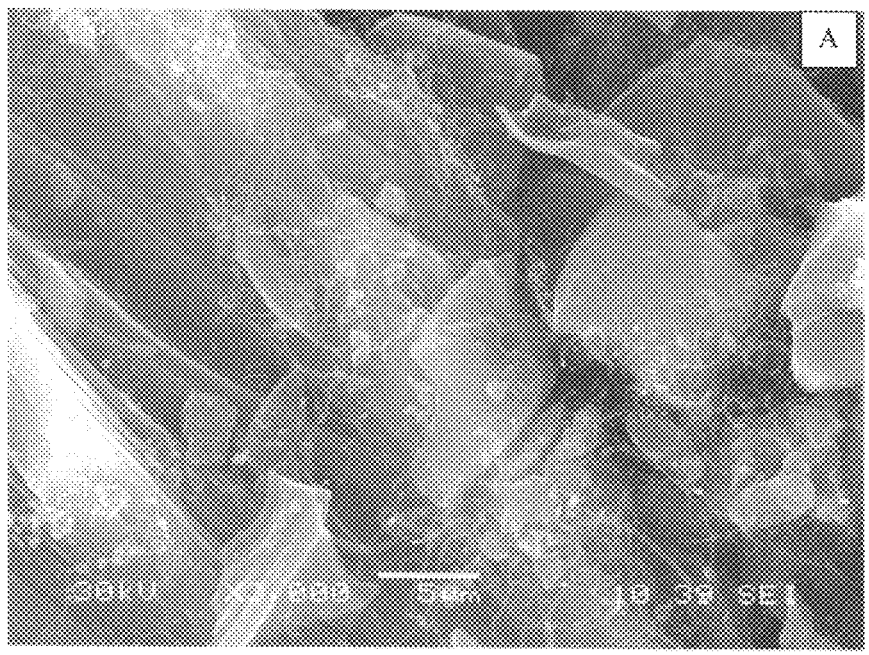
Figure 30:
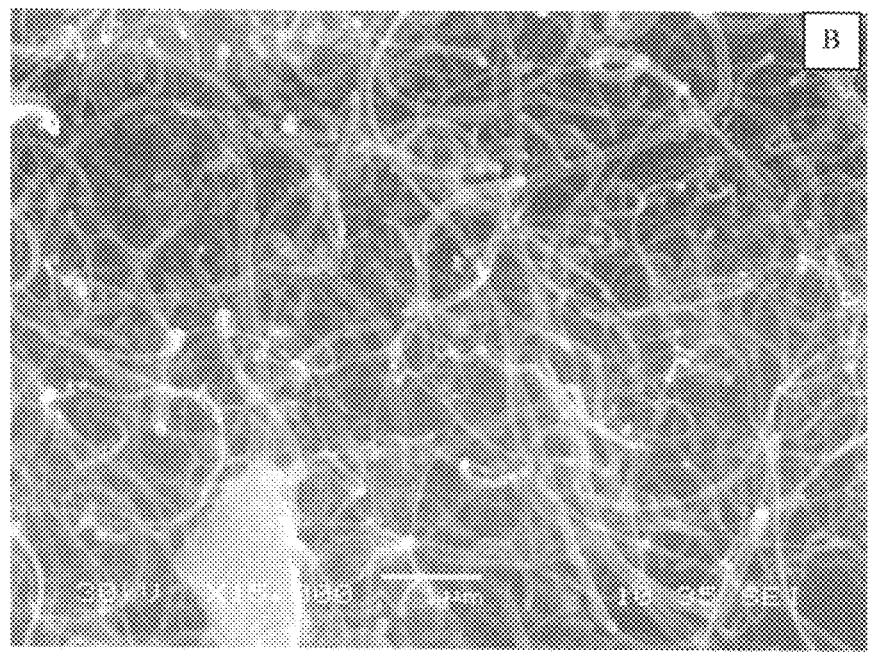
Figure 31:
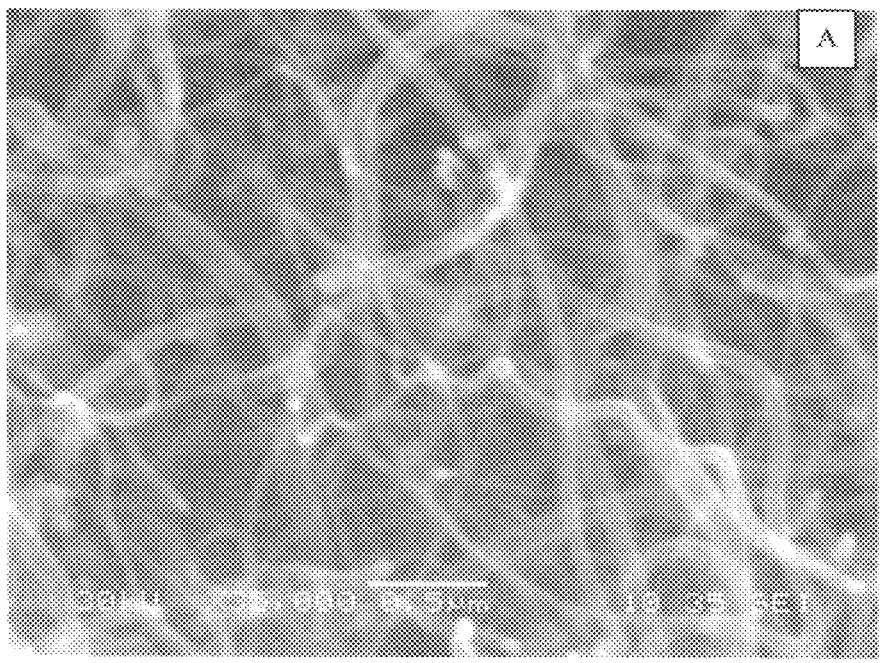
Figure 32:

FIGS. 27 and 28 are SEM images showing a view of the powder of Sample 1 and a cross-sectional view, respectively. FIGS. 29 and 30 are SEM images showing the distribution of carbon nanotubes on the surface of the carbon substrate and the morphology of the carbon nanotubes, respectively. FIGS. 31 and 32 are SEM images showing the carbon nanoutubes of the powder sample of Sample 1.

Figure 33:
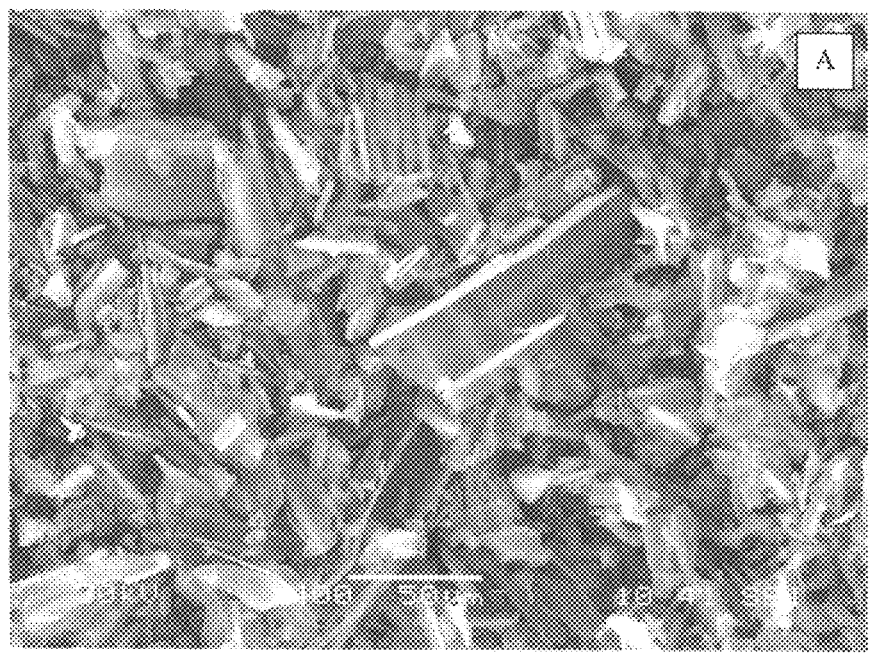
Figure 34:
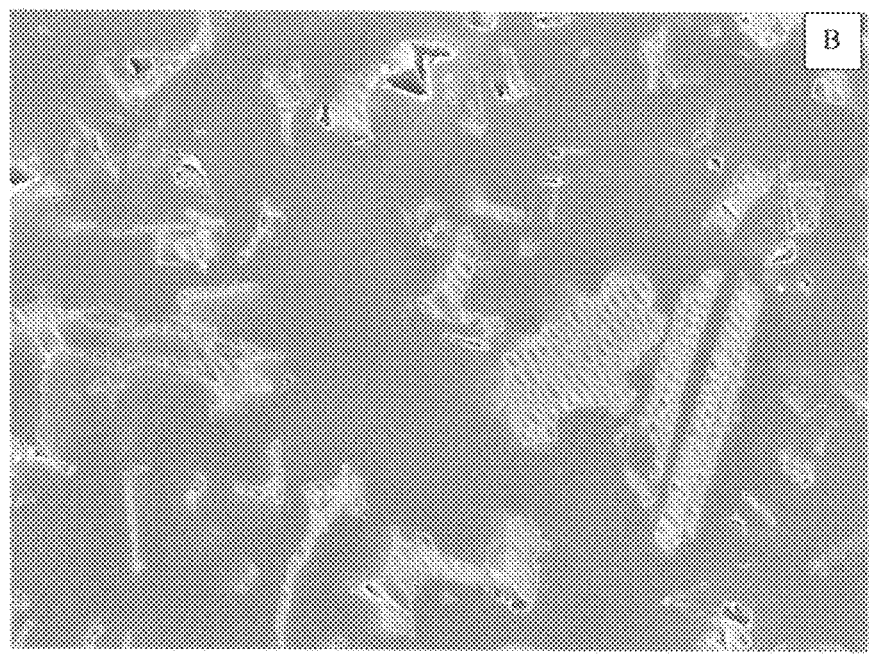
Figure 35:
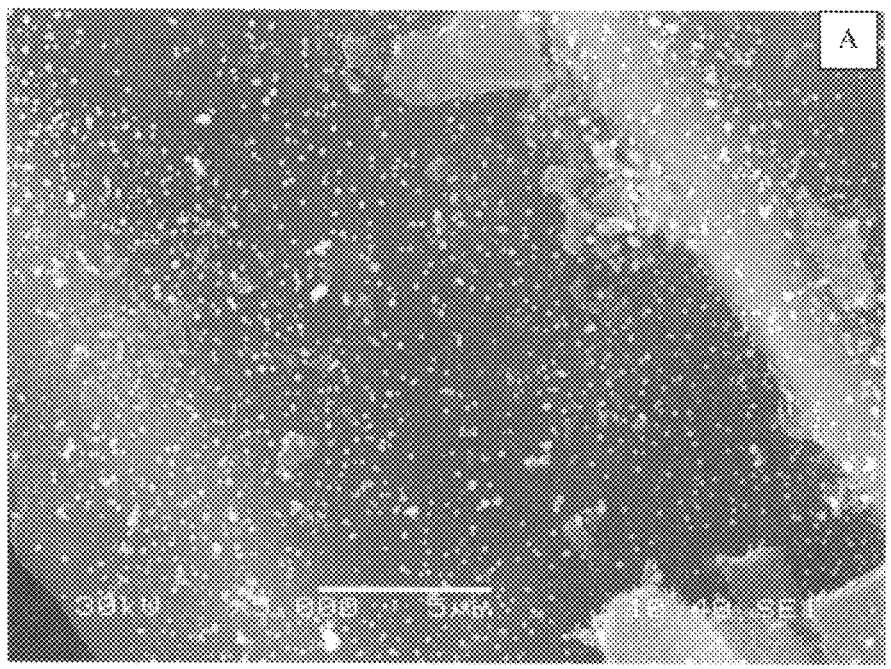
Figure 36:
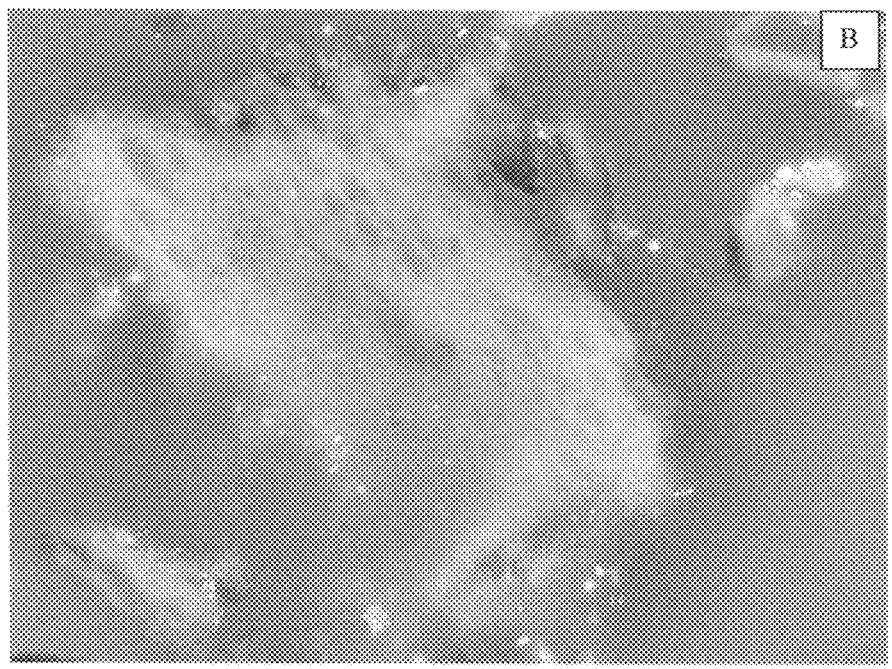
Figure 37:
Figure 38:
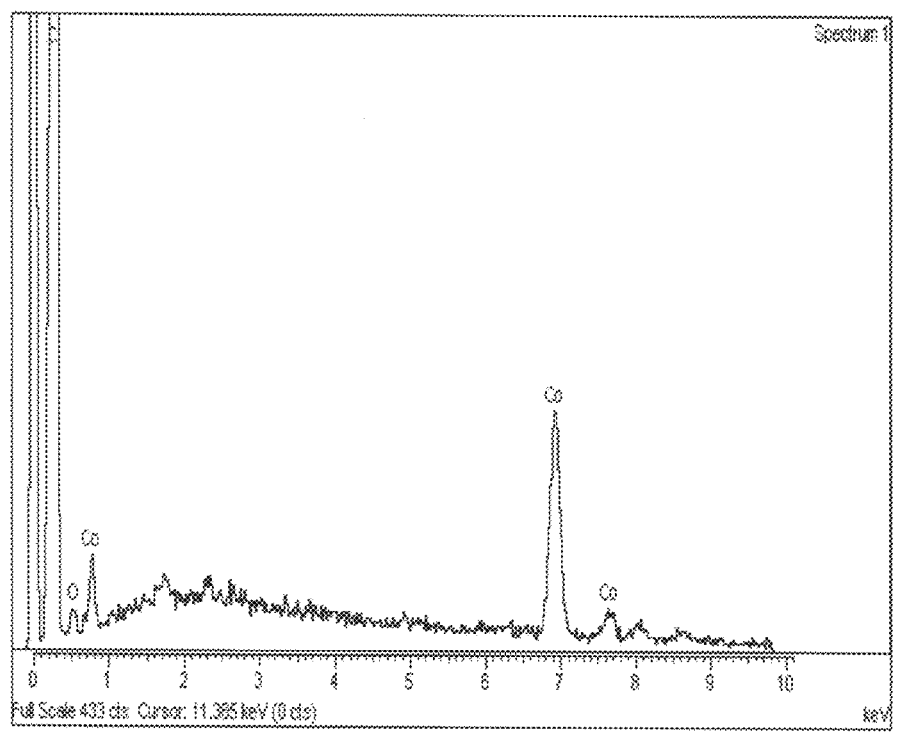
FIG. 38 is an Energy dispersive X-ray analysis spectroscopy (EDS) spectrum of a catalyst sample analyzed as described in Example 31.

FIGS. 33 and 34 are SEM images showing a view of the powder of Sample 2 and a cross-sectional view, respectively. FIGS. 35 and 36 are SEM images showing the distribution of the cobalt particles on the powder sample of Sample 2 and cross-sectional view, respectively. FIG. 37 is an SEM image showing the carbon nanotubes on the surface of the carbon support. FIG. 38 is an Energy dispersive X-ray analysis spectroscopy (EDS) spectrum of the powder sample of Sample 2. The EDS spectrum of Sample 2 was determined using an Oxford energy dispersive X-ray spectroscopy system.

Figure 39:
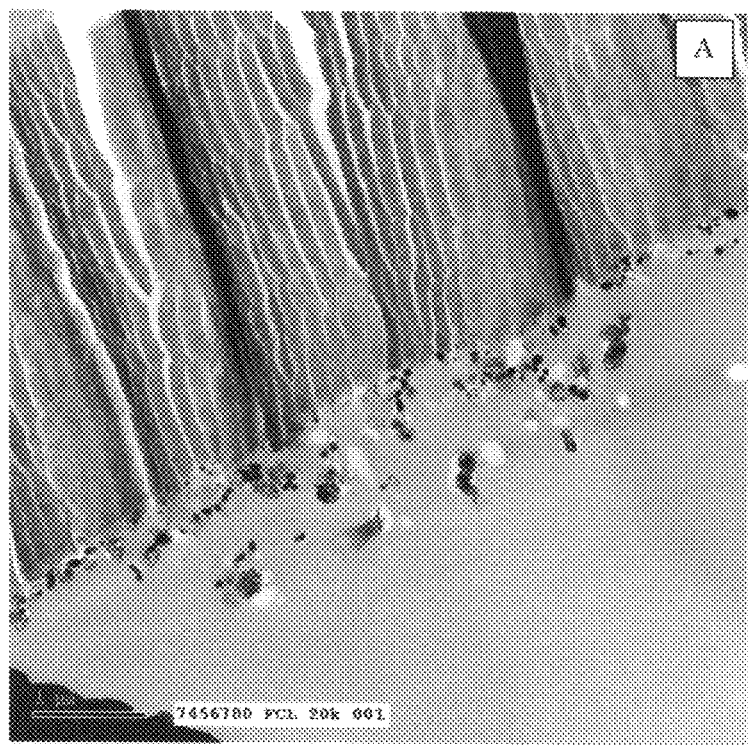
FIGS. 39 and 40 are TEM images of catalyst samples analyzed as described in Example 31.
Figure 40:
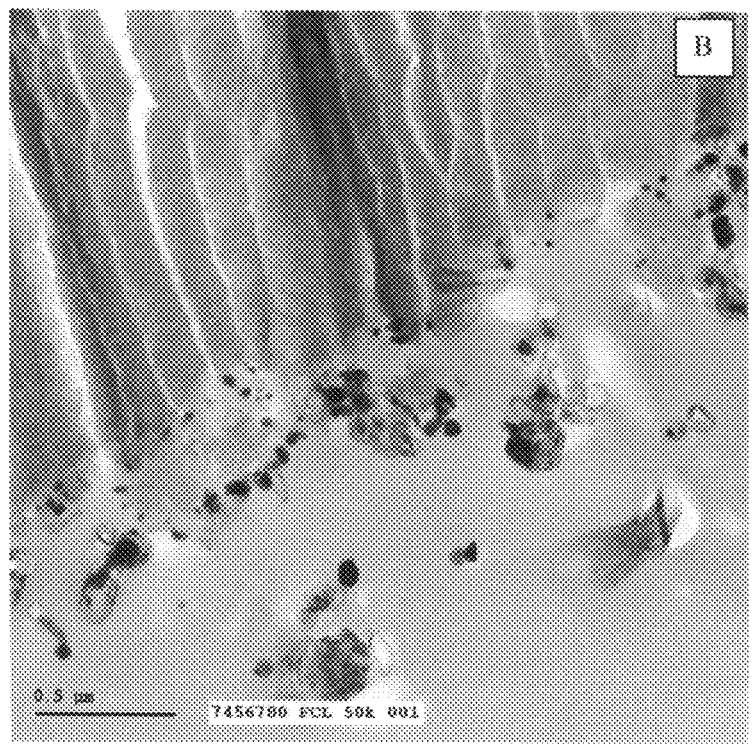
Figure 41:
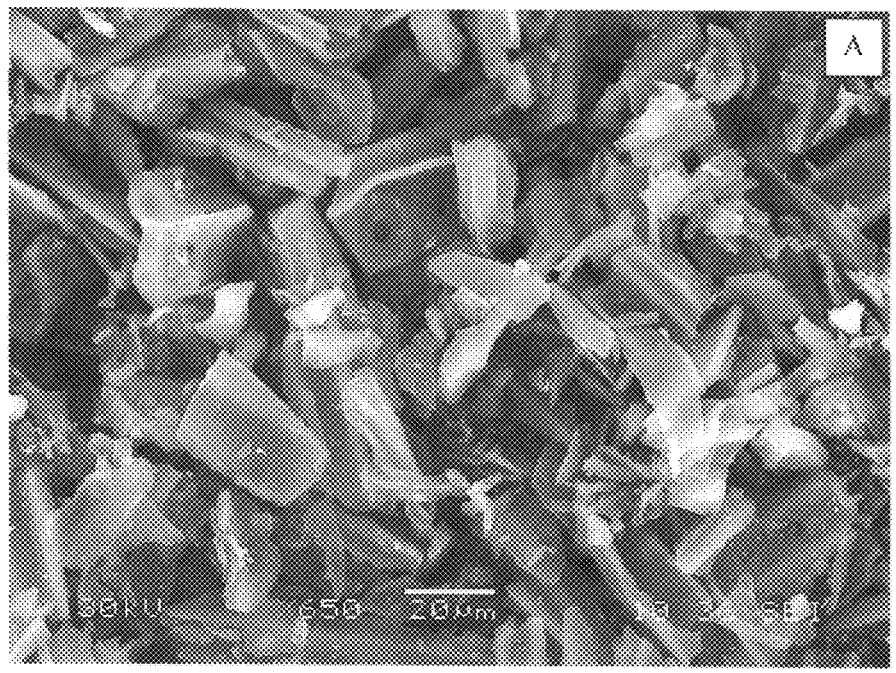
FIGS. 41 and 42 are SEM Images of catalyst samples analyzed as described in Example 31.
Figure 42:
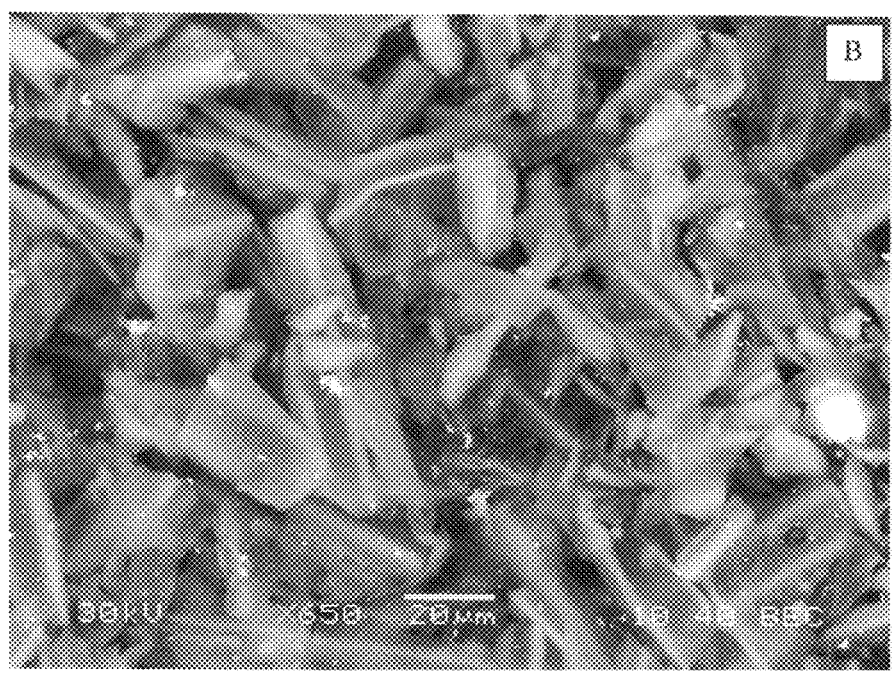
Figure 43:
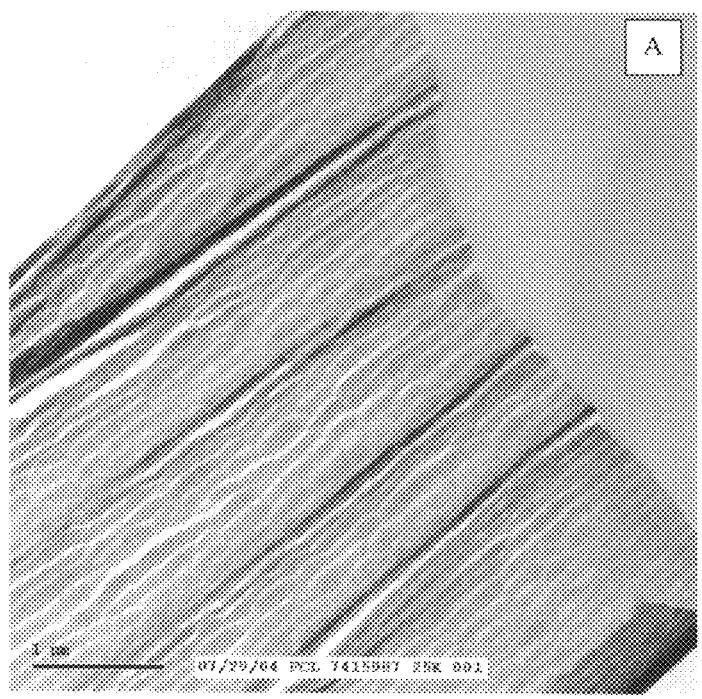
FIGS. 43 and 44 are TEM images of catalyst samples analyzed as described in Example 31.
Figure 44:
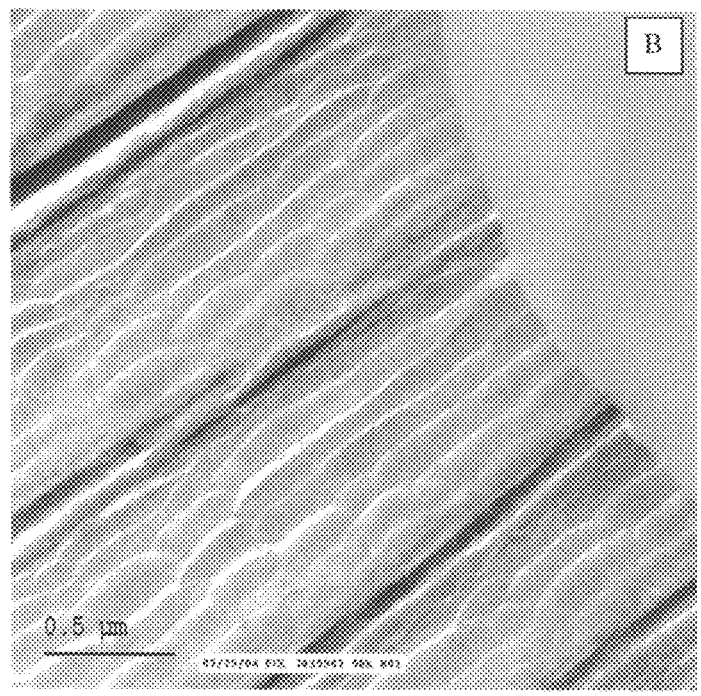

FIGS. 39 and 40 are TEM image images of Sample 4 at low and high magnification, respectively. FIG. 41 is an SEM image of a powder sample of Sample 7. FIG. 42 is a backscattered electron image of the powder sample of Sample 7. FIGS. 43 and 44 are TEM images showing a cross-sectional view of Sample 7.

Figure 45:
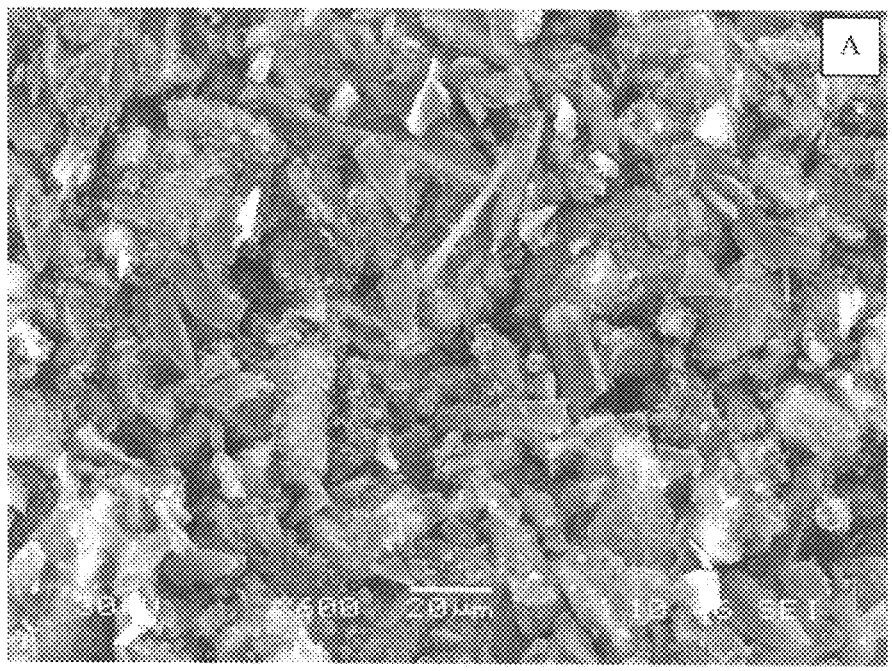
FIGS. 45-48 are SEM Images of catalyst samples analyzed as described in Example 31.
Figure 46:
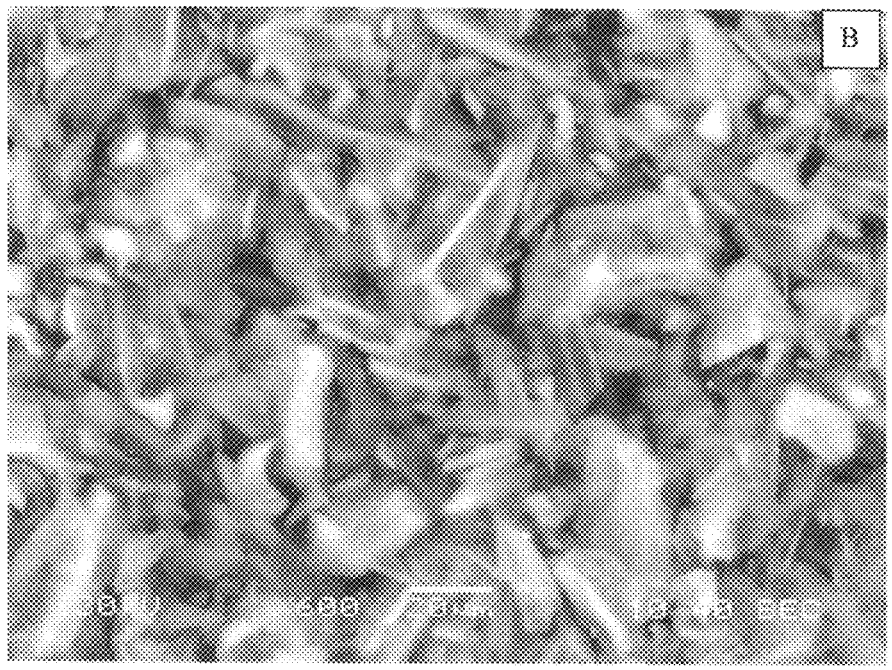
Figure 47:
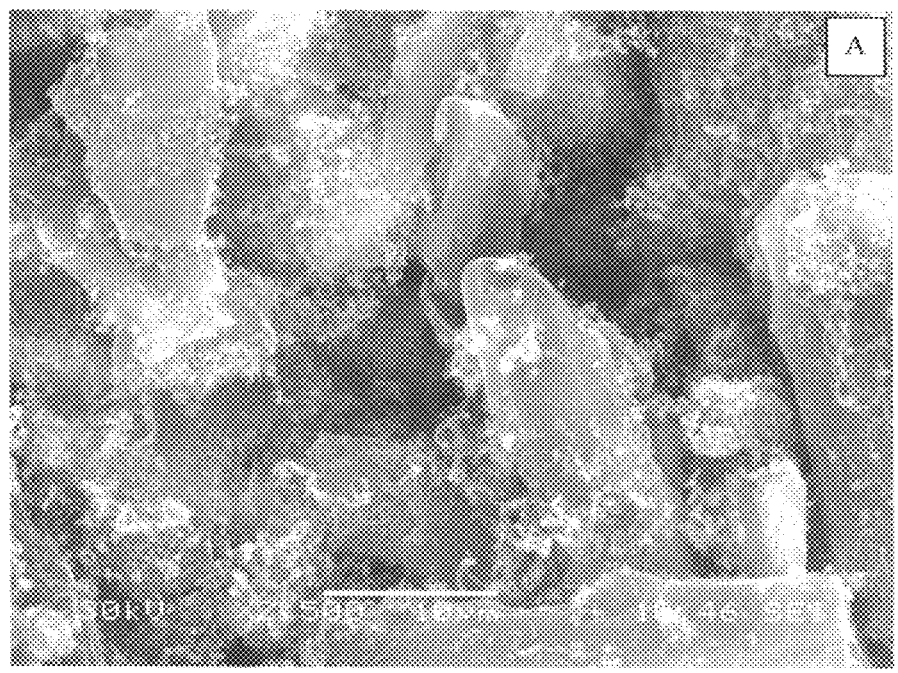
Figure 48:
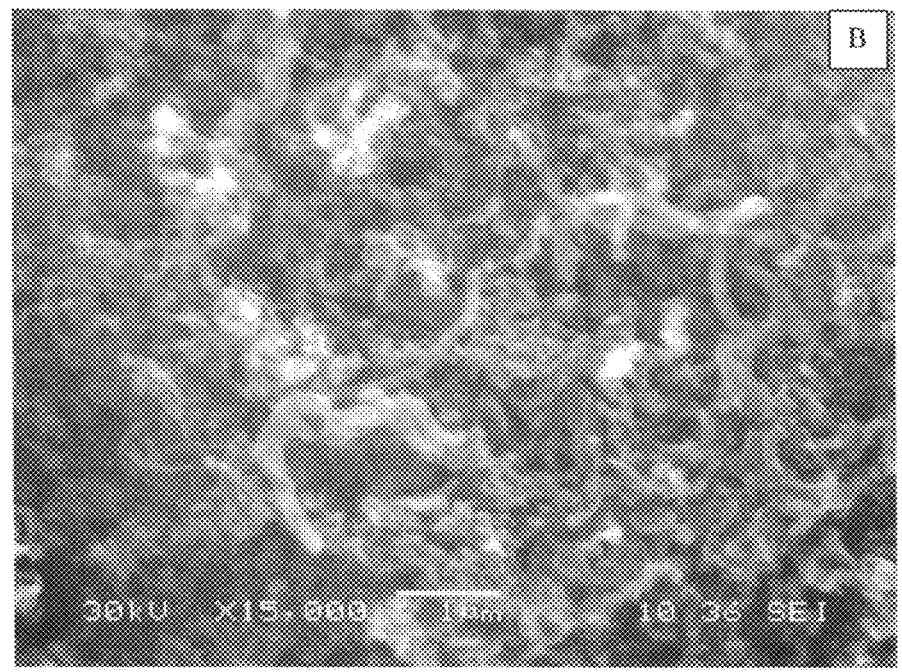
Figure 49:
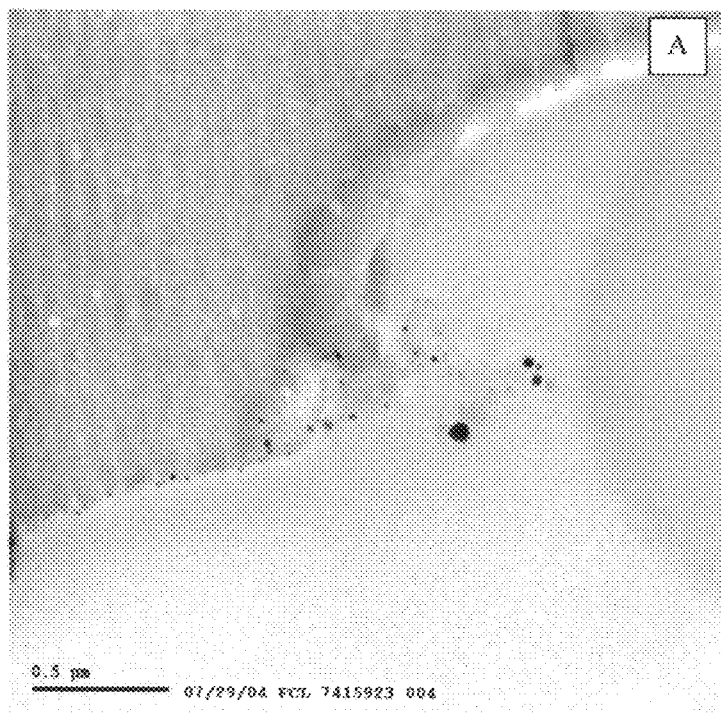
FIGS. 49 and 50 are TEM images of catalyst samples analyzed as described in Example 31.
Figure 50:
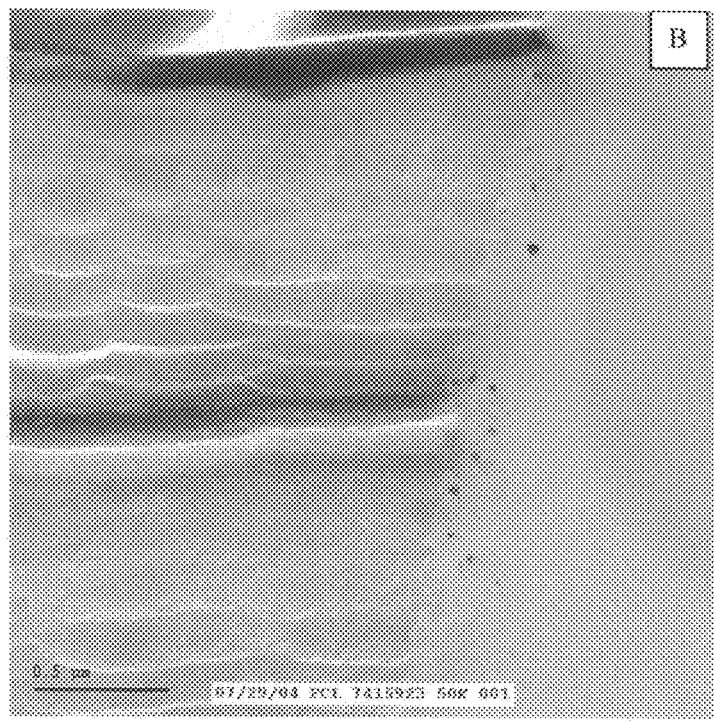

FIG. 45 is an SEM image of a powder sample of Sample 8. FIG. 46 is a backscattered electron image of the powder sample of Sample 8. FIGS. 47 and 48 are high magnification SEM images of powder sample 8 showing the growth of carbon nanotubes on the carbon support. FIGS. 49 and 50 are TEM images providing a cross-sectional view of Sample 8.

EXAMPLE 32

This examples details X-ray Photoelectron Spectroscopy Analysis (XPS) of the samples described above in Example 30 (detailed in Table 15).

The XPS analysis was performed under the analytical conditions set forth in Table 19.

TABLE 19

| Instrument | Physical Electronics Quantum 2000 Scanning XPS |
| --- | --- |
| X-ray source | Monochromatic Al Kα |
| Analysis areas | 0.4 mm × 0.4 mm |
| Take-off angle | 45 degrees |
| Charge correction | C—C, C—H in C1s spectra set to 284.8 eV |
| Charge Neutralization | Low energy electron and ion floods |

Figure 51:
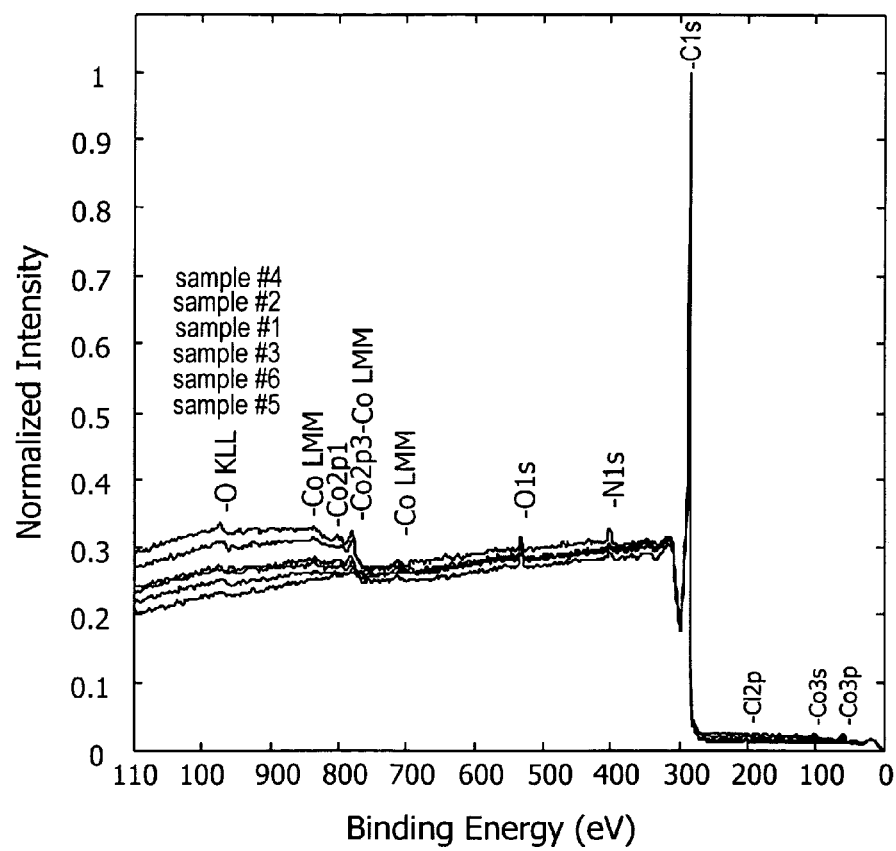
FIGS. 51 and 52 are X-ray Photoelectron Spectroscopy (XPS) results for samples analyzed as described in Example 32.
Figure 52:
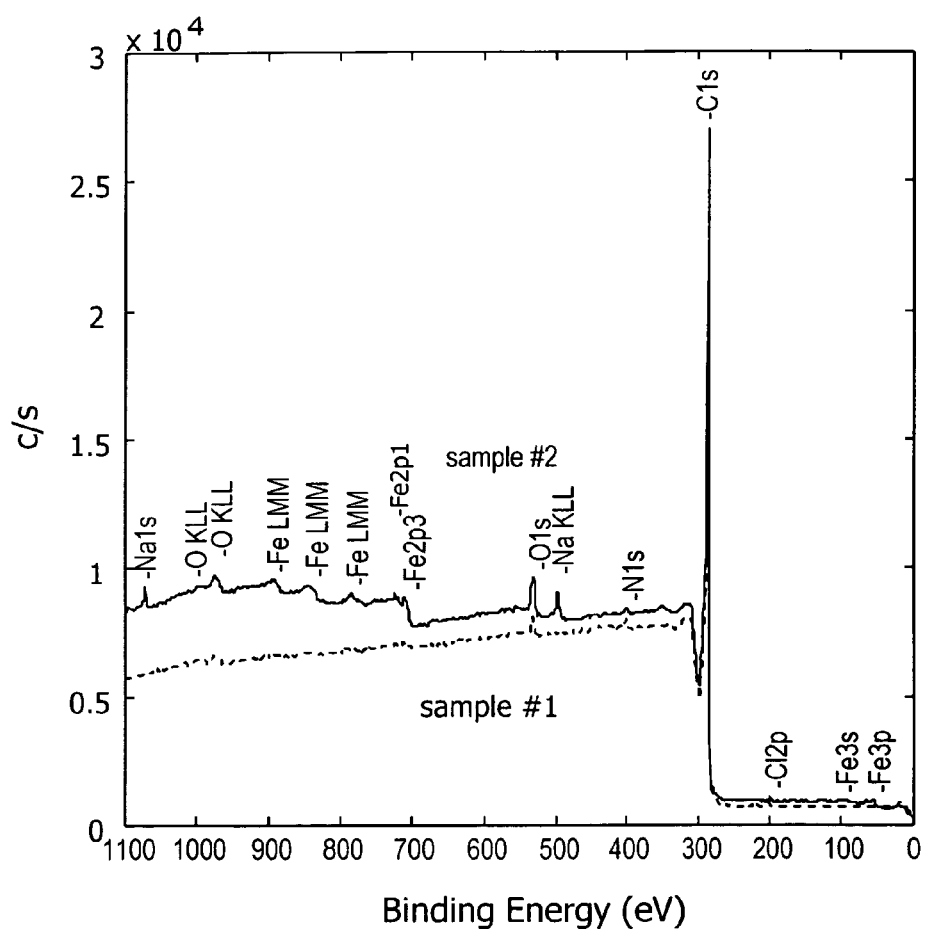

Surface concentration results (area comment) for Samples 1-6 in terms of Atomic % and Weight % are detailed below in Tables 20 and 21, respectively. The spectra are set forth in FIGS. 51 and 52.

TABLE 20

| Sample | C | N | O | Cl | Co |
|---|---|---|---|---|---|
| 1 | 97.3 | 1.2 | 1.0 | 0.07 | 0.42 |
| 2 | 97.9 | 0.2 | 1.3 | 0.09 | 0.52 |
| 3 | 97.9 | 0.7 | 0.9 | 0.05 | 0.41 |
| 4 | 97.7 | 0.4 | 1.2 | 0.08 | 0.73 |
| 5 | 97.3 | 1.8 | 0.8 | 0.07 | — |
| 6 | 98.5 | 0.4 | 0.8 | 0.10 | 0.19 |

TABLE 21

| Sample | C | N | O | Cl | Co |
|---|---|---|---|---|---|
| 1 | 95.1 | 1.4 | 1.3 | 0.2 | 2.0 |
| 2 | 95.4 | 0.3 | 1.6 | 0.3 | 2.5 |
| 3 | 95.9 | 0.8 | 1.2 | 0.1 | 2.0 |
| 4 | 94.4 | 0.4 | 1.5 | 0.2 | 3.5 |
| 5 | 96.6 | 2.1 | 1.1 | 0.2 | — |
| 6 | 97.3 | 0.5 | 1.0 | 0.3 | 0.9 |

EXAMPLE 33

This example details preparing a carbon-supported titanium-containing catalyst precursor.

Add a particulate carbon support (10.0 g) having a Langmuir surface area of approximately 1500 m$^2$/g to a 1 liter flask containing deionized water (400 ml) to form a slurry. The pH of the slurry is approximately 8.0 and the temperature approximately 20° C.

Add tittanium (III) sulfate ($Ti_2(SO_4)_3$) (0.40 g) to a 100 ml beaker containing deionized water (30 ml) to form a clear solution. Add the titanium solution to the support slurry over the course of 15 minutes (i.e., at a rate of approximately 2 ml/minute). Maintain the pH of the carbon slurry at from about 7.5 to about 8.0 by co-addition of a 0.1 wt. % solution of sodium hydroxide (Aldrich Chemical Co., Milwaukee, Wis.). Monitor the pH of the slurry using a pH meter (Thermo Orion Model 290).

After addition of the titanium solution to the carbon slurry is complete, stir the slurry for 30 minutes using a mechanical stirring rod (at 50% output) (IKA-Werke RW16 Basic) and monitor the pH of the slurry using the pH meter and maintain the pH at approximately 8.0 by dropwise addition of 0.1% sodium hydroxide or 0.1 wt. % $HNO_3$.

Heat slurry under a nitrogen blanket to 45° C. at a rate of about 2° C. per minute while maintaining the pH at 8.0 by dropwise addition of 0.1 wt. % sodium hydroxide (1 ml) or 0.1 wt. % $HNO_3$ (1 ml). Upon reaching 45° C., stir the slurry using the mechanical stirring bar described above for 20 minutes at constant temperature of 45° C. and a pH of 8.0. Heat the slurry to 50° C. and adjust its pH to 8.5 by addition of 0.1 wt. % sodium hydroxide solution (5 ml); maintain the slurry at these conditions for approximately 20 minutes. Heat the slurry to 60° C., adjust its pH to 9.0 by addition of 0.1 wt. % sodium hydroxide solution (5 ml) and maintain at these conditions for approximately 10 minutes.

Filter the resulting mixture and wash with a plentiful amount of deionized water (approximately 500 ml) and dry the wet cake for approximately 16 hours in a vacuum oven at 120° C. The precursor contains approximately 1.0% by weight titanium.

EXAMPLE 34

This example details preparation of a carbon-supported cobalt and titanium-containing catalyst precursor containing 1% by weight cobalt and 1% by weight titanium.

Add a particulate carbon support containing 1% by weight titanium prepared as described above in Example 33 (10.0 g) to a 1 liter flask containing deionized water (400 ml) to form a slurry. The pH of the slurry is approximately 8.0 and the temperature approximately 20° C.

Add cobalt chloride ($CoCl_2.2H_2O$) (0.285 g) (Sigma-Aldrich, St. Louis, Mo.) to a 100 ml beaker containing deionized water (60 ml) to form a clear solution. Add the cobalt solution to the carbon-supported titanum slurry incrementally over the course of 30 minutes (i.e., at a rate of approximately 2 ml/minute). Maintain the pH of the carbon slurry at from about 7.5 and about 8.0 during addition of the cobalt solution by co-addition of a 0.1 wt % solution of sodium hydroxide (Aldrich Chemical Co., Milwaukee, Wis.). Add approximately 1 ml of 0.1 wt. % sodium hydroxide solution to the carbon slurry during addition of the cobalt solution. Monitor the pH of the slurry a pH meter (Thermo Orion, Model 290).

After addition of the cobalt solution to the carbon-supported titanum slurry is complete, stir the slurry using a mechanical stirring rod operating at 50% of output (Model IKA-Werke RW16 Basic) for approximately 30 minutes; monitor the pH of the slurry using the pH meter and maintain at about 8.0 by dropwise addition of 0.1 wt. % sodium hydroxide (1 ml) or 0.1 wt. % $HNO_3$ (1 ml). Heat the slurry under a nitrogen blanket to 45° C. at a rate of about 2° C. per minute and maintain the pH at 8.0 by dropwise addition of 0.1 wt. % sodium hydroxide (1 ml) or 0.1 wt. % $HNO_3$ (1 ml). Upon reaching 45° C., stir the slurry using the mechanical stirring bar described above for 20 minutes at constant temperature of 45° C. and a pH of 8.0. Heat the slurry to 50° C. and adjust its pH to 8.5 by addition of 0.1 wt. % sodium hydroxide solution (5 ml); maintain the slurry at these conditions for approximately 20 minutes. Heat the slurry to 60° C., adjust its pH to 9.0 by addition of 0.1 wt. % sodium hydroxide solution (5 ml) and maintain at these conditions for approximately 10 minutes.

Filter the resulting mixture and wash with a plentiful amount of deionized water (approximately 500 ml) and dry the wet cake for approximately 16 hours in a vacuum oven at 120° C. The precursor contains approximately 1.0% by weight cobalt and 1% by weight titanium.

EXAMPLE 35

This example details preparation of a carbon-supported cobalt and titanium-containing catalyst precursor containing 1% by weight cobalt and 1% by weight titanium by concurrent deposition of cobalt and titanium.

Add a particulate carbon support (10.0 g) having a Langmuir surface area of approximately 1500 m$^2$/g to a 1 liter flask containing deionized water (400 ml) to form a slurry. The pH of the slurry is approximately 8.0 and the temperature approximately 20° C.

Add titanium (III) sulfate ($Ti_2(SO_4)_3$) (0.40 g) and cobalt chloride ($COCl_2.2H_2O$) (0.285 g) (Sigma-Aldrich, St. Louis, Mo.) to a 100 ml beaker containing deionized water (60 ml) to form a clear solution. Add the titanium-cobalt solution to the carbon slurry incrementally over the course of 30 minutes (i.e., at a rate of approximately 2 ml/minute). Maintain the pH of the carbon slurry at from about 7.5 and about 8.0 during addition of the titanium-cobalt solution by co-addition of a 0.1 wt % solution of sodium hydroxide (Aldrich Chemical Co., Milwaukee, Wis.). Add approximately 1 ml of 0.1 wt. % sodium hydroxide solution to the carbon slurry during addition of the titanium-cobalt solution. Monitor the pH of the slurry using a pH meter (Thermo Orion, Model 290).

After addition of the titanium-cobalt solution to the carbon slurry is complete, stir the slurry using a mechanical stirring rod operating at 50% of output (Model IKA-Werke RW16 Basic) for approximately 30 minutes; monitor the pH of the slurry using the pH meter and maintain the pH at about 8.0 by dropwise addition of 0.1 wt. % sodium hydroxide (1 ml) or 0.1 wt. % $HNO_3$ (1 ml). Heat the slurry under a nitrogen blanket to 45° C. at a rate of about 2° C. per minute while maintaining the pH at 8.0 by dropwise addition of 0.1 wt. % sodium hydroxide (1 ml) or 0.1 wt. % $HNO_3$ (1 ml). Upon reaching 45° C., stir the slurry using the mechanical stirring bar described above for 20 minutes at constant temperature of 45° C. and a pH of 8.0. Heat the slurry to 50° C. and adjust its pH to 8.5 by addition of 0.1 wt. % sodium hydroxide solution (5 ml); maintain the slurry at these conditions for approximately 20 minutes. Heat the slurry to 60° C., adjust its pH to 9.0 by addition of 0.1 wt. % sodium hydroxide solution (5 ml) and maintain at these conditions for approximately 10 minutes.

Filter the resulting mixture and wash with a plentiful amount of deionized water (approximately 500 ml) and dry the wet cake for approximately 16 hours in a vacuum oven at 120° C. The precursor contains approximately 1.0% by weight cobalt and 1% by weight titanium.

EXAMPLE 36

This example details preparing a carbon-supported titanium and cobalt-containing catalyst precursor.

Add a particulate carbon support having cobalt deposited in accordance with the method described in Example 12 (10 g) to a 1 liter flask containing deionized water (400 ml) to form a slurry. The pH of the slurry is approximately 8.0 and the temperature approximately 20° C.

Add titanium (III) sulfate ($Ti_2(SO_4)_3$) (0.40 g) to a 100 ml beaker containing deionized water (30 ml) to form a clear solution. Add the titanium solution incrementally over the course of 15 minutes (i.e., at a rate of approximately 2 ml/minute). Maintain the pH of the carbon slurry at from about 7.5 to about 8.0 by co-addition of a 0.1 wt. % solution of sodium hydroxide (Aldrich Chemical Co., Milwaukee, Wis.). Monitor the pH of the slurry using a pH meter (Thermo Orion Model 290).

After addition of the titanium solution to the carbon-supported cobalt precursor slurry is complete, stir the slurry for 30 minutes using a mechanical stirring rod (at 50% output) (IKA-Werke RW16 Basic) and monitor the pH of the slurry using the pH meter and maintain the pH at approximately 8.0 by dropwise addition of 0.1 wt. % sodium hydroxide or 0.1 wt. % $HNO_3$.

Heat the slurry under a nitrogen blanket to 45° C. at a rate of about 2° C. per minute while maintaining the pH at 8.0 by dropwise addition of 0.1 wt. % sodium hydroxide (1 ml) or 0.1 wt. % $HNO_3$ (1 ml). Upon reaching 45° C., the stir slurry using the mechanical stirring bar described above for 20 minutes at constant temperature of 45° C. and a pH of 8.0. Heat the slurry to 50° C. and adjust its pH to 8.5 by addition of 0.1 wt. % sodium hydroxide solution (5 ml); maintain the slurry at these conditions for approximately 20 minutes. Heat the slurry to 60° C., adjust its pH to 9.0 by addition of 0.1 wt. % sodium hydroxide solution (5 ml) and maintain at these conditions for approximately 10 minutes.

Filter the resulting mixture and wash with a plentiful amount of deionized water (approximately 500 ml) and dry the wet cake for approximately 16 hours in a vacuum oven at 120° C. The precursor contains approximately 1% by weight cobalt and 1.0% by weight titanium.

EXAMPLE 37

This example details the preparation of a carbon-supported titanium catalyst in which the titanium is deposited on the carbon support as described in Example 33.

Charge titanium-containing precursor (5.0 g) into a Hastelloy C tube reactor packed with high temperature insulation material. Purge the reactor with argon introduced to the reactor at a rate of approximately 100 $cm^3$/min at approximately 20° C. for approximately 15 minutes. Insert a thermocouple into the center of the reactor for charging the precursor material.

Raise the temperature of the reactor to approximately 300° C. over the course of approximately 15 minutes during which time a 10%/90% (v/v) mixture of acetonitrile and argon (Airgas, Inc., Radnor, Pa.) is introduced to the reactor at a rate of approximately 100 $cm^3$/minute. Increase the temperature of the reactor to approximately 950° C. over the course of 30 minutes during which time the 10%/90% (v/v) mixture of acetonitrile and argon flow through the reactor at a rate of approximately 100 $cm^3$/minute. Maintain the temperature of the reactor at approximately 950° C. for approximately 120 minutes.

Cool the reactor to approximately 20° C. over the course of 90 minutes under a flow of argon at approximately 100 $cm^3$/minute. The catalyst contains approximately 1% by weight titanium.

EXAMPLE 38

This example details the preparation of a carbon-supported cobalt and titanium-containing catalyst in which the cobalt and titanium may be deposited on the carbon support using one or more of the methods described in Examples 33 through 36.

Charge cobalt and titanium-containing precursor (5.0 g) into a Hastelloy C tube reactor packed with high temperature insulation material. Purge the reactor with argon introduced to the reactor at a rate of approximately 100 $cm^3$/min at approximately 20° C. for approximately 15 minutes. Insert a thermocouple into the center of the reactor for charging the precursor material.

Raise the temperature of the reactor to approximately 300° C. over the course of approximately 15 minutes during which time a 10%/90% (v/v) mixture of acetonitrile and argon (Airgas, Inc., Radnor, Pa.) is introduced to the reactor at a rate of approximately 100 $cm^3$/minute. Increase the temperature of the reactor to approximately 950° C. over the course of 30 minutes during which time the 10%/90% (v/v) mixture of acetonitrile and argon flow through the reactor at a rate of approximately 100 $cm^3$/minute. Maintain the temperature of the reactor at approximately 950° C. for approximately 120 minutes.

Allow the reactor to cool to approximately 20° C. over the course of 90 minutes under a flow of argon at approximately 100 $cm^3$/minute.

The catalyst contains approximately 1% by weight cobalt and approximately 1% by weight titanium.

EXAMPLE 39

This example details preparation of a carbon-supported titanium and cobalt-containing catalyst in which cobalt is deposited on a titanium-containing catalyst prepared as described in Example 37. Deposit cobalt on the titanium-containing catalyst as described in Example 34. After depositing cobalt on the titanium-containing catalyst, heat treat the catalyst using an acetonitrile-containing environment as described in Example 38.

EXAMPLE 40

This example details the preparation of a carbon-supported cobalt and titanium-containing catalyst. Titanium is deposited as described in Example 36 onto a 1% cobalt-containing catalyst prepared using acetonitrile as described in Examples 12 and 13. Charge the 1% cobalt catalyst having titanium deposited thereon (5.0 g) into the tube reactor described above in Example 13. Purge the reactor with argon introduced to the reactor at a rate of approximately 100 cm$^3$/min at approximately 20° C. for approximately 15 minutes. Insert a thermocouple into the center of the reactor for charging the catalyst.

Increase the temperature of the reactor to approximately 850° C. over the course of 30 minutes during which time a 5%/95% (v/v) mixture of hydrogen and argon flows through the reactor at a rate of approximately 100 cm$^3$/minute. Maintain the temperature of the reactor at approximately 850° C. for approximately 120 minutes.

Allow the reactor to cool to approximately 20° C. over the course of 90 minutes under a flow of argon at approximately 100 cm$^3$/minute.

The resulting catalyst contains approximately 1% by weight cobalt and approximately 1% by weight titanium.

EXAMPLE 41

This example details the preparation of a carbon-supported cobalt and titanium-containing catalyst. Titanium is deposited as described in Example 36 onto a 1% cobalt-containing catalyst prepared using acetonitrile as described in Examples 12 and 13. Charge the 1% cobalt catalyst having titanium deposited thereon (5.0 g) into the tube reactor described above in Example 13. Purge the reactor with argon introduced to the reactor at a rate of approximately 100 cm$^3$/min at approximately 20° C. for approximately 15 minutes. Insert a thermocouple into the center of the reactor for charging the catalyst.

Increase the temperature of the reactor to approximately 850° C. over the course of 120 minutes during which time argon flows through the reactor at a rate of approximately 100 cm$^3$/minute. Maintain the temperature of the reactor at approximately 850° C. for approximately 120 minutes.

Allow the reactor to cool to approximately 20° C. over the course of 90 minutes under a flow of argon at approximately 100 cm$^3$/minute.

The resulting catalyst contains approximately 1% by weight cobalt and approximately 1% by weight titanium.

EXAMPLE 42

This example details preparation of a cobalt-containing catalyst on a silica support. A silica support ($SiO_2$) (Sigma-Aldrich, St. Louis, Mo.) (10 g) having a Langmuir surface area of approximately 255 m$^2$/g was added to a 1 liter flask containing deionized water (400 ml) to form a slurry. The pH of the slurry was approximately 7.0 and the temperature approximately 20° C.

Cobalt chloride ($COCl_2 \cdot 2H_2O$) (0.285 g) (Sigma-Aldrich, St. Louis, Mo.) was added to a 100 ml beaker containing deionized water (60 ml) to form a clear solution. The cobalt solution was added to the silica slurry incrementally over the course of 30 minutes (i.e., at a rate of approximately 2 ml/minute). The pH of the silica slurry was maintained at from about 7.5 to about 8.0 during addition of the cobalt solution by co-addition of a 0.1 wt % solution of sodium hydroxide (Aldrich Chemical Co., Milwaukee, Wis.). The pH of the slurry was monitored using a pH meter (Thermo Orion, Model 290).

After addition of the cobalt solution to the silica slurry is complete, the slurry is stirred using a mechanical stirring rod operating at 50% of output (Model IKA-Werke RW16 Basic) for approximately 30 minutes; the pH of the slurry was monitored using the pH meter and maintained at about 8.0 by dropwise addition of 0.1 wt. % sodium hydroxide (1 ml) or 0.1 wt. % $HNO_3$ (1 ml).

The resulting mixture was filtered and washed with a plentiful amount of deionized water (approximately 500 ml) and the wet cake dried for approximately 16 hours in a vacuum oven at 120° C. The precursor contained approximately 1.0% by weight cobalt.

To prepare the catalyst, the cobalt-containing precursor was heat treated as described in Example 13.

EXAMPLE 43

This example details the performance of various cobalt-containing catalysts in the oxidation of PMIDA to N-(phosphonomethyl)glycine.

Two catalyst samples were prepared as described in Example 6 of International Publication No. WO 03/068387 using cobalt tetramethoxyphenyl prophyrin (TMPP) as the source of cobalt. One sample contained 1.5% cobalt on a carbon support designated MC-10 and the other 1.5% cobalt on a carbon support designated CP-117. Hereinafter, the catalysts are designated 1.5% CoTMPP/MC-10 and 1.5% CoTMPP/CP-117, respectively. MC-10 carbon support is described, for example, in Examples 1, 4, and 5 of International Publication No. WO 03/068387 and in U.S. Pat. No. 4,696,772 to Chou.

The performance of these catalysts was compared to the performance of a 1.5% CoCN/C catalyst prepared as described in Example 14 above. MC-10 carbon support was also tested in PMIDA oxidation. All catalyst samples were tested in PMIDA oxidation under the conditions set forth above in Example 10. The maximum $CO_2$ percentage in the exit gas and the cumulative amount of $CO_2$ generated were used as indices of catalyst performance. The results are shown in Table 22.

TABLE 22

| Catalyst | Cat. charge (g) | Runtime (min) | Cycle# | CO$_2$ % Max in offgas | Total CO$_2$ at 50 m (cc) | GI (%) | Gly (%) | FM (ppm) | FA (ppm) |
|---|---|---|---|---|---|---|---|---|---|
| 1.5% CoCN/C | 0.21 | 50 | 1 | 38.45 | 1611 | 0.013 | 4.22 | 1683 | 8476 |
| | | | 2 | 33.63 | 1571 | 0.016 | 4.45 | 1634 | 9261 |
| | | | 3 | 31.97 | 1556 | 0.016 | 4.47 | 1569 | 9665 |
| | | | 4 | 30.97 | 1550 | 0.015 | 4.39 | 1495 | 9516 |
| 1.5% CoTMPP/CP117 | 0.21 | 50 | 1 | 13.75 | 993 | 2.172 | 2.74 | 3879 | 1469 |
| | | | 2 | 12.7 | 936 | 2.407 | 2.62 | 3717 | 1328 |
| | | | 3 | 12.4 | 906 | 2.684 | 2.65 | 3739 | 1388 |
| | | | 4 | 12.09 | 883 | 2.641 | 2.47 | 3462 | 1314 |
| 1.5% CoTMPP/MC10 | 0.21 | 50 | 1 | 36.24 | 1939 | 0.037 | 3.83 | 5480 | 2799 |
| | | | 2 | 33.38 | 1846 | 0.026 | 3.75 | 5219 | 3817 |
| MC10 | 0.21 | 50 | 1 | 20.02 | 1256 | 0.416 | 3.59 | 4398 | 2922 |
| | | | 2 | 16.04 | 953 | 0.410 | 3.61 | 4439 | 2956 |
| MC10 | 0.21 | 65 | 1 | 19.69 | 1526 | 0.023 | 3.89 | 4620 | 3365 |
| MC10 | .40 | 50 | 1 | 27.41 | 1551 | 0.026 | 3.86 | 5413 | 2962 |

As shown in Table 22, the 1.5% CoCN/C prepared as described in Example 14 using CH$_3$CN exhibited high activity for oxidation of both PMIDA and formaldehyde. The 1.5% CoTMPP/CP117 and 1.5% CoTMPP/MC10 samples exhibited much lower formaldehyde oxidation activity than this sample. The 1.5% CoTMPP/CP117 sample also exhibited much lower activity for PMIDA oxication activity as compared to the 1.5% CoCN/C prepared as described in Example 14. Although the 1.5% CoTMPP/MC10 appeared to demonstrate similar PMIDA oxidation activity as compared to the 1.5% CoCN/C sample, it is presently believed that a substantial amount of the PMIDA activity of this catalyst was attributable to the MC-10 support. To test the effectiveness of the MC-10 carbon support for PMIDA oxidation, some modifications were made to the standard testing conditions: either runtime was increased or catalyst loading was increased. At a similar PMIDA conversion level, the MC10 catalyst demonstrated similar formaldehyde oxidation activity as the 1.5% CoTMPP/MC10 catalyst.

EXAMPLE 44

Various carbon-supported transition metal-containing catalysts and their supports were analyzed to determine their Langmuir surface areas as described in Example 28. The analysis of the catalyst and carbon support surface areas included the total Langmuir surface area, Langmuir surface area attributed to micropores, and Langmuir surface area attributed to mesopores and macropores.

Catalysts and supports tested included:
(1) a carbon support having a Langmuir surface area of approximately 1600 m$^2$/g; (2) a 1% FeCN/C catalyst prepared on support (1) as described in Examples 8 and 9; (3) a 1.5% CoCN/C catalyst prepared on support (1) as described in Example 14; (4) a 1% cobalt phthalocyanine (CoPLCN) catalyst prepared on support (1) prepared as described in Examples 22 and 23; (5) a particulate carbon support sold under the trade name CP-117 (Engelhard Corp., Iselin, N.J.) and described in Example 2 of International Publication No. WO 03/068387; (6) a 1.1% FeTPP (iron tetraphenylporphyrin) catalyst prepared on the CP-117 support as described in Example 2 of International Publication No. WO 03/068387; (7) a 1.5% cobalt tetramethoxyphenyl porphyrin (TMPP) catalyst prepared on a CP-117 support as described in Example 6 of International Publication No. WO 03/068387; (8) a particulate carbon catalyst designated MC-10 prepared in accordance with U.S. Pat. No. 4,696,772 to Chou and described in Example 1 of International Publication No. WO 03/068387; and (9) a 1.5% cobalt tetramethoxyphenyl porphyrin (TMPP) catalyst prepared on a MC-10 support as described in Example 6 of International Publication No. WO 03/068387. The results are shown in Table 23.

TABLE 23

| Catalyst/Support | | Surface area (SA) (m$^2$/g) | Micropore SA (m$^2$/g) | Meso-& Macropore SA(m$^2$/g) |
|---|---|---|---|---|
| Support | | 1597 | 1294 | 280 |
| 1% FeCN/C | | 1164 | 935 | 229 |
| | percentage of support SA | 72.9% | 72.3% | 81.8% |
| 1.5% CoCN/C | | 1336 | 1066 | 251 |
| | percentage of support SA | 83.7% | 82.4% | 89.6% |
| 1% CoPLCN/C | | 1337 | 1082 | 250 |
| | percentage of support SA | 83.7% | 83.6% | 89.3% |
| CP117 support | | 1603 | 1329 | 274 |
| 1.1% FeTPP/CP117 | | 888 | 696 | 192 |
| | percentage of support SA | 55.4% | 52.4% | 70.1% |
| 1.5% CoTMPP/CP117 | | 1163 | 915 | 240 |
| | percentage of support SA | 72.6% | 68.8% | 87.6% |
| MC-10 support | | 2704 | 1944 | 760 |
| 1.5% CoTMPP/MC10 | | 2045 | 1330 | 715 |
| | percentage of support SA | 75.6% | 68.4% | 94.1% |

Iron Catalysts

For the Fe-based catalysts with similar metal loading, the 1% FeCN/C prepared using CH$_3$CN exhibited significantly higher total Langmuir surface area as compared to the 1% FeTPP/CP117 catalyst (1164 vs. 888 m$^2$/g). The 1% FeCN/C catalyst prepared using CH$_3$CN possessed 72.9% of the total surface area of the carbon support; the 1.1% FeTPP/CP117 catalysts possessed 55.4% of the total surface area of CP117. These results indicate the 1% FeCN/C catalyst exhibited higher metal dispersion than 1.1% FeTPP/CP117 catalyst.

The pore surface area analysis demonstrated the decrease in surface area between the two catalysts is due primarily to the substantial loss of micropore surface area (i.e., surface area attributed to pores having a diameter of less than 20 Å) and some loss in mesopore and macropore surface area (i.e., pores having a diameter between 20 and 80 Å).

The 1% FeCN/C catalyst exhibited a micropore surface area of 935 m²/g while the 1.1% FeTPP/CP117 catalyst exhibited a micropore surface area of 696 m²/g. It is presently believed the 1% FeCN/C catalyst contained a much higher proportion of micropores, mesopores and macropores than the 1.1% FeTPP/CPl17 catalyst.

Cobalt Catalysts

For the Co-based catalysts with similar metal loading, the 1.5% CoCN/C catalyst prepared using $CH_3CN$ exhibited much higher total Langmuir surface area than the 1.5% CoTMPP/CP117 catalyst prepared from the CoTMPP organometallic precursor (1336 vs. 1163 m²/g). The 1.5% CoCN/C catalyst possessed 83.7% of the total Langmuir surface area of its carbon support; the 1.5% CoTMPP/CP117 catalyst possessed 72.6% of the total surface area of the CP117 support. These results indicated the 1.5% CoCN/C catalyst exhibited higher metal dispersion than the 1.5% CoTMPP/CP117 catalyst. The pore surface area analysis demonstrated the reduced surface area of the 1.5% CoTMPP/CP117 catalyst was primarily due to the loss of micropore surface area and some loss in mesopore and macropore surface area.

The 1.5% CoCN/C catalyst exhibited a micropore surface area of 1066 m²/g while the 1.5% CoTMPP/CP117 catalyst exhibited a micropore surface area of 915 m²/g. The higher micropore SA observed in 1.5% CoCN/C implies the catalyst has much more micropore than 1.5% CoTMPP/CP117. The results also showed 1.5% CoCN/C had similar amount of meso- and macropore as 1.5% CoTMPP/CP117. It is presently believed the 1.5% CoCN/C catalyst contained a much higher proportion of micropores, mesopores and macropores than the 1.5% CoTMPP/CP117 catalyst.

Comparison of the 1.5% CoTMPP/MC10 catalyst with the 1.5% CoCN/C catalyst is difficult due to MC10 having a much higher surface area than the carbon support used for the 1.5% CoCN/C catalyst. However, useful information can be extracted if we compare the catalysts' surface area as a percentage of the surface area of its carbon support. The 1.5% CoCN/C catalyst possessed 83.7% of the total surface area of its carbon support; the 1.5% CoTMPP/MC10 possessed 75.6% of the total surface area of the MC10 carbon support. These results suggested that the 1.5% CoCN/C catalysts have higher metal dispersion than the 1.5% CoTMPP/MC10 catalysts. This conclusion is supported by the microscopy study of these catalysts described in Example 47.

Based on the foregoing, it is currently believed that metal carbide-nitride or, carbo-nitride, catalysts prepared in accordance with the present invention using $CH_3CN$ exhibit significantly higher surface area and metal dispersion than catalysts prepared from porphyrin or organometallic precursors. Moreover, metal carbide-nitride or, carbo-nitride, catalysts also exhibit a greater proportion of micropores than catalysts prepared from porphyrin or organometallic precursors.

EXAMPLE 45

Various catalysts were analyzed by Inductively Coupled Plasma (ICP) analysis to determine their nitrogen and transition metal content. The analysis was carried out using a Thermo Jarrell Ash (TJA), IRIS Advantage Duo View inductively coupled plasma optical emission spectrometer. The results are shown in Table 24. Catalyst samples analyzed included:
(1) a 1.1% FeTPP (iron tetraphenylporphyrin) catalyst on a CP-117 support prepared generally as described in Example 2 of International Publication No. WO 03/068387; (2) a 1% FeCN/C catalyst on a carbon support having a Langmuir surface area of approximately 1600 m²/g; prepared generally as described in Examples 8 and 9; (3) a 1.5% cobalt tetramethoxyphenyl porphyrin (TMPP) catalyst on a CP-117 support prepared generally as described in Example 6 of International Publication No. WO 03/068387; (4) a 1.5% cobalt tetramethoxyphenyl porphyrin (TMPP) catalyst on a MC-10 support prepared generally as described in Example 6 of International Publication No. WO 03/068387; (5) a 1% cobalt phthalocyanine (CoPLCN) catalyst on a carbon support having a Langmuir surface area of approximately 1600 m²/g prepared generally as described in Examples 22 and 23; (6) a 1.5% cobalt phthalocyanine (CoPLCN) catalyst on a carbon support having a Langmuir surface area of approximately 1600 m²/g prepared generally as described in Examples 22 and 23, with precursor deposition modified to provide 1.5% CoPLCN loading; (7) a 5% cobalt phthalocyanine (CoPLCN) catalyst on a carbon support having a Langmuir surface area of approximately 1600 m²/g prepared generally as described in Examples 22 and 23, with precursor deposition modified to provide 5% CoPLCN loading; (8) a 1% CoCN/C catalyst on a carbon support having a Langmuir surface area of approximately 1600 m²/g prepared generally as described in Example 14; (9) a 1.5% CoCN/C catalyst on a carbon support having a Langmuir surface area of approximately 1600 m²/g prepared generally as described in Example 14; (10) a 3% CoCN/C catalyst on a carbon support having a Langmuir surface area of approximately 1600 m²/g prepared generally as described in Example 14, with precursor deposition modified to provide 3% cobalt loading; (11) a 5% CoCN/C catalyst on a carbon support having a Langmuir surface area of approximately 1600 m²/g prepared generally as described in Example 14, with precursor deposition modified to provide 5% cobalt loading; and (12) a 10% CoCN/C catalyst on a carbon support having a Langmuir surface area of approximately 1600 m²/g prepared generally as described in Example 14, with precursor deposition modified to provide 10% cobalt loading.

TABLE 24

| Catalyst | Fe(or Co) (wt %) | N(wt %) | C + O + H(wt %) |
|---|---|---|---|
| 1.1% FeTPP/CP117[a] | 1.1 | 1.9 | 97.0 |
| 1% FeCN/C[b] | 1.0 | 2.3 | 96.7 |
| 1.5% CoTMPP/CP117[a] | 1.5 | 2.8 | 95.7 |
| 1.5% CoTMPP/MC10[a] | 1.5 | 3.3 | 95.2 |
| 1% CoPLCN/C[c] | 1.0 | 1.5 | 97.5 |
| 1.5% CoPLCN/C[c] | 1.5 | 1.5 | 97.0 |
| 5% CoPLCN/C[c] | 5.0 | 1.6 | 93.4 |
| 1% CoCN/C[b] | 1.0 | 1.4 | 97.6 |
| 1.5% CoCN/C[b] | 1.5 | 2.0 | 96.5 |
| 3% CoCN/C[b] | 3.0 | 1.6 | 95.4 |
| 5% CoCN/C[b] | 5.0 | 1.5 | 93.5 |
| 10% CoCN/C[b] | 10.0 | 1.2 | 88.8 | a. Catalysts were synthesized by depositing organometallic compounds on carbon; the precursors were then calcined at 800° C. under argon for 2 hours as described in Examples 1, 2 and 6 of International Publication No. WO 03/068387.
b. Catalysts were synthesized by depositing $CoCl_2$ on carbon; the precursors were then calcined at 950° C. under an $CH_3CN$ environment for 2 hours.
c. Catalysts were synthesized by depositing the organometallic compound on carbon; the precursors were then calcined at 950° C. under argon for 2 hours.

EXAMPLE 46

Various catalysts were characterized by Time-of-Flight Secondary Ion Mass Spectrometry (ToF SIMS). Catalyst samples analyzed included: (1) a 1.1% FeTPP/CP117 catalyst prepared generally as described in Example 2 of International Publication No. WO 03/068387; (2) a 1% FeCN/C catalyst on a carbon support having a Langmuir surface area of approximately 1600 $m^2/g$; prepared generally as described in Examples 8 and 9; (3) a 1.5% CoTMPP/CP117 catalyst prepared generally as described in Example 6 of International Publication No. WO 03/068387; (4) a 1.5% CoTMPP/MC10 catalyst prepared generally as described in Example 6 of International Publication No. WO 03/068387; (5) a 1% CoCN/C catalyst on a carbon support having a Langmuir surface area of approximately 1600 $m^2/g$ prepared generally as described in Example 14; (6) a 1.5% CoCN/C catalyst on a carbon support having a Langmuir surface area of approximately 1600 $m^2/g$ prepared generally as described in Example 14; (7) a 5% CoCN/C catalyst on a carbon support having a Langmuir surface area of approximately 1600 $m^2/g$ prepared generally as described in Example 14, with precursor deposition modified to provide 5% cobalt loading; and (8) a 10% CoCN/C catalyst on a carbon support having a Langmuir surface area of approximately 1600 $m^2/g$ prepared generally as described in Example 14, with precursor deposition modified to provide 10% cobalt loading.
(9) a 1% cobalt phthalocyanine (CoPLCN) catalyst on a carbon support having a Langmuir surface area of approximately 1600 $m^2/g$ prepared generally as described in Examples 22 and 23.

The surface of each catalyst sample was secured to double sided tape and analyzed by ToF SIMS (Charles-Evans and Associates) under the following conditions. The ToF SIMS analysis depth was ~10 Å. The method described in this example is referenced in this specification and appended claims as "Protocol A."
Instrument: Physical Electronics TRIFT III
Primary Ion Beam: $^{69}$Ga LMIG (bunched)
Primary Beam Potential: 18 kV
Primary Ion Current (DC): ~2 nA
Nominal Analysis Region: 300×300 µm
Charge Neutralization (~20 eV): Yes
Post Acceleration: 5 kV
Masses Blanked: No
Energy Filter/Contrast Diaphragm: No/No ToF SIMS analysis is also described, for example, in LEFÈVRE, M., et al., "$O_2$ Reduction in PEM Fuel Cells: Activity and Active Site Structural Information for Catalysts Obtained by the Pyrolysis at High Temperature of Fe Precursors," *Journal of Physical Chemistry B*, 2000, Pages 11238-11247, Volume 104, American Chemical Society; and LEFÈVRE, M., et al., "Molecular Oxygen Reduction in PEM Fuel Cells: Evidence for the Simultaneous Presence of Two Active Sites in Fe-Based Catalysts," *Journal of Physical Chemistry*, 2002, Pages 8705-8713, Volume 106.

The results for samples (1) and (2) are shown below in Table 25 and the results for samples (3)-(8) are shown below in Table 26.

Figure 54:
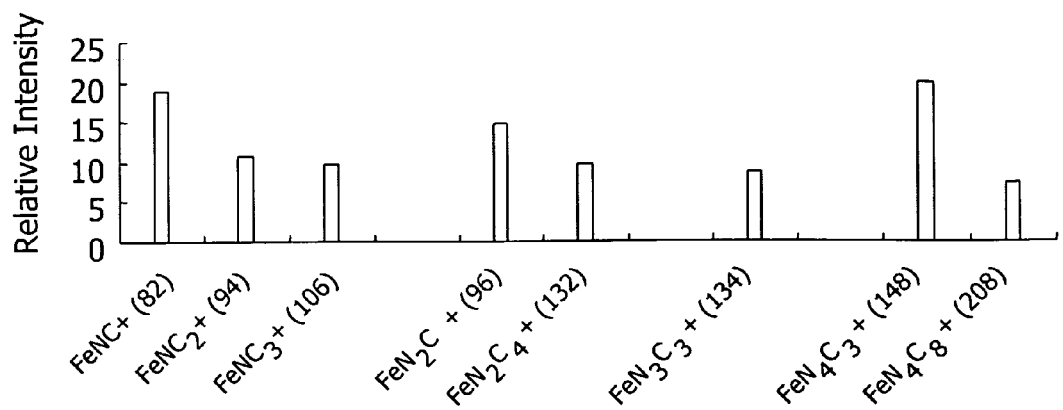
FIGS. 54, 55, 56 and 57 show the intensities of ion species detected during ToF SIMS analysis of a 1.1% iron tetraphenyl porphyrin (FeTPP), a 1.0% iron carbide-nitride (FeCN), a 1.5% cobalt tetramethoxy phenylporphyrin (CoTMPP) catalyst, and a 1.0% cobalt carbide-nitride (CoCN) catalyst, respectively, as described in Example 46.
Figure 55:
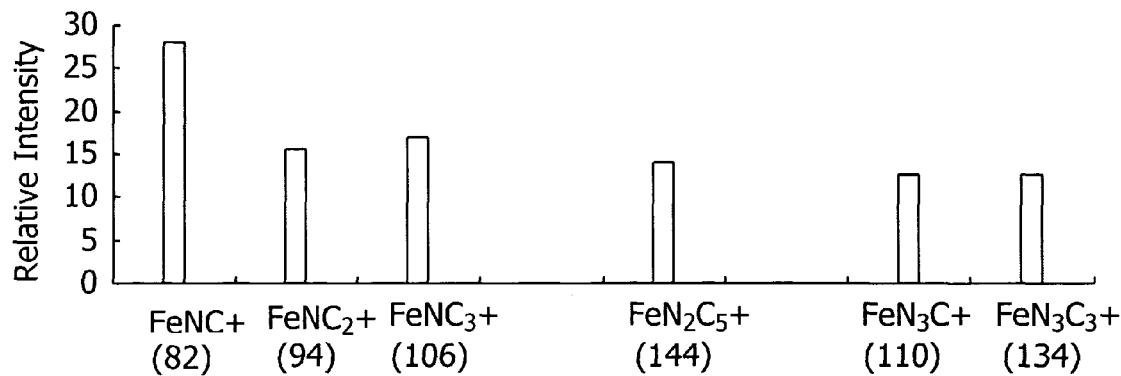

FIGS. 54 and 55 show the intensities of ion species detected during analysis of the 1.1% FeTPP/CP117 and 1% FeCN/C samples, respectively. The relative intensity in Table 25 indicates the proportion of the total intensity associated with each species.

TABLE 25

| Catalyst | Ion Family | Ions | Mass (m/z) | Relative intensity (%) | Relative abundance of ion family (%) |
|---|---|---|---|---|---|
| 1.1% FeTPP/CP117 | $FeNC_y$ | $FeNC^+$ | 82 | 18.9 | 39.4 |
| | | $FeNC_2^+$ | 94 | 10.8 | |
| | | $FeNC_3^+$ | 106 | 9.7 | |
| | $FeN_2C_y$ | $FeN_2C^+$ | 96 | 14.9 | 24.6 |
| | | $FeN_2C_4^+$ | 132 | 9.7 | |
| | $FeN_3C_y$ | $FeN_3C_3^+$ | 134 | 8.6 | 8.6 |
| | $FeN_4C_y$ | $FeN_4C_3^+$ | 148 | 20.0 | 27.4 |
| | | $FeN_4C_8^+$ | 208 | 7.4 | |
| 1% FeCN/C | $FeNC_y$ | $FeNC^+$ | 82 | 28.1 | 60.5 |
| | | $FeNC_2^+$ | 94 | 15.5 | |
| | | $FeNC_3^+$ | 106 | 16.9 | |
| | $FeN_2C_y$ | $FeN_2C_5^+$ | 144 | 14.1 | 14.1 |
| | $FeN_3C_y$ | $FeN_3C^+$ | 110 | 12.7 | 25.4 |
| | | $FeN_3C_3^+$ | 134 | 12.7 | |
| | $FeN_4C_y$ | Not detected | | | 0 |

As shown in Table 25, for the 1.1% FeTPP/CP117 prepared using a FeTPP organometallic precursor, the majority of $FeN_xC_y^+$ ions existed in $FeNC_y^+$, $FeN_2C_y^+$, and $FeN_4C_y^+$. A minor portion of $FeN_3C_y^+$ ions was also detected. For the 1% FeCN/C catalyst prepared using acetonitrile, the majority of the $FeN_xC_y^+$ ions existed in the form of $FeNC_y^+$, $FeN_2C_y^+$, or $FeN_3C_y^+$ ions. Analysis of the 1% FeCN/C catalyst prepared using acetonitrile did not detect $FeN_4C_y^+$ ions.

Table 26 shows the relative intensity of various detectable ions and the relative abundance of different ion families for Co-based catalysts.

TABLE 26

| Catalyst | Ion Family | Ions | Mass (m/z) | Relative intensity (%) | Relative abundance of ion family (%) |
|---|---|---|---|---|---|
| 1.5% CoTMPP/CP117 | $CoNC_y$ | $CoNC^+$ | 85 | 18.6 | 18.6 |
| | | Not detected | | | 0 |
| | $CoN_2C_y$ | $CoN_3C_5^+$ | 161 | 16.9 | 16.9 |
| | $CoN_3C_y$ | $CoN_4C_6^+$ | 187 | 50.5 | 64.5 |
| | $CoN_4C_y$ | $CoN_4C_7^+$ | 199 | 14.0 | |
| 1.5% CoTMPP/MC10 | $CoNC_y$ | Not detected | | | 0 |
| | $CoN_2C_y$ | Not detected | | | 0 |
| | $CoN_3C_y$ | Not detected | | | 0 |
| | $CoN_4C_y$ | Not detected | | | 0 |
| 1.0% CoCN/C | $CoNC_y$ | $CoNC^+$ | 85 | 22.1 | 40.7 |
| | | $CoNC_2^+$ | 97 | 10.9 | |
| | | $CoNC_3^+$ | 109 | 7.7 | |
| | $CoN_2C_y$ | $CoN_2C^+$ | 99 | 10.0 | 36.8 |
| | | $CoN_2C_2^+$ | 111 | 7.7 | |

TABLE 26-continued

| Catalyst | Ion Family | Ions | Mass (m/z) | Relative intensity (%) | Relative abundance of ion family (%) |
|---|---|---|---|---|---|
| | | $CoN_2C_4^+$ | 135 | 8.3 | |
| | | $CoN_2C_5^+$ | 147 | 10.8 | |
| | $CoN_3C_y$ | $CoN_3C^+$ | 113 | 14.1 | 22.5 |
| | | $CoN_3C_4^+$ | 149 | 8.4 | |
| | $CoN_4C_y$ | Not detected | | | 0 |
| 1.5% CoCN/C | $CoNC_y$ | $CoNC^+$ | 85 | 23.1 | 34.6 |
| | | $CoNC_2^+$ | 97 | 11.5 | |
| | $CoN_2C_y$ | $CoN_2C^+$ | 99 | 15.4 | 35.9 |
| | | $CoN_2C_4^+$ | 135 | 20.5 | |
| | $CoN_3C_y$ | $CoN_3C^+$ | 113 | 18.0 | 29.5 |
| | | $CoN_3C_3^+$ | 137 | 11.5 | |
| | $CoN_4C_y$ | Not detected | | | 0 |
| 5.0% CoCN/C | $CoNC_y$ | $CoNC^+$ | 85 | 17.9 | 17.9 |
| | $CoN_2C_y$ | $CoN_2C_4^+$ | 135 | 26.1 | 51.5 |
| | | $CoN_2C_5^+$ | 147 | 25.4 | |
| | $CoN_3C_y$ | $CoN_3C_4^+$ | 149 | 18.2 | 18.2 |
| | $CoN_4C_y$ | $CoN_4C_3^+$ | 151 | 12.4 | 12.4 |
| 10.0% CoCN/C | $CoNC_y$ | $CoNC^+$ | 85 | 17.3 | 24.8 |
| | | $CoNC_2^+$ | 97 | 7.5 | |
| | $CoN_2C_y$ | $CoN_2C^+$ | 99 | 11.8 | 27.4 |
| | | $CoN_2C_4^+$ | 135 | 15.6 | |
| | $CoN_3C_y$ | $CoN_3C^+$ | 113 | 10.2 | 32.2 |
| | | $CoN_3C_3^+$ | 137 | 7.1 | |
| | | $CoN_3C_4^+$ | 149 | 14.9 | |
| | $CoN_4C_y$ | $CoN_4C_3^+$ | 151 | 15.6 | 15.6 |
| 1.0% CoPLCN/C | $CoNC_y$ | CoNC+ | 85 | 45.1 | 78.5 |
| | | $CoNC_{2+}$ | 97 | 16.7 | |
| | | $CoNC_{3+}$ | 109 | 16.7 | |
| | $CoN_2C_y$ | CoN_2C+ | 99 | 9.8 | 21.6 |
| | | $CoN_2C_{2+}$ | 111 | 11.8 | |
| | $CoN_3C_y$ | Not detected | | | |
| | $CoN_4C_y$ | Not detected | | | |

Figure 53:
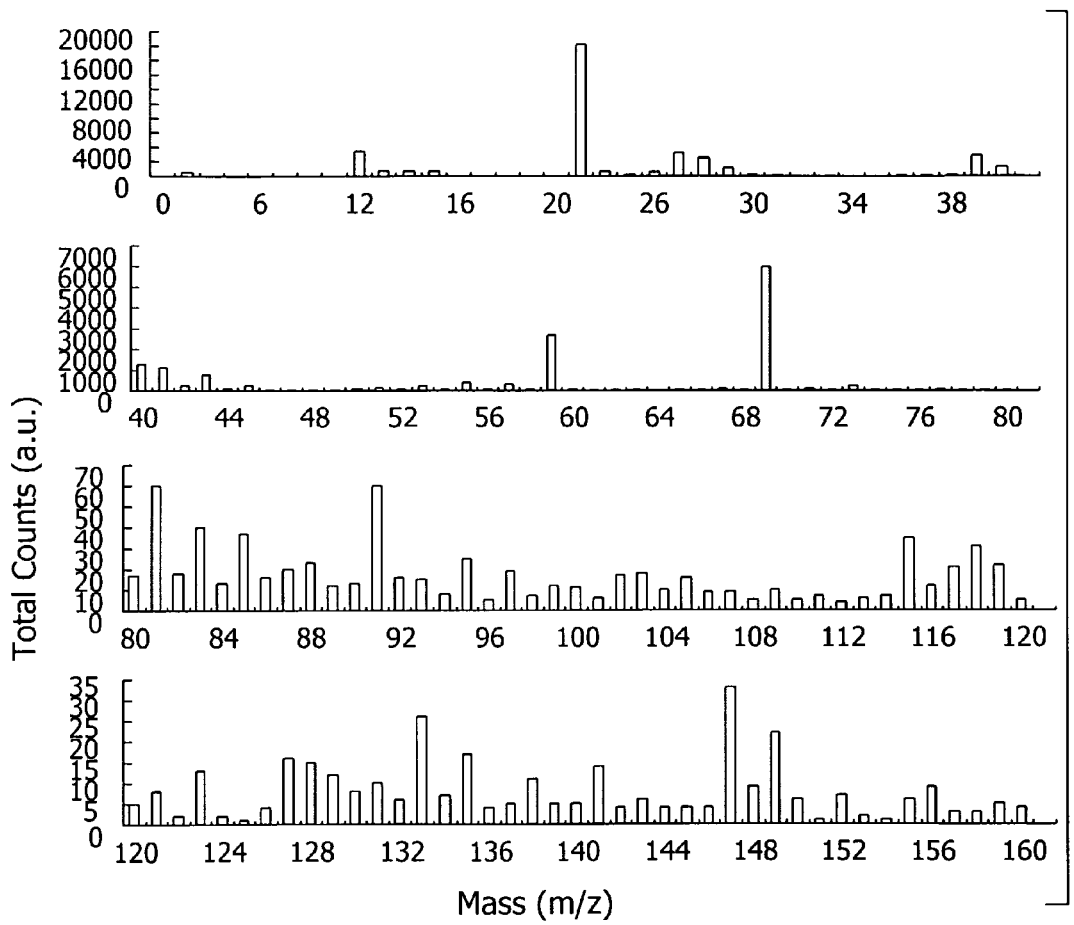
FIG. 53 is a Time-of-Flight Secondary Ion Mass Spectrometry (ToF SIMS) for a 1.5% cobalt carbide-nitride (CoCN) catalyst analyzed as described in Example 46.
Figure 56:
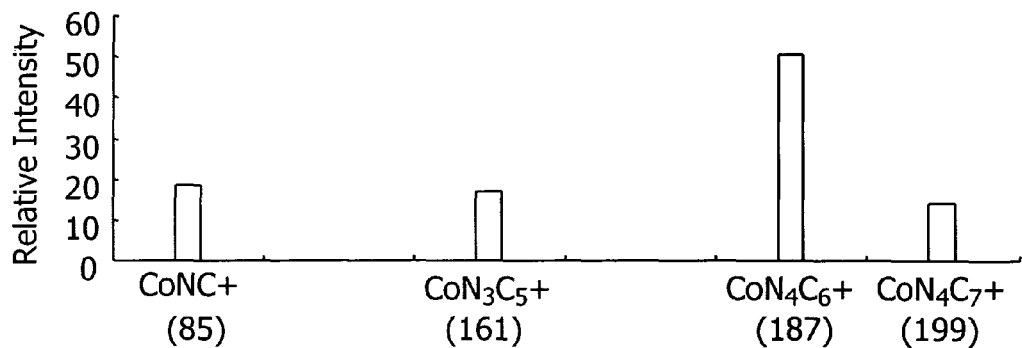
Figure 57:
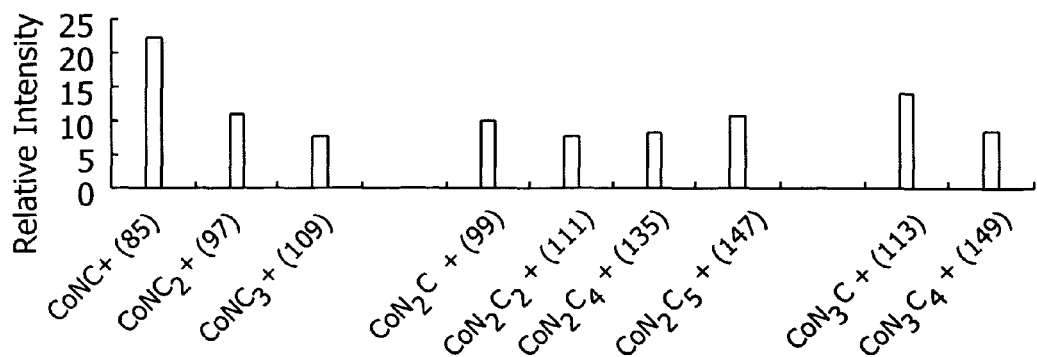
Figure 58:
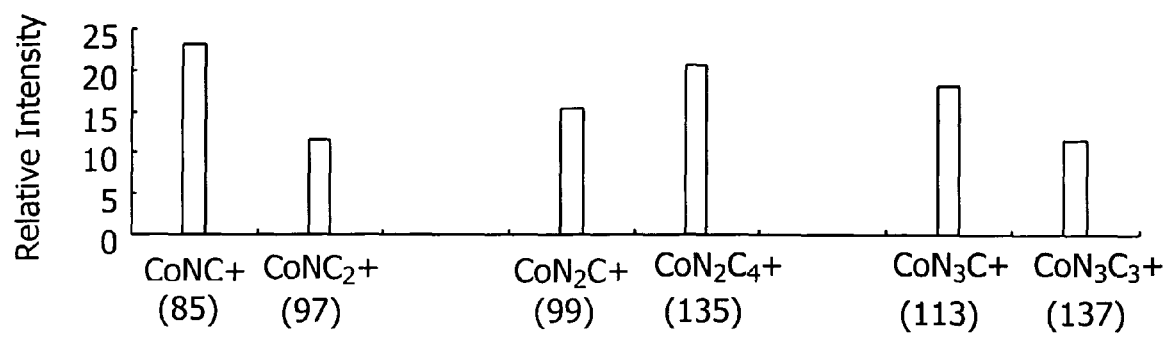
FIGS. 58, 59 and 60 show the intensities of ion species detected during ToF SIMS analysis of 1.5%, 5% and 10% cobalt carbide-nitride (CoCN) catalysts, respectively, as described in Example 46.
Figure 59:
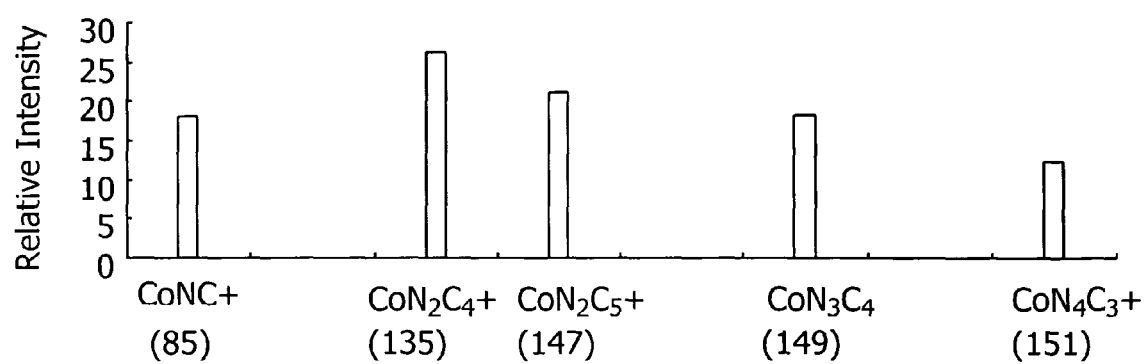
Figure 60:
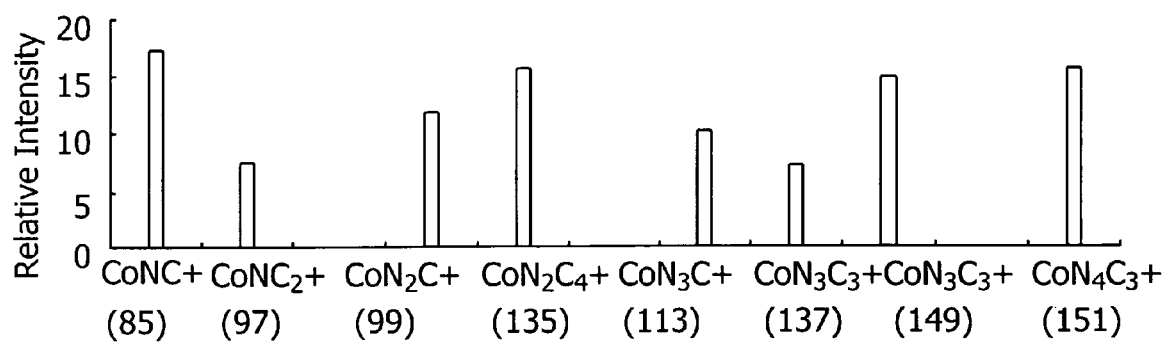
Figure 61:
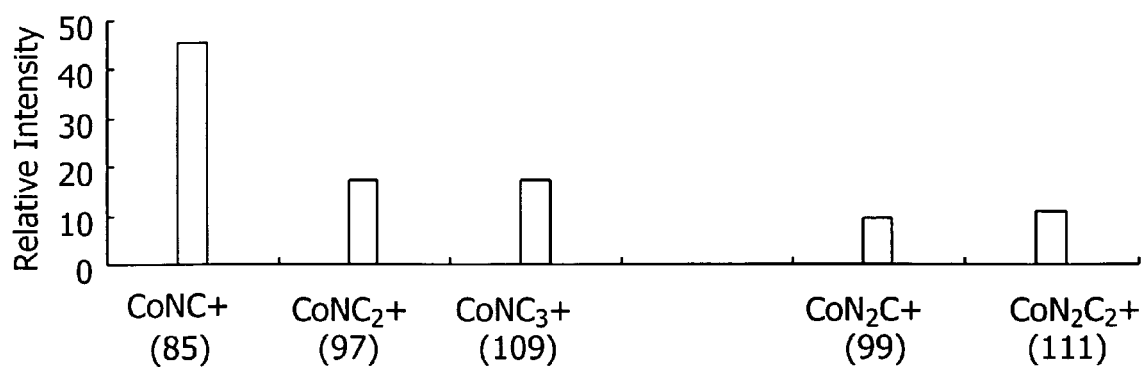
FIG. 61 shows the intensities of ion species detected during ToF SIMS analysis of a 1.0% cobalt phthalocyanine (Co-PLCN) catalyst as described in Example 46.
Figure 62A:
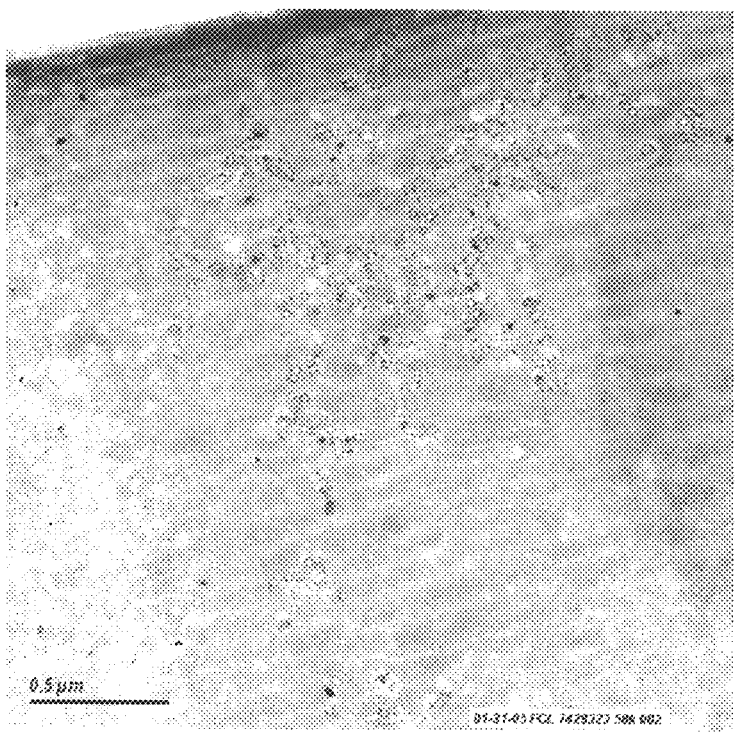
FIGS. 62A, 62B, 63A and 63B are TEM images for a 1% cobalt phthalocyanine (CoPLCN) catalyst analyzed as described in Example 47.
Figure 62B:
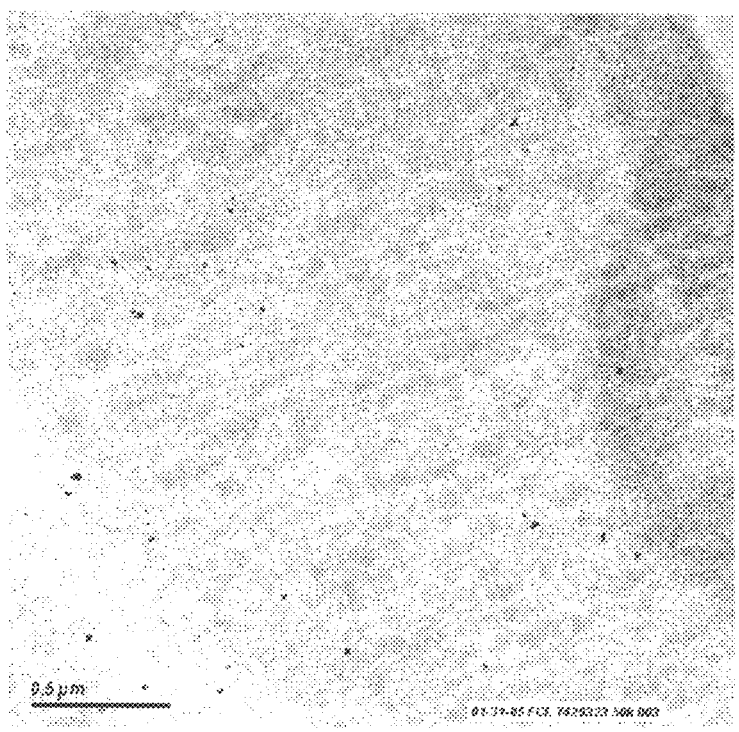
Figure 63A:
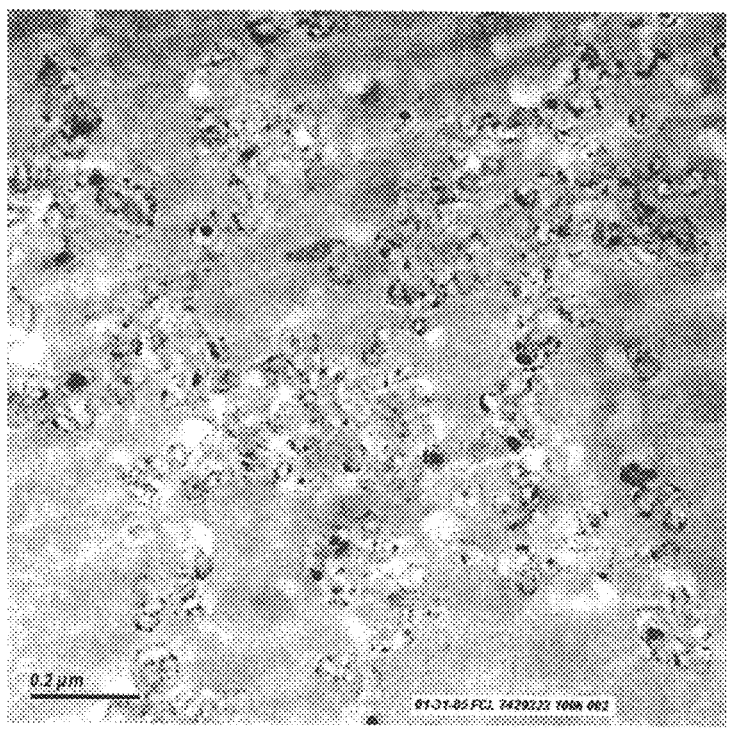
Figure 63B:
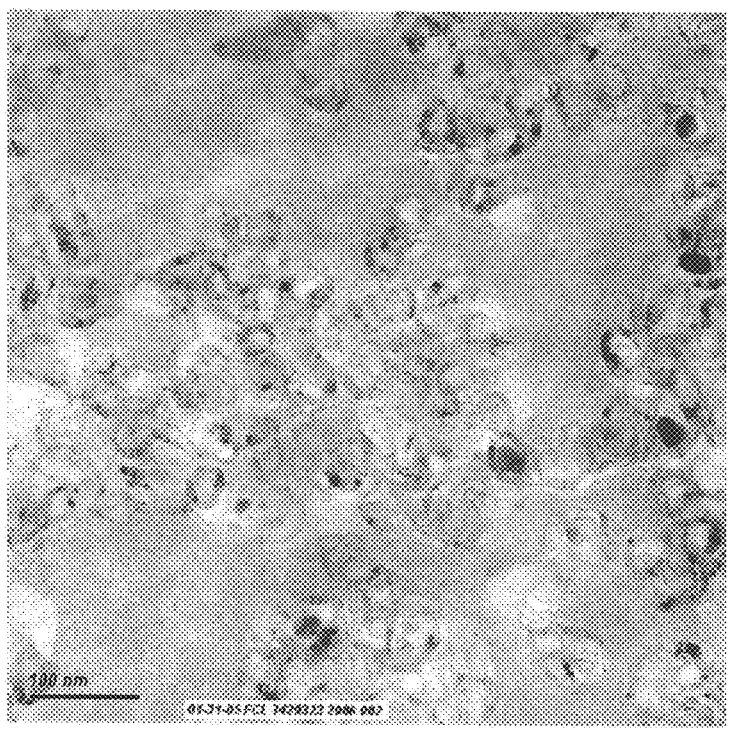

FIG. 53 shows the ToF SIMS spectrum for the 1.5% CoCN/C sample. FIG. 56 shows the intensities of ion species detected during analysis of the 1.5% CoTMPP/CP117 sample. FIG. 57 shows the intensities of ion species detected during analysis of the 1.0% CoCN/C sample. FIG. 58 shows the intensities of ion species detected during analysis of the 1.5% CoCN/C sample. FIG. 59 shows the intensities of ion species detected during analysis of the 5% CoCN/C sample. FIG. 60 shows the intensities of ion species detected during analysis of the 10% CoCN/C sample. FIG. 61 shows the intensities of ion species detected during analysis of the 1.0% CoPLCN/C sample. Relative intensities for each of the samples (given in Table 26) were determined as described above for the iron samples.

As shown in Table 26, for the 1.5% CoTMPP/CP117 catalyst prepared using a CoTMPP organometallic precursor, the majority of the $CoN_xC_y^+$ ions existed in the form of $CoN_4C_y^+$ ions along with a minor portion of $CoNC_y^+$ and $CoN_3C_y^+$ ions. $CoN_2C_y^+$ ions were not detected in the analysis of the 1.5% CoTMPP/CP117 catalyst.

For the 1.5% CoTMPP/MC10 catalyst, $CoN_xC_y^+$ ion signals were not identified, possibly due to the high surface area (2704 m²/g) of the MC10 carbon support. Although the 1.5% CoTMPP/CP117 and 1.5% CoTMPP/MC10 catalysts have the same cobalt loading, the 1.5% CoTMPP/MC10 catalyst will exhibit less cobalt species than the 1.5% CoTMPP/CP117 catalyst when comparison is made on a normalized surface area due to the higher surface area MC10 carbon support. ToF SIMS is a surface sensitive technique which collects signals from a fixed surface area for different samples. Thus, the results for the 1.5% CoTMPP/MC10 catalyst are likely due to the effect of the support surface area on cobalt density. However, a similar $CoN_xC_y^+$ ion population would be expected in for both 1.5% CoTMPP/MC10 and 1.5% CoTMPP/CP117 as the surface area of the support is not expected to affect ion formation and distribution.

Regardless of the carbon support used, existence of a major portion of $CoN_4C_y^+$ species in the CoTMPP catalysts is not surprising due to the nature of the metal porphyrin in which the metal centers are coordinated to four nitrogen atoms on the porphyrin rings.

Similar $CoN_xC_y^+$ ions and ion distribution were observed for the 1.0% CoCN/C and 1.5% CoCN/C catalysts. For each, the majority of the $CoN_xC_y^+$ ions existed as $CoNC_y^+$ and $CoN_2C_y^+$ ions along with $CoN_3C_y^+$ ions. $CoN_4C_y^+$ ions were not detected in analysis of either sample.

As cobalt loading increased, the proportion of $CoNC_y^+$ ions decreased and $CoN_4C_y^+$ ions were observed in analysis of the 5% CoCN/C and 10% CoCN/C samples. Significant amounts of $CoN_2C_y^+$ and $CoN_3C_y^+$ ions were detected for each of these samples.

As shown in Example 43, the CoCN/C catalysts exhibited superior reaction performance (i.e., higher PMIDA and formaldehyde oxidation activity) as compared to the CoTMPP/C catalysts.

As shown in Example 24, reaction performance of CoCN/C catalysts decreased slightly as cobalt loading increased (i.e., those CoCN/C samples in which $CoN_4C_y^+$ ions were observed exhibited decreased performance as compared to those CoCN/C samples in which $CoN_4C_y^+$ ions were not observed). Based on these results, it is believed that the $CoNC_y^+$ are the major catalytic sites for PMIDA and formaldehyde oxidation with $CoNC_y^+$ also contributing catalytic activity.

EXAMPLE 47

This example details transmission electron microscopy (TEM) analysis of various catalyst samples following the procedure described in Example 31. Samples analyzed included: (1) a 1% cobalt phthalocyanine (CoPLCN) catalyst on a carbon support having a Langmuir surface area of approximately 1600 m²/g prepared generally as described in Examples 22 and 23; (2) a 1.5% CoTMPP/MC10 catalyst prepared generally as described in Example 6 of International Publication No. WO 03/068387; (3) a 1.5% CoTMPP/CP117 catalyst prepared generally as described in Example 6 of International Publication No. WO 03/068387.

FIGS. 62A, 62B, 63A and 63B are TEM images for the 1% CoPLCN/C sample. High magnification TEM analysis reveals that most of the Co-related particles are associated with some graphitic features (see FIG. 62A), suggesting that during the catalyst preparation process, Co stimulates the graphitization of the carbon substrates (see FIGS. 63A and 63B). From some low-density carbon substrates, larger cobalt-based particles of 10-16 nm in diameter have been observed.

Figure 64A:
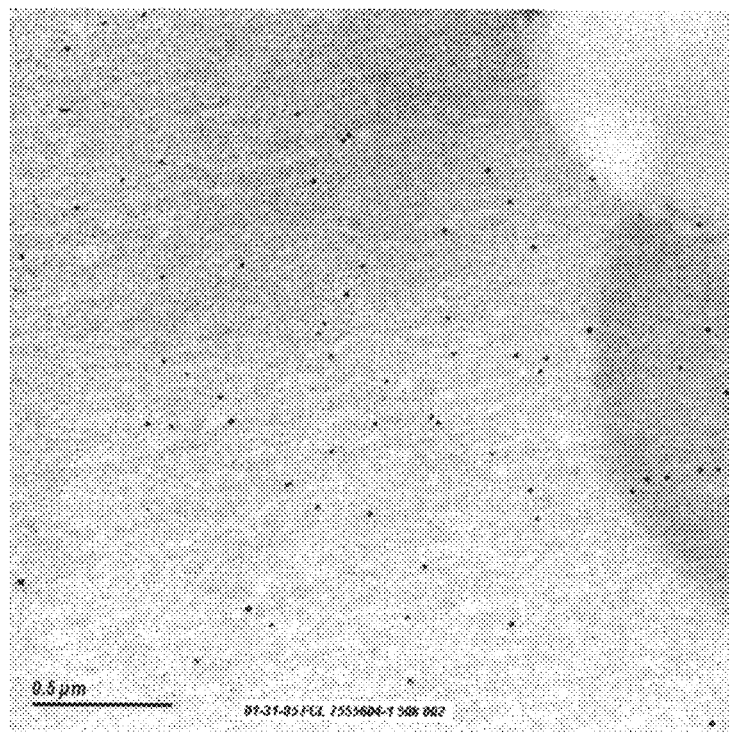
FIGS. 64A and 64B are TEM images for a 1.5% cobalt tetramethoxy phenylporphyrin (CoTMPP) catalyst analyzed as described in Example 47.
Figure 64B:
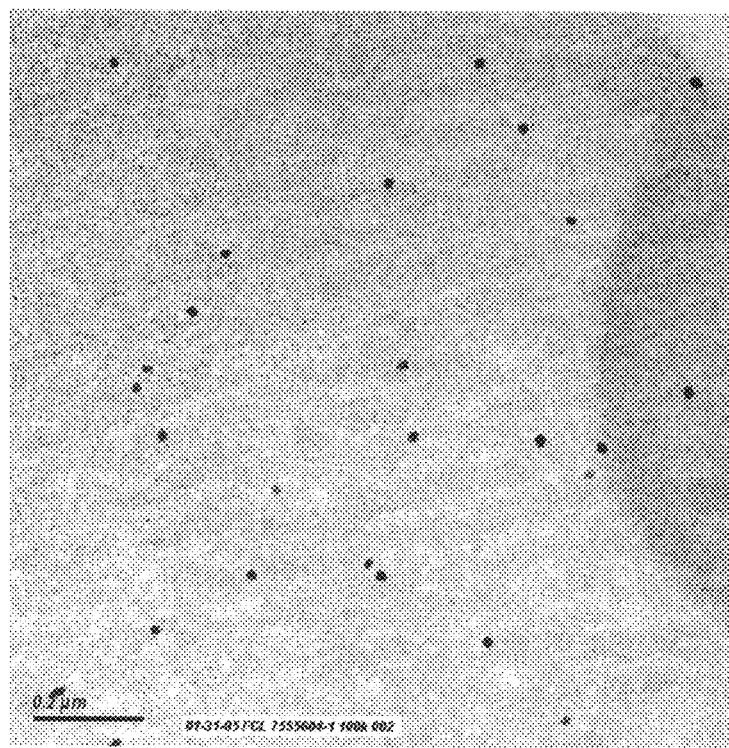

FIGS. 64A and 64B are TEM images for the 1.5% CoTMPP/MC10 sample. Many larger particles of from 18-20 nm in diameter were detected in the TEM analysis for the 1.5% CoTMPP/MC10 sample. In contrast, as shown in FIGS. 27-33 (Example 31), Co-based particles of a size above the detection limit (1 nm in diameter) of this SEM analysis were not detected for the 1.5% CoCN/C catalyst. Based on the foregoing, it is currently believed that the cobalt species in this sample likely exist in an amorphous form or in particles of a size below 1 nm.

Figure 65A:
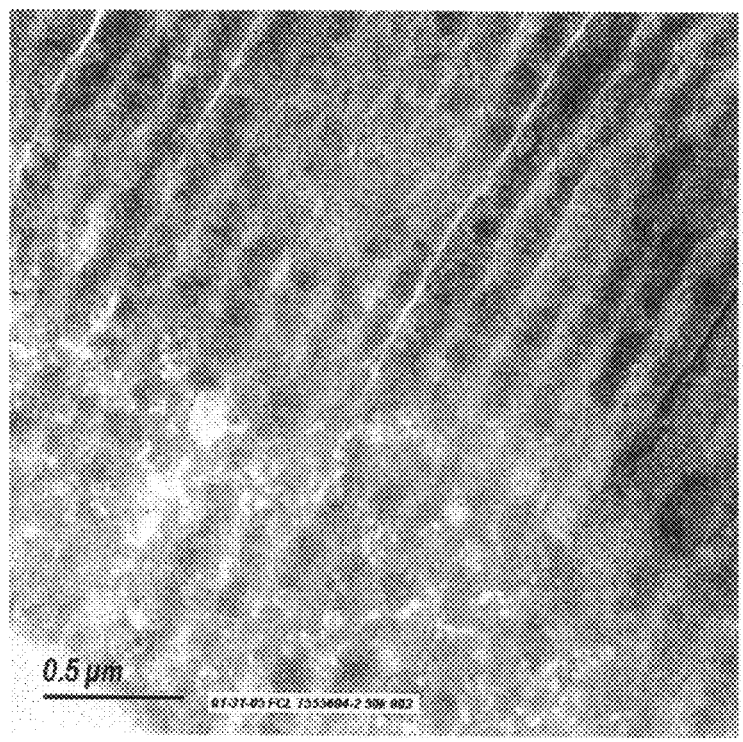
FIGS. 65A and 65B are TEM images for a 1.5% cobalt tetramethoxy phenylporphyrin (CoTMPP) catalyst analyzed as described in Example 47.
Figure 65B:
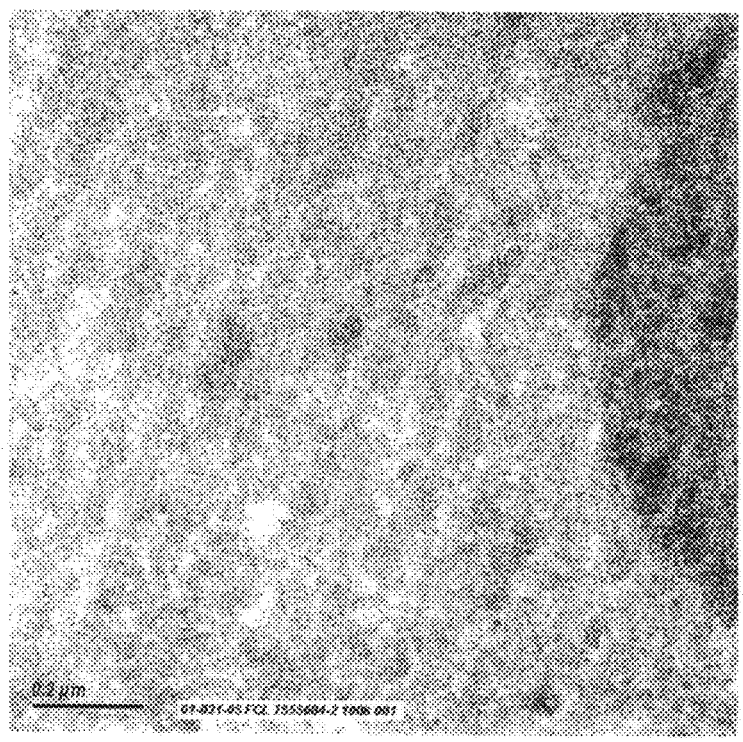

FIGS. 65A and 65B are TEM images for the 1.5% CoTMPP/CP117 sample. No Co-based particles within our TEM detecting limit of 1 nm in diameter were detected (see FIGS. 65A and 65B).

EXAMPLE 48

The following example details CO chemisorption analysis used to determine exposed metal surface areas for various iron-based catalysts, cobalt-based catalysts, and carbon supports. The method described in this example is referenced in this specification and appended claims as "Protocol B."

This protocol subjects a single sample to two sequential CO chemisorption cycles.

Cycle 1 measures initial exposed metal (e.g., cobalt) at zero valence state. The sample is vacuum degassed and treated with oxygen. Next, residual, un-adsorbed oxygen is removed and the catalyst is then exposed to CO. The volume of CO taken up irreversibly is used to calculate metal (e.g., $Co^0$) site density.

Cycle 2 measures total exposed metal. Without disturbing the sample after cycle 1, it is again vacuum degassed and then treated with flowing hydrogen, and again degassed. Next the sample is treated with oxygen. Finally, residual, non-adsorbed oxygen is removed and the catalyst is then again exposed to CO. The volume of CO taken up irreversibly is used to calculate total exposed metal (e.g., $Co^0$) site density. See, for example, Webb et al., *Analytical Methods in Fine Particle Technology*, Micromeritics Instrument Corp., 1997, for a description of chemisoprtion analysis. Sample preparation, including degassing, is described, for example, at pages 129-130.

Equipment: Micromeritics (Norcross, Ga.) ASAP 2010-static chemisorption instrument; Required gases: UHP hydrogen; carbon monoxide; UHP helium; oxygen (99.998%); Quartz flow through sample tube with filler rod; two stoppers; two quartz wool plugs; Analytical balance.

Preparation: Insert quartz wool plug loosely into bottom of sample tube. Obtain tare weight of sample tube with 1st wool plug. Pre-weigh approximately 0.25 grams of sample then add this on top of the 1st quartz wool plug. Precisely measure initial sample weight. Insert 2nd quartz wool plug above sample and gently press down to contact sample mass, then add filler rod and insert two stoppers. Measure total weight (before degas): Transfer sample tube to degas port of instrument then vacuum to <10 µm Hg while heating under vacuum to 150° C. for approximately 8-12 hours. Release vacuum. Cool to ambient temperature and reweigh. Calculate weight loss and final degassed weight (use this weight in calculations).

Cycle 1: Secure sample tube on analysis port of static chemisorption instrument. Flow helium (approximately 85 cm³/minute) at ambient temperature and atmospheric pressure through sample tube, then heat to 150° C. at 5° C./minute. Hold at 150° C. for 30 minutes. Cool to 30° C.

Evacuate sample tube to <10 µm Hg at 30° C. Hold at 30° C. for 15 minutes. Close sample tube to vacuum pump and run leak test. Evacuate sample tube while heating to 70° C. at 5° C./min. Hold for 20 minutes at 70° C.

Flow oxygen (approximately 75 cm³/minute) through sample tube at 70° C. and atmospheric pressure for 50 minutes.

Evacuate sample tube at 70° C. for 5 minutes.

Flow helium (approximately 85 cm³/minute) through sample tube at atmospheric pressure and increase to 80° C. at 5° C./minute. Hold at 80° C. for 15 minutes.

Evacuate sample tube at 80° C. for 60 minutes and hold under vacuum at 80° C. for 60 minutes. Cool sample tube to 30° C. and continue evacuation at 30° C. for 30 minutes. Close sample tube to vacuum pump and run leak test.

Evacuate sample tube at 30° C. for 30 minutes and hold under vacuum at 30° C. for 30 minutes.

For a first CO analysis, CO uptakes are measured under static chemisorption conditions at 30° C. and starting manifold pressures of 50, 100, 150, 200, 250, 300, 350 and 400 mm Hg (gauge) to determine the total amount of CO adsorbed (i.e., both chemisorbed and physisorbed).

Pressurize manifold to the starting pressure (e.g., 50 mm Hg). Open valve between manifold and sample tube allowing CO to contact the sample in the sample tube. Allow the pressure in the sample tube to equilibrate. The reduction in pressure from the starting manifold pressure to equilibrium pressure in the sample tube indicates the volume of CO uptake by the sample.

Close valve between the manifold and sample tube and pressurize the manifold to the next starting pressure (e.g., 100 mm Hg). Open valve between manifold and sample tube allowing CO to contact the sample in the sample tube. Allow the pressure in the sample tube to equilibrate to determine the volume of CO uptake by the sample. Perform for each starting manifold pressure.

Evacuate sample tube at 30° C. for 30 minutes.

For a second CO analysis, CO uptakes are measured under static chemisorption conditions at 30° C. and starting manifold pressures of 50, 100, 150, 200, 250, 300, 350 and 400 mm Hg (gauge) as described above for the first CO analysis to determine the total amount of CO physisorbed.

Cycle 2: After the second CO analysis of Cycle 1, flow helium (approximately 85 cm³/minute) at 30° C. and atmospheric pressure through sample tube then heat to 150° C. at 5° C./minute. Hold at 150° C. for 30 minutes.

Cool to 30° C. Evacuate sample tube to <10 μm Hg at 30° C. for 15 minutes. Hold at 30° C. for 15 minutes.

Close sample tube to vacuum pump and run leak test.

Evacuate sample tube at 30° C. for 20 minutes.

Flow hydrogen (approximately 150 cm³/minute) through sample tube at atmospheric pressure while heating to 150° C. at 10° C./min. Hold at 150° C. for 15 minutes.

Evacuate sample tube at 150° C. for 60 minutes. Cool sample tube to 70° C. Hold at 70° C. for 15 minutes.

Flow oxygen (approximately 75 cm³/minute) through sample tube at atmospheric pressure and 70° C. for 50 minutes.

Evacuate sample tube at 70° C. for 5 minutes.

Flow helium (approximately 85 cm³/minute) through sample tube at atmospheric pressure and increase temperature to 80° C. at 5° C./minute. Hold at 80° C. for 15 minutes. Evacuate sample tube at 80° C. for 60 minutes. Hold under vacuum at 80° C. for 60 minutes.

Cool sample tube to 30° C. and continue evacuation at 30° C. for 30 minutes. Close sample tube to vacuum pump and run leak test.

Evacuate sample tube at 30° C. for 30 minutes and hold for 30 minutes.

For a first CO analysis, CO uptakes are measured under static chemisorption conditions at 30° C. and starting manifold pressures of 50, 100, 150, 200, 250, 300, 350 and 400 mm Hg (gauge) to determine the total amount of CO adsorbed (i.e., both chemisorbed and physisorbed).

Pressurize manifold to the starting pressure (e.g., 50 mm Hg). Open valve between manifold and sample tube allowing CO to contact the sample in the sample tube. Allow the pressure in the sample tube to equilibrate. The reduction in pressure from the starting manifold pressure to equilibrium pressure in the sample tube indicates the volume of CO uptake by the sample.

Close valve between the manifold and sample tube and pressurize the manifold to the next starting pressure (e.g., 100 mm Hg). Open valve between manifold and sample tube allowing CO to contact the sample in the sample tube. Allow the pressure in the sample tube to equilibrate to determine the volume of CO uptake by the sample. Perform for each starting manifold pressure.

Evacuate sample tube at 30° C. for 30 minutes.

For a second CO analysis, CO uptakes are measured under static chemisorption conditions at 30° C. and starting manifold pressures of 50, 100, 150, 200, 250, 300, 350 and 400 mm Hg (gauge) as described above for the first CO analysis to determine the total amount of CO physisorbed.

Calculations: Plot first and second analysis lines in each cycle: volume CO physically adsorbed and chemisorbed (1st analysis) and volume CO physically adsorbed (2nd analysis) (cm³/g at STP) versus target CO pressures (mm Hg). Plot the difference between First and Second analysis lines at each target CO pressure. Extrapolate the difference line to its intercept with the Y-axis. In Cycle 1, total exposed metal (e.g., Co⁰) (μmole CO/g)=Y-intercept of difference line/22.414× 1000. In Cycle 2, total exposed metal (μmole CO/g)=Y-intercept of difference line/22.414×1000.

The results for Cycle 2 uptake for various iron-based catalysts, carbon-based catalysts, and carbon supports (described in greater detail in Example 46) are shown below in Table 27. Both the untreated and treated carbon supports were particulate carbon supports having a Langmuir surface area of approximately 1600 m²/g. The treated carbon support was treated in an acetonitrile environment in accordance with the description in, for example, Example 9.

TABLE 27

| Catalyst | CO uptake (μmol CO/g) |
|---|---|
| 1.5% CoCN/C | 1.0 |
|  | 0.8 |
| 1.5% CoTMPP/MC10 | 1.6 |
| 1.5% CoTMPP/CP117 | 0 |
| 1.1% FeTPP/CP117 | 0 |
| 1% CoPLCN/C | 2.1 |
| 1% FeCN/C | <1 |
| Treated carbon support | <1 |
| Untreated carbon support | <1 |
| MC10 carbon support | <1 |
| CP117 carbon support | 0 |

EXAMPLE 49

A 1.5% cobalt catalyst prepared as described in Examples 12-14 and a catalyst prepared as described in U.S. Ser. No. 60/627,500 (Attorney Docket No. 39-21(52910)C, MTC 6879.2) containing 5% platinum and 0.5% iron deposited on a carbon support (5% Pt/0.5% Fe catalyst) were tested in the oxidation of N-(phosphonomethyl)iminodiacetic acid (PMIDA).

The PMIDA oxidation was conducted in a 200 ml glass reactor containing a total reaction mass (200 g) which included water (188.3 g), 5.74% by weight PMIDA (11.48 g) and 0.11% catalyst (0.21 g). The oxidation was conducted at a temperature of 100° C., a pressure of 60 psig, (a stir rate of 1000 revolutions per minute (rpm)), under an oxygen flow of 100 cm³/minute and under a nitrogen flow of 100 cm³/min.

As shown in Table 28, 6 reaction cycles to varying degrees of conversion (i.e., varying residual PMIDA concentration in the reactor) were carried out with each of the catalysts. Oxidation of PMIDA was monitored by electrochemical detection (ECD) using a dual probe ECD electrode mounted in the bottom of the reactor. The voltage required to maintain a select current density between the electrodes was monitored throughout the cycle to the varied residual PMIDA contents in the reaction mixture. The change in ECD values (i.e., ΔECD) was determined from the maximum and minimum ECD voltages observed during each cycle. The results are provided in Table 28.

TABLE 28

| Endpoint | ΔECD(V) | | | | | | | |
|---|---|---|---|---|---|---|---|---|
| Catalyst | 0.90 | 0.95 | 1.00 | 1.05 | 1.10 | 1.15 | 1.20 | 1.30 |
| Residual PMIDA(% by weight) for 5% Pt/0.5% Fe | | | 0.439 | 0.210 | 0.181 | 0.121 | 0.066 | 0.037 |
| Residual PMIDA (% by weight) for 1.5% CoCN/C | 0.283 | 0.139 | 0.091 | 0.054 | 0.034 | 0.023 | | |

The performance of each of the catalyst samples in PMIDA oxidation (under the conditions set forth above) was analyzed by allowing the reaction to proceed to pre-determined ΔECD values; the ΔECD value endpoints selected were those corresponding to a residual PMIDA content in the reactor of approximately 0.1% by weight as shown in Table 28 above. The ΔECD value for the 1.5% cobalt catalyst was approximately 1.00V and the ΔECD value for the 5% Pt/0.5% Fe catalyst was approximately 1.18V. 5 reaction cycles were carried out using the 1.5% Co catalyst while 6 cycles were carried out using the 5% Pt/0.5% Fe catalyst.

Figure 66:
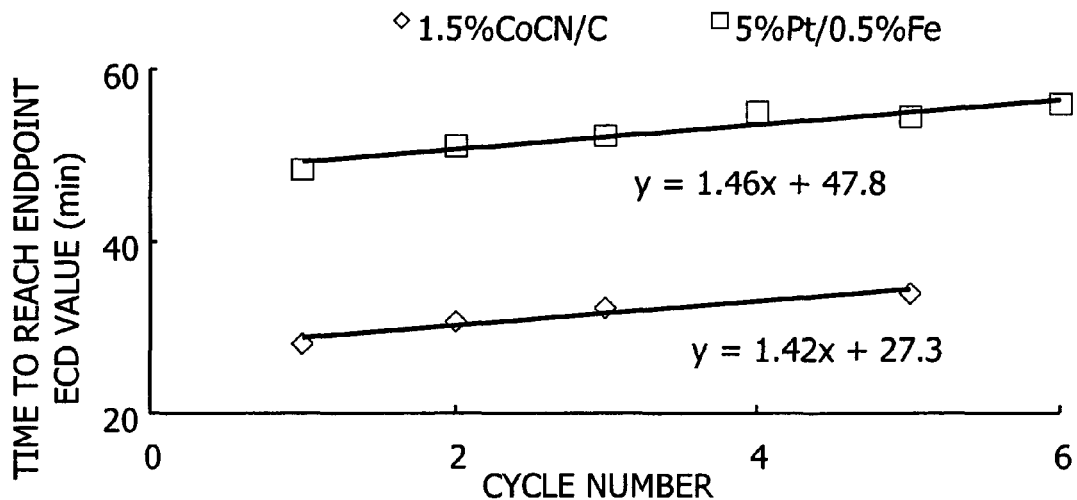
FIGS. 66 and 67 show PMIDA oxidation results described in Example 49.

FIG. 66 shows a plot of time to reach the target ΔECD value versus reaction cycle (i.e., reaction runtime plot) as an indicator of catalyst stability with stability increasing as the slope of the plot decreases. The slope of the plot for the 1.5% Co catalyst was 1.42 while the slope of the plot for the 5% Pt/0.5% Fe catalyst was 1.46. Table 29 provides a comparison of the selectivity of the catalysts to conversion of PMIDA, N-formylglyphosate (NFG), formaldehyde (FM), formic acid (FA), iminodiacetic acid (IDA), aminomethylphosphonic acid (AMPA), N-methy-N-(phosphonomethyl)glycine (NMG), imino-bis-(methylene)-bis-phosphonic acid (iminobis), phosphate ion (PO$_4$), glycine and methyl aminomethylphosphonic acid (MAMPA) based on the endpoint concentration of each of these components in the reaction mixture (determined by High Performance Liquid Chromatography) observed when using each of the catalysts.

Cobalt nitrate hexahydrate (Co(NO$_3$)$_2$.6H$_2$O) (0.773 g) (available from Aldrich Chemical Co., Milwaukee, Wis.) was introduced to 60 ml of a 50/50 (v/v) mixture of diglyme (diethylene glycol dimethyl ether) (also available from Aldrich Chemical Co., Milwaukee, Wis.) and deionized water in a 100 ml beaker.

The cobalt-diglyme mixture was added to the carbon slurry incrementally over the course of approximately 30 minutes (i.e., at a rate of approximately 2 ml/minute) to produce a cobalt-diglyme-carbon mixture. The pH of the carbon slurry was maintained at from about 7.5 to about 8.0 during addition of the cobalt solution by co-addition of a 0.1 wt % solution of sodium hydroxide (Aldrich Chemical Co., Milwaukee, Wis.). Approximately 1 ml of 0.1 wt. % sodium hydroxide solution was added to the carbon slurry during addition of the cobalt solution. The pH of the slurry was monitored using a pH meter (Thermo Orion, Model 290).

TABLE 29

| Catalyst | Cycle # | PMIDA (%) | Gly (%) | NFG (ppm) | FM (ppm) | FA (ppm) | IDA (ppm) | AMPA (ppm) | NMG (ppm) | Iminobis (ppm) | PO$_4$ (ppm) | Glycine (ppm) | MAMPA (ppm) |
|---|---|---|---|---|---|---|---|---|---|---|---|---|---|
| 5% Pt/ | 1 | 0.170 | 4.016 | 769 | 2244 | 4693 | 360 | 4 | 246 | 260 | 255 | 2 | 111 |
| 0.5% Fe | 2 | 0.108 | 4.173 | 836 | 2356 | 4947 | 280 | 10 | 249 | 279 | 218 | 5 | 122 |
| Endpoint | 4 | 0.121 | 4.213 | 885 | 2515 | 5521 | 220 | 98 | 294 | 386 | 192 | 53 | 42 |
| (ΔECD = | 6 | 0.150 | 4.099 | 806 | 2526 | 5330 | 180 | 108 | 304 | 295 | 171 | 54 | 36 |
| 1.18 V) | Average | | 4.125 | | 2410 | 5123 | | | | | | | |
| 1.5% | 1 | 0.250 | 4.092 | 695 | 2863 | 6560 | 60 | 155 | 172 | 271 | 91 | 61 | 38 |
| CoCN/C | 2 | 0.092 | 4.346 | 808 | 2633 | 7479 | 80 | 174 | 171 | 296 | 147 | 77 | 47 |
| Endpoint | 4 | 0.087 | 4.211 | 799 | 2313 | 7950 | 80 | 177 | 187 | 291 | 170 | 95 | 50 |
| (ΔECD = | 5 | 0.083 | 4.254 | 832 | 2251 | 8148 | 80 | 191 | 189 | 291 | 187 | 103 | 50 |
| 1.00 V) | Average | | 4.226 | | 2515 | 7534 | | | | | | | |

Figure 67:
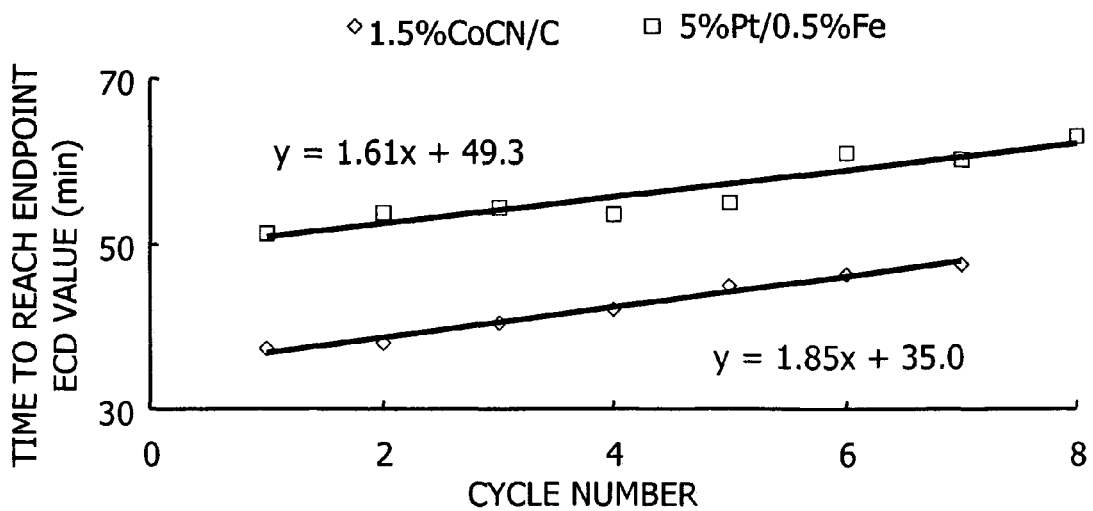

The performance of each of the catalyst samples in PMIDA oxidation (under the conditions set forth above) was also analyzed by allowing the reaction to proceed for an additional 12 minutes after reaching the pre-determined ΔECD value endpoints described above. 7 reaction cycles were carried out using each of the catalysts. FIG. 67 shows the reaction endpoint runtime plots; the slope of the plot for the 1.5% cobalt catalyst was 1.85 while the slope of the plot for the 5% Pt/0.5% Fe catalyst was 1.61. Table 30 provides a comparison of the selectivity towards oxidation of the various compounds set forth above based on the endpoint concentration of the compounds at the reaction endpoint (as determined by HPLC) observed when using each of the catalysts.

The cobalt-diglyme-carbon mixture was stirred using a mechanical stirring rod operating at 50% of output (Model IKA-Werke RW16 Basic) for approximately 30 minutes; the pH of the mixture was monitored using the pH meter and maintained at approximately 8.0 by dropwise addition of 0.1 wt. % sodium hydroxide or 0.1 wt. % HNO$_3$. The mixture was then heated under a nitrogen blanket to approximately 45° C. at a rate of approximately 2° C. per minute while maintaining the pH at approximately 8.0 by dropwise addition of 0.1 wt. % sodium hydroxide or 0.1 wt. % HNO$_3$. Upon reaching approximately 45° C., the mixture was stirred using the mechanical stirring bar described above for 20 minutes at a

TABLE 30

| Catalyst | Cycle # | PMIDA (%) | Gly (%) | NFG (ppm) | FM (ppm) | FA (ppm) | IDA (ppm) | AMPA (ppm) | NMG (ppm) | Iminobis (ppm) | PO$_4$ (ppm) | Glycine (ppm) | MAMPA (ppm) |
|---|---|---|---|---|---|---|---|---|---|---|---|---|---|
| 5% Pt/0.5% Fe | 1 | 0.085 | 4.040 | 905 | 1719 | 4154 | 390 | 158 | 209 | 273 | 303 | 46 | 72 |
| Endpoint | 2 | 0.076 | 4.210 | 930 | 1770 | 4359 | 280 | 173 | 219 | 256 | 208 | 48 | 99 |
| (ΔECD = 1.18 V) | 4 | 0.073 | 4.170 | 922 | 2036 | 4715 | 210 | 171 | 263 | 260 | 178 | 48 | 83 |
| +12 min | 7 | 0.058 | 4.298 | 938 | 2403 | 5018 | 150 | 174 | 362 | 276 | 151 | 55 | 79 |
| 1.5% CoCN/C | 1 | 0.090 | 4.305 | 1357 | 2160 | 7579 | 60 | 579 | 223 | 269 | 178 | 90 | 186 |
| Endpoint | 2 | 0.086 | 4.203 | 1494 | 1959 | 8248 | 70 | 519 | 212 | 269 | 232 | 112 | 190 |
| (ΔECD = 1.00 V) | 4 | 0.078 | 4.019 | 1547 | 1698 | 8197 | 80 | 455 | 181 | 239 | 283 | 129 | 154 |
| +12 min | 7 | 0.080 | 3.955 | 1615 | 1506 | 8502 | 80 | 441 | 170 | 243 | 339 | 154 | 137 |

EXAMPLE 50

A particulate carbon support designated D1097 (10.00 g) having a Langmuir surface area of approximately 1500 m$^2$/g was added to a 1 liter flask containing deionized water (400 ml) to form a slurry.

constant temperature of approximately 45° C. and a pH of approximately 8.0. The mixture was then heated to approximately 50° C. and its pH was adjusted to approximately 8.5 by addition of 0.1 wt. % sodium hydroxide solution; the mixture was maintained at these conditions for approximately 20 minutes. The slurry was then heated to approximately 60° C., its pH adjusted to 9.0 by addition of 0.1 wt. % sodium hydroxide solution (5 ml) and maintained at these conditions for approximately 10 minutes.

The resulting mixture was filtered and washed with a plentiful amount of deionized water (approximately 500 ml) and the wet cake was dried for approximately 16 hours in a vacuum oven at approximately 120° C. to provide a catalyst precursor.

Cobalt-containing catalyst precursor (5 g) was charged into the center of a Hastelloy C tube reactor packed with high temperature insulation material; thermocouple was inserted to monitor the temperature. The reactor was purged with argon that was introduced to the reactor at a rate of approximately 100 cm$^3$/min at approximately 20° C. for approximately 15 minutes.

The temperature of the reactor was then raised to approximately 30° C. during which time acetonitrile (available from Aldrich Chemical Co. (Milwaukee, Wis.) was introduced to the reactor at a rate of approximately 10 cm$^3$/minute. The reactor was maintained at approximately 950° C. for approximately 120 minutes.

The reactor was cooled to approximately 20° C. over the course of 90 minutes under a flow of argon at approximately 100 cm$^3$/minute.

The resulting catalyst contained approximately 1.5% by weight cobalt.

A second catalyst containing approximately 3% by weight cobalt was prepared in this manner by doubling the amount of cobalt source (i.e., 1.545 g of cobalt nitrate hexahydrate).

The 1.5% and 3% cobalt catalysts prepared using diglyme were tested in PMIDA oxidation under the conditions set forth in Example 49 that was monitored by electrochemical detection (ECD) and their performance was compared to that of the 5% Pt/0.5% Fe catalyst prepared as described in U.S. Ser. No. 60/627,500 (Attorney Docket No. 39-21(52910)C, MTC 6879.2). The target ΔECD value for the 1.5% cobalt and 3% cobalt catalysts was approximately 1.00 V. As in Example 49, the ΔECD value for the 5% Pt/0.5% Fe catalyst was approximately 1.18V.

Figure 68:
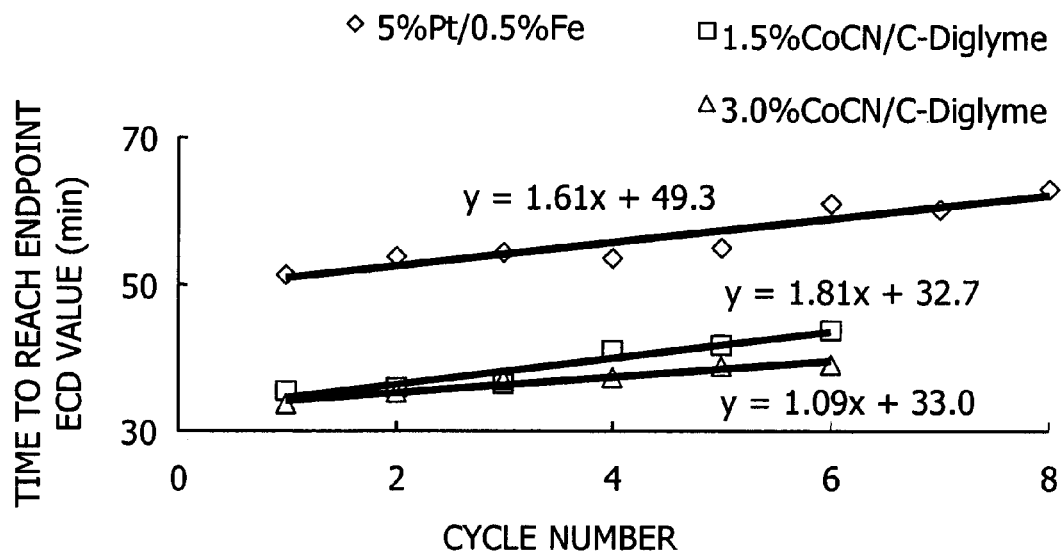
FIGS. 68 and 69 show PMIDA oxidation results described in Example 50.

The cobalt-containing catalysts were tested in each of 6 PMIDA reaction cycles while the 5% Pt/0.5% Fe catalyst was tested in each of 8 reaction cycles. FIG. 68 shows the reaction endpoint runtime plots for each catalyst. The slope of the plot for the 1.5% cobalt catalyst was 1.81, the slope of the plot for the 5% Pt/0.5% Fe catalyst was 1.61 while the slope of the plot for the 3% cobalt catalyst was 1.09.

Figure 69:
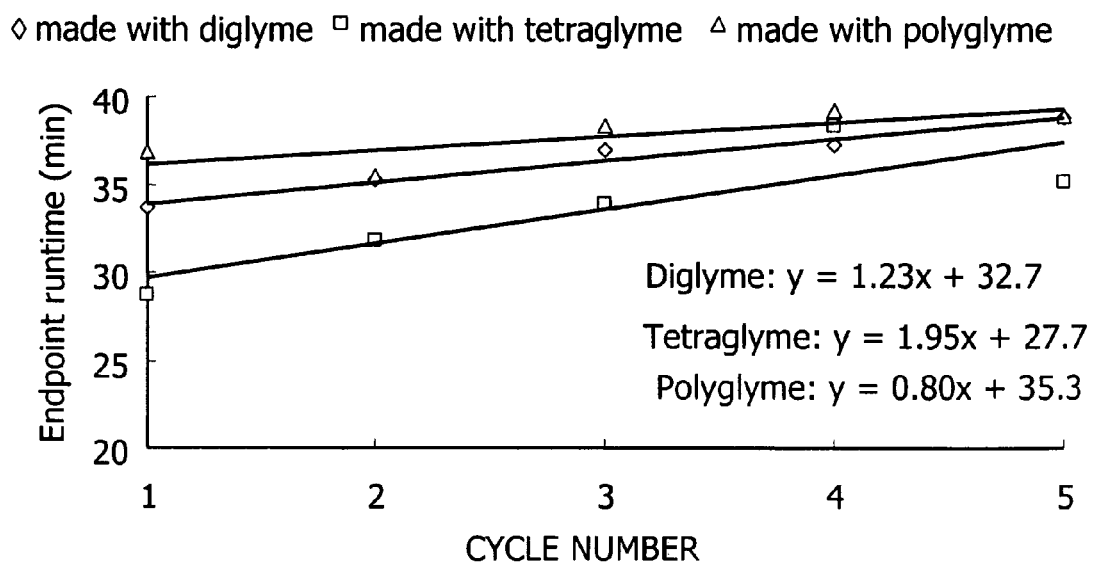

Another catalyst (1) containing 3% cobalt was prepared as described above using diglyme. Two catalysts containing 3% cobalt were also prepared as described above using tetraglyme (2) and polyglyme (3) rather than diglyme. Each of the catalysts was tested in PMIDA oxidation under the conditions set forth in Example 49 in each of 5 reaction cycles. For each reaction cycle, the reaction was carried out for an additional 12 minutes after reaching the predetermined ΔECD value of 1.00 V for each of the catalysts. FIG. 69 shows a plot of time to reach the predetermined endpoint versus reaction cycle for each of the catalysts. As shown in FIG. 69, the time axis-intercept for the plot for the catalyst prepared using diglyme was approximately 32.7 and its slope was approximately 1.23; the time axis-intercept for the plot for the catalyst prepared using tetraglyme was approximately 27.7 and its slope was approximately 1.95; the time axis-intercept for the plot for the catalyst prepared using polyglyme was approximately 35.3 and its slope was approximately 0.80.

EXAMPLE 51

This Example details preparation of various iron and cobalt-containing catalysts prepared generally as described in Example 50.

Catalysts containing 3% iron were prepared generally in accordance with the method described in Example 50. A particulate carbon support (10 g) having a Langmuir surface area of approximately 1500 m$^2$/g described in Example 50 was was added to a 1 liter flask containing deionized water (400 ml) to form a slurry. Iron chloride (FeCl$_3$.H$_2$O) (1.497 g) (available from Aldrich Chemical Co., Milwaukee, Wis.) was introduced to 60 ml of a 50/50 (v/v) mixture of diglyme (diethylene glycol dimethyl ether) (also available from Aldrich Chemical Co., Milwaukee, Wis.) and deionized water in a 100 ml beaker. The iron-diglyme mixture was added to the carbon slurry incrementally over the course of approximately 30 minutes (i.e., at a rate of approximately 2 ml/minute) to produce an iron-diglyme-carbon mixture. The pH of the carbon slurry was maintained at from about 4.0 and about 4.4 during addition of the iron-diglyme mixture to the carbon slurry by co-addition of sodium hydroxide solution (Aldrich Chemical Co., Milwaukee, Wis.). The iron-diglyme-carbon mixture was stirred using a mechanical stirring rod operating at 50% of output (Model IKA-Werke RW16 Basic) for approximately 30 minutes; the pH of the mixture was monitored using the pH meter and maintained at approximately 4.4 by dropwise addition of 0.1 wt. % sodium hydroxide. The mixture was then heated under a nitrogen blanket to approximately 70° C. at a rate of approximately 2° C. per minute while maintaining the pH at approximately 4.4 by dropwise addition of 0.1 wt. % sodium hydroxid. Upon reaching approximately 70° C., the pH of the mixture was raised by addition of a 0.1 wt. % sodium hydroxide solution according to the following pH profile: 10 minutes at pH of approximately 5.0, 20 minutes at pH of approximately 5.5, followed by continued stirring at pH of 6.0 until the pH became relatively constant. The resulting mixture was filtered and washed with a plentiful amount of deionized water and the wet cake was dried for approximately 16 hours in a vacuum oven at 120° C. to provide a catalyst precursor. Iron-containing catalyst precursor (5 g) was charged into the Hastelloy C tube reactor and heat treated as described above regarding preparation of the cobalt-containing catalysts. A catalyst containing 3% iron was also prepared using this method using polyglyme in place of diglyme. (Entries 1 and 2 in Table 31)

Catalysts containing 3% cobalt were also prepared in accordance with the method detailed in Example 50 using various liquid media. For each 3% cobalt catalyst, cobalt nitrate hexahydrate (1.545 g) was introduced to 60 ml of a 50/50 (v/v) of water and an additional component.

The liquid media used included 50/50 (v/v) mixtures of water and diethylene glycol diethyl ether, diethylene glycol ethyl ether acetate, Dipropylene glycol methyl ether, 12-crown-4 (1,4,7,10-tetraoxacyclododecane) (a crown analog to polyglyme), 18-crown-6 (1,4,7,10,13,16-hexaoxacylclooctadecane, and tetraethylene glycol. (Entries 6, 7, and 9-12 in Table 31) (Entries 3 and 16 in Table 31 correspond to 3% Co catalysts prepared as described in Example 50 using diglyme while entries 4 and 5 correspond to 3% Co catalysts prepared using tetraglyme and polyglyme, respectively)

A catalyst containing 0.5% Co was prepared by introducing cobalt nitrate hexahydrate (0.258 g) to 60 ml of a 50/50 (v/v) mixture of water and N,N,N',N',N" Pentamethyldiethylenetriamine. (Entry 8 in Table 31)

In addition, a 3% Co catalyst was prepared by introducing cobalt nitrate hexahydrate (1.545 g) to a mixture containing 30 ml of a 50/50 (v/v) mixture of water and ethanol and 30 ml of diglyme. (Entry 13 in Table 31)

A 3% Co catalyst was also prepared by introducing cobalt nitrate hexahydrate (1.545 g) to 60 ml of a 50/50 (v/v) mixture of ethanol and diglyme. (Entry 14 in Table 31) A 3% Co catalyst was also prepared by introducing cobalt nitrate hexahydrate (1.545 g) to 60 ml of ethanol. (Entry 15 in Table 31)

A 4% Co catalyst was prepared generally as described in Example 50 by introducing cobalt nitrate hexahydrate (2.06 g) to 60 ml of a 50/50 (v/v) mixture of polyglyme and deionized water. (Entry 17 in Table 31)

A catalyst containing 3% Co and 1% nickel was prepared by introducing cobalt nitrate hexahydrate (1.545 g) and nickel dichloride hexahydrate ($NiCl_2.6H_2O$) (0.422 g) to a 50/50 (v/v) mixture of diglyme and deionized water. (Entry 18 in Table 31)

A 3% Co catalyst was also prepared by introducing cobalt nitrate hexahydrate (1.545 g) to 60 ml of n-butanol. (Entry 19 in Table 31)

Each of the catalysts was tested in PMIDA oxidation was conducted in a 200 ml glass reactor containing a total reaction mass (200 g) which included water (188.3 g), 5.74% by weight PMIDA (11.48 g) and 0.15% catalyst (0.30 g). The oxidation was conducted at a temperature of 100° C., a pressure of 60 psig, (a stir rate of 1000 revolutions per minute (rpm)), under an oxygen flow of 175 $cm^3$/minute and under a nitrogen flow of 175 $cm^3$/min. The performance of each of the catalyst samples in PMIDA oxidation was analyzed over the course of 6 reaction cycles by allowing the reaction to proceed to 12 minutes past the pre-determined ΔECD values determined as set forth above in Example 49. The predetermined ΔECD value for each of the catalyst samples was 1.00 V. The intercepts and slopes of the plots of time to reach the predetermined LECD value versus reaction cycle are provided in Table 31.

TABLE 31

| Entry | Catalyst | Liquid Medium (see below for solvents Nos. 1-10) | Intercept | Slope |
|---|---|---|---|---|
| 1 | 3% FeCN/C | $H_2O$/1 | 31.5 | 10.13 |
| 2 | 3% FeCN/C | $H_2O$/2 | 35.7 | 11.93 |
| 3 | 3% CoCN/C | $H_2O$/1 | 29.7 | 0.69 |
| 4 | 3% CoCN/C | $H_2O$/3 | 29.3 | 1.09 |
| 5 | 3% CoCN/C | $H_2O$/2 | 30.0 | 0.70 |
| 6 | 3% CoCN/C | $H_2O$/4 | 32.2 | 1.24 |
| 7 | 3% CoCN/C | $H_2O$/5 | 31.8 | 1.45 |
| 8 | 0.5% CoCN/C | $H_2O$/6 | 26.2 | 0.95 |
| 9 | 3% CoCN/C | $H_2O$/7 | 28.9 | 0.78 |
| 10 | 3% CoCN/C | $H_2O$/8 | 24.5 | 1.80 |
| 11 | 3% CoCN/C | $H_2O$/9 | 33.3 | 3.17 |
| 12 | 3% CoCN/C | $H_2O$/10 | >120 | NA |
| 13 | 3% CoCN/C | EtOH/$H_2O$/1 | 26.2 | 1.33 |
| 14 | 3% CoCN/C | EtOH/1 | 30.2 | 0.8 |
| 15 | 3% CoCN/C | EtOH | 31.6 | 0.72 |
| 16 | 3% CoCN/C | $H_2O$/1 | 33.4 | 0.91 |
| 17 | 4% CoCN/C | $H_2O$/2 | 30.6 | 1.36 |
| 18 | (3% Co/1% Ni)CN/C | $H_2O$/1 | 32.1 | 3.78 |
| 19 | 3% CoCN/C | n-butanol | 30.2 | 0.89 |

Ethanol (EtOH)
1 Diglyme
2 Polyglyme (with an averaged Mn of 1000)
3 Tetraglyme
4 Diethylene glycol diethyl ether
5 Diethylene glycol ethyl ether acetate
6 N,N,N',N',N" Pentamethyldiethylenetriamine
7 Dipropylene glycol methyl ether
8 12-crown-4 (1,4,7,10-tetraoxacyclododecane) (a crown analog to polygylme)
9 18-crown-6 (1,4,7,10,13,16-hexaoxacylclooctadecane
10 Tetraethylene glycol 1% FeCN/C, 1.5. % CoCN/C, 1.1% FeTPP/CP117, and 1.5% CoTMPP/CP117 catalysts were also tested in PMIDA oxidation; these catalysts exhibited lower activity and stability than those catalysts set forth in Table 31.

EXAMPLE 52

The catalysts prepared as described in Examples 50 and 51 were analyzed to determine their Langmuir surface areas (e.g., total Langmuir surface area, Langmuir surface area attributed to micropores, and Langmuir surface area attributed to mesopores and macropores) as described in Example 28. The results are shown in Table 32.

For comparison purposes, a catalyst prepared as described in Example 50 by introducing cobalt nitrate (1.545 g) to 60 ml of diglyme was prepared and analyzed; neat carbon support used in Examples 50 and 51 was heat treated as described in Example 50 was also analyzed.

TABLE 32

(Entry Nos. are with reference to Table 31)

| Catalyst/Support | | Langmuir SA ($m^2$/g) | Micropore SA ($m^2$/g) <20 Å | Meso- & Macropore SA ($m^2$/g) Å |
|---|---|---|---|---|
| Support | | 1597 | 1294 | 280 |
| Support treated with $CH_3CN$ | Percentage of support SA | 1272 79.6% | 1030 79.6% | 238 85% |
| 3% CoCN/ 50% diglyme (Entry No. 3) | Percentage of support SA | 1080 67.6% | 889 68.7% | 191 68.2% |
| 3% CoCN/ 100% diglyme | Percentage of support SA | 1158 72.5% | 950 73.4% | 208 74.3% |
| 3% CoCN/ 50% tetraglyme (Entry No. 4) | Percentage of support SA | 1002 62.7% | 819 63.3% | 183 65.4% |
| 3% CoCN/ 50% polyglyme (Entry No. 5) | Percentage of support SA | 829 51.9% | 663 51.2% | 166 59.3% |
| Entry No. 6 | Percentage of support SA | 1162 78% | 956 79% | 206 74% |
| Entry No. 8 | Percentage of support SA | 1080 72% | 857 70% | 223 80% |
| Entry No. 9 | Percentage of support SA | 954 64% | 753 62% | 201 72% |
| Entry No. 10 | Percentage of support SA | 1116 75% | 888 73% | 228 81% |
| Entry No. 14 | Percentage of support SA | 1098 73% | 874 72% | 224 80% |
| Entry No. 15 | Percentage of support SA | 1121 75% | 887 73% | 234 84% |

Figure 70:
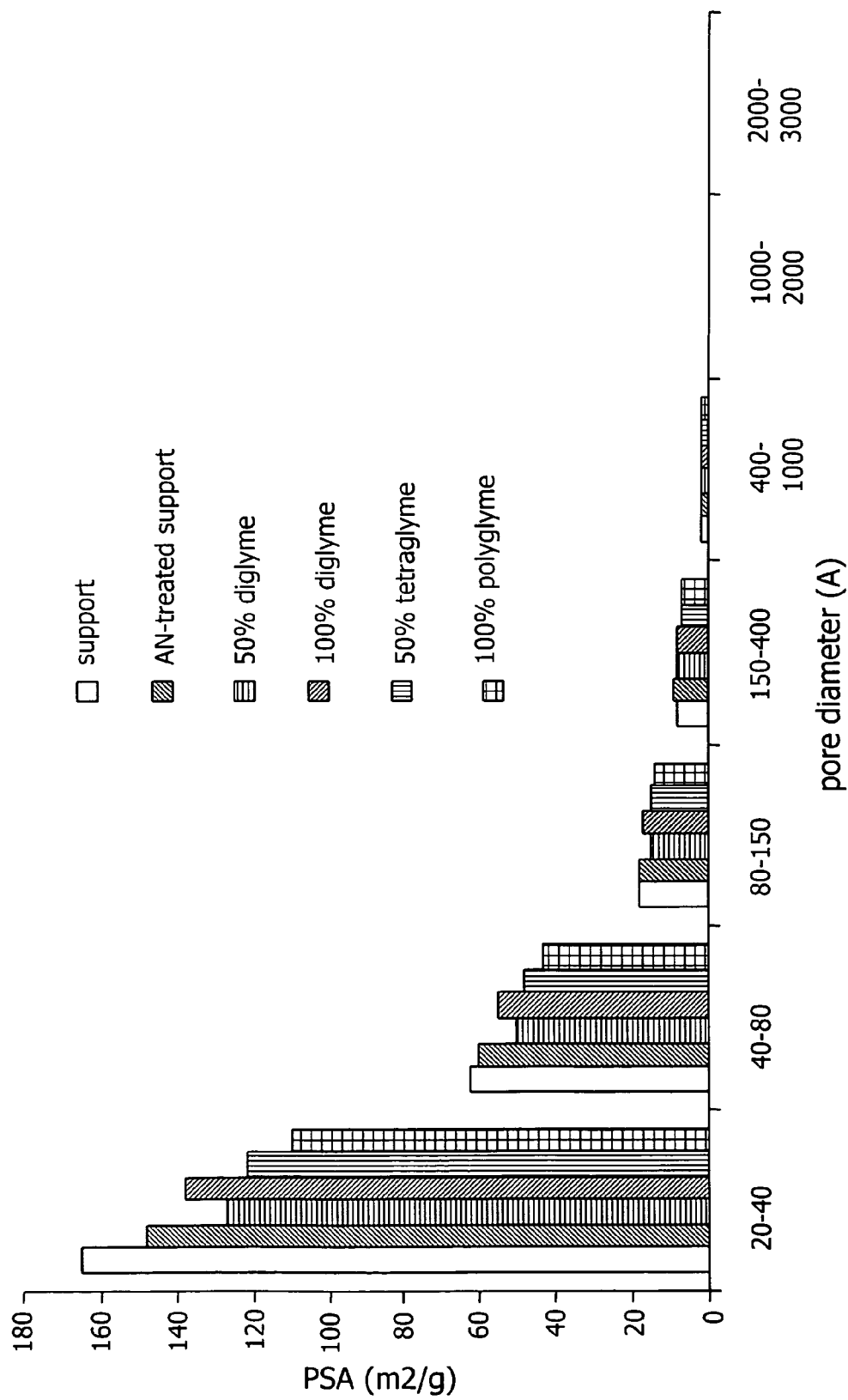
FIG. 70 shows pore volume distributions for catalysts analyzed as described in Example 52.

FIG. 70 shows the pore volume distribution for samples the carbon support, the acetonitrile-treated support, the 3% Co catalyst prepared using 100% diglyme, and Entry Nos. 3-5.

Table 33 shows the pore volume distribution (pore surface areas, PSA) for Entry Nos. 6, 8, 9, 10, 14, and 15 in Table 31.

TABLE 33

| PSA (m2/g) | Support | Support | Entry #6 | Entry #8 | Entry #9 | Entry #10 | Entry #14 | Entry #15 |
|---|---|---|---|---|---|---|---|---|
| 20-40 | 178.065 | 172.633 | 134.252 | 138.632 | 126.478 | 148.574 | 140.927 | 148.403 |
| 40-80 | 74.298 | 74.605 | 54.141 | 56.876 | 50.714 | 59.824 | 56.931 | 59.689 |
| 80-150 | 24.009 | 24.994 | 18.314 | 19.025 | 17.494 | 19.757 | 19.039 | 19.72 |
| 150-400 | 10.904 | 11.172 | 9.187 | 8.872 | 8.77 | 9.321 | 9.185 | 9.318 |
| 400-1000 | 1.955 | 1.873 | 1.914 | 1.971 | 1.916 | 1.743 | 1.976 | 1.767 |
| 1000-2000 | 0.528 | 0.459 | 0.425 | 0.276 | 0.286 | 0.464 | 0.366 | 0.41 |
| 2000-3000 | 0.089 | 0 | 0.152 | 0.145 | 0.008 | 0.067 | 0.114 | 0 |
| Total meso-/macro-pore SA (m2/g) | 289.848 | 285.736 | 218.385 | 225.797 | 205.666 | 239.75 | 228.538 | 239.307 |

Table 34 provides a comparison of the samples analyzed to determine their surface areas in this Example and Examples 28 and 44.

TABLE 34

| Catalyst/Support | | Surface area (SA) (m²/g) | Micropore SA (m²/g)<20 Å | Meso-& Macropore SA(m²/g) |
|---|---|---|---|---|
| Example 8 Support | | 1584 | 1329 | 256 |
| 1% FeCN/C | | 1142 | 937 | 205 |
| | percentage of support SA | 72% | 70% | 80% |
| 1% CoCN/C | | 1263 | 1051 | 212 |
| | percentage of support SA | 79% | 79% | 82% |
| Example 28 Support | | 1623 | 1365 | 258 |
| | percentage of support SA | 97.5% | 97.3% | 99% |
| 1.1% FeTPP/C | | 888 | 717 | 171 |
| | percentage of support SA | 56% | 53.9% | 66.7% |
| Support | | 1597 | 1294 | 280 |
| 1% FeCN/C | | 1164 | 935 | 229 |
| | percentage of support SA | 72.9% | 72.3% | 81.8% |
| 1.5% CoCN/C | | 1336 | 1066 | 251 |
| | percentage of support SA | 83.7% | 82.4% | 89.6% |
| 1% CoPLCN/C | | 1337 | 1082 | 250 |
| | percentage of support SA | 83.7% | 83.6% | 89.3% |
| CP117 Support | | 1603 | 1329 | 274 |
| 1.1% FeTPP/CP117 | | 888 | 696 | 192 |
| | percentage of support SA | 55.4% | 52.4% | 70.1% |
| 1.5% CoTMPP/CP117 | | 1163 | 915 | 240 |
| | percentage of support SA | 72.6% | 68.8% | 87.6% |
| MC-10 Support | | 2704 | 1944 | 760 |
| 1.5% CoTMPP/MC10 | | 2045 | 1330 | 715 |
| | percentage of support SA | 75.6% | 68.4% | 94.1% |
| Support | | 1597 | 1294 | 280 |
| Support treated with CH₃CN | | 1272 | 1030 | 238 |
| | Percentage of support SA | 79.6% | 79.6% | 85% |

TABLE 34-continued

| Catalyst/Support | | Surface area (SA) (m²/g) | Micropore SA (m²/g)<20 Å | Meso-& Macropore SA(m²/g) |
|---|---|---|---|---|
| 3% CoCN/ 50% diglyme (Entry No. 3) | | 1080 | 889 | 191 |
| | Percentage of support SA | 67.6% | 68.7% | 68.2% |
| 3% CoCN/ 100% diglyme | | 1158 | 950 | 208 |
| | Percentage of support SA | 72.5% | 73.4% | 74.3% |
| 3% CoCN/ 50% tetraglyme (Entry No. 4) | | 1002 | 819 | 183 |
| | Percentage of support SA | 62.7% | 63.3% | 65.4% |
| 3% CoCN/ 50% polyglyme (Entry No. 5) | | 829 | 663 | 166 |
| | Percentage of support SA | 51.9% | 51.2% | 59.3% |
| Entry No. 6 | | 1162 | 956 | 206 |
| | Percentage of support SA | 78% | 79% | 74% |
| Entry No. 8 | | 1080 | 857 | 223 |
| | Percentage of support SA | 72% | 70% | 80% |
| Entry No. 9 | | 954 | 753 | 201 |
| | Percentage of support SA | 64% | 62% | 72% |
| Entry No. 10 | | 1116 | 888 | 228 |
| | Percentage of support SA | 75% | 73% | 81% |
| Entry No. 14 | | 1098 | 874 | 224 |
| | Percentage of support SA | 73% | 72% | 80% |
| Entry No. 15 | | 1121 | 887 | 234 |
| | Percentage of support SA | 75% | 73% | 84% |

EXAMPLE 53

Catalysts prepared as described in Examples 51 and 52 were analyzed by Inductively Coupled Plasma (ICP) analysis as described in Example 29 to determine their transition metal and nitrogen content. The results are shown in Table 35.

TABLE 35

| Catalyst | Co(wt %) | N(wt %) | C + O + H(wt %) |
|---|---|---|---|
| 3% CoCN/50% diglyme (Entry No. 3) | 3.0 | 2.1 | 94.9 |
| 30% CoCN/100% diglyme | 3.0 | 2.1 | 94.9 |
| 3% CoCN/50% tetraglyme (Entry No. 4) | 3.0 | 2.1 | 94.9 |
| 3% CoCN/50% polyglyme (Entry No. 5) | 3.0 | 1.9 | 95.1 |

EXAMPLE 54

This example details scanning electron microscopy (SEM) and transmission electron microscopy (TEM) of various catalysts prepared as described in Examples 50 and 51. Table 36 lists the catalysts analyzed and the corresponding FIGS. providing the results. A 3% Co catalyst prepared generally as described in Example 50 in which the cobalt source was introduced to a liquid medium consisting of water was also prepared and analyzed.

TABLE 36

(Entry Nos. are with reference to Table 31)

Figure 71A:
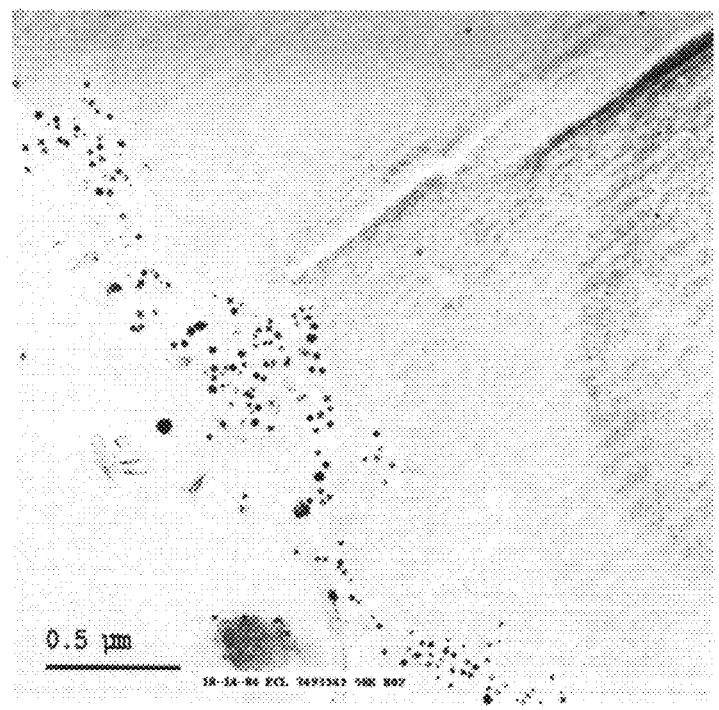
FIGS. 71A-87B are SEM and TEM images of catalysts analyzed as described in Example 54.
Figure 71B:
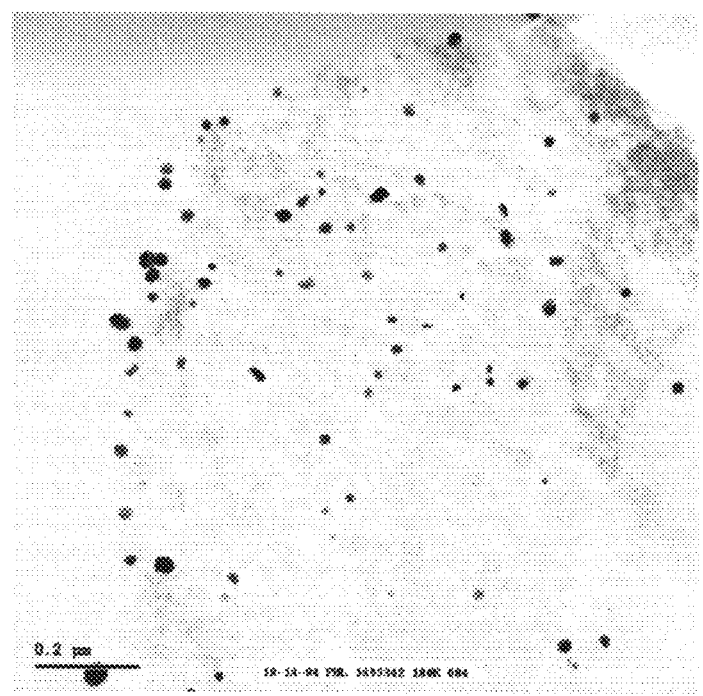
Figure 72A:
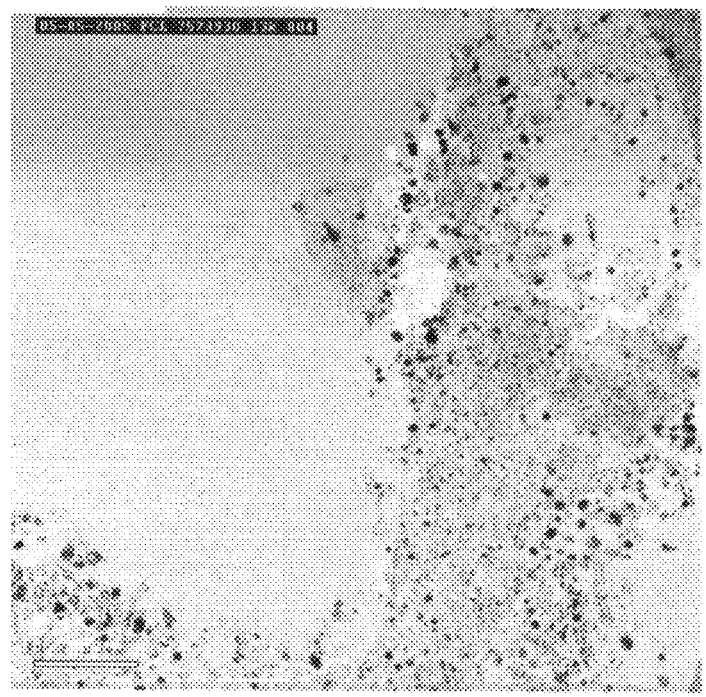
Figure 72B:
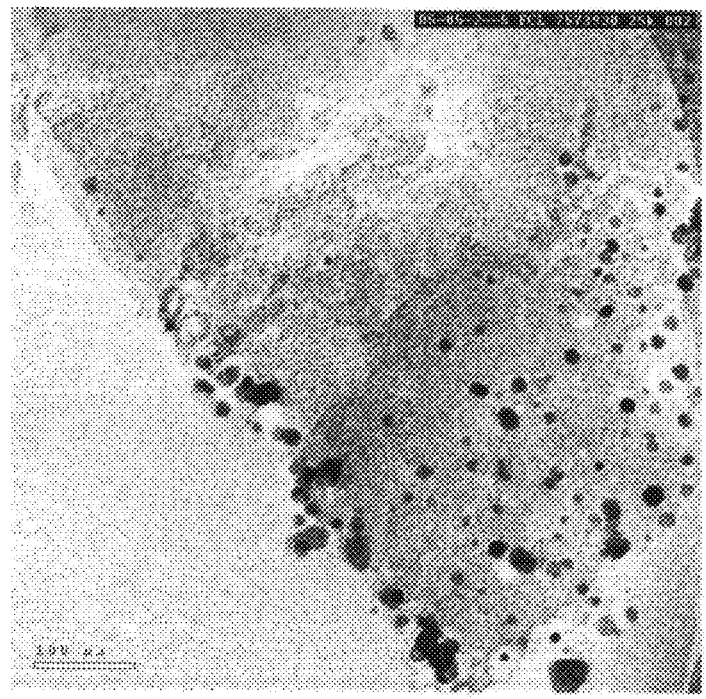
Figure 73A:
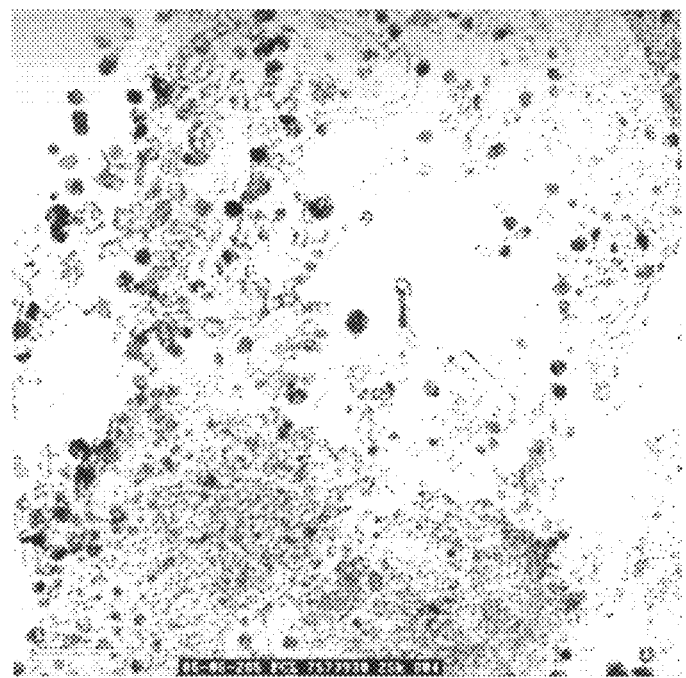
Figure 73B:
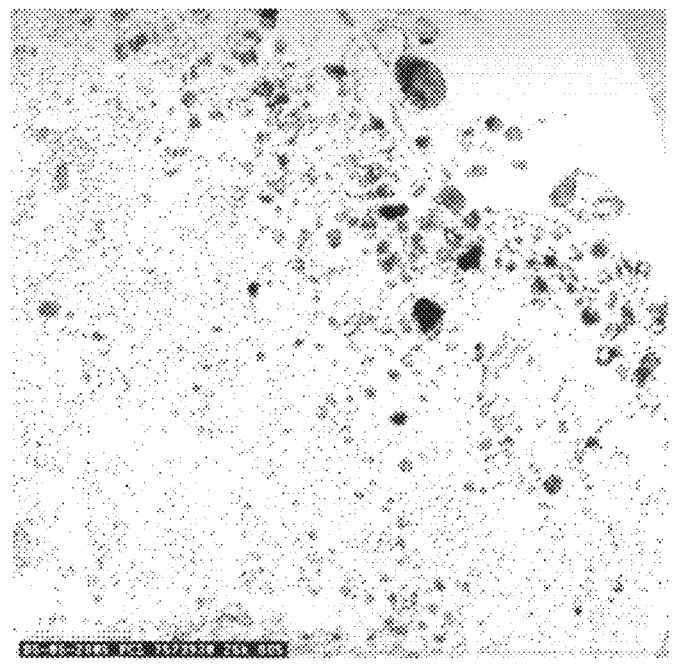
Figure 74A:
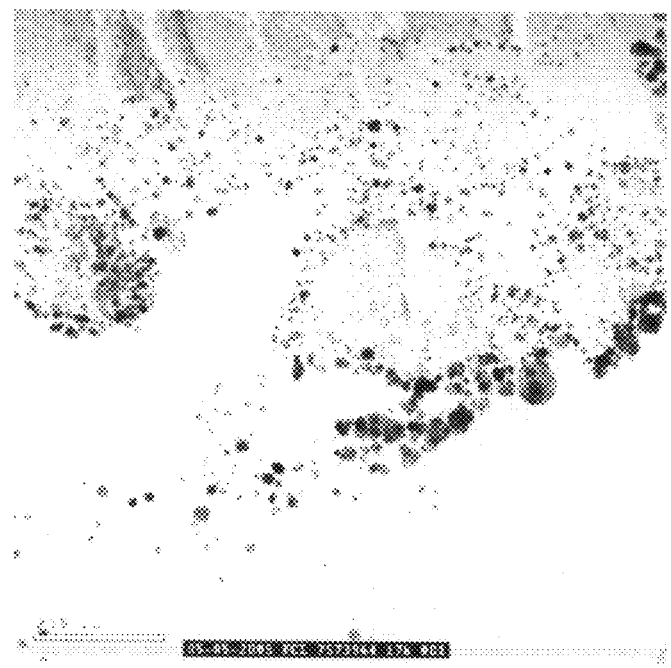
Figure 74B:
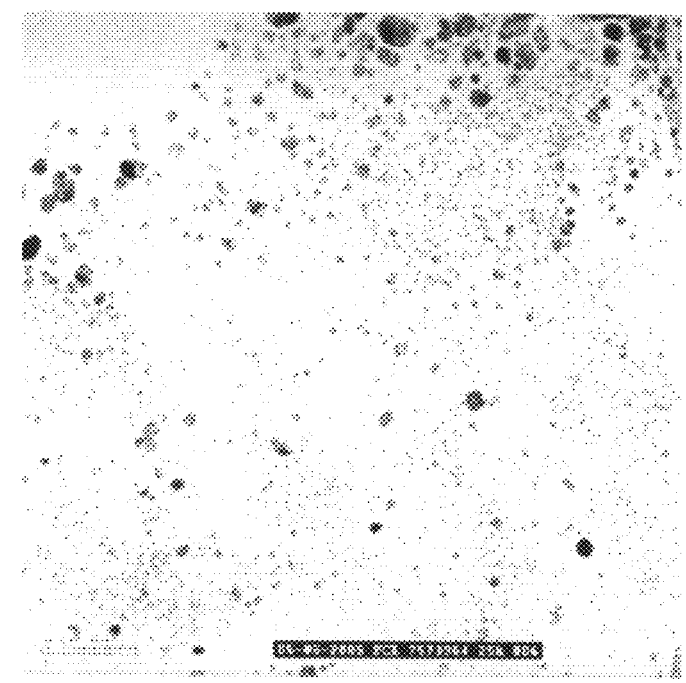
Figure 75A:
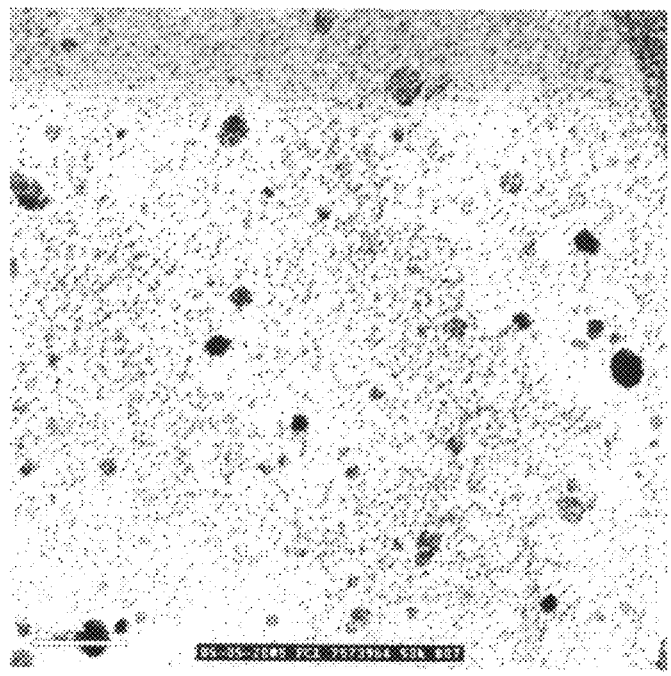
Figure 75B:
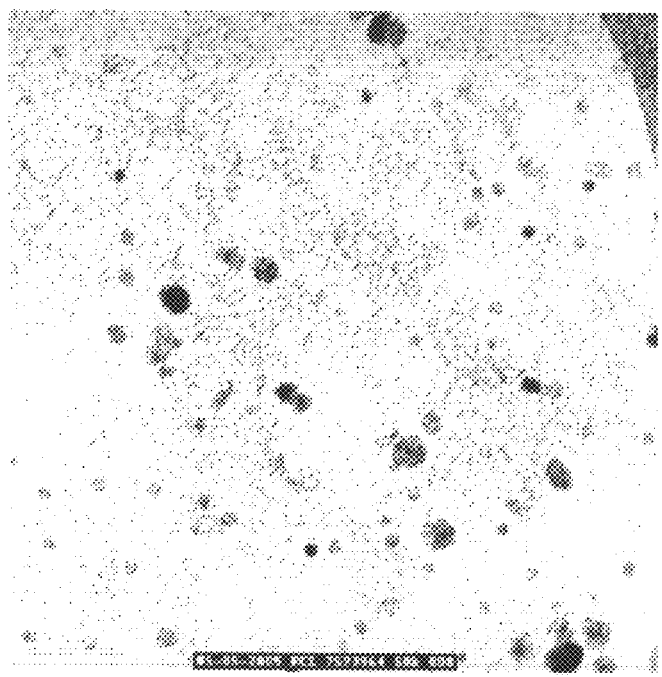
Figure 76A:
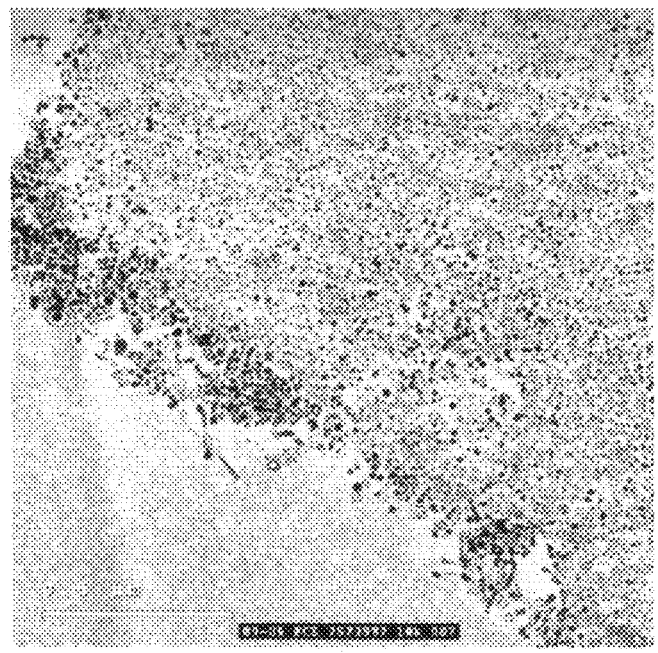
Figure 76B:
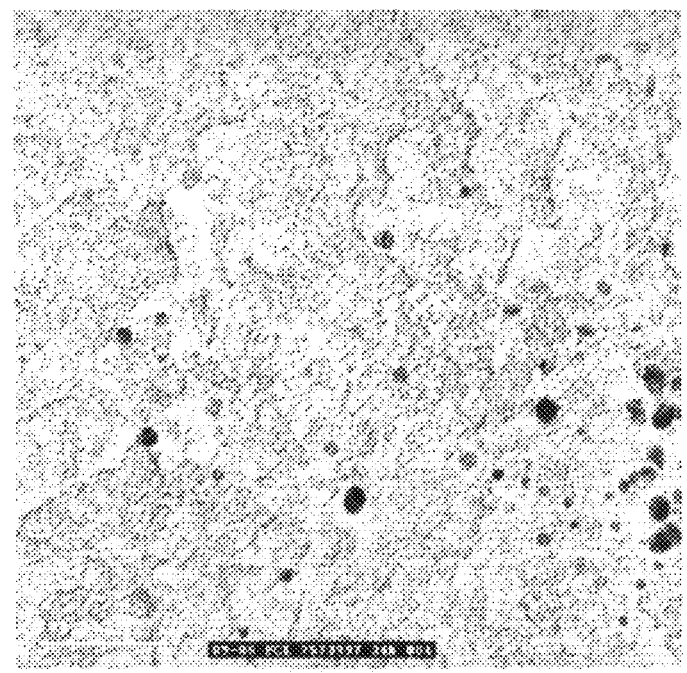
Figure 77A:
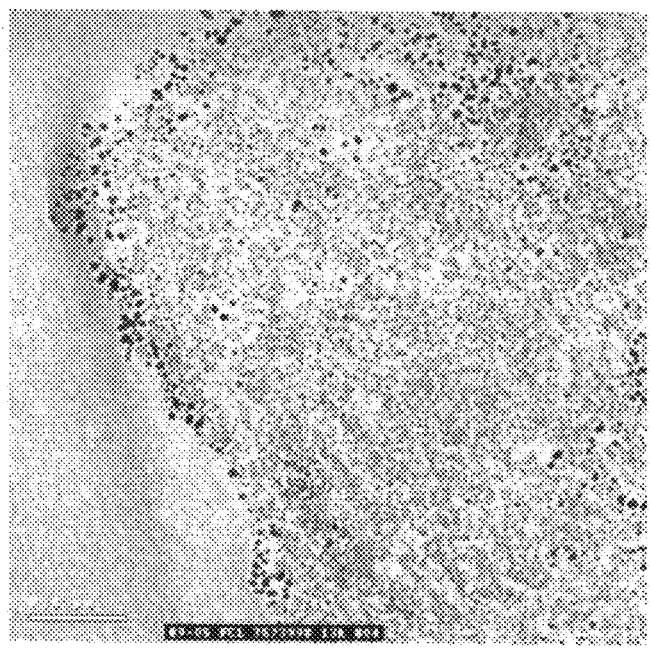
Figure 77B:
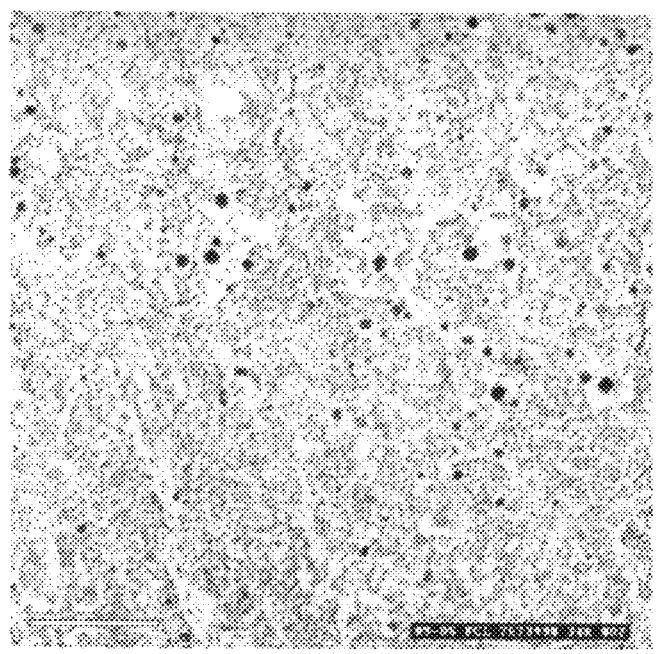
Figure 78A:
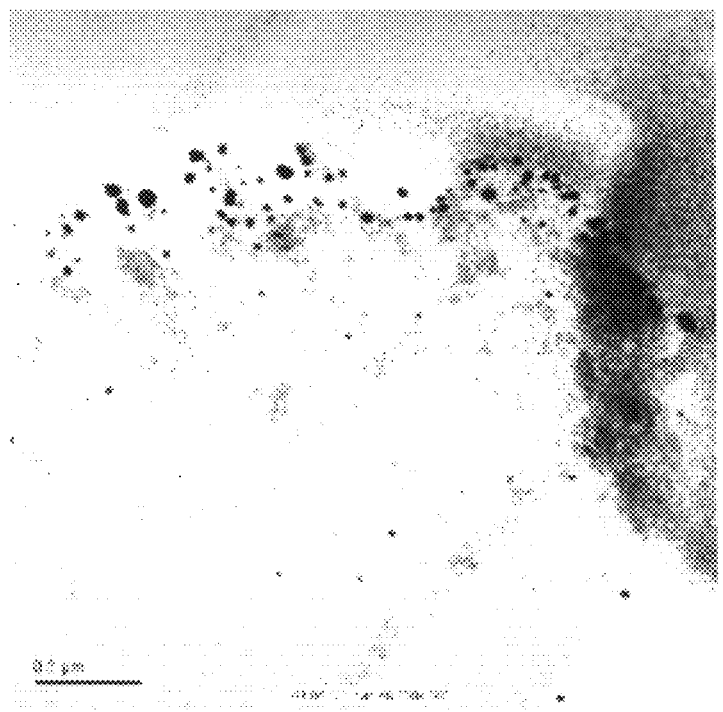
Figure 78B:
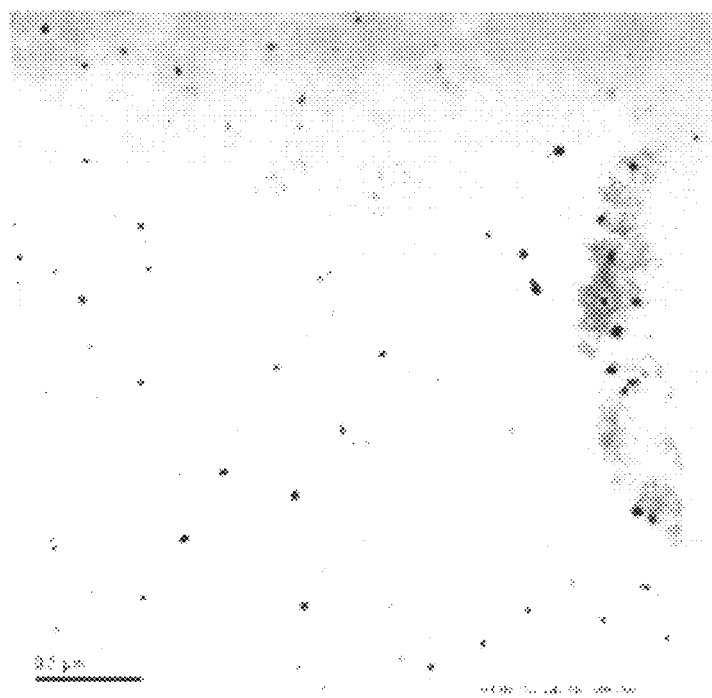
Figure 79A:
Figure 79B:
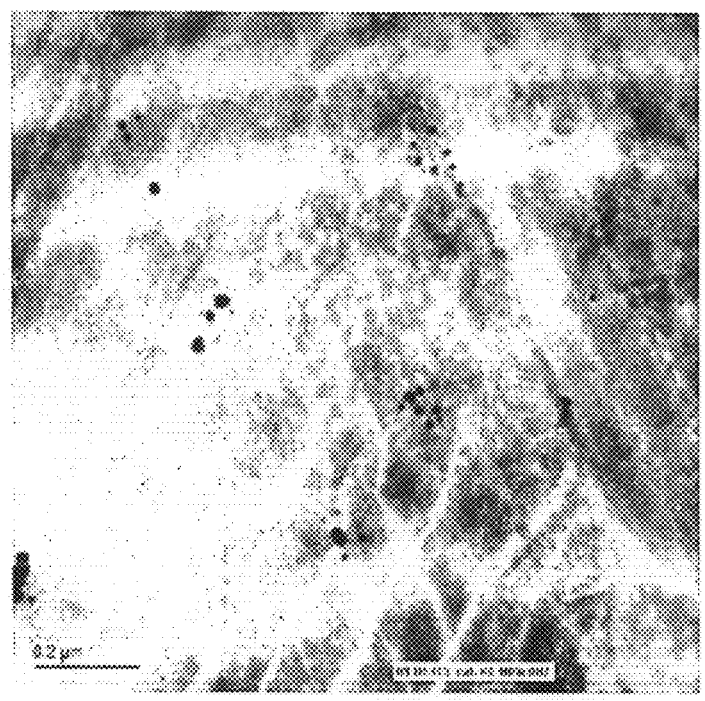
Figure 80A:
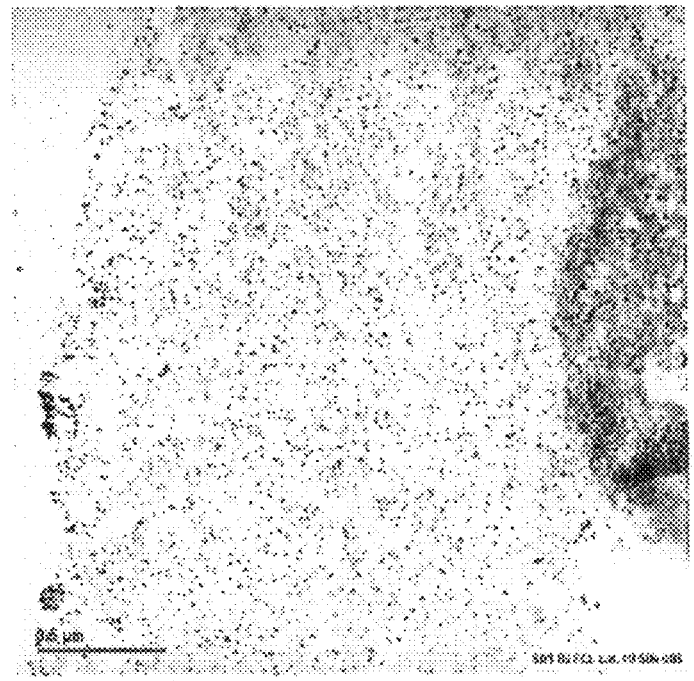
Figure 80B:
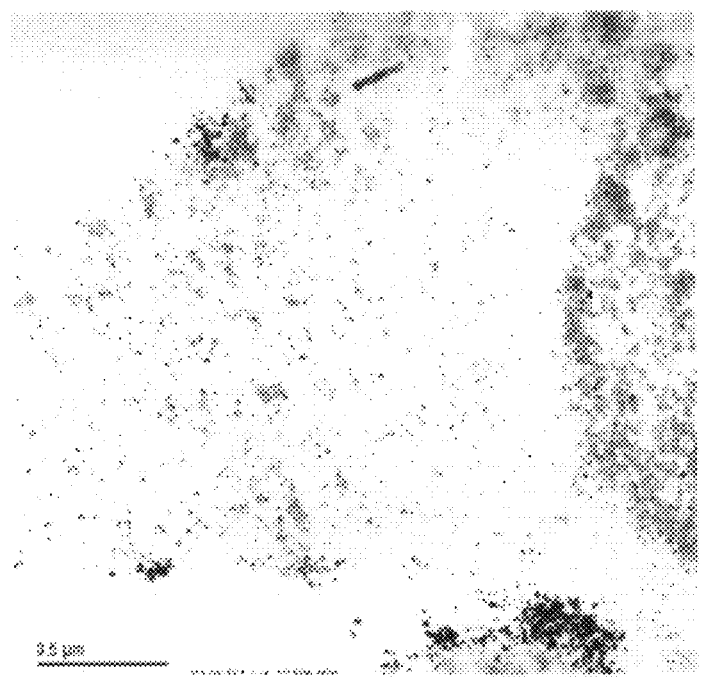
Figure 81A:
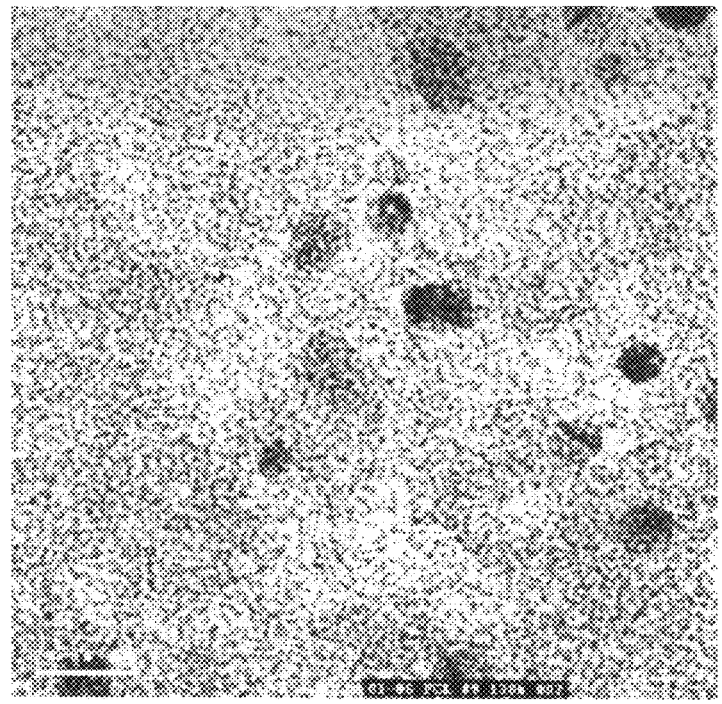
Figure 81B:
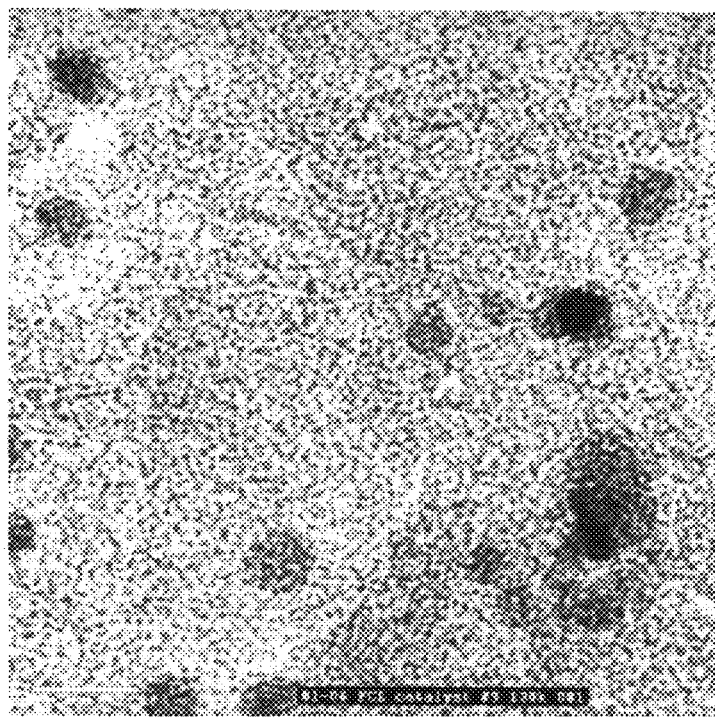
Figure 82A:
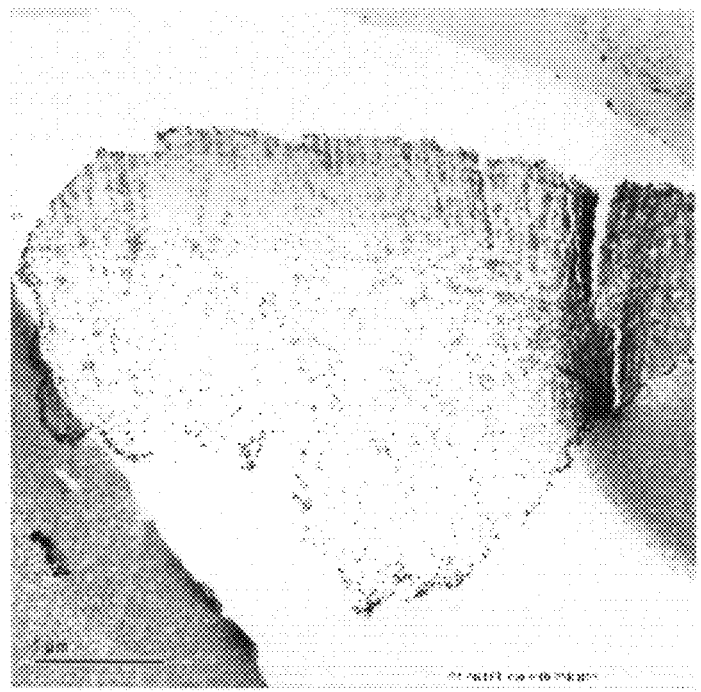
Figure 82B:
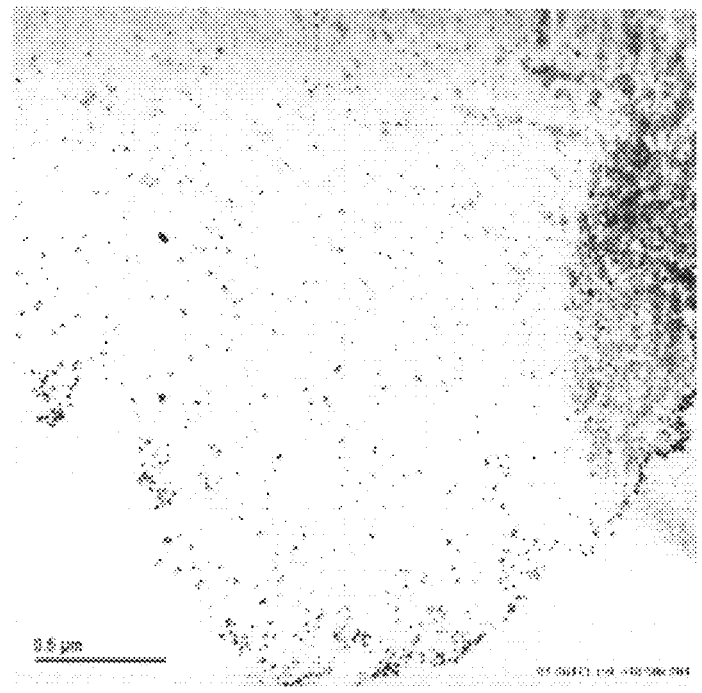
Figure 83A:
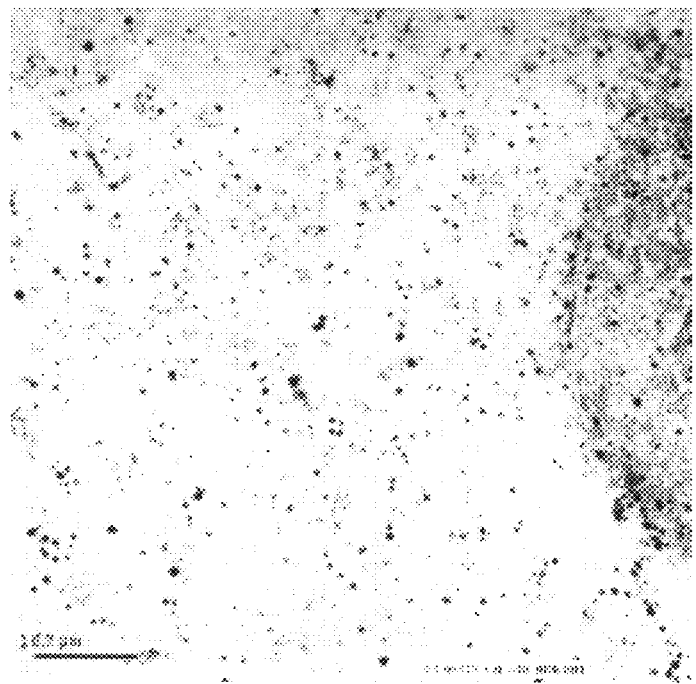
Figure 83B:
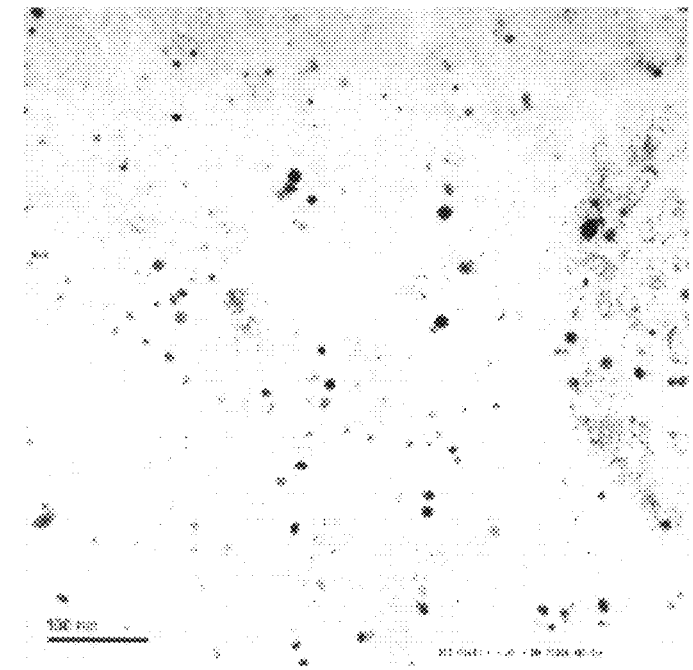
Figure 84A:
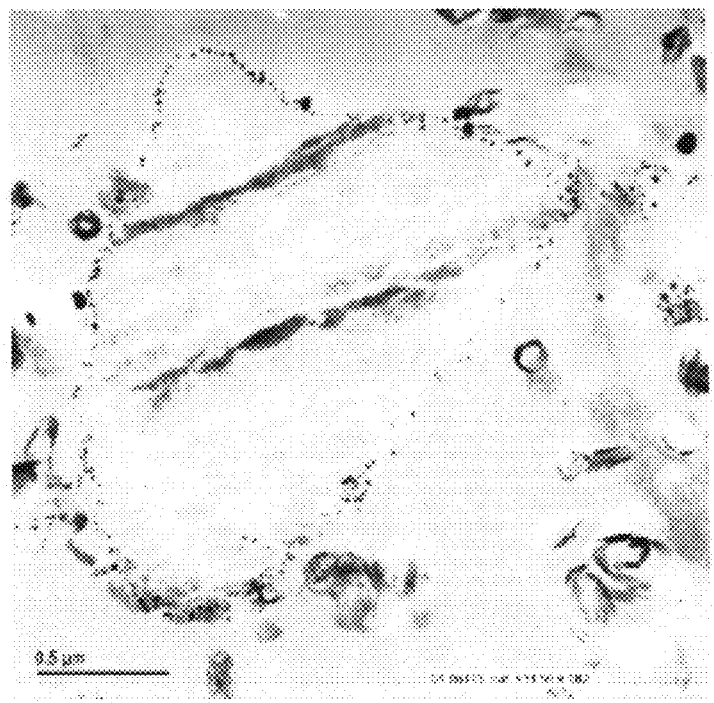
Figure 84B:
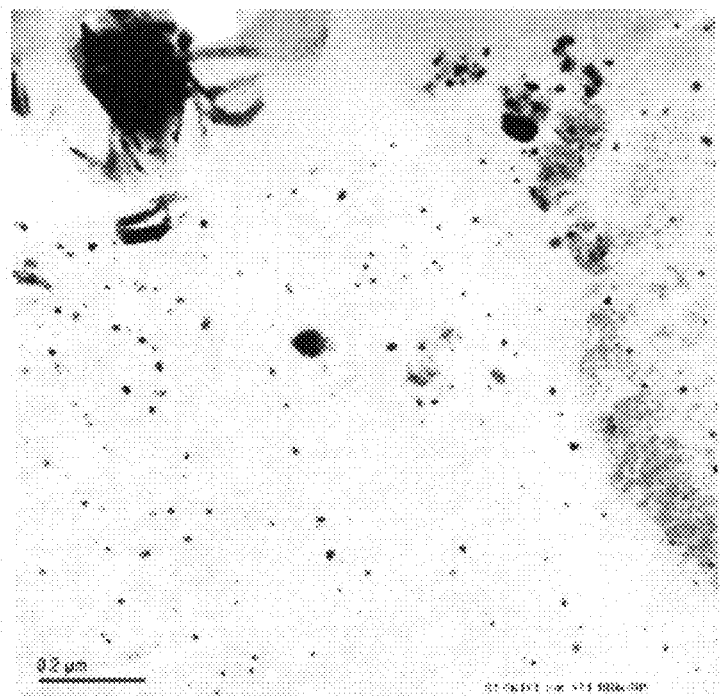
Figure 85A:
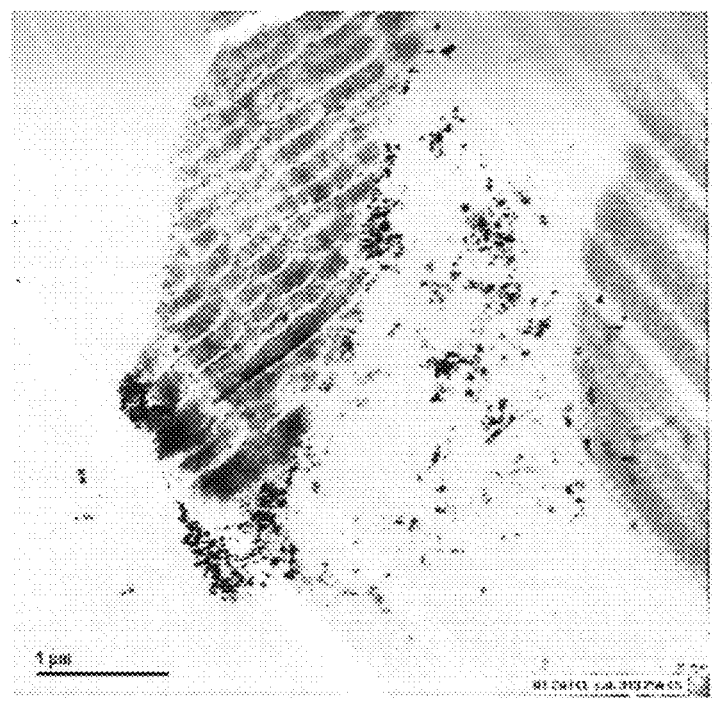
Figure 85B:
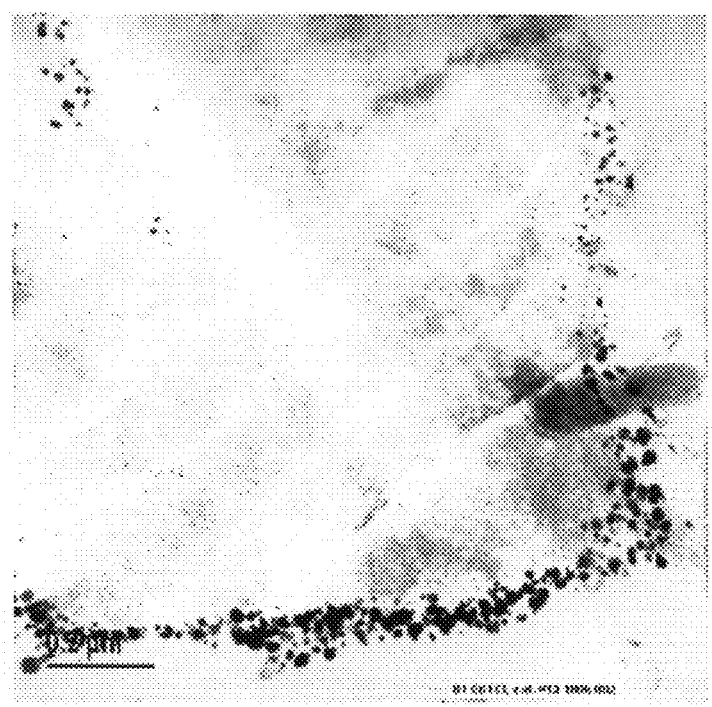
Figure 86A:
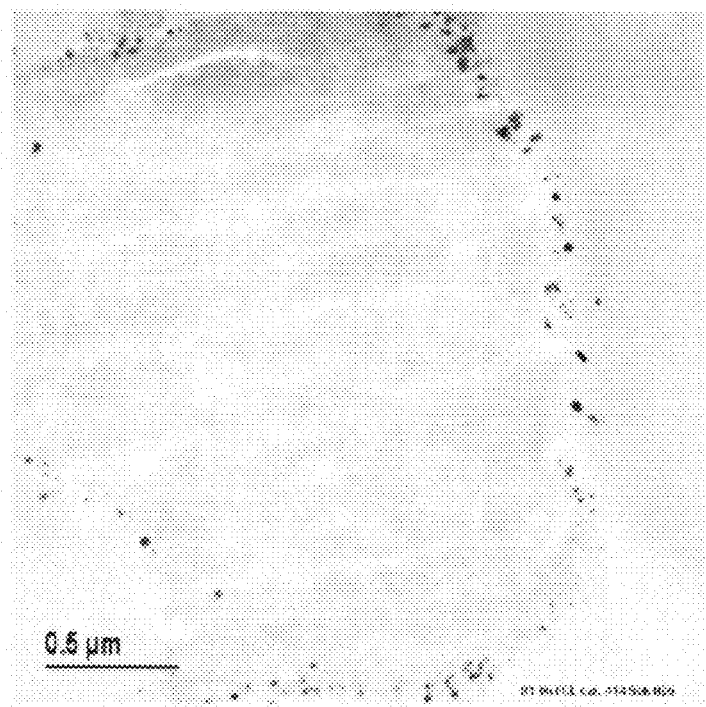
Figure 86B:
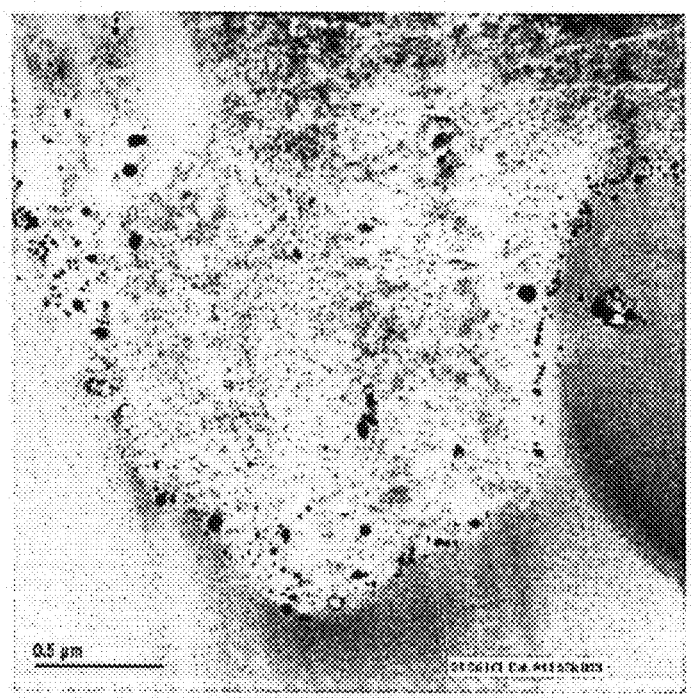
Figure 87A:
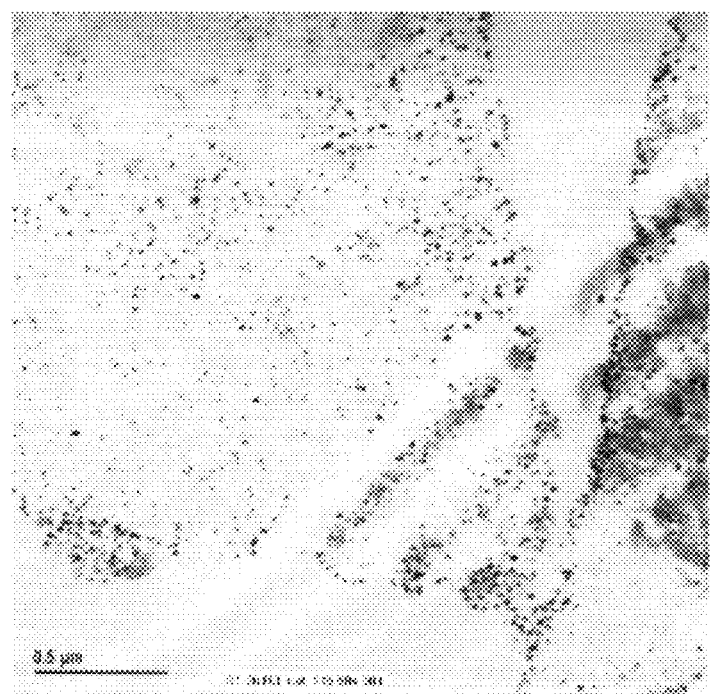
Figure 87B:
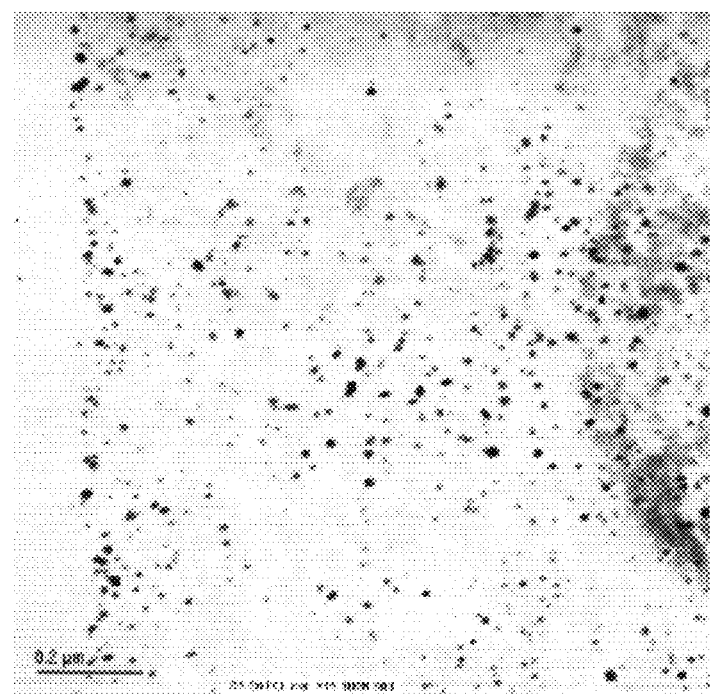

| Catalyst | Figures |
|---|---|
| 3% CoCN/C water | FIGS. 71A/B |
| 3% CoCN/100% diglyme | FIGS. 72A-73B |
| 3% CoCN/50% diglyme (Entry No. 3) | FIGS. 74A-75B |
| 3% CoCN/50% tetraglyme (Entry No. 4) | FIGS. 76A-B |
| 3% CoCN/50% polyglyme (Entry No. 5) | FIGS. 77A-B |
| Entry No. 6 | FIGS. 78A-B |
| Entry No. 8 | FIGS. 79A-B |
| Entry No. 9 | FIGS. 80A-81B |
| Entry No. 10 | FIGS. 82A-83B |
| Entry No. 11 | FIGS. 84A-B |
| Entry No. 13 | FIGS. 85A-B |
| Entry No. 14 | FIGS. 86A-B |
| Entry No. 15 | FIGS. 87A-B |

EXAMPLE 55

Various catalysts prepared as described in Examples 50, 51, and 54 were analyzed by small angle X-ray scattering (SAXS) analysis. FeTPP/CP117, CoTMPP/CP117, and CoTMPP/MC10 catalysts prepared in accordance with Examples 2 and 6 of International Publication No. WO 03/068387 were also analyzed by SAXS. SAXS is a technique for studying structural features of nanoparticles. It is performed by focusing a low divergence x-ray beam onto a sample and observing a coherent scattering pattern that arises from electron density inhomogeneities within the sample. Since the dimensions typically analyzed are much larger than the wavelength of the typical x-ray used (e.g., 1.54°, for Cu), dimensions from tens to thousands of angstroms can be analyzed within a narrow angular scattering range. This angular range or pattern is analyzed using the inverse relationship between particle size and scattering angle to distinguish characteristic shape and size features within a given sample. The instrument used for the SAXS analysis was the Rigaku Ultima III X-ray diffraction and/or scattering system configured with a line source for standard and high-resolution materials analysis. The system has variable slits, which are ideal for low angle diffraction or scattering. The stages include a six position sample changer, thin-film stage and a small-angle transmission stage. A two-bounce germanium monochromator makes the system suitable for high resolution rocking curves and reflectivity, and a multilayer mirror for grazing incident studies or reflectomatry can also condition the incident beam. For the SAXS analysis, the X-ray is generated from a copper target operated at 40 kV and 100 mA, and the irradiated area is approximately 100 $mm^2$. The scanning speed of the X-ray beam is 0.1 degree per minute. The dry catalyst powder can be directly analyzed and no special sample preparation is required.

Table 37 shows the samples analyzed and the corresponding Figure(s) showing the observed particle size distribution.

TABLE 37

(Entry Nos. are with reference to Table 31)

Figure 88A:
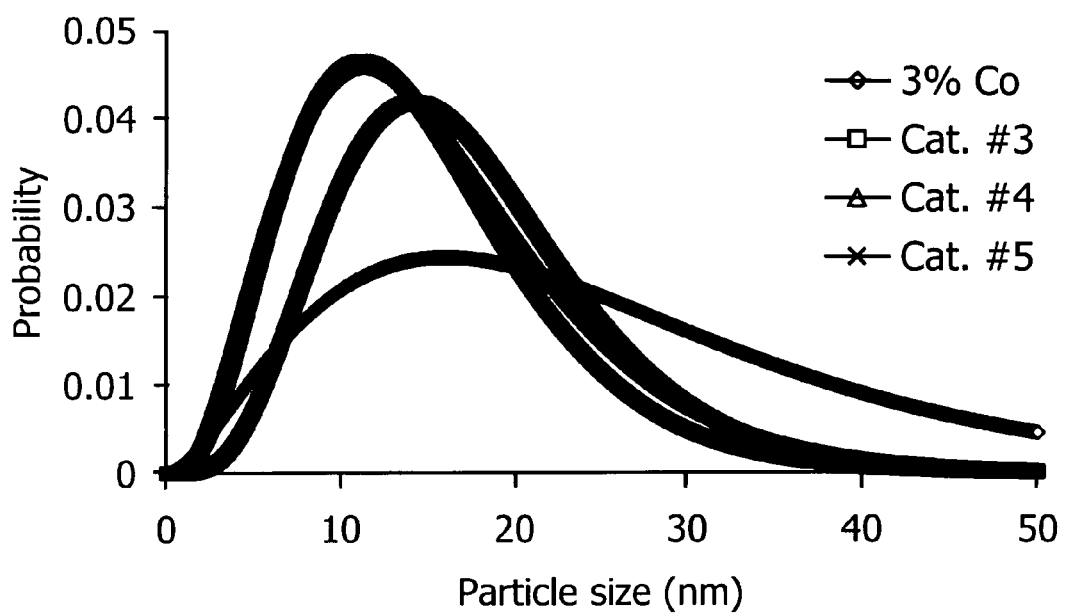
FIGS. 88A-93 show Small Angle X-Ray Scattering (SAXS) results for catalysts analyzed as described in Example 55.
Figure 88B:
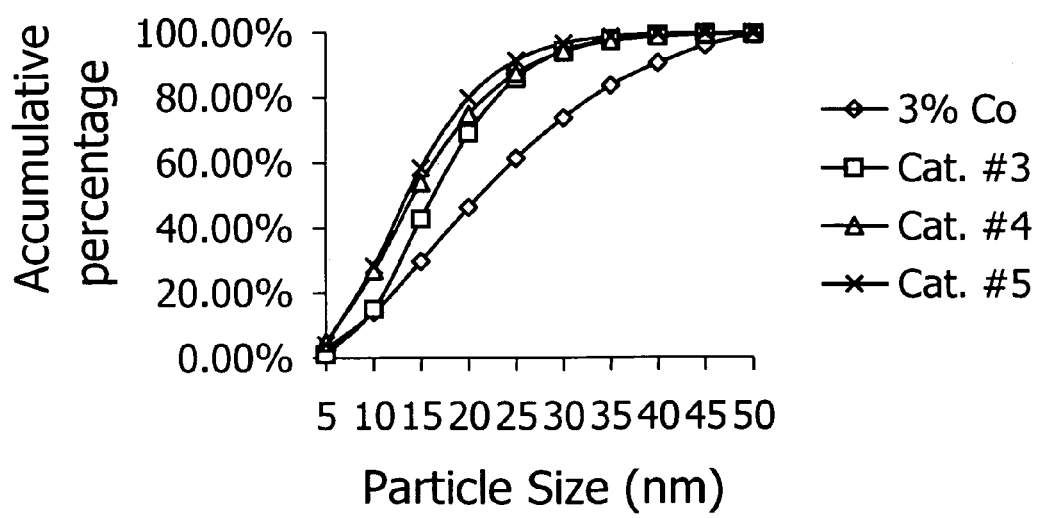
Figure 89:
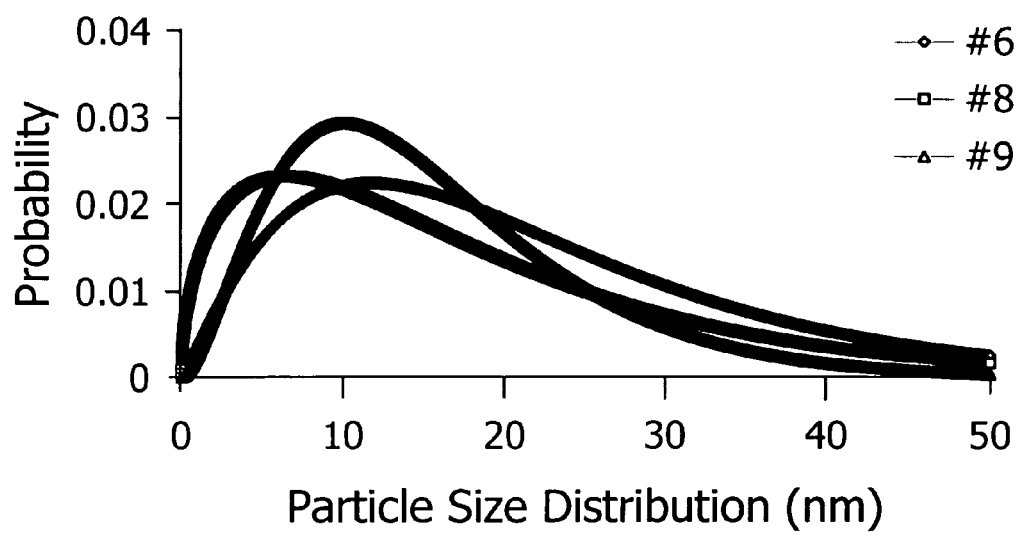
Figure 90:
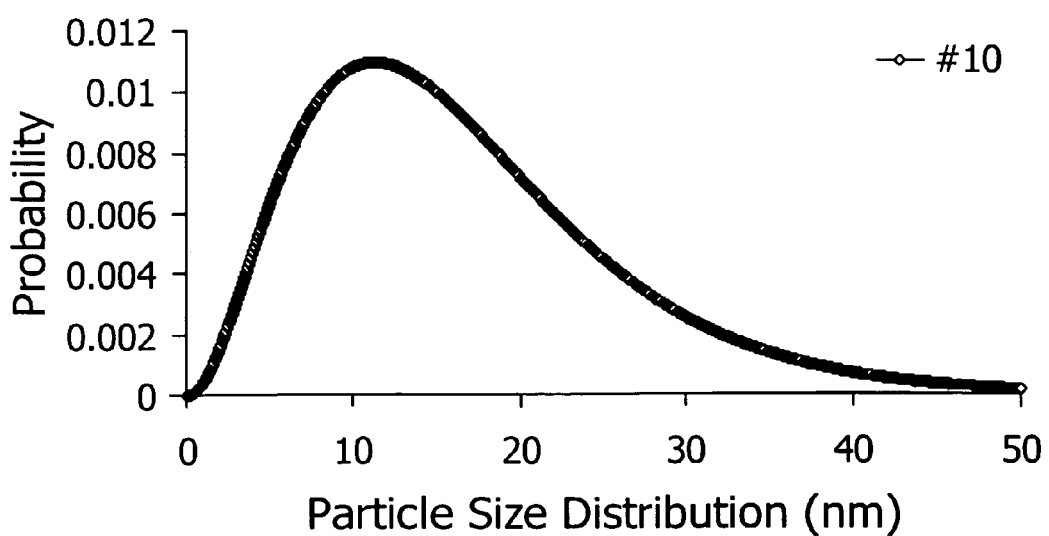
Figure 91:
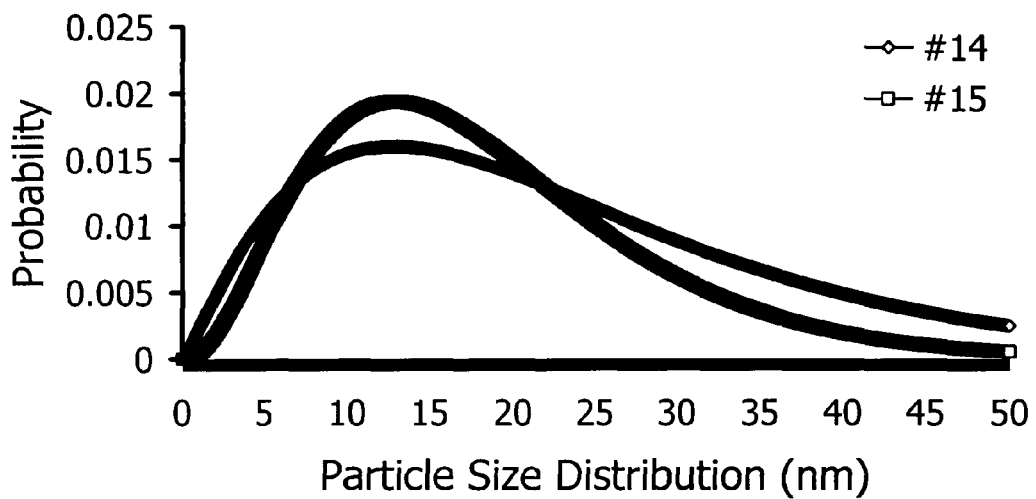
Figure 92:
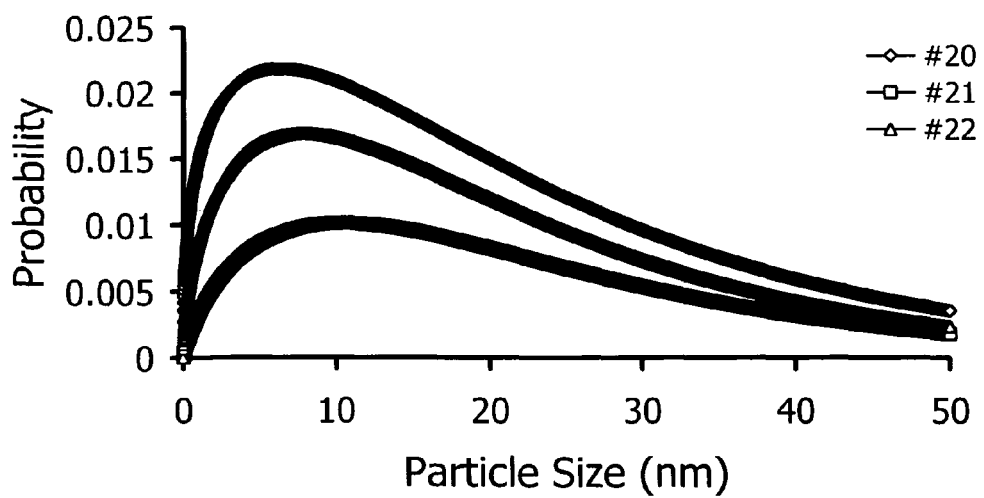
Figure 93:
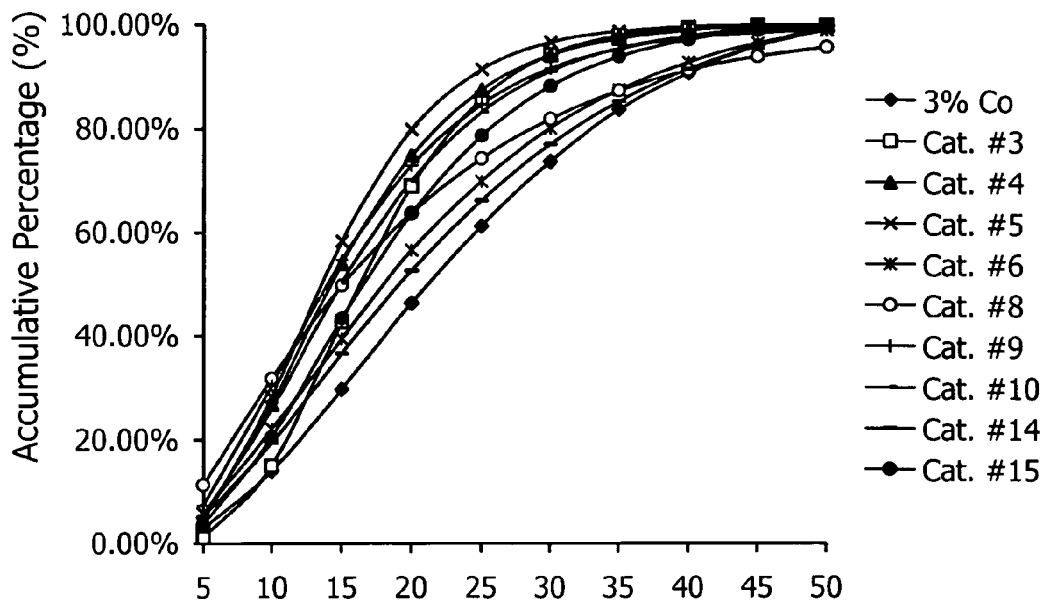

| Catalyst | Figures |
|---|---|
| 3% CoCN/water | FIGS. 88A-B, 93 |
| 3% CoCN/50% diglyme (Entry No. 3) | FIGS. 88A-B, 93 |
| 3% CoCN/50% tetraglyme (Entry No. 4) | FIGS. 88A-B, 93 |
| 3% CoCN/50% polyglyme (Entry No. 5) | FIGS. 88A-B, 93 |
| Entry No. 6 | FIG. 89, 93 |
| Entry No. 8 | FIG. 89, 93 |
| Entry No. 9 | FIG. 89, 93 |
| Entry No. 10 | FIG. 90, 93 |
| Entry No. 14 | FIG. 91, 93 |
| Entry No. 15 | FIG. 91, 93 |
| 1.5% CoCN/C | FIG. 92 (#20) |
| 1.1% FeTPP/CP117 | FIG. 92 (#21) |
| 1.5% CoTMPP/CP117 | FIG. 92 (#22) |

Table 37A provides particle size distributions for various catalysts analyzed by SAXS.

TABLE 37A (Entry Nos. are with reference to Table 31.)

| | | 3% CoCN/water | Entry No. 3 | Entry No. 4 | Entry No. 5 | Entry No. 6 | Entry No. 8 | Entry No. 9 | Entry No. 10 | Entry No. 14 | Entry No. 15 | 1.1% FeTPP/CP117 | 1.5% CoTMPP/CP117 |
|---|---|---|---|---|---|---|---|---|---|---|---|---|---|
| 2-5 nm | 5 | 2.83% | 1.10% | 4.74% | 4.23% | 5.87% | 11.31% | 7.32% | 5.33% | 5.08% | 3.64% | 7.05% | 9.15% |
| <10 nm | 10 | 14.00% | 14.94% | 26.90% | 28.25% | 22.09% | 31.82% | 30.48% | 25.97% | 19.44% | 20.53% | 22.87% | 26.80% |
| <15 nm | 15 | 29.77% | 42.71% | 53.96% | 58.33% | 39.41% | 49.70% | 54.67% | 50.30% | 36.59% | 43.31% | 39.22% | 43.38% |
| <20 nm | 20 | 46.31% | 68.96% | 74.72% | 79.79% | 56.60% | 63.75% | 72.95% | 69.98% | 52.60% | 63.68% | 53.92% | 57.44% |
| <25 nm | 25 | 61.29% | 85.74% | 87.37% | 91.32% | 69.88% | 74.25% | 84.58% | 83.10% | 66.16% | 78.53% | 66.25% | 68.79% |
| <30 nm | 30 | 73.68% | 94.22% | 94.08% | 96.56% | 80.10% | 81.87% | 91.51% | 91.03% | 76.97% | 88.12% | 76.17% | 77.67% |
| <35 nm | 35 | 83.67% | 97.89% | 97.33% | 98.68% | 87.41% | 87.30% | 95.34% | 95.44% | 85.24% | 93.84% | 83.95% | 84.51% |
| <40 nm | 40 | 90.63% | 99.31% | 98.80% | 99.47% | 92.67% | 91.11% | 97.34% | 97.72% | 91.34% | 97.05% | 89.95% | 89.70% |

TABLE 37A-continued (Entry Nos. are with reference to Table 31.)

|  | | 3% CoCN/ water | Entry No. 3 | Entry No. 4 | Entry No. 5 | Entry No. 6 | Entry No. 8 | Entry No. 9 | Entry No. 10 | Entry No. 14 | Entry No. 15 | 1.1% FeTPP/ CP117 | 1.5% CoTMPP/ CP117 |
|---|---|---|---|---|---|---|---|---|---|---|---|---|---|
| <45 nm | 45 | 95.91% | 99.80% | 99.43% | 99.77% | 96.34% | 93.80% | 98.34% | 99.09% | 95.83% | 98.78% | 94.50% | 93.61% |
| <50 nm | 50 | 99.67% | 99.80% | 99.70% | 99.85% | 98.84% | 95.63% | 98.92% | 99.50% | 99.02% | 99.69% | 98.89% | 96.51% |

EXAMPLE 56

This example details X-ray Photoelectron Spectroscopy (XPS) analysis of various catalysts prepared as described in Example 52 under the conditions set forth in Table 38. The samples analyzed and the FIGS. providing the corresponding spectra are set forth in Table 39. An iron-contiaining catalyst prepared as described in Example 9 above and a FeTPP/CP117 catalyst prepared in accordance with Example 2 of International Publication No. WO 03/068387 were also analyzed.

TABLE 38

| Instrument | Physical Electronics Quantum 2000 Scanning XPS |
|---|---|
| X-ray source | Monochromatic Al $K_\alpha$ 1486 eV |
| Analysis areas | 1.4 mm × 0.6 mm |
| Take-off angle | ~90° (achieved by "banking" the powder sample rather than laying it flat within the sample holder receptacle) |
| Charge correction | C—C, C—H in C1s spectra set to 284.8 eV |
| Charge Neutralization | Low energy electron and ion floods |

TABLE 39

(Entry Nos. are with reference to Table 31)

Figure 94:
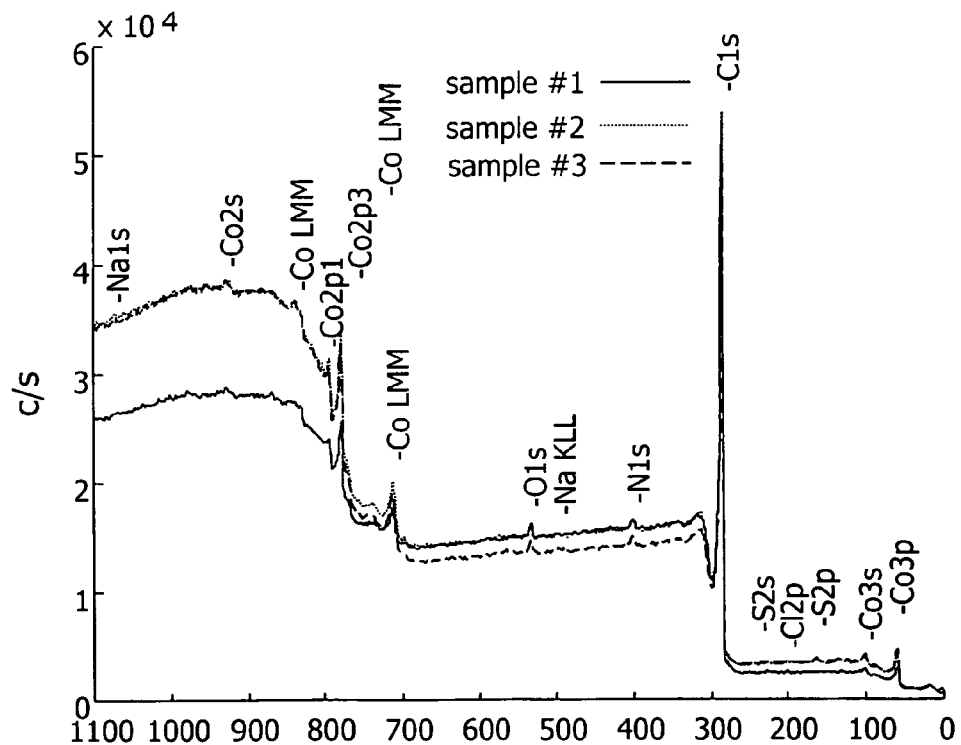
FIGS. 94-104 are X-Ray Photoelectron Spectroscopy spectra for catalysts analyzed as described in Example 56.
Figure 95:
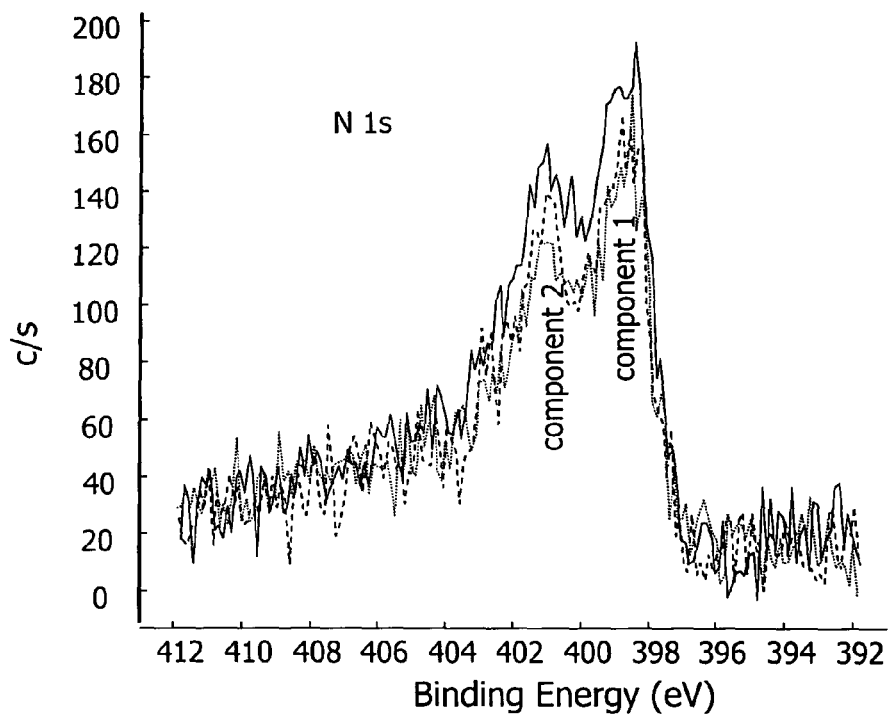
Figure 96:
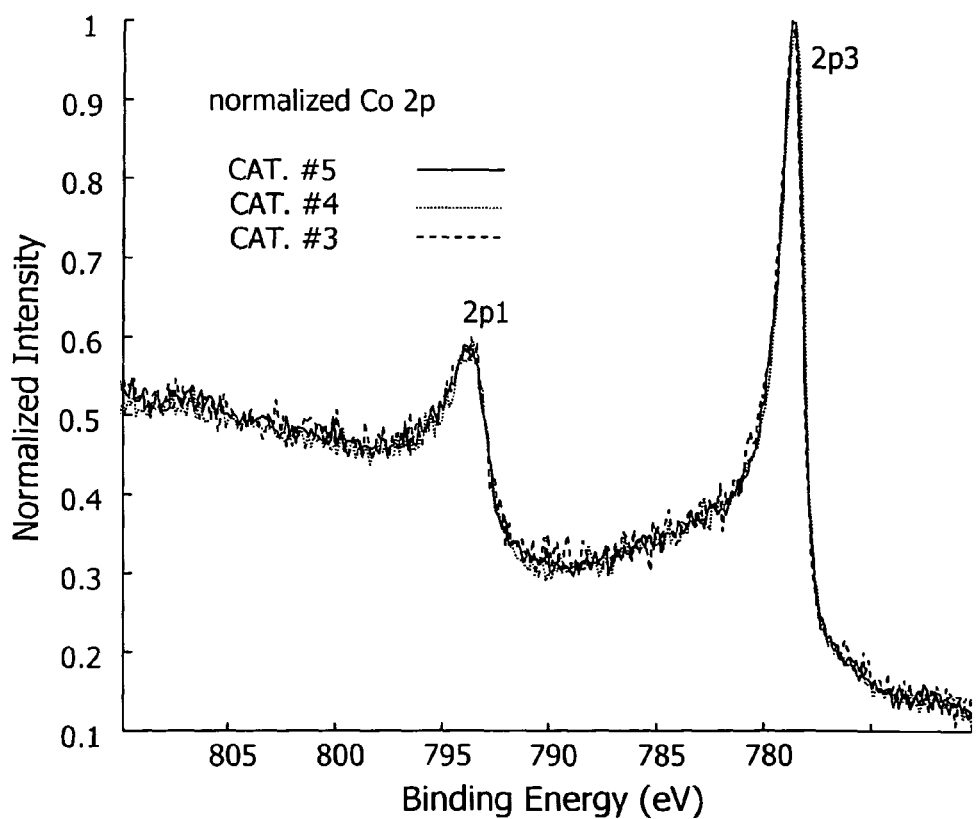
Figure 97:
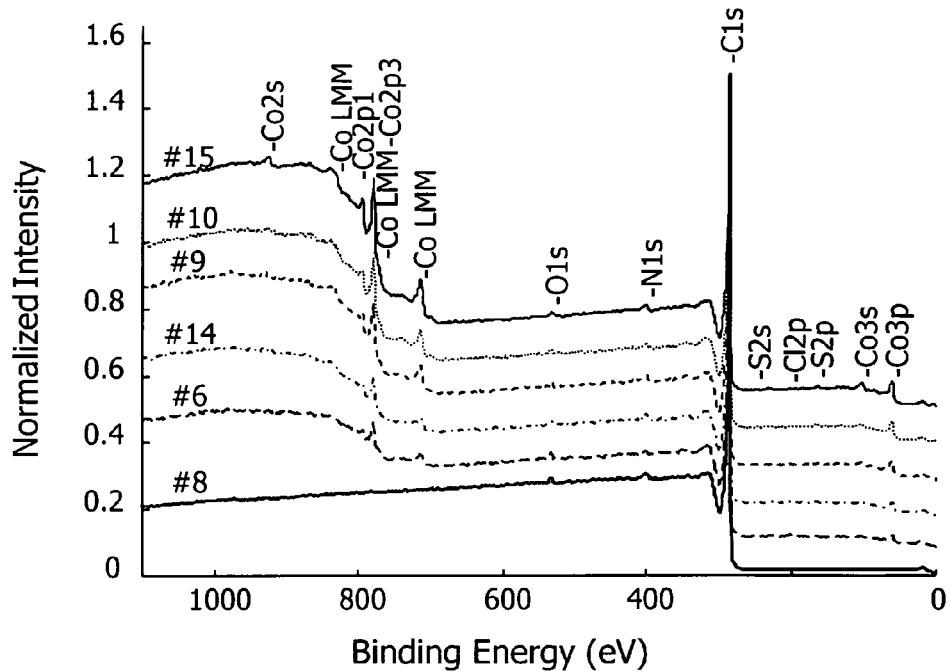
Figure 98:
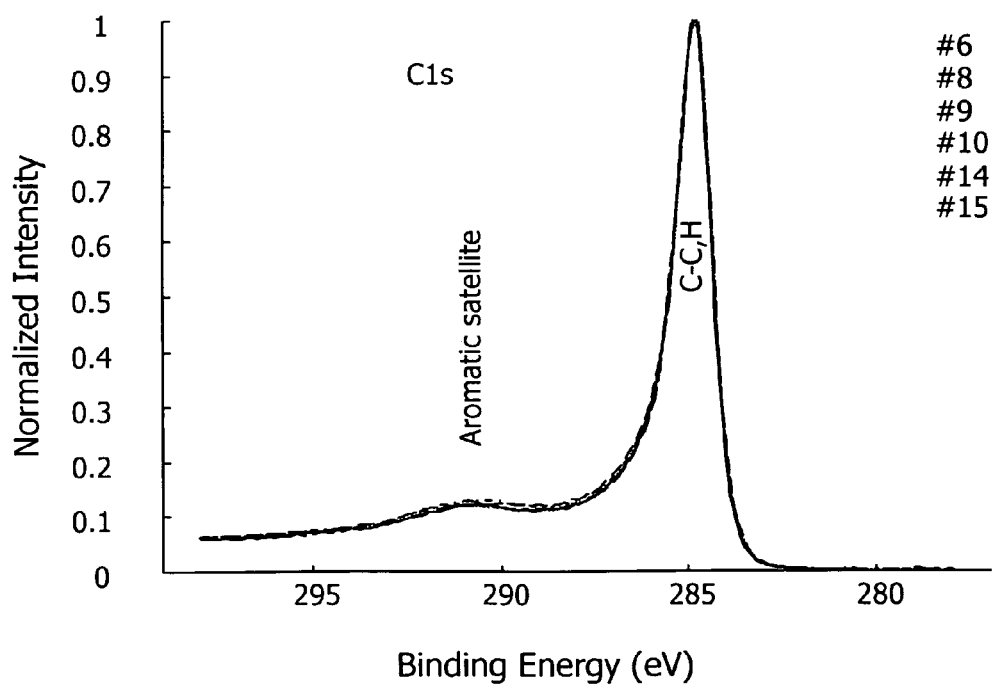
Figure 99:
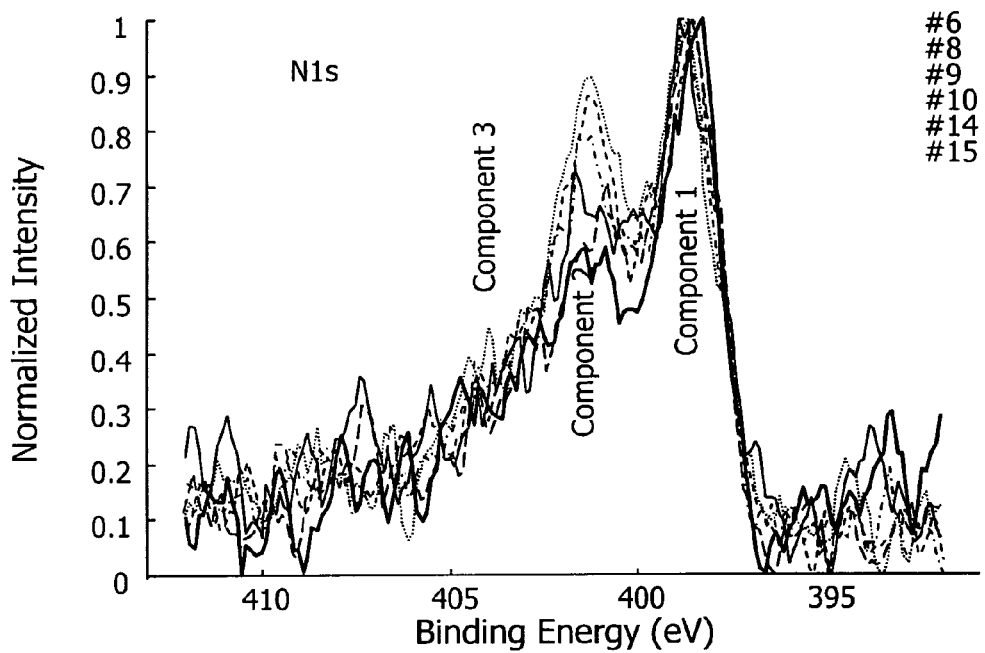
Figure 100:
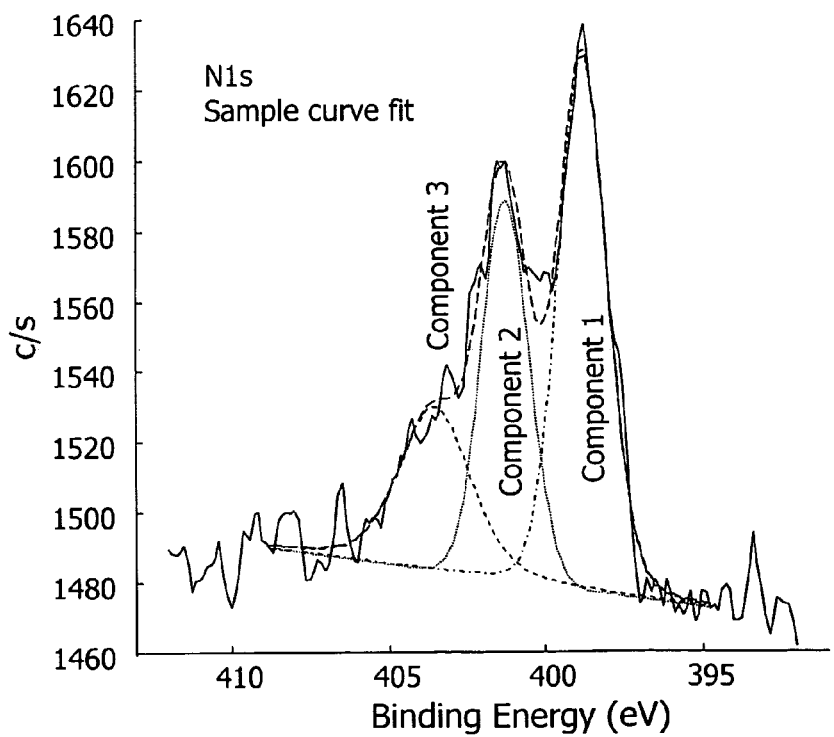
Figure 101:
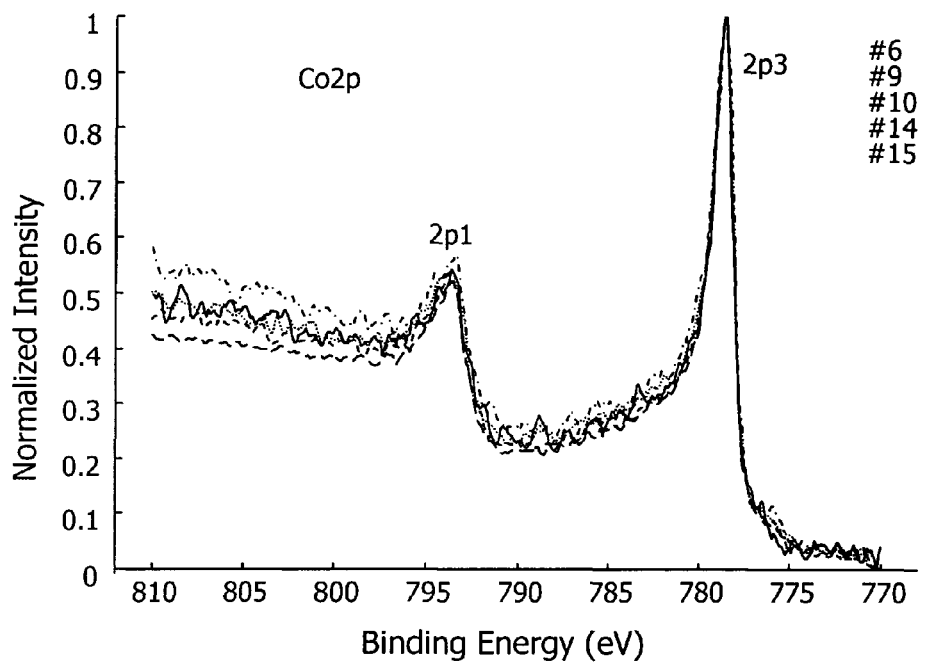
Figure 102:
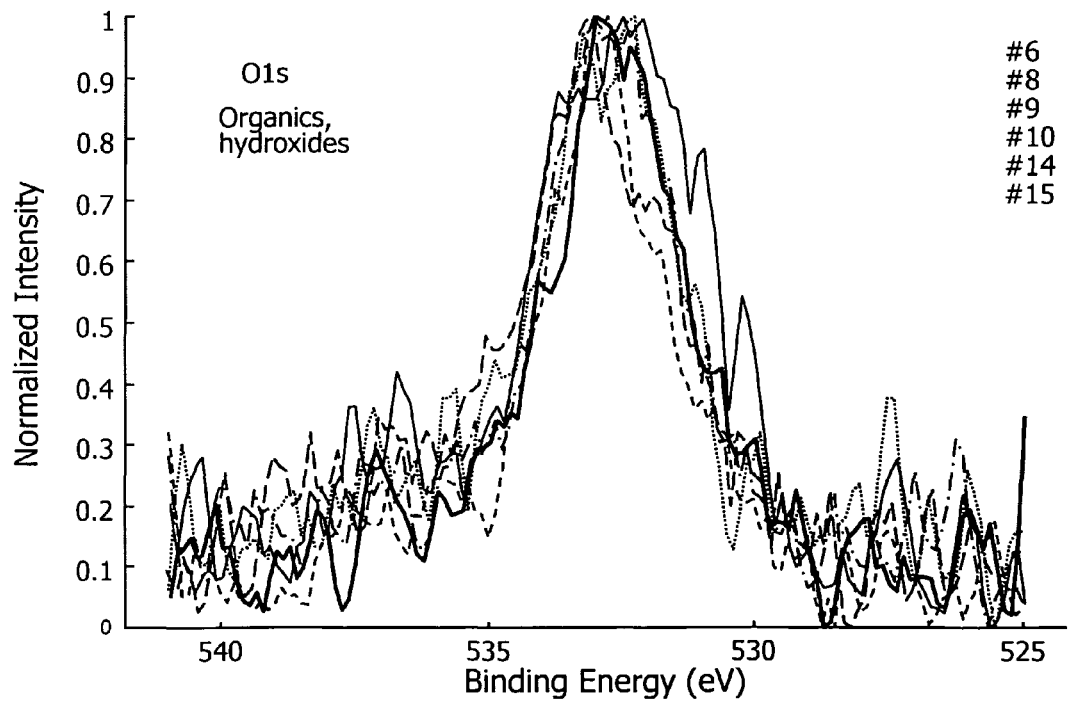
Figure 103:
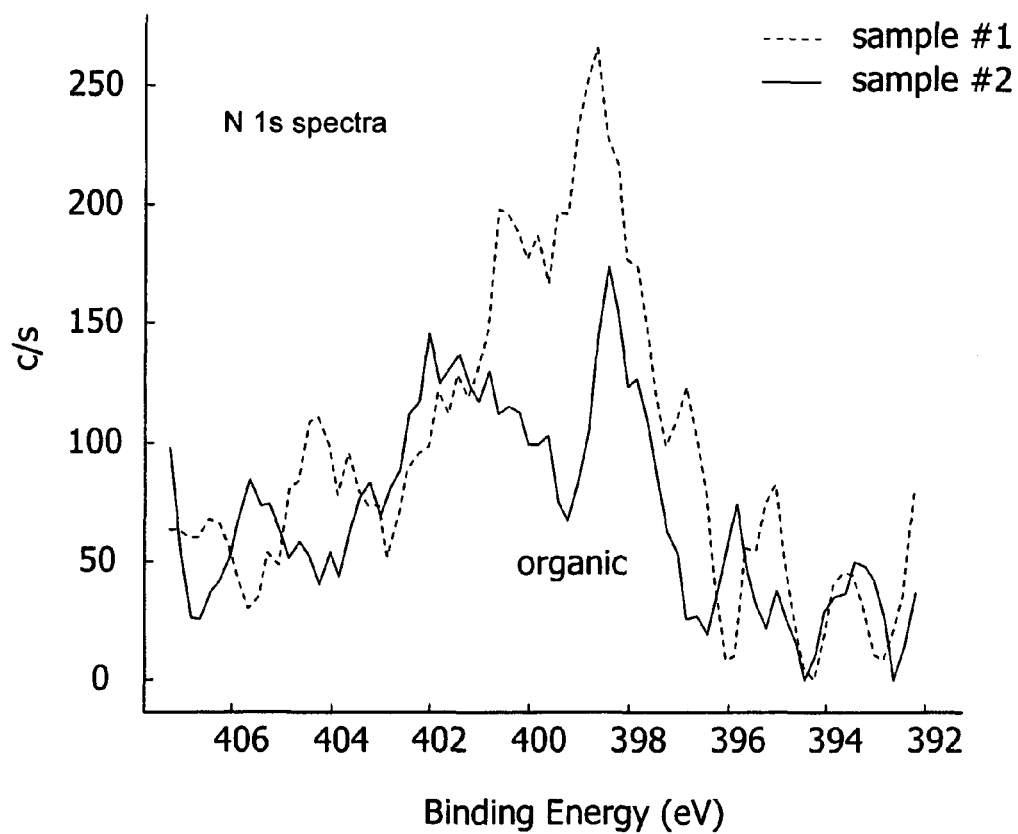
Figure 104:
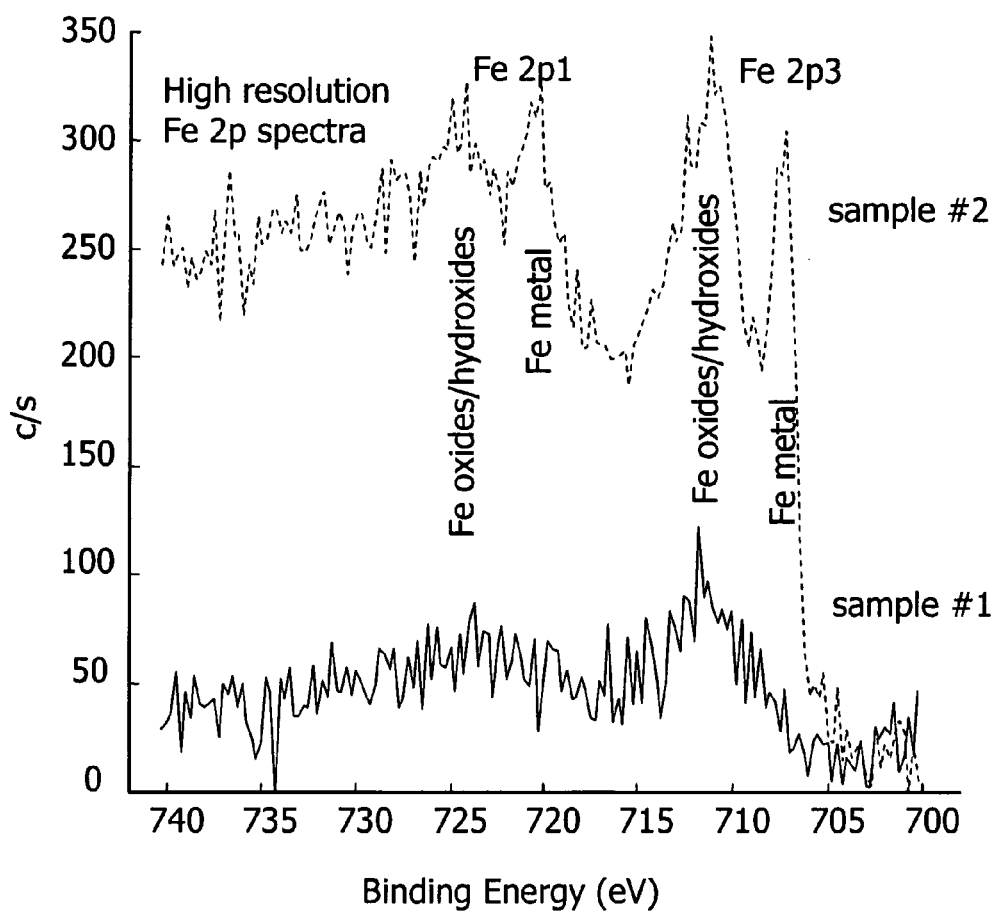

| Catalyst | Figures |
|---|---|
| 3% CoCN/50% diglyme (Entry No. 3) | FIGS. 94-96 |
| 3% CoCN/50% tetraglyme (Entry No. 4) | FIG. 94-96 |
| 3% CoCN/50% polyglyme (Entry No. 5) | FIG. 94-96 |
| Entry No. 6 | FIGS. 97-102 |
| Entry No. 8 | FIGS. 97-102 |
| Entry No. 9 | FIGS. 97-102 |
| Entry No. 10 | FIGS. 97-102 |
| Entry No. 14 | FIGS. 97-102 |
| Entry No. 15 | FIGS. 97-102 |
| 1.1% FeTPP/CP117 | FIGS. 103-104 |
| 1% FeCN/C | FIGS. 103-104 |

EXAMPLE 57

Figure 108:
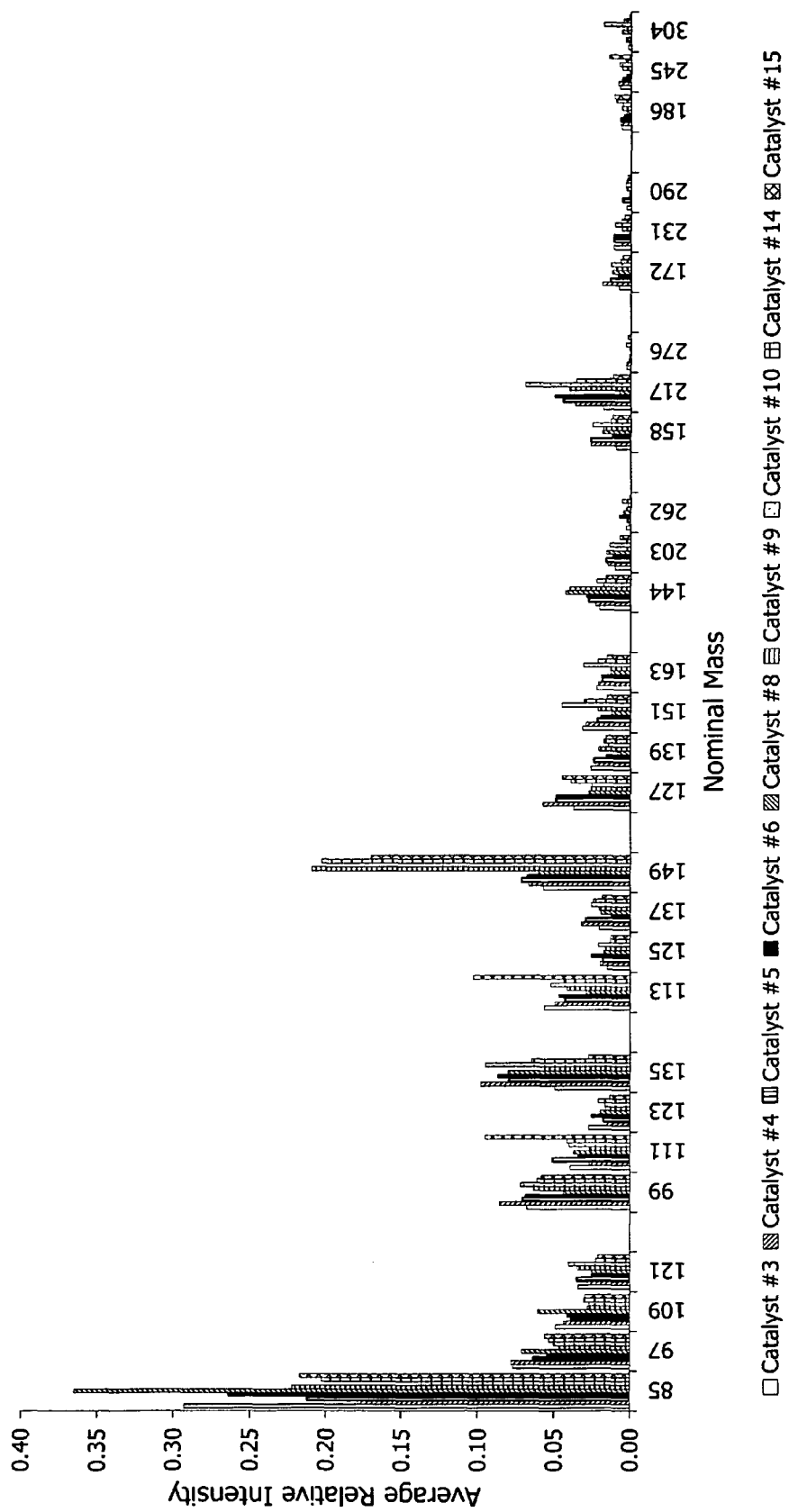

Various catalysts prepared in accordance with one of the preceding examples were analyzed by Time-of-Flight Secondary Ion Mass Spectrometry (ToF SIMS) as described in Example 46. The samples analyzed and the corresponding tables providing ion family information and corresponding figures showing intensity of ion species are shown in Table 40. FIG. 108 shows the average relative intensity for various ion species for various samples analyzed.

TABLE 40

Figure 105:
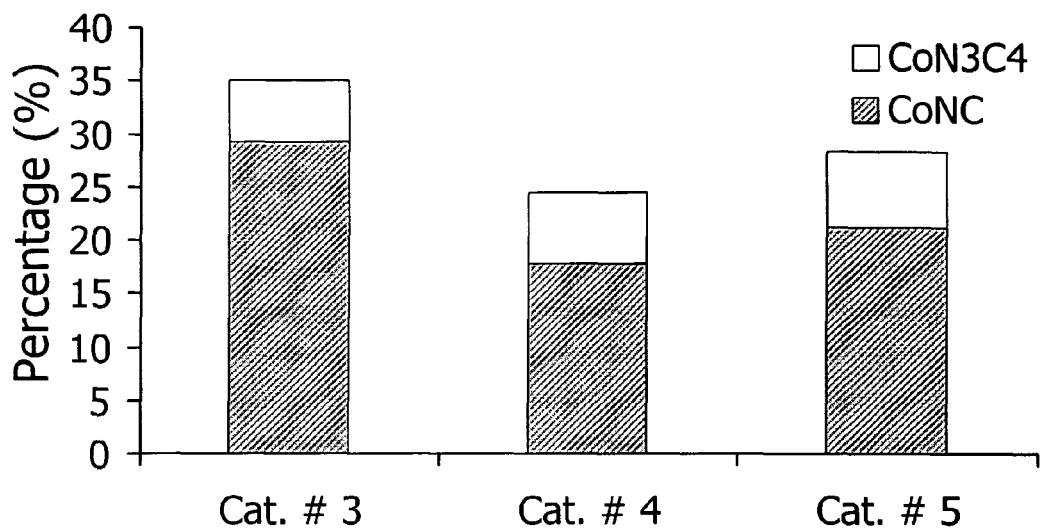
FIGS. 105-108 shows Time-of-Flight Secondary Ion Mass Spectroscopy (ToF SIMS) results for various catalysts analyzed as described in Example 57.
Figure 106:
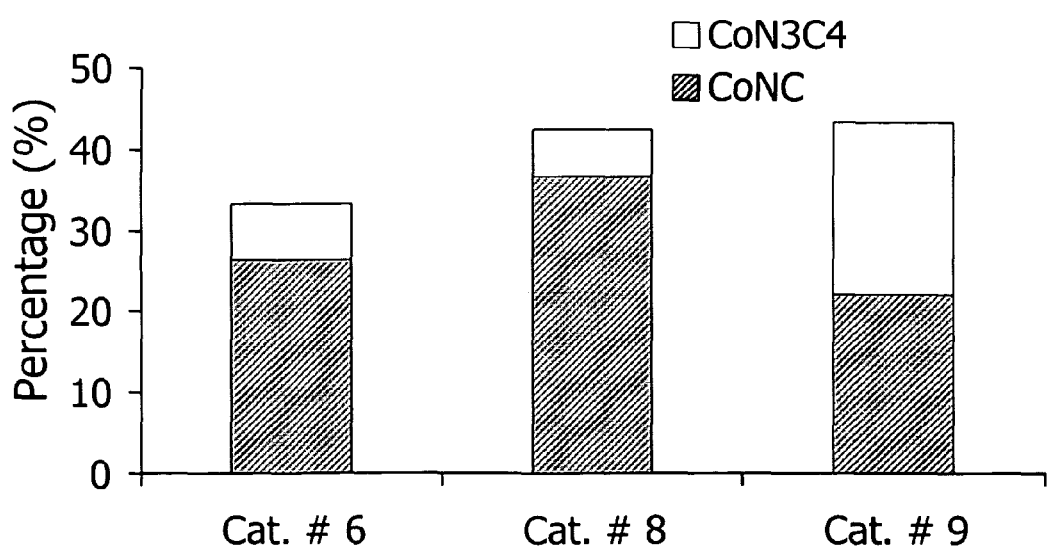
Figure 107:
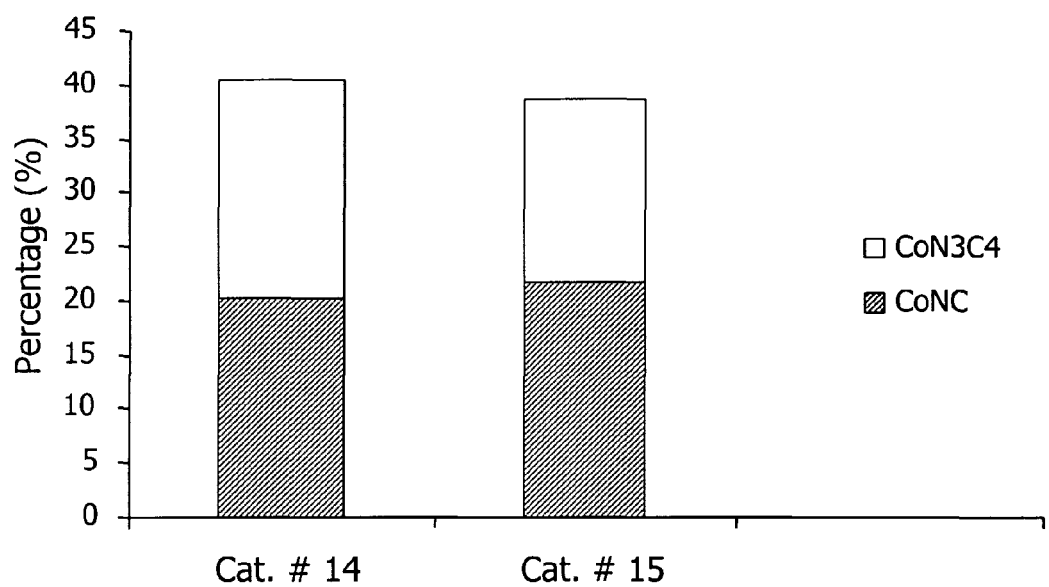

| Catalyst | Table | Figures |
|---|---|---|
| 1% CoCN/C | 41 | |
| 1.5% CoCN/C | 41 | |
| 5% CoCN/C | 41 | |
| 10% CoCN/C | 41 | |
| 1.5% CoTMPP/CP117 | 41 | |
| 3% CoCN/50% diglyme (Entry No. 3) | 42 | FIGS. 105, 108 |
| 3% CoCN/50% tetraglyme (Entry No. 4) | 42 | FIGS. 105, 108 |
| 3% CoCN/50% polyglyme (Entry No. 5) | 42 | FIGS. 105, 108 |
| Entry No. 6 | 42 | FIGS. 106, 108 |
| Entry No. 8 | 42 | FIGS. 106, 108 |
| Entry No. 9 | 42 | FIGS. 106, 108 |
| Entry No. 10 | 42 | FIG. 108 |
| Entry No. 14 | 42 | FIGS. 107-108 |
| Entry No. 15 | 42 | FIGS. 107-108 |

TABLE 41

| Catalyst | Ion Family | Relative Abundance of Ion Family (%) |
|---|---|---|
| 1% CoCN/C | $CoNC_y$ | 40.7 |
|  | $CoN_2C_y$ | 36.8 |
|  | $CoN_3C_y$ | 22.5 |
|  | $CoN_4C_y$ | 0 |
| 1.5% CoCN/C | $CoNC_y$ | 34.6 |
|  | $CoN_2C_y$ | 35.9 |
|  | $CoN_3C_y$ | 29.5 |
|  | $CoN_4C_y$ | 0 |
| 5% CoCN/C | $CoNC_y$ | 17.9 |
|  | $CoN_2C_y$ | 51.5 |
|  | $CoN_3C_y$ | 18.2 |
|  | $CoN_4C_y$ | 12.4 |
| 10% CoCN/C | $CoNC_y$ | 24.8 |
|  | $CoN_2C_y$ | 27.4 |
|  | $CoN_3C_y$ | 32.2 |
|  | $CoN_4C_y$ | 15.6 |
| 1.5% CoTMPP/CP117 | $CoNC_y$ | 18.6 |
|  | $CoN_2C_y$ | 0 |
|  | $CoN_3C_y$ | 16.9 |
|  | $CoN_4C_y$ | 64.5 |

TABLE 42

| Ions | Exact Mass | Nominal Mass Tabulated | Catalyst # - area #3-1 Integrated Peak Counts | Relative Intensity | #3-2 Integrated Peak Counts | Relative Intensity | #3-3 Average Intensity | Ions |
|---|---|---|---|---|---|---|---|---|
| CoNC | 84.9363 | 85 | 205 | 0.264 | 342 | 0.321 | 0.293 | CoNC |
| $CoNC_2$ | 96.9363 | 97 | 65 | 0.084 | 74 | 0.070 | 0.077 | $CoNC_2$ |
| $CoNC_3$ | 108.9363 | 109 | 35 | 0.045 | 56 | 0.053 | 0.049 | $CoNC_3$ |
| $CoNC_4$ | 120.9363 | 121 | 27 | 0.035 | 35 | 0.033 | 0.034 | $CoNC_4$ |
| $CoN_2C$ | 98.9394 | 99 | 56 | 0.072 | 67 | 0.063 | 0.068 | $CoN_2C$ |
| $CoN_2C_2$ | 110.9394 | 111 | 25 | 0.032 | 49 | 0.046 | 0.039 | $CoN_2C_2$ |
| $CoN_2C_3$ | 122.9394 | 123 | 24 | 0.031 | 25 | 0.023 | 0.027 | $CoN_2C_3$ |
| $CoN_2C_4$ | 134.9394 | 135 | 40 | 0.051 | 50 | 0.047 | 0.049 | $CoN_2C_4$ |
| $CoN_3C$ | 112.9425 | 113 | 57 | 0.073 | 42 | 0.039 | 0.056 | $CoN_3C$ |
| $CoN_3C_2$ | 124.9425 | 125 | 12 | 0.015 | 15 | 0.014 | 0.015 | $CoN_3C_2$ |
| $CoN_3C_3$ | 136.9425 | 137 | 12 | 0.015 | 27 | 0.025 | 0.020 | $CoN_3C_3$ |
| $CoN_3C_4$ | 148.9425 | 149 | 36 | 0.046 | 72 | 0.068 | 0.057 | $CoN_3C_4$ |
| $CoN_4C$ | 126.9456 | 127 | 30 | 0.039 | 37 | 0.035 | 0.037 | $CoN_4C$ |
| $CoN4C_2$ | 138.9456 | 139 | 23 | 0.030 | 24 | 0.023 | 0.026 | $CoN4C_2$ |
| $CoN_4C_3$ | 150.9456 | 151 | 31 | 0.040 | 24 | 0.023 | 0.031 | $CoN_4C_3$ |
| $CoN_4C_4$ | 162.9456 | 163 | 18 | 0.023 | 22 | 0.021 | 0.022 | $CoN_4C_4$ |
| $Co_2NC$ | 143.8695 | 144 | 14 | 0.018 | 24 | 0.023 | 0.020 | $Co_2NC$ |
| $Co_3NC$ | 202.8027 | 203 | 9 | 0.012 | 9 | 0.008 | 0.010 | $Co_3NC$ |
| $Co_4NC$ | 261.7359 | 262 | 2 | 0.003 | 4 | 0.004 | 0.003 | $Co_4NC$ |
| $Co_2N_2C$ | 157.8725 | 158 | 8 | 0.010 | 9 | 0.008 | 0.009 | $Co_2N_2C$ |
| $Co_3N_2C$ | 216.8057 | 217 | 15 | 0.019 | 18 | 0.017 | 0.018 | $Co_3N_2C$ |
| $Co_4N_2C$ | 275.7389 | 276 | 1 | 0.001 | 4 | 0.004 | 0.003 | $Co_4N_2C$ |
| $Co_2N_3C$ | 171.8756 | 172 | 5 | 0.006 | 10 | 0.009 | 0.008 | $Co_2N_3C$ |
| $Co_3N_3C$ | 230.8088 | 231 | 12 | 0.015 | 7 | 0.007 | 0.011 | $Co_3N_3C$ |
| $Co_4N_3C$ | 289.742 | 290 | 1 | 0.001 | 5 | 0.005 | 0.003 | $Co_4N_3C$ |
| $Co_2N_4C$ | 185.8787 | 186 | 5 | 0.006 | 6 | 0.006 | 0.006 | $Co_2N_4C$ |
| $Co_3N_4C$ | 244.8119 | 245 | 8 | 0.010 | 4 | 0.004 | 0.007 | $Co_3N_4C$ |
| $Co_4N_4C$ | 303.7451 | 304 | 1 | 0.001 | 3 | 0.003 | 0.002 | $Co_4N_4C$ |
| Total | | | 777 | 1 | 1064 | 1 | | |

| Ions | Exact Mass | Nominal Mass Tabulated | Catalyst # - area #4-1 Integrated Peak Counts | Relative Intensity | #4-2 Integrated Peak Counts | Relative Intensity | #4-3 Average Intensity | Ions |
|---|---|---|---|---|---|---|---|---|
| CoNC | 84.9363 | 85 | 73 | 0.173 | 106 | 0.183 | 0.178 | CoNC |
| $CoNC_2$ | 96.9363 | 97 | 36 | 0.086 | 41 | 0.071 | 0.078 | $CoNC_2$ |
| $CoNC_3$ | 108.9363 | 109 | 16 | 0.038 | 28 | 0.048 | 0.043 | $CoNC_3$ |
| $CoNC_4$ | 120.9363 | 121 | 9 | 0.021 | 20 | 0.035 | 0.028 | $CoNC_4$ |
| $CoN_2C$ | 98.9394 | 99 | 39 | 0.093 | 46 | 0.080 | 0.086 | $CoN_2C$ |
| $CoN_2C_2$ | 110.9394 | 111 | 7 | 0.017 | 21 | 0.036 | 0.026 | $CoN_2C_2$ |
| $CoN_2C_3$ | 122.9394 | 123 | 5 | 0.012 | 13 | 0.022 | 0.017 | $CoN_2C_3$ |
| $CoN_2C_4$ | 134.9394 | 135 | 46 | 0.109 | 50 | 0.087 | 0.098 | $CoN_2C_4$ |
| $CoN_3C$ | 112.9425 | 113 | 19 | 0.045 | 31 | 0.054 | 0.049 | $CoN_3C$ |
| $CoN_3C_2$ | 124.9425 | 125 | 10 | 0.024 | 9 | 0.016 | 0.020 | $CoN_3C_2$ |
| $CoN_3C_3$ | 136.9425 | 137 | 16 | 0.038 | 15 | 0.026 | 0.032 | $CoN_3C_3$ |
| $CoN_3C_4$ | 148.9425 | 149 | 32 | 0.076 | 33 | 0.057 | 0.067 | $CoN_3C_4$ |
| $CoN_4C$ | 126.9456 | 127 | 20 | 0.048 | 39 | 0.067 | 0.057 | $CoN_4C$ |
| $CoN4C_2$ | 138.9456 | 139 | 9 | 0.021 | 14 | 0.024 | 0.023 | $CoN4C_2$ |
| $CoN_4C_3$ | 150.9456 | 151 | 10 | 0.024 | 20 | 0.035 | 0.029 | $CoN_4C_3$ |
| $CoN_4C_4$ | 162.9456 | 163 | 7 | 0.017 | 15 | 0.026 | 0.021 | $CoN_4C_4$ |
| $Co_2NC$ | 143.8695 | 144 | 10 | 0.024 | 13 | 0.022 | 0.023 | $Co_2NC$ |
| $Co_3NC$ | 202.8027 | 203 | 6 | 0.014 | 9 | 0.016 | 0.015 | $Co_3NC$ |
| $Co_4NC$ | 261.7359 | 262 | 1 | 0.002 | 0 | 0.000 | 0.001 | $Co_4NC$ |
| $Co_2N_2C$ | 157.8725 | 158 | 11 | 0.026 | 15 | 0.026 | 0.026 | $Co_2N_2C$ |
| $Co_3N_2C$ | 216.8057 | 217 | 21 | 0.050 | 13 | 0.022 | 0.036 | $Co_3N_2C$ |
| $Co_4N_2C$ | 275.7389 | 276 | 1 | 0.002 | 2 | 0.003 | 0.003 | $Co_4N_2C$ |
| $Co_2N_3C$ | 171.8756 | 172 | 12 | 0.029 | 5 | 0.009 | 0.019 | $Co_2N_3C$ |
| $Co_3N_3C$ | 230.8088 | 231 | 0 | 0.000 | 7 | 0.012 | 0.006 | $Co_3N_3C$ |
| $Co_4N_3C$ | 289.742 | 290 | 0 | 0.000 | 1 | 0.002 | 0.001 | $Co_4N_3C$ |
| $Co_2N_4C$ | 185.8787 | 186 | 0 | 0.000 | 8 | 0.014 | 0.007 | $Co_2N_4C$ |
| $Co_3N_4C$ | 244.8119 | 245 | 4 | 0.010 | 4 | 0.007 | 0.008 | $Co_3N_4C$ |
| $Co_4N_4C$ | 303.7451 | 304 | 1 | 0.002 | 0 | 0.000 | 0.001 | $Co_4N_4C$ |
| Total | | | 421 | 1 | 578 | 1 | | |

TABLE 42-continued

| Ions | Exact Mass | Nominal Mass Tabulated | Catalyst # - area #5-1 Integrated Peak Counts | Relative Intensity | #5-2 Integrated Peak Counts | Relative Intensity | #5-3 Average Intensity | Ions |
|---|---|---|---|---|---|---|---|---|
| CoNC | 84.9363 | 85 | 86 | 0.193 | 110 | 0.231 | 0.212 | CoNC |
| CoNC$_2$ | 96.9363 | 97 | 31 | 0.070 | 27 | 0.057 | 0.063 | CoNC$_2$ |
| CoNC$_3$ | 108.9363 | 109 | 17 | 0.038 | 18 | 0.038 | 0.038 | CoNC$_3$ |
| CoNC$_4$ | 120.9363 | 121 | 15 | 0.034 | 17 | 0.036 | 0.035 | CoNC$_4$ |
| CoN$_2$C | 98.9394 | 99 | 29 | 0.065 | 36 | 0.076 | 0.070 | CoN$_2$C |
| CoN$_2$C$_2$ | 110.9394 | 111 | 30 | 0.067 | 16 | 0.034 | 0.051 | CoN$_2$C$_2$ |
| CoN$_2$C$_3$ | 122.9394 | 123 | 6 | 0.013 | 10 | 0.021 | 0.017 | CoN$_2$C$_3$ |
| CoN$_2$C$_4$ | 134.9394 | 135 | 36 | 0.081 | 37 | 0.078 | 0.079 | CoN$_2$C$_4$ |
| CoN$_3$C | 112.9425 | 113 | 24 | 0.054 | 15 | 0.032 | 0.043 | CoN$_3$C |
| CoN$_3$C$_2$ | 124.9425 | 125 | 10 | 0.022 | 6 | 0.013 | 0.018 | CoN$_3$C$_2$ |
| CoN$_3$C$_3$ | 136.9425 | 137 | 13 | 0.029 | 14 | 0.029 | 0.029 | CoN$_3$C$_3$ |
| CoN$_3$C$_4$ | 148.9425 | 149 | 41 | 0.092 | 24 | 0.050 | 0.071 | CoN$_3$C$_4$ |
| CoN$_4$C | 126.9456 | 127 | 17 | 0.038 | 28 | 0.059 | 0.049 | CoN$_4$C |
| CoN4C$_2$ | 138.9456 | 139 | 11 | 0.025 | 11 | 0.023 | 0.024 | CoN4C$_2$ |
| CoN$_4$C$_3$ | 150.9456 | 151 | 11 | 0.025 | 9 | 0.019 | 0.022 | CoN$_4$C$_3$ |
| CoN$_4$C$_4$ | 162.9456 | 163 | 7 | 0.016 | 10 | 0.021 | 0.018 | CoN$_4$C$_4$ |
| Co$_2$NC | 143.8695 | 144 | 13 | 0.029 | 12 | 0.025 | 0.027 | Co$_2$NC |
| Co$_3$NC | 202.8027 | 203 | 2 | 0.004 | 13 | 0.027 | 0.016 | Co$_3$NC |
| Co$_4$NC | 261.7359 | 262 | 2 | 0.004 | 0 | 0.000 | 0.002 | Co$_4$NC |
| Co$_2$N$_2$C | 157.8725 | 158 | 10 | 0.022 | 14 | 0.029 | 0.026 | Co$_2$N$_2$C |
| Co$_3$N$_2$C | 216.8057 | 217 | 14 | 0.031 | 27 | 0.057 | 0.044 | Co$_3$N$_2$C |
| Co$_4$N$_2$C | 275.7389 | 276 | 1 | 0.002 | 0 | 0.000 | 0.001 | Co$_4$N$_2$C |
| Co$_2$N$_3$C | 171.8756 | 172 | 7 | 0.016 | 5 | 0.011 | 0.013 | Co$_2$N$_3$C |
| Co$_3$N$_3$C | 230.8088 | 231 | 6 | 0.013 | 4 | 0.008 | 0.011 | Co$_3$N$_3$C |
| Co$_4$N$_3$C | 289.742 | 290 | 2 | 0.004 | 3 | 0.006 | 0.005 | Co$_4$N$_3$C |
| Co$_2$N$_4$C | 185.8787 | 186 | 2 | 0.004 | 4 | 0.008 | 0.006 | Co$_2$N$_4$C |
| Co$_3$N$_4$C | 244.8119 | 245 | 2 | 0.004 | 3 | 0.006 | 0.005 | Co$_3$N$_4$C |
| Co$_4$N$_4$C | 303.7451 | 304 | 0 | 0.000 | 3 | 0.006 | 0.003 | Co$_4$N$_4$C |
| Total | | | 445 | 1 | 476 | 1 | | |

| Ions | Exact Mass | Nominal Mass Tabulated | Catalyst # - area #6-1 Integrated Peak Counts | Relative Intensity | #6-2 Integrated Peak Counts | Relative Intensity | #6-3 Average Intensity | Ions |
|---|---|---|---|---|---|---|---|---|
| CoNC | 84.9363 | 85 | 66 | 0.175 | 211 | 0.354 | 0.264 | CoNC |
| CoNC$_2$ | 96.9363 | 97 | 19 | 0.050 | 35 | 0.059 | 0.054 | CoNC$_2$ |
| CoNC$_3$ | 108.9363 | 109 | 16 | 0.042 | 24 | 0.040 | 0.041 | CoNC$_3$ |
| CoNC$_4$ | 120.9363 | 121 | 9 | 0.024 | 16 | 0.027 | 0.025 | CoNC$_4$ |
| CoN$_2$C | 98.9394 | 99 | 26 | 0.069 | 41 | 0.069 | 0.069 | CoN$_2$C |
| CoN$_2$C$_2$ | 110.9394 | 111 | 11 | 0.029 | 23 | 0.039 | 0.034 | CoN$_2$C$_2$ |
| CoN$_2$C$_3$ | 122.9394 | 123 | 10 | 0.026 | 15 | 0.025 | 0.026 | CoN$_2$C$_3$ |
| CoN$_2$C$_4$ | 134.9394 | 135 | 42 | 0.111 | 38 | 0.064 | 0.087 | CoN$_2$C$_4$ |
| CoN$_3$C | 112.9425 | 113 | 21 | 0.056 | 23 | 0.039 | 0.047 | CoN$_3$C |
| CoN$_3$C$_2$ | 124.9425 | 125 | 10 | 0.026 | 15 | 0.025 | 0.026 | CoN$_3$C$_2$ |
| CoN$_3$C$_3$ | 136.9425 | 137 | 4 | 0.011 | 9 | 0.015 | 0.013 | CoN$_3$C$_3$ |
| CoN$_3$C$_4$ | 148.9425 | 149 | 31 | 0.082 | 32 | 0.054 | 0.068 | CoN$_3$C$_4$ |
| CoN$_4$C | 126.9456 | 127 | 18 | 0.048 | 30 | 0.050 | 0.049 | CoN$_4$C |
| CoN4C$_2$ | 138.9456 | 139 | 9 | 0.024 | 5 | 0.008 | 0.016 | CoN4C$_2$ |
| CoN$_4$C$_3$ | 150.9456 | 151 | 6 | 0.016 | 14 | 0.023 | 0.020 | CoN$_4$C$_3$ |
| CoN$_4$C$_4$ | 162.9456 | 163 | 10 | 0.026 | 7 | 0.012 | 0.019 | CoN$_4$C$_4$ |
| Co$_2$NC | 143.8695 | 144 | 11 | 0.029 | 17 | 0.029 | 0.029 | Co$_2$NC |
| Co$_3$NC | 202.8027 | 203 | 5 | 0.013 | 6 | 0.010 | 0.012 | Co$_3$NC |
| Co$_4$NC | 261.7359 | 262 | 5 | 0.013 | 1 | 0.002 | 0.007 | Co$_4$NC |
| Co$_2$N$_2$C | 157.8725 | 158 | 6 | 0.016 | 5 | 0.008 | 0.012 | Co$_2$N$_2$C |
| Co$_3$N$_2$C | 216.8057 | 217 | 24 | 0.063 | 22 | 0.037 | 0.050 | Co$_3$N$_2$C |
| Co$_4$N$_2$C | 275.7389 | 276 | 1 | 0.003 | 0 | 0.000 | 0.001 | Co$_4$N$_2$C |
| Co$_2$N$_3$C | 171.8756 | 172 | 4 | 0.011 | 4 | 0.007 | 0.009 | Co$_2$N$_3$C |
| Co$_3$N$_3$C | 230.8088 | 231 | 8 | 0.021 | 1 | 0.002 | 0.011 | Co$_3$N$_3$C |
| Co$_4$N$_3$C | 289.742 | 290 | 1 | 0.003 | 0 | 0.000 | 0.001 | Co$_4$N$_3$C |
| Co$_2$N$_4$C | 185.8787 | 186 | 3 | 0.008 | 1 | 0.002 | 0.005 | Co$_2$N$_4$C |
| Co$_3$N$_4$C | 244.8119 | 245 | 2 | 0.005 | 1 | 0.002 | 0.003 | Co$_3$N$_4$C |
| Co$_4$N$_4$C | 303.7451 | 304 | 0 | 0.000 | 0 | 0.000 | 0.000 | Co$_4$N$_4$C |
| Total | | | 378 | 1 | 596 | 1 | | |

TABLE 42-continued

| Ions | Catalyst # - area Exact Mass | Nominal Mass Tabulated | #8-1 Integrated Peak Counts | Relative Intensity | #8-2 Integrated Peak Counts | Relative Intensity | #8-3 Average Intensity | Ions |
|---|---|---|---|---|---|---|---|---|
| CoNC | 84.9363 | 85 | 274 | 0.436 | 134 | 0.293 | 0.365 | CoNC |
| $CoNC_2$ | 96.9363 | 97 | 44 | 0.070 | 33 | 0.072 | 0.071 | $CoNC_2$ |
| $CoNC_3$ | 108.9363 | 109 | 33 | 0.053 | 31 | 0.068 | 0.060 | $CoNC_3$ |
| $CoNC_4$ | 120.9363 | 121 | 19 | 0.030 | 9 | 0.020 | 0.025 | $CoNC_4$ |
| $CoN_2C$ | 98.9394 | 99 | 26 | 0.041 | 21 | 0.046 | 0.044 | $CoN_2C$ |
| $CoN_2C_2$ | 110.9394 | 111 | 19 | 0.030 | 20 | 0.044 | 0.037 | $CoN_2C_2$ |
| $CoN_2C_3$ | 122.9394 | 123 | 11 | 0.018 | 10 | 0.022 | 0.020 | $CoN_2C_3$ |
| $CoN_2C_4$ | 134.9394 | 135 | 50 | 0.080 | 37 | 0.081 | 0.080 | $CoN_2C_4$ |
| $CoN_3C$ | 112.9425 | 113 | 14 | 0.022 | 16 | 0.035 | 0.029 | $CoN_3C$ |
| $CoN_3C_2$ | 124.9425 | 125 | 6 | 0.010 | 11 | 0.024 | 0.017 | $CoN_3C_2$ |
| $CoN_3C_3$ | 136.9425 | 137 | 10 | 0.016 | 10 | 0.022 | 0.019 | $CoN_3C_3$ |
| $CoN_3C_4$ | 148.9425 | 149 | 37 | 0.059 | 28 | 0.061 | 0.060 | $CoN_3C_4$ |
| $CoN_4C$ | 126.9456 | 127 | 15 | 0.024 | 14 | 0.031 | 0.027 | $CoN_4C$ |
| $CoN4C_2$ | 138.9456 | 139 | 8 | 0.013 | 2 | 0.004 | 0.009 | $CoN4C_2$ |
| $CoN_4C_3$ | 150.9456 | 151 | 7 | 0.011 | 6 | 0.013 | 0.012 | $CoN_4C_3$ |
| $CoN_4C_4$ | 162.9456 | 163 | 2 | 0.003 | 10 | 0.022 | 0.013 | $CoN_4C_4$ |
| $Co_2NC$ | 143.8695 | 144 | 18 | 0.029 | 26 | 0.057 | 0.043 | $Co_2NC$ |
| $Co_3NC$ | 202.8027 | 203 | 9 | 0.014 | 8 | 0.018 | 0.016 | $Co_3NC$ |
| $Co_4NC$ | 261.7359 | 262 | 2 | 0.003 | 3 | 0.007 | 0.005 | $Co_4NC$ |
| $Co_2N_2C$ | 157.8725 | 158 | 11 | 0.018 | 9 | 0.020 | 0.019 | $Co_2N_2C$ |
| $Co_3N_2C$ | 216.8057 | 217 | 2 | 0.003 | 5 | 0.011 | 0.007 | $Co_3N_2C$ |
| $Co_4N_2C$ | 275.7389 | 276 | 0 | 0.000 | 0 | 0.000 | 0.000 | $Co_4N_2C$ |
| $Co_2N_3C$ | 171.8756 | 172 | 7 | 0.011 | 6 | 0.013 | 0.012 | $Co_2N_3C$ |
| $Co_3N_3C$ | 230.8088 | 231 | 0 | 0.000 | 1 | 0.002 | 0.001 | $Co_3N_3C$ |
| $Co_4N_3C$ | 289.742 | 290 | 0 | 0.000 | 1 | 0.002 | 0.001 | $Co_4N_3C$ |
| $Co_2N_4C$ | 185.8787 | 186 | 1 | 0.002 | 2 | 0.004 | 0.003 | $Co_2N_4C$ |
| $Co_3N_4C$ | 244.8119 | 245 | 1 | 0.002 | 0 | 0.000 | 0.001 | $Co_3N_4C$ |
| $Co_4N_4C$ | 303.7451 | 304 | 2 | 0.003 | 4 | 0.009 | 0.006 | $Co_4N_4C$ |
| Total | | | 628 | 1 | 457 | 1 | | |

| Ions | Catalyst # - area Exact Mass | Nominal Mass Tabulated | #9-1 Integrated Peak Counts | Relative Intensity | #9-2 Integrated Peak Counts | Relative Intensity | #9-3 Average Intensity | Ions |
|---|---|---|---|---|---|---|---|---|
| CoNC | 84.9363 | 85 | 142 | 0.215 | 136 | 0.229 | 0.222 | CoNC |
| $CoNC_2$ | 96.9363 | 97 | 33 | 0.050 | 26 | 0.044 | 0.047 | $CoNC_2$ |
| $CoNC_3$ | 108.9363 | 109 | 22 | 0.033 | 13 | 0.022 | 0.028 | $CoNC_3$ |
| $CoNC_4$ | 120.9363 | 121 | 22 | 0.033 | 21 | 0.035 | 0.034 | $CoNC_4$ |
| $CoN_2C$ | 98.9394 | 99 | 46 | 0.070 | 34 | 0.057 | 0.063 | $CoN_2C$ |
| $CoN_2C_2$ | 110.9394 | 111 | 24 | 0.036 | 10 | 0.017 | 0.027 | $CoN_2C_2$ |
| $CoN_2C_3$ | 122.9394 | 123 | 14 | 0.021 | 6 | 0.010 | 0.016 | $CoN_2C_3$ |
| $CoN_2C_4$ | 134.9394 | 135 | 31 | 0.047 | 39 | 0.066 | 0.056 | $CoN_2C_4$ |
| $CoN_3C$ | 112.9425 | 113 | 20 | 0.030 | 31 | 0.052 | 0.041 | $CoN_3C$ |
| $CoN_3C_2$ | 124.9425 | 125 | 11 | 0.017 | 9 | 0.015 | 0.016 | $CoN_3C_2$ |
| $CoN_3C_3$ | 136.9425 | 137 | 17 | 0.026 | 9 | 0.015 | 0.020 | $CoN_3C_3$ |
| $CoN_3C_4$ | 148.9425 | 149 | 139 | 0.210 | 124 | 0.209 | 0.210 | $CoN_3C_4$ |
| $CoN_4C$ | 126.9456 | 127 | 20 | 0.030 | 13 | 0.022 | 0.026 | $CoN_4C$ |
| $CoN4C_2$ | 138.9456 | 139 | 12 | 0.018 | 14 | 0.024 | 0.021 | $CoN4C_2$ |
| $CoN_4C_3$ | 150.9456 | 151 | 15 | 0.023 | 12 | 0.020 | 0.021 | $CoN_4C_3$ |
| $CoN_4C_4$ | 162.9456 | 163 | 5 | 0.008 | 11 | 0.019 | 0.013 | $CoN_4C_4$ |
| $Co_2NC$ | 143.8695 | 144 | 24 | 0.036 | 26 | 0.044 | 0.040 | $Co_2NC$ |
| $Co_3NC$ | 202.8027 | 203 | 0 | 0.000 | 3 | 0.005 | 0.003 | $Co_3NC$ |
| $Co_4NC$ | 261.7359 | 262 | 3 | 0.005 | 1 | 0.002 | 0.003 | $Co_4NC$ |
| $Co_2N_2C$ | 157.8725 | 158 | 9 | 0.014 | 13 | 0.022 | 0.018 | $Co_2N_2C$ |
| $Co_3N_2C$ | 216.8057 | 217 | 29 | 0.044 | 22 | 0.037 | 0.040 | $Co_3N_2C$ |
| $Co_4N_2C$ | 275.7389 | 276 | 1 | 0.002 | 0 | 0.000 | 0.001 | $Co_4N_2C$ |
| $Co_2N_3C$ | 171.8756 | 172 | 7 | 0.011 | 5 | 0.008 | 0.010 | $Co_2N_3C$ |
| $Co_3N_3C$ | 230.8088 | 231 | 4 | 0.006 | 3 | 0.005 | 0.006 | $Co_3N_3C$ |
| $Co_4N_3C$ | 289.742 | 290 | 2 | 0.003 | 2 | 0.003 | 0.003 | $Co_4N_3C$ |
| $Co_2N_4C$ | 185.8787 | 186 | 2 | 0.003 | 5 | 0.008 | 0.006 | $Co_2N_4C$ |
| $Co_3N_4C$ | 244.8119 | 245 | 4 | 0.006 | 3 | 0.005 | 0.006 | $Co_3N_4C$ |
| $Co_4N_4C$ | 303.7451 | 304 | 3 | 0.005 | 3 | 0.005 | 0.005 | $Co_4N_4C$ |
| Total | | | 661 | 1 | 594 | 1 | | |

TABLE 42-continued

| Ions | Catalyst # - area | | #10-1 | | #10-2 | | #10-3 | Ions |
|---|---|---|---|---|---|---|---|---|
| | Exact Mass | Nominal Mass Tabulated | Integrated Peak Counts | Relative Intensity | Integrated Peak Counts | Relative Intensity | Average Intensity | |
| CoNC | 84.9363 | 85 | 69 | 0.120 | 140 | 0.153 | 0.136 | CoNC |
| $CoNC_2$ | 96.9363 | 97 | 32 | 0.056 | 41 | 0.045 | 0.050 | $CoNC_2$ |
| $CoNC_3$ | 108.9363 | 109 | 21 | 0.037 | 15 | 0.016 | 0.026 | $CoNC_3$ |
| $CoNC_4$ | 120.9363 | 121 | 23 | 0.040 | 37 | 0.040 | 0.040 | $CoNC_4$ |
| $CoN_2C$ | 98.9394 | 99 | 33 | 0.057 | 79 | 0.086 | 0.072 | $CoN_2C$ |
| $CoN_2C_2$ | 110.9394 | 111 | 28 | 0.049 | 29 | 0.032 | 0.040 | $CoN_2C_2$ |
| $CoN_2C_3$ | 122.9394 | 123 | 8 | 0.014 | 17 | 0.019 | 0.016 | $CoN_2C_3$ |
| $CoN_2C_4$ | 134.9394 | 135 | 52 | 0.090 | 91 | 0.099 | 0.095 | $CoN_2C_4$ |
| $CoN_3C$ | 112.9425 | 113 | 26 | 0.045 | 54 | 0.059 | 0.052 | $CoN_3C$ |
| $CoN_3C_2$ | 124.9425 | 125 | 13 | 0.023 | 17 | 0.019 | 0.021 | $CoN_3C_2$ |
| $CoN_3C_3$ | 136.9425 | 137 | 15 | 0.026 | 23 | 0.025 | 0.026 | $CoN_3C_3$ |
| $CoN_3C_4$ | 148.9425 | 149 | 66 | 0.115 | 120 | 0.131 | 0.123 | $CoN_3C_4$ |
| $CoN_4C$ | 126.9456 | 127 | 14 | 0.024 | 24 | 0.026 | 0.025 | $CoN_4C$ |
| $CoN4C_2$ | 138.9456 | 139 | 10 | 0.017 | 10 | 0.011 | 0.014 | $CoN4C_2$ |
| $CoN_4C_3$ | 150.9456 | 151 | 22 | 0.038 | 48 | 0.052 | 0.045 | $CoN_4C_3$ |
| $CoN_4C_4$ | 162.9456 | 163 | 14 | 0.024 | 34 | 0.037 | 0.031 | $CoN_4C_4$ |
| $Co_2NC$ | 143.8695 | 144 | 11 | 0.019 | 14 | 0.015 | 0.017 | $Co_2NC$ |
| $Co_3NC$ | 202.8027 | 203 | 10 | 0.017 | 9 | 0.010 | 0.014 | $Co_3NC$ |
| $Co_4NC$ | 261.7359 | 262 | 1 | 0.002 | 2 | 0.002 | 0.002 | $Co_4NC$ |
| $Co_2N_2C$ | 157.8725 | 158 | 15 | 0.026 | 22 | 0.024 | 0.025 | $Co_2N_2C$ |
| $Co_3N_2C$ | 216.8057 | 217 | 48 | 0.083 | 50 | 0.055 | 0.069 | $Co_3N_2C$ |
| $Co_4N_2C$ | 275.7389 | 276 | 2 | 0.003 | 3 | 0.003 | 0.003 | $Co_4N_2C$ |
| $Co_2N_3C$ | 171.8756 | 172 | 11 | 0.019 | 6 | 0.007 | 0.013 | $Co_2N_3C$ |
| $Co_3N_3C$ | 230.8088 | 231 | 11 | 0.019 | 1 | 0.001 | 0.010 | $Co_3N_3C$ |
| $Co_4N_3C$ | 289.742 | 290 | 1 | 0.002 | 5 | 0.005 | 0.004 | $Co_4N_3C$ |
| $Co_2N_4C$ | 185.8787 | 186 | 3 | 0.005 | 5 | 0.005 | 0.005 | $Co_2N_4C$ |
| $Co_3N_4C$ | 244.8119 | 245 | 6 | 0.010 | 4 | 0.004 | 0.007 | $Co_3N_4C$ |
| $Co_4N_4C$ | 303.7451 | 304 | 10 | 0.017 | 16 | 0.017 | 0.017 | $Co_4N_4C$ |
| Total | | | 575 | 1 | 916 | 1 | | |

| Ions | Catalyst # - area | | #14-1 | | #14-2 | | #14-3 | Ions |
|---|---|---|---|---|---|---|---|---|
| | Exact Mass | Nominal Mass Tabulated | Integrated Peak Counts | Relative Intensity | Integrated Peak Counts | Relative Intensity | Average Intensity | |
| CoNC | 84.9363 | 85 | 89 | 0.227 | 89 | 0.178 | 0.202 | CoNC |
| $CoNC_2$ | 96.9363 | 97 | 25 | 0.064 | 21 | 0.042 | 0.053 | $CoNC_2$ |
| $CoNC_3$ | 108.9363 | 109 | 11 | 0.028 | 16 | 0.032 | 0.030 | $CoNC_3$ |
| $CoNC_4$ | 120.9363 | 121 | 9 | 0.023 | 11 | 0.022 | 0.022 | $CoNC_4$ |
| $CoN_2C$ | 98.9394 | 99 | 25 | 0.064 | 29 | 0.058 | 0.061 | $CoN_2C$ |
| $CoN_2C_2$ | 110.9394 | 111 | 23 | 0.059 | 12 | 0.024 | 0.041 | $CoN_2C_2$ |
| $CoN_2C_3$ | 122.9394 | 123 | 6 | 0.015 | 13 | 0.026 | 0.021 | $CoN_2C_3$ |
| $CoN_2C_4$ | 134.9394 | 135 | 20 | 0.051 | 39 | 0.078 | 0.064 | $CoN_2C_4$ |
| $CoN_3C$ | 112.9425 | 113 | 16 | 0.041 | 23 | 0.046 | 0.043 | $CoN_3C$ |
| $CoN_3C_2$ | 124.9425 | 125 | 6 | 0.015 | 5 | 0.010 | 0.013 | $CoN_3C_2$ |
| $CoN_3C_3$ | 136.9425 | 137 | 4 | 0.010 | 19 | 0.038 | 0.024 | $CoN_3C_3$ |
| $CoN_3C_4$ | 148.9425 | 149 | 59 | 0.151 | 128 | 0.255 | 0.203 | $CoN_3C_4$ |
| $CoN_4C$ | 126.9456 | 127 | 18 | 0.046 | 16 | 0.032 | 0.039 | $CoN_4C$ |
| $CoN4C_2$ | 138.9456 | 139 | 8 | 0.020 | 7 | 0.014 | 0.017 | $CoN4C_2$ |
| $CoN_4C_3$ | 150.9456 | 151 | 17 | 0.043 | 9 | 0.018 | 0.031 | $CoN_4C_3$ |
| $CoN_4C_4$ | 162.9456 | 163 | 12 | 0.031 | 6 | 0.012 | 0.021 | $CoN_4C_4$ |
| $Co_2NC$ | 143.8695 | 144 | 11 | 0.028 | 8 | 0.016 | 0.022 | $Co_2NC$ |
| $Co_3NC$ | 202.8027 | 203 | 1 | 0.003 | 2 | 0.004 | 0.003 | $Co_3NC$ |
| $Co_4NC$ | 261.7359 | 262 | 2 | 0.005 | 3 | 0.006 | 0.006 | $Co_4NC$ |
| $Co_2N_2C$ | 157.8725 | 158 | 3 | 0.008 | 9 | 0.018 | 0.013 | $Co_2N_2C$ |
| $Co_3N_2C$ | 216.8057 | 217 | 17 | 0.043 | 14 | 0.028 | 0.036 | $Co_3N_2C$ |
| $Co_4N_2C$ | 275.7389 | 276 | 0 | 0.000 | 0 | 0.000 | 0.000 | $Co_4N_2C$ |
| $Co_2N_3C$ | 171.8756 | 172 | 3 | 0.008 | 3 | 0.006 | 0.007 | $Co_2N_3C$ |
| $Co_3N_3C$ | 230.8088 | 231 | 2 | 0.005 | 4 | 0.008 | 0.007 | $Co_3N_3C$ |
| $Co_4N_3C$ | 289.742 | 290 | 0 | 0.000 | 3 | 0.006 | 0.003 | $Co_4N_3C$ |
| $Co_2N_4C$ | 185.8787 | 186 | 2 | 0.005 | 7 | 0.014 | 0.010 | $Co_2N_4C$ |
| $Co_3N_4C$ | 244.8119 | 245 | 0 | 0.000 | 4 | 0.008 | 0.004 | $Co_3N_4C$ |
| $Co_4N_4C$ | 303.7451 | 304 | 3 | 0.008 | 1 | 0.002 | 0.005 | $Co_4N_4C$ |
| Total | | | 392 | 1 | 501 | 1 | | |

TABLE 42-continued

| Ions | Exact Mass | Nominal Mass Tabulated | #15-1 Integrated Peak Counts | #15-1 Relative Intensity | #15-2 Integrated Peak Counts | #15-2 Relative Intensity | #15-3 Average Intensity | Ions |
|---|---|---|---|---|---|---|---|---|
| CoNC | 84.9363 | 85 | 210 | 0.185 | 500 | 0.249 | 0.217 | CoNC |
| $CoNC_2$ | 96.9363 | 97 | 59 | 0.052 | 120 | 0.060 | 0.056 | $CoNC_2$ |
| $CoNC_3$ | 108.9363 | 109 | 38 | 0.034 | 51 | 0.025 | 0.029 | $CoNC_3$ |
| $CoNC_4$ | 120.9363 | 121 | 27 | 0.024 | 35 | 0.017 | 0.021 | $CoNC_4$ |
| $CoN_2C$ | 98.9394 | 99 | 66 | 0.058 | 117 | 0.058 | 0.058 | $CoN_2C$ |
| $CoN_2C_2$ | 110.9394 | 111 | 119 | 0.105 | 171 | 0.085 | 0.095 | $CoN_2C_2$ |
| $CoN_2C_3$ | 122.9394 | 123 | 16 | 0.014 | 24 | 0.012 | 0.013 | $CoN_2C_3$ |
| $CoN_2C_4$ | 134.9394 | 135 | 30 | 0.026 | 56 | 0.028 | 0.027 | $CoN_2C_4$ |
| $CoN_3C$ | 112.9425 | 113 | 111 | 0.098 | 218 | 0.108 | 0.103 | $CoN_3C$ |
| $CoN_3C_2$ | 124.9425 | 125 | 12 | 0.011 | 30 | 0.015 | 0.013 | $CoN_3C_2$ |
| $CoN_3C_3$ | 136.9425 | 137 | 18 | 0.016 | 42 | 0.021 | 0.018 | $CoN_3C_3$ |
| $CoN_3C_4$ | 148.9425 | 149 | 218 | 0.192 | 300 | 0.149 | 0.171 | $CoN_3C_4$ |
| $CoN_4C$ | 126.9456 | 127 | 48 | 0.042 | 97 | 0.048 | 0.045 | $CoN_4C$ |
| $CoN4C_2$ | 138.9456 | 139 | 17 | 0.015 | 34 | 0.017 | 0.016 | $CoN4C_2$ |
| $CoN_4C_3$ | 150.9456 | 151 | 13 | 0.011 | 38 | 0.019 | 0.015 | $CoN_4C_3$ |
| $CON_4C_4$ | 162.9456 | 163 | 21 | 0.019 | 24 | 0.012 | 0.015 | $CoN_4C_4$ |
| $Co_2NC$ | 143.8695 | 144 | 22 | 0.019 | 26 | 0.013 | 0.016 | $Co_2NC$ |
| $Co_3NC$ | 202.8027 | 203 | 9 | 0.008 | 13 | 0.006 | 0.007 | $Co_3NC$ |
| $Co_4NC$ | 261.7359 | 262 | 0 | 0.000 | 4 | 0.002 | 0.001 | $Co_4NC$ |
| $Co_2N_2C$ | 157.8725 | 158 | 16 | 0.014 | 19 | 0.009 | 0.012 | $Co_2N_2C$ |
| $Co_3N_2C$ | 216.8057 | 217 | 14 | 0.012 | 21 | 0.010 | 0.011 | $Co_3N_2C$ |
| $Co_4N_2C$ | 275.7389 | 276 | 3 | 0.003 | 4 | 0.002 | 0.002 | $Co_4N_2C$ |
| $Co_2N_3C$ | 171.8756 | 172 | 3 | 0.003 | 16 | 0.008 | 0.005 | $Co_2N_3C$ |
| $Co_3N_3C$ | 230.8088 | 231 | 6 | 0.005 | 7 | 0.003 | 0.004 | $Co_3N_3C$ |
| $Co_4N_3C$ | 289.742 | 290 | 4 | 0.004 | 2 | 0.001 | 0.002 | $Co_4N_3C$ |
| $Co_2N_4C$ | 185.8787 | 186 | 15 | 0.013 | 15 | 0.007 | 0.010 | $Co_2N_4C$ |
| $Co_3N_4C$ | 244.8119 | 245 | 19 | 0.017 | 24 | 0.012 | 0.014 | $Co_3N_4C$ |
| $Co_4N_4C$ | 303.7451 | 304 | 0 | 0.000 | 4 | 0.002 | 0.001 | $Co_4N_4C$ |
| Total | | | 1134 | 1 | 2012 | 1 | | |

EXAMPLE 58

This example details Electron Paramagnetic Resonance (EPR) Spectroscopy analysis of various catalysts prepared as described in Examples 50 and 51. Entry Nos. 3-6, 8-10, 14, and 15 of Table 31 above were analyzed. For comparison purposes, the following samples were analyzed as well:
(1) a carbon support having a Langmuir surface area of approximately 1500 m²/g impregnated with Co phthalocyanine that was calcined in Argon for 2 hours;
(2) a 1.5% CoTMPP/MC10 catalyst prepared in accordance with Example 6 of WO 03/068387; and
(3) catalysts containing 1.5% and 3% cobalt prepared in accordance with Example 50 in which the cobalt source was mixed with the carbon support in a liquid medium consisting of deionized water prior to heat treatment.

Each catalyst was dried to obtain a constant amount of catalyst per centimeter in the EPR tube. A catalyst sample (0.05 g) was diluted 10:1 on a weight basis with silica gel (Grade 15, Aldrich stock no. 21,448-8, 30-60 mesh) in a vial that was vigorously shaken. The diluted catalyst sample was then ground for further mixing of the catalyst and diluent.

Q-band EPR spectra for each sample were collected at room temperature (approximately 20-25° C.) using a Varian E-15 spectrometer Q-band having a TE011 cavity. The magnetic fields were calibrated using a Varian NMR Gaussmeter and the microwave frequency was measured with an EIP Model 578 frequency counter equipped with a high-frequency option.

The EPR signal for each catalyst is a first derivative curve that is integrated once to provide an absorption signal and integrated once more to provide the area under the absorption curve that corresponds to the EPR signal intensity. Thus, EPR signal intensity is reported as a "double integral." Accordingly, the EPR signal intensity varies as the inverse square of the linewidth if the shape of the line does not change.

The samples were analyzed using a spectral window of either from 7000 to 17,000 Gauss or from 6806 to 15,376 Gauss. The absorbance for the samples extended beyond the spectral window. The absorbances were modeled using a mixed Gaussian-Lorentzian lineshape. The thus modeled lineshapes were highly anisotropic, particularly with respect to their linewidth. FIGS. 109A and 109B show the spectra thus obtained.

The number of spins/gram for each sample was determined. As a standard, copper sulfate pentahydrate ($CuSO_4.5H_2O$, MW: 249.69 g/mol) was analyzed. The molecular weight of the $CuSO_4.5H_2O$ sample corresponds to approximately $2.41*10^{21}$ spins per gram based on the number of $Cu^{2+}$ ions per gram of the compound. The spins/gram of this strong pitch standard was measured by the above method to be $2.30*10^{21}$ spins per gram was measured. A $Co_3O_4$ standard was also analyzed and, as shown in Table 43, exhibited approximately 1.64E23 spins per mole cobalt that also generally agrees with the spins/mole cobalt expected based on stoichiometry. That is, the standard has one mole of $Co^{2+}$ and two moles $Co^{3+}$ ions per mole of material, but only the $Co^{2+}$ ions give an EPR signal; thus, in theory, one expects 2.01E23 (0.333*6.022E23) spins/mole cobalt.

As shown in Table 43, spins/gram catalyst and spins/mole cobalt readings were not detected for the Co phthalocyanine-impregnated support and the 1.5% CoTMPP/MC10 catalyst. The observed spins/gram catalyst and spins/mole cobalt for the remaining samples were found to be higher than would be expected based on the stoichiometry.

The method described in this example is referenced in this specification and appended claims as "Protocol C."

TABLE 43

| Sample | Spectral Window | Double integral/Gain[1] | p-p linewidth (Gauss)[2] | Spins/Gram catalyst | Spins/mole Co |
|---|---|---|---|---|---|
| Co-Phthalocyanine impregnated support | B | | A | A | |
| CoTMPP/MC10 | B | 1645 | A | A | 2.18E25 |
| 3% Co/water | B | 82,260 | 1413 | 7.07E22 | 1.39E26 |
| 1.5% Co/water | B | 82,990 | 1270 | 6.37E22 | 2.50E26 |
| Entry No. 3 (diglyme) | B | 34,150 | 2039 | 2.62E22 | 1.03E26 |
| Entry No. 4 (tetraglyme) | B | 30,990 | 2340 | 3.58E22 | 7.03E25 |
| Entry No. 5 (polyglyme) | B | 59,640 | 2550 | 4.85E22 | 9.53E25 |
| Entry No. 6 | C | 74,200 | 2319 | 7.32E22 | 1.44E26 |
| Entry No. 8 | C | 1700 | 4200 | 1.02E22 | 1.20E26 |
| Entry No. 9 | C | 88,100 | 2612 | 8.24E22 | 1.62E26 |
| Entry No. 10 | C | 105,000 | 2491 | 9.86E22 | 1.94E26 |
| Entry No. 14 | C | 55,500 | 2473 | 7.01E22 | 1.38E26 |
| Entry No. 15 | C | 101,000 | 1465 | 8.40E22 | 1.65E26 |
| $Co_3O_4$ | C | 59,100 | 2439 | 1.62E21 | 1.64E23 |

[1]Double integral over the spectral window divided by the gain
[2]Distance (in Gauss) between the positive and negative peaks in the derivative spectrum
A = Signal too weak to quantify
B = 7000-17,000 Gauss
C = 6806-15,376 Gauss C=6806-15,376 Gauss

EXAMPLE 59

A 3% CoCN/C catalyst prepared as described in Example 50 and 1.5% CoTMPP/MC10 and 1.5% CoTMPP/CP117 catalysts prepared in accordance with Example 6 of WO 03/068387 were tested in PMIDA oxidation under the conditions set forth in Example 51.

The reaction was run for the times set forth in Table 44 for each of 6 cycles for the 3% CoCN/C catalyst and for the times set forth in Table 44 for each of 3 reaction cycles for the 1.5% CoTMPP/MC10 catalyst. The metal content of the reaction mixture was determined upon completion of each reaction cycle. For the 1.5% CoTMPP/CP117 catalyst, the reaction was discontinued after a reaction time of approximately 100 minutes due to plugging of the gas frit used to sparge the oxygen and nitrogen into the reaction. The metal content of the reaction mixture was determined after the reaction was discontinued. The metal content of the reaction mixtures was determined by ICP-MS using using a VG PQ ExCell Inductively Coupled Plasma-Mass Spectrometer.

As shown in Table 44, the 3% CoCN/C catalyst exhibited low metal leaching over the course of the 6 reaction cycles while the 1.5% CoTMPP/MC10 catalyst exhibited significantly higher metal leaching during its first reaction as compared to the 3% CoCN/C catalyst. The 1.5% CoTMPP/CP117 exhibited relatively low metal leaching; however, this is currently believed to be due the fact that the reaction medium had not yet reached a relatively high oxidation potential associated with a relatively high conversion of PMIDA that tends to promote metal leaching. In contrast, the degree of conversion achieved with the 3% CoCN/C catalyst would subject the catalyst to a relatively high reaction potential. However, this catalyst exhibited resistance to metal leaching under these conditions.

TABLE 44

| Catalyst | Cycle Number | Endpoint runtime (min) | Metal leaching as percentage of total metal (%) | Slope |
|---|---|---|---|---|
| 3% CoCN/C | 1 | 30.13 | 1.61 | |
| | 2 | 30.90 | <0.6* | |
| | 3 | 31.81 | | 0.69 |
| | 4 | 32.43 | <0.6* | |
| | 5 | 32.91 | | |
| | 6 | 33.60 | <0.06* | |
| 1.5% CoTMPP/MC10 | 1 | 29.60 | 28.4 | |
| | 2 | 33.73 | | 2.67 |
| | 3 | 34.93 | 1.8 | |
| 1.5% CoTMPP/CP117 | 1 | >100 (reaction stopped) | 2.7 (reaction stopped) | NA |

*Below detection limit.

EXAMPLE 60

This example details the preparation of a carbon-supported iron-containing catalyst precursor using a solid impregnation technique.

Add a articulate carbon support (100 g) having a Langmuir surface area of approximately 1500 m$^2$/g and approximately 3% moisture to a 500 ml flask under a nitrogen blanket at a temperature of approximately 20° C.

Add iron chloride ($FeCl_3.6H_2O$) (4.89 g) to a 100 ml beaker containing deionized water (30 ml) to form an iron solution. Add the iron solution to the carbon support at a rate of approximately 1 ml/minute with vigorous shaking of the flask containing the carbon powder, over the course of approximately 30 minutes and under the nitrogen blanket.

Add approximately 25 ml of a 0.2% by weight sodium hydroxide solution (Aldrich Chemical Co., Milwaukee, Wis.) to the iron solution and carbon support mixture at a rate of approximately 1 ml/minute with vigorous shaking of the flask containing the carbon powder, over the course of approximately 25 minutes and under the nitrogen blanket.

Heat the resulting mixture under a nitrogen blanket to 70° C. at a rate of about 2° C. per minute. Upon reaching 70° C., add 25 ml of 0.2% by weight sodium hydroxide at a rate of approximately 1 ml/minute with vigorous shaking of the flask, over the course of approximately 25 minutes and under the nitrogen blanket.

Dry the resulting wet cake for approximately 16 hours in a vacuum oven at approximately 120° C. to produce a catalyst precursor that contains approximately 1.0% by weight iron.

Charge iron-containing precursor (5.0 g) into a Hastelloy C tube reactor packed with high temperature insulation material. Purge the reactor with argon by introducing to the reactor at a rate of approximately 100 cm$^3$/min at approximately 20° C. for approximately 15 minutes. Insert a thermocouple into the center of the reactor for charging the precursor.

After introduction of the precursor, increase the temperature of the reactor to approximately 300° C. over the course of approximately 15 minutes. During this time, introduce a 10%/90% (v/v) mixture of acetonitrile and argon (Airgas, Inc., Radnor, Pa.) to the reactor at a rate of approximately 100 cm$^3$/minute. Then increase the reactor to approximately 950° C. over the course of 30 minutes while flowing a 10%/90% (v/v) mixture of acetonitrile and argon through the reactor at a rate of approximately 100 cm$^3$/minute. Maintain the reactor at approximately 950° C. for approximately 120 minutes. Cool the reactor to approximately 20° C. over the course of approximately 90 minutes under a flow of argon at approximately 100 cm$^3$/minute.

The resulting catalyst contains approximately 1% by weight iron.

EXAMPLE 61

This example details hydrogen generation during PMIDA oxidation conducted under the conditions set forth in Example 49 using different catalysts. The catalysts tested included a 3% cobalt catalyst prepared as described in Example 50, a 5% Pt/0.5% Fe catalyst prepared as described in U.S. Ser. No. 60/627,500, and a particulate carbon catalyst described in U.S. Pat. No. 4,696,772 to Chou.

Figure 110:
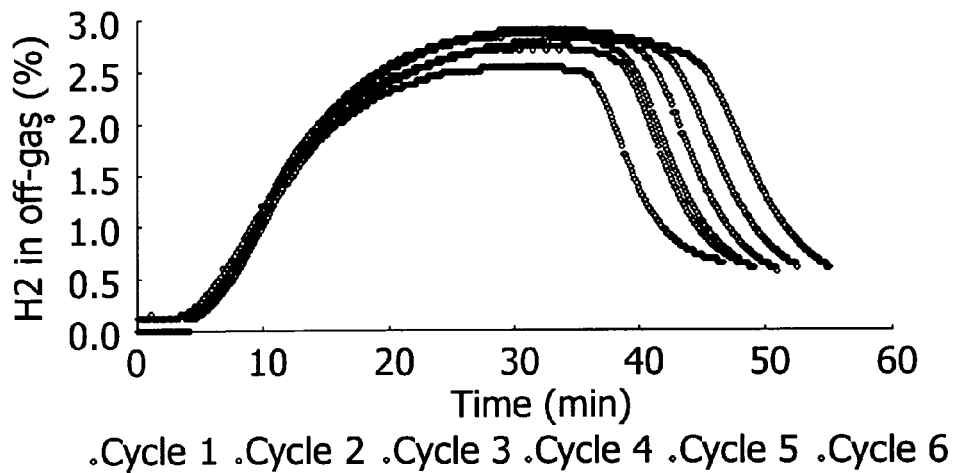
FIGS. 110-112 show PMIDA reaction testing results as described in Example 61.

FIG. 110 shows the hydrogen generation profiles for the 3% cobalt catalyst over the course of the 6 reaction cycles.

Figure 111:
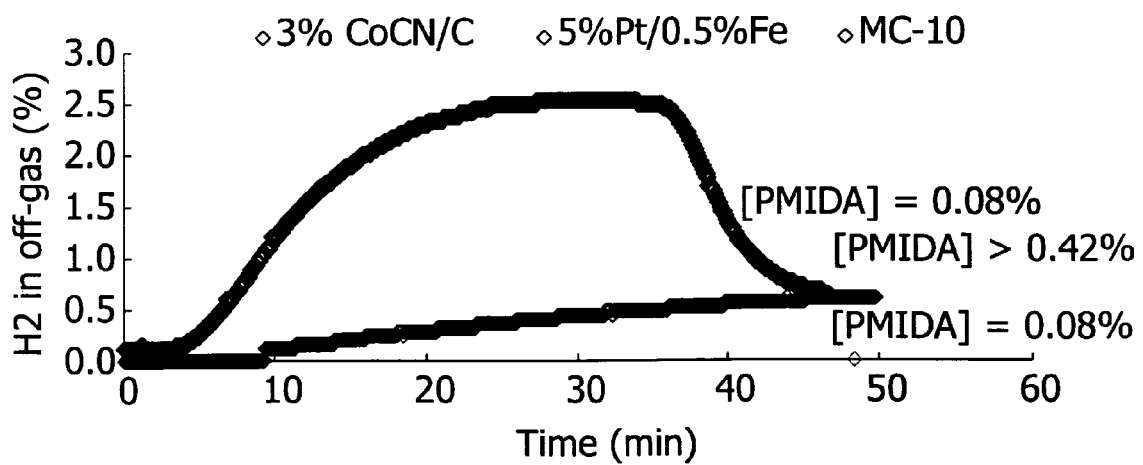

FIG. 111 shows the first cycle hydrogen generation profile for each of the three catalysts for a reaction time of approximately 50 minutes. At this reaction time, very low residual levels of PMIDA were observed with the 3% cobalt catalyst and the 5% Pt/0.5% Fe catalyst.

Figure 112:
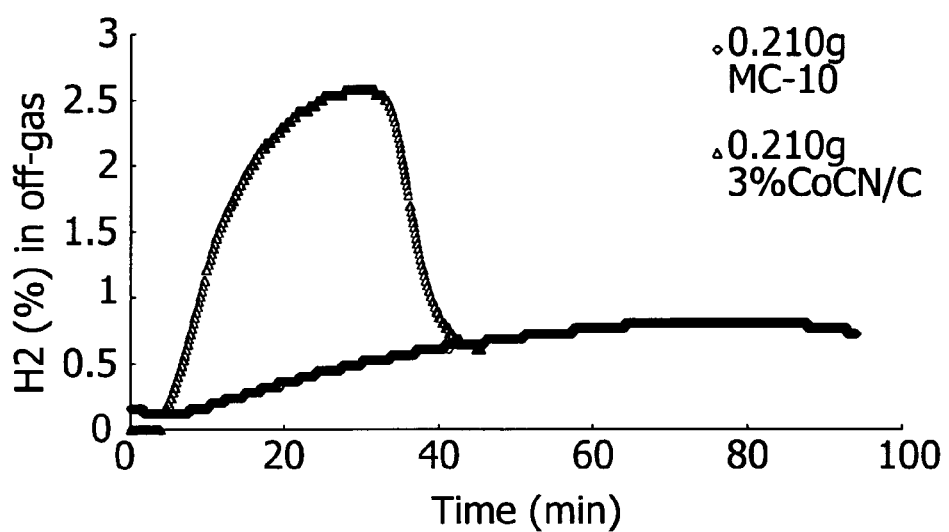

FIG. 112 shows the first cycle hydrogen generation profile for the 3% cobalt catalyst and the 4,696,772 catalyst at similar PMIDA conversion levels (i.e., at a reaction time of approximately 50 minutes for the 3% cobalt catalyst and a reaction time of approximately 95 minutes for the 4,696,772 catalyst) The maximum hydrogen generation for the 3% cobalt catalyst was approximately three times that of the 4,696,772 catalyst] while the total amount of hydrogen generated with the 3% cobalt catalyst was approximately 37% higher than observed with the 4,696,772 catalyst.

EXAMPLE 62

This example details detection of hydrogen peroxide in the PMIDA reaction product of PMIDA oxidation catalyzed using a 3% CoCN/C catalyst prepared using diglyme as described in Example 50. The protocol relies on oxidation of $VO^{+2}$ by hydrogen peroxide to produce a diperoxo anion (e.g., $VO(O-O)]^-$ in a neutral medium yielding a yellowish medium and oxidation to produce a diperoxo cation (e.g., $VO(O-O)]^+$ in an acidic medium to produce a reddish medium.

20 ml of the reaction product (taken at a reaction time of approximately 50 minutes) was mixed with 10 ml of an aqueous solution containing 1% $VOSO_4$ and the color of the resulting solution was recorded. The color of the solution was yellowish green, indicating hydrogen peroxide was present in the reaction product. As an estimate of the hydrogen peroxide content, a solution of similar color was prepared by mixing approximately 625 ppm of hydrogen peroxide with the $VOSO_4$ solution.

IR spectra of the reaction product were determined. Two wavelengths of hydrogen peroxide (e.g., 2828 and 1362 $cm^{-1}$) were used to determine the presence of hydrogen peroxide. No clear hydrogen peroxide peaks were identified, possibly due to the presence of glyphosate and other reaction products in the samples. Since the detection limit of hydrogen peroxide was estimated to be approximately 3000 ppm and based on the 625 ppm used to prepare the yellowish green solution, the hydrogen peroxide concentration in the 50 minute reaction runtime product was estimated to be from approximately 625 to approximately 3000 ppm.

The present invention is not limited to the above embodiments and can be variously modified. The above description of the preferred embodiments, including the Examples, is intended only to acquaint others skilled in the art with the invention, its principles, and its practical application so that others skilled in the art may adapt and apply the invention in its numerous forms, as may be best suited to the requirements of a particular use.

With reference to the use of the word(s) comprise or comprises or comprising in this entire specification (including the claims below), unless the context requires otherwise, those words are used on the basis and clear understanding that they are to be interpreted inclusively, rather than exclusively, and applicants intend each of those words to be so interpreted in construing this entire specification.

What is claimed is:

1. A process for the oxidation of N-(phosphonomethyl) iminodiacetic acid or a salt thereof, the process comprising contacting said N-(phosphonomethyl)iminodiacetic acid or a salt thereof with an oxidant in the presence of a catalyst, wherein the catalyst comprises a carbon support having formed thereon a transition metal composition comprising a transition metal (M) and nitrogen, the transition metal being selected from the group consisting of copper, silver, vanadium, chromium, molybdenum, tungsten, manganese, cobalt, nickel, cerium, and combinations thereof, wherein the catalyst is characterized as generating ions corresponding to the formula $MN_xC_y^+$ when the catalyst is analyzed by Time-of-Flight Secondary Ion Mass Spectrometry (ToF SIMS) as described in Protocol A and the relative abundance of ions in which x is 1 is at least 20%.

2. A process as set forth in claim 1 wherein said catalyst comprises an activated carbon support.

3. A process as set forth in claim 2 wherein the total Langmuir surface area of said carbon support prior to formation of said transition metal composition thereon is from about 1000 $m^2/g$ to about 1600 $m^2/g$.

4. A process as set forth in claim 3 wherein the catalyst has a total Langmuir surface area of from about 600 $m^2/g$ to about 1400 $m^2/g$.

5. A process as set forth in claim 4 wherein the total Langmuir surface area of said catalyst is from about 60 to about 80% of the total Langmuir surface area of said carbon support prior to formation of said transition metal composition thereon.

6. A process as set forth in claim 2 wherein the micropore Langmuir surface area of said catalyst is from about 750 $m^2/g$ to about 1100 $m^2/g$.

7. A process as set forth in claim 6 wherein the micropore Langmuir surface area of said catalyst is from about 55% to about 80% of the micropore Langmuir surface area of said carbon support prior to formation of said transition metal composition thereon.

8. A process as set forth in claim 2 wherein the combined mesopore and macropore Langmuir surface area of said catalyst is from about 175 to about 300 $m^2/g$.

9. A process as set forth in claim 8 wherein the combined mesopore and macropore Langmuir surface area of said catalyst is from about 70% to about 90% of the combined mesopore and macropore Langmuir surface area of said carbon support prior to formation of said transition metal composition thereon.

10. A process as set forth in claim 1 wherein the transition metal constitutes at least about 1.0% by weight of the catalyst.

11. A process as set forth in claim 10 wherein the transition metal constitutes less than about 5% by weight of the catalyst.

12. A process as set forth in claim 10 wherein the transition metal constitutes at least about 2.0% by weight of the catalyst.

13. A process as set forth in claim 12 wherein the transition metal constitutes less than about 5% by weight of the catalyst.

14. A process as set forth in claim 1 wherein said transition metal composition formed on said carbon support is present in a proportion of from about 0.1% to about 20% by weight of the catalyst.

15. A process as set forth in claim 1 wherein said nitrogen of said transition metal composition formed on said carbon support is present in a proportion of from about 0.1% to about 20% by weight of the catalyst.

16. A process as set forth in claim 1 wherein the transition metal composition comprises a transition metal nitride.

17. A process as set forth in claim 16 wherein the transition metal composition further comprises carbon.

18. A process as set forth in claim 17 wherein the transition metal composition comprises a transition metal nitride, transition metal carbide, a transition metal carbide-nitride, or combinations thereof.

19. A process as set forth in claim 16 wherein the transition metal comprises cobalt and the transition metal composition comprises cobalt nitride.

20. A process as set forth in claim 1 wherein the relative abundance of ions in which x is 1 is at least about 30%.

21. A process as set forth in claim 20 wherein the relative abundance of ions in which x is 1 is at least about 42%.

22. A process as set forth in claim 20 wherein the relative abundance of ions in which x is 1 is less than about 90%.

23. A process as set forth in claim 1 wherein the relative abundance of ions in which x is 1 and y is 1 is at least about 10%.

24. A process as set forth in claim 23 wherein the relative abundance of ions in which x is 1 and y is 1 is from about 10% to about 40%.

25. A process as set forth in claim 1 wherein the weighted molar average value of x is from about 0.5 to about 5.0.

26. A process as set forth in claim 25 wherein the weighted molar average value of x is from about 0.5 to about 3.0.

27. A process as set forth in claim 26 wherein the weighted molar average value of x is from about 0.5 to about 2.10.

28. A process as set forth in claim 1 wherein the weighted molar average value of y is from about 0.5 to about 5.0.

29. A process as set forth in claim 28 wherein the weighted molar average value of y is from about 0.5 to about 2.6.

30. A process as set forth in claim 1 wherein $MN_xC_y^+$ ions in which the weighted molar average value of x is from 4.0 to about 8.0 constitute no more than about 60 mole percent of said $MN_xC_y^+$ ions generated during said ToFSIMS analysis.

31. A process as set forth in claim 1 wherein said transition metal composition comprises cobalt, and the catalyst is characterized such that the catalyst exhibits at least about $2.50 \times 10^{25}$ spins/mole cobalt when the catalyst is analyzed by Electron Paramagnetic Resonance (EPR) Spectroscopy as described in Protocol C.

32. A process as set forth in claim 31 wherein the catalyst is characterized such that the catalyst exhibits at least about $6.50 \times 10^{25}$ spins/mole cobalt when the catalyst is analyzed by Electron Paramagnetic Resonance (EPR) Spectroscopy as described in Protocol C.

33. A process as set forth in claim 32 wherein the catalyst is characterized such that the catalyst exhibits at least about $1.0 \times 10^{26}$ spins/mole cobalt when the catalyst is analyzed by Electron Paramagnetic Resonance (EPR) Spectroscopy as described in Protocol C.

34. A process as set forth in claim 31 wherein the catalyst is characterized such that the catalyst exhibits less than about $1.0 \times 10^{27}$ spins/mole cobalt when the catalyst is analyzed by Electron Paramagnetic Resonance (EPR) Spectroscopy as described in Protocol C.

35. A process as set forth in claim 1 wherein said transition metal composition comprises cobalt, and the catalyst is characterized such that, when the catalyst is analyzed by X-Ray Photoelectron Spectroscopy (XPS):
the C 1s spectra includes a component having a binding energy of from about 284.6 eV to about 285 eV,
the N 1s spectra includes a component having a binding energy of from about 398.4 eV to about 398.8 eV,
the Co 2p spectra includes a component having a binding energy of from about 778.4 eV to about 778.8 eV, and/or
the O 1s spectra includes a component having a binding energy of from about 532.5 eV to about 533.7 eV.

36. A process as set forth in claim 1 wherein said catalyst functions to catalyze both the oxidation of said N-(phosphonomethyl)iminodiacetic acid or a salt thereof and the further oxidation of formaldehyde and formic acid produced as by-products of the oxidation of said N-(phosphonomethyl)iminodiacetic acid or a salt thereof.

37. A process as set forth in claim 36 wherein contacting N-(phosphonomethyl)iminodiacetic acid with an oxidant in the presence of said catalyst produces N-(phosphonomethyl)glycine, the process further comprising preparing an agronomically acceptable salt of N-(phosphonomethyl) glycine.

38. A process as set forth in claim 37 wherein a concentrate is prepared comprising a salt of N-(phosphonomethyl)glycine in a concentration of at least 240 gpl, a.e.

39. A process as set forth in claim 38 wherein the concentrate further comprises a surfactant.

40. A process as set forth in claim 39 wherein the surfactant comprises an alkoxylated alkylamine or an alkoxylated etheramine.

41. A process for the oxidation of N-(phosphonomethyl)iminodiacetic acid or a salt thereof, the process comprising contacting said N-(phosphonomethyl)iminodiacetic acid or a salt thereof with an oxidant in the presence of a catalyst, wherein the catalyst comprises a carbon support having formed thereon a transition metal composition comprising a transition metal (M) and nitrogen, the transition metal being selected from the group consisting of copper, silver, vanadium, chromium, molybdenum, tungsten, manganese, cobalt, nickel, cerium, and combinations thereof, wherein: the catalyst is characterized as generating ions corresponding to the formula $MN_xC_y^+$ when the catalyst is analyzed by Time-of-Flight Secondary Ion Mass Spectrometry (ToF SIMS) as described in Protocol A, the weighted molar average value of x being from about 0.5 to about 3.0 and the weighted molar average value of y being from about 0.5 to about 8.0.

42. A process as set forth in claim 41 wherein the transition metal constitutes from about 1.0% to about 5% by weight of the catalyst.

43. A process as set forth in claim 42 wherein the transition metal constitutes from about 2% to about 5% by weight of the catalyst.

44. A process as set forth in claim 41 wherein the transition metal composition comprises a transition metal nitride.

45. A process as set forth in claim 44 wherein the transition metal composition further comprises carbon.

46. A process as set forth in claim 45 wherein the transition metal composition comprises a transition metal nitride, transition metal carbide, a transition metal carbide-nitride, or combinations thereof.

47. A process as set forth in claim 41 wherein the transition metal comprises cobalt and the transition metal composition comprises cobalt nitride.

48. A process as set forth in claim 41 wherein the relative abundance of ions in which x is 1 is at least about 30%.

49. A process as set forth in claim 41 wherein the relative abundance of ions in which x is 1 and y is 1 is at least about 10%.

50. A process as set forth in claim 41 wherein the weighted molar average value of x is from about 0.5 to about 2.10.

51. A process as set forth in claim 41 wherein $MN_xC_y^+$ ions in which the weighted molar average value of x is from 4.0 to about 8.0 constitute no more than about 60 mole percent of said $MN_xC_y^+$ ions generated during said ToFSIMS analysis.

52. A process as set forth in claim 41 wherein said transition metal composition comprises cobalt, and the catalyst is characterized such that the catalyst exhibits at least about $2.50 \times 10^{25}$ spins/mole cobalt when the catalyst is analyzed by Electron Paramagnetic Resonance (EPR) Spectroscopy as described in Protocol C.

53. A process as set forth in claim 41 wherein said transition metal composition comprises cobalt, and the catalyst is characterized such that, when the catalyst is analyzed by X-Ray Photoelectron Spectroscopy (XPS):
the C 1s spectra includes a component having a binding energy of from about 284.6 eV to about 285 eV,
the N 1s spectra includes a component having a binding energy of from about 398.4 eV to about 398.8 eV,
the Co 2p spectra includes a component having a binding energy of from about 778.4 eV to about 778.8 eV, and/or
the O 1s spectra includes a component having a binding energy of from about 532.5 eV to about 533.7 eV.

54. A process as set forth in claim 41 wherein said catalyst functions to catalyze both the oxidation of said N-(phosphonomethyl)iminodiacetic acid or a salt thereof and the further oxidation of formaldehyde and formic acid produced as by-products of the oxidation of said N-(phosphonomethyl)iminodiacetic acid or a salt thereof.

55. A process for the oxidation of N-(phosphonomethyl) iminodiacetic acid or a salt thereof, the process comprising contacting said N-(phosphonomethyl)iminodiacetic acid or a salt thereof with an oxidant in the presence of a catalyst, wherein the catalyst comprises a carbon support having formed thereon a transition metal composition comprising a transition metal (M) and nitrogen, the transition metal (M) constituting at least 1.6% by weight of the catalyst, wherein: the catalyst is characterized as generating ions corresponding to the formula $MN_xC_y^+$ when the catalyst is analyzed by Time-of-Flight Secondary Ion Mass Spectrometry (ToF SIMS) as described in Protocol A; the weighted molar average value of x being from about 0.5 to about 8 and the weighted molar average value of y being from about 0.5 to about 8.

56. A process as set forth in claim 55 wherein the transition metal is selected from the group consisting of Group IB, Group VB, Group VIB, Group VIIB, Group VIII, lanthanide series metals, and combinations thereof.

57. A process as set forth in claim 55 wherein the transition metal is selected from the group consisting of copper, silver, vanadium, chromium, molybdenum, tungsten, manganese, iron, cobalt, nickel, ruthenium, cerium, and combinations thereof.

58. A process as set forth in claim 55 wherein the transition metal is selected from the group consisting of copper, silver, vanadium, chromium, molybdenum, tungsten, manganese, cobalt, nickel, ruthenium, cerium, and combinations thereof.

59. A process as set forth in claim 55 wherein said transition metal is selected from the group consisting of chromium, iron, cobalt, and combinations thereof.

60. A process as set forth in claim 55 wherein the transition metal comprises iron.

61. A process as set forth in claim 55 wherein the transition metal comprises cobalt.

62. A process as set forth in claim 55 wherein the transition metal constitutes less than about 5% by weight of the catalyst.

63. A process as set forth in claim 55 wherein the transition metal constitutes at least about 2.0% by weight of the catalyst.

64. A process as set forth in claim 63 wherein the transition metal constitutes less than about 5% by weight of the catalyst.

65. A process as set forth in claim 55 wherein the transition metal composition comprises a transition metal nitride.

66. A process as set forth in claim 65 wherein the transition metal composition further comprises carbon.

67. A process as set forth in claim 66 wherein the transition metal composition comprises a transition metal nitride, transition metal carbide, a transition metal carbide-nitride, or combinations thereof.

68. A process as set forth in claim 65 wherein the transition metal is cobalt and the transition metal composition comprises cobalt nitride.

69. A process as set forth in claim 55 wherein the weighted molar average value of x is from about 0.5 to about 5.0.

70. A process as set forth in claim 69 wherein the weighted molar average value of x is from about 0.5 to about 3.0.

71. A process as set forth in claim 70 wherein the weighted molar average value of x is from about 0.5 to about 2.20.

72. A process as set forth in claim 55 wherein the relative abundance of ions in which x is 1 is at least about 20%.

73. A process as set forth in claim 55 wherein the relative abundance of ions in which x is 1 and y is 1 is at least about 10%.

74. A process as set forth in claim 55 wherein $MN_xC_y^+$ ions in which the weighted molar average value of x is from 4.0 to about 8.0 constitute no more than about 60 mole percent of said $MN_xC_y^+$ ions generated during said ToFSIMS analysis.

75. A process as set forth in claim 55 wherein said transition metal composition comprises cobalt, and the catalyst is characterized such that the catalyst exhibits at least about $2.50 \times 10^{25}$ spins/mole cobalt when the catalyst is analyzed by Electron Paramagnetic Resonance (EPR) Spectroscopy as described in Protocol C.

76. A process as set forth in claim 55 wherein said transition metal composition comprises cobalt, and the catalyst is characterized such that, when the catalyst is analyzed by X-Ray Photoelectron Spectroscopy (XPS):
the C 1s spectra includes a component having a binding energy of from about 284.6 eV to about 285 eV,
the N 1s spectra includes a component having a binding energy of from about 398.4 eV to about 398.8 eV,
the Co 2p spectra includes a component having a binding energy of from about 778.4 eV to about 778.8 eV, and/or
the O 1s spectra includes a component having a binding energy of from about 532.5 eV to about 533.7 eV.

77. A process as set forth in claim 55 wherein said catalyst functions to catalyze both the oxidation of said N-(phosphonomethyl)iminodiacetic acid or a salt thereof and the further oxidation of formaldehyde and formic acid produced as by-products of the oxidation of said N-(phosphonomethyl)iminodiacetic acid or a salt thereof.

78. A process for the oxidation of N-(phosphonomethyl) iminodiacetic acid or a salt thereof, the process comprising contacting said N-(phosphonomethyl)iminodiacetic acid or a salt thereof with an oxidant in the presence of a catalyst, wherein said catalyst comprises a carbon support having formed thereon a transition metal composition comprising a transition metal (M) and nitrogen and the catalyst is characterized as generating ions corresponding to the formula $MN_xC_y^+$ when the catalyst is analyzed by Time-of-Flight Secondary Ion Mass Spectrometry (ToF SIMS) as described in Protocol A, the weighted molar average value of x being from about 0.5 to 2.10 and the weighted molar average value of y being from about 0.5 to about 8.0.

79. A process as set forth in claim 78 wherein the transition metal is selected from the group consisting of copper, silver, vanadium, chromium, molybdenum, tungsten, manganese, iron, cobalt, nickel, ruthenium, cerium, and combinations thereof.

80. A process as set forth in claim 78 wherein the transition metal is selected from the group consisting of copper, silver, vanadium, chromium, molybdenum, tungsten, manganese, cobalt, nickel, ruthenium, cerium, and combinations thereof.

81. A process as set forth in claim 78 wherein the transition metal comprises cobalt.

82. A process as set forth in claim 78 wherein the transition metal constitutes from about 1.0% to about 5% by weight of the catalyst.

83. A process as set forth in claim 78 wherein the transition metal constitutes from about 2% to about 5% by weight of the catalyst.

84. A process as set forth in claim 78 wherein the transition metal composition comprises a transition metal nitride.

85. A process as set forth in claim 84 wherein the transition metal composition further comprises carbon.

86. A process as set forth in claim 85 wherein the transition metal composition comprises a transition metal nitride, transition metal carbide, a transition metal carbide-nitride, or combinations thereof.

87. A process as set forth in claim 84 wherein the transition metal is cobalt and the transition metal composition comprises cobalt nitride.

88. A process as set forth in claim 78 wherein the relative abundance of ions in which x is 1 is at least about 20%.

89. A process as set forth in claim 78 wherein the relative abundance of ions in which x is 1 and y is 1 is at least about 10%.

90. A process as set forth in claim 78 wherein $MN_xC_y^+$ ions in which the weighted molar average value of x is from 4.0 to about 8.0 constitute no more than about 60 mole percent of said $MN_xC_y^+$ ions generated during said ToFSIMS analysis.

91. A process as set forth in claim 78 wherein said transition metal composition comprises cobalt, and the catalyst is characterized such that the catalyst exhibits at least about $2.50 \times 10^{25}$ spins/mole cobalt when the catalyst is analyzed by Electron Paramagnetic Resonance (EPR) Spectroscopy as described in Protocol C.

92. A process as set forth in claim 78 wherein said transition metal composition comprises cobalt, and the catalyst is characterized such that, when the catalyst is analyzed by X-Ray Photoelectron Spectroscopy (XPS):

the C 1s spectra includes a component having a binding energy of from about 284.6 eV to about 285 eV,
the N 1s spectra includes a component having a binding energy of from about 398.4 eV to about 398.8 eV,
the Co 2p spectra includes a component having a binding energy of from about 778.4 eV to about 778.8 eV, and/or
the O 1s spectra includes a component having a binding energy of from about 532.5 eV to about 533.7 eV.

93. A process as set forth in claim 78 wherein said catalyst functions to catalyze both the oxidation of said N-(phosphonomethyl)iminodiacetic acid or a salt thereof and the further oxidation of formaldehyde and formic acid produced as by-products of the oxidation of said N-(phosphonomethyl)iminodiacetic acid or a salt thereof.

94. A process for the oxidation of N-(phosphonomethyl)iminodiacetic acid or a salt thereof, the process comprising contacting said N-(phosphonomethyl)iminodiacetic acid or a salt thereof with an oxidant in the presence of a catalyst, wherein the catalyst comprises a carbon support having formed thereon a transition metal composition comprising cobalt and nitrogen, wherein cobalt constitutes from about 2% to about 5% by weight of the catalyst and the catalyst is characterized such that, when the catalyst is analyzed by X-Ray Photoelectron Spectroscopy (XPS), the C 1s spectra includes a component having a binding energy of from about 284.6 eV to about 285 eV,
the N 1s spectra includes a component having a binding energy of from about 398.4 eV to about 398.8 eV,
the Co 2p spectra includes a component having a binding energy of from about 778.4 eV to about 778.8 eV, and/or
the O 1s spectra includes a component having a binding energy of from about 532.5 eV to about 533.7 eV.

95. A process for the oxidation of N-(phosphonomethyl)iminodiacetic acid or a salt thereof, the process comprising contacting said N-(phosphonomethyl)iminodiacetic acid or a salt thereof with an oxidant in the presence of a catalyst, wherein the catalyst comprises a carbon support having formed thereon a transition metal composition comprising cobalt and nitrogen, the catalyst being characterized such that the catalyst exhibits at least about $2.50 \times 10^{25}$ spins/mole cobalt when the catalyst is analyzed by Electron Paramagnetic Resonance (EPR) Spectroscopy as described in Protocol C.

96. A process as set forth in claim 1 wherein the transition metal comprises cobalt.

97. A process as set forth in claim 41 wherein the transition metal comprises cobalt.

98. A process as set forth in claim 78 wherein the transition metal comprises cobalt.

* * * * *